(12) United States Patent
Yin et al.

(10) Patent No.: US 10,208,120 B2
(45) Date of Patent: Feb. 19, 2019

(54) ANTI-FGFR2/3 ANTIBODIES AND METHODS USING SAME

(71) Applicant: Genentech, Inc., South San Francisco, CA (US)

(72) Inventors: Yiyuan Yin, Fremont, CA (US); Avi Ashkenazi, San Mateo, CA (US); Paul J. Carter, Hillsborough, CA (US); Mark Chen, San Mateo, CA (US); Junichiro Sonoda, Lafayette, CA (US)

(73) Assignee: GENENTECH, INC., South San Francisco, CA (US)

( * ) Notice: Subject to any disclaimer, the term of this patent is extended or adjusted under 35 U.S.C. 154(b) by 130 days.

(21) Appl. No.: 14/934,059

(22) Filed: Nov. 5, 2015

(65) Prior Publication Data
US 2016/0244525 A1 Aug. 25, 2016

Related U.S. Application Data

(60) Provisional application No. 62/075,740, filed on Nov. 5, 2014.

(51) Int. Cl.
A61K 39/00 (2006.01)
C07K 16/28 (2006.01)
C07K 16/30 (2006.01)
C07K 16/40 (2006.01)
C12P 21/02 (2006.01)

(52) U.S. Cl.
CPC .......... C07K 16/2863 (2013.01); C07K 16/30 (2013.01); C07K 16/303 (2013.01); C07K 16/3015 (2013.01); C07K 16/3023 (2013.01); C07K 16/3069 (2013.01); C07K 16/40 (2013.01); C12P 21/02 (2013.01); A61K 2039/505 (2013.01); C07K 2317/21 (2013.01); C07K 2317/31 (2013.01); C07K 2317/34 (2013.01); C07K 2317/565 (2013.01); C07K 2317/73 (2013.01); C07K 2317/76 (2013.01)

(58) Field of Classification Search
CPC ............... C07K 16/2863; A61K 2039/505
See application file for complete search history.

(56) References Cited

U.S. PATENT DOCUMENTS

| 3,773,919 A | 11/1973 | Boswell et al. |
|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,675,187 A | 6/1987 | Konishi et al. |
| 4,676,980 A | 6/1987 | Segal et al. |
| 4,683,195 A | 7/1987 | Mullis et al. |
| 4,683,203 A | 7/1987 | Anton et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 4,970,198 A | 11/1990 | Lee et al. |
| 4,975,278 A | 12/1990 | Senter et al. |
| 5,053,394 A | 10/1991 | Ellestad et al. |
| 5,079,233 A | 1/1992 | Lee |
| 5,122,469 A | 6/1992 | Mather et al. |
| 5,208,020 A | 5/1993 | Chari et al. |

(Continued)

FOREIGN PATENT DOCUMENTS

EP 0332435 A2 9/1989
EP 0 404 097 A2 12/1990

(Continued)

OTHER PUBLICATIONS

Ahmad et al., "Mechanisms of FGFR-mediated carcinogenesis", Biochimica et Biophysica Acta, Molecular Cell Research 1823(4):850-860 (Jan. 10, 2012).
Annex to Invitation to Pay Additional Fees dated Feb. 26, 2016 in International Application No. PCT/US2015/059335.
International Search Report and Written Opinion dated May 10, 2016 in International Application No. PCT/US2015/059335.
Qing et al., "Antibody-based targeting of FGFR3 in bladder carcinoma and t(4;14)-positive multiple myeloma in mice", Journal of Clinical Investigation 119(5):1216-1229 (May 1, 2009).
Sharpe et al., "FGFR Signaling Promotes the Growth of Triple-Negative and Basal-Like Breast Cancer Cell Lines Both In Vitro and In Vivo", Clinical Cancer Research 17(16):5275-5286 (Jun. 28, 2011).

(Continued)

Primary Examiner — Ruixiang Li
(74) Attorney, Agent, or Firm — Baker Botts, L.L.P.

(57) ABSTRACT

The invention provides dual specific anti-FGFR2 and FGFR3 (FGFR2/3) antibodies, and compositions comprising and methods of using these antibodies.

10 Claims, 26 Drawing Sheets
(12 of 26 Drawing Sheet(s) Filed in Color)
Specification includes a Sequence Listing.

(56) References Cited

U.S. PATENT DOCUMENTS

| | | | |
|---|---|---|---|
| 5,264,365 | A | 11/1993 | Georgiou et al. |
| 5,362,852 | A | 11/1994 | Geoghegan et al. |
| 5,416,064 | A | 5/1995 | Chari et al. |
| 5,500,362 | A | 3/1996 | Robinson et al. |
| 5,508,192 | A | 4/1996 | Georgiou et al. |
| 5,571,894 | A | 11/1996 | Wels et al. |
| 5,585,089 | A | 12/1996 | Queen et al. |
| 5,587,458 | A | 12/1996 | King et al. |
| 5,606,040 | A | 2/1997 | Mcgahren et al. |
| 5,624,821 | A | 4/1997 | Winter et al. |
| 5,635,483 | A | 6/1997 | Pettit et al. |
| 5,639,635 | A | 6/1997 | Joly |
| 5,641,870 | A | 6/1997 | Rinderknecht et al. |
| 5,648,237 | A | 7/1997 | Carter |
| 5,648,260 | A | 7/1997 | Winter et al. |
| 5,663,149 | A | 9/1997 | Pettit et al. |
| 5,693,762 | A | 12/1997 | Queen et al. |
| 5,712,374 | A | 1/1998 | Kuntsmann et al. |
| 5,714,586 | A | 2/1998 | Kuntsmann et al. |
| 5,739,116 | A | 4/1998 | Hamann et al. |
| 5,739,277 | A | 4/1998 | Presta et al. |
| 5,767,285 | A | 6/1998 | Hamann et al. |
| 5,770,701 | A | 6/1998 | Mcgahren et al. |
| 5,770,710 | A | 6/1998 | Mcgahren et al. |
| 5,773,001 | A | 6/1998 | Hamann et al. |
| 5,780,588 | A | 7/1998 | Pettit et al. |
| 5,821,337 | A | 10/1998 | Carter et al. |
| 5,837,243 | A | 11/1998 | Deo et al. |
| 5,869,046 | A | 2/1999 | Presta et al. |
| 5,869,245 | A | 2/1999 | Yeung |
| 5,877,296 | A | 3/1999 | Hamann et al. |
| 5,922,845 | A | 7/1999 | Deo et al. |
| 6,027,888 | A | 2/2000 | Georgiou et al. |
| 6,083,715 | A | 7/2000 | Georgiou et al. |
| 6,194,551 | B1 | 2/2001 | Idusogie et al. |
| 6,407,213 | B1 | 6/2002 | Carter et al. |
| 6,602,684 | B1 | 8/2003 | Umana et al. |
| 6,737,056 | B1 | 5/2004 | Presta |
| 8,410,250 | B2 * | 4/2013 | Ashkenazi ......... C07K 16/2863 530/387.1 |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0123546 | A1 | 6/2005 | Umana et al. |
| 2005/0147612 | A1 | 7/2005 | Yayon et al. |
| 2010/0291114 | A1 | 11/2010 | Wiesmann |
| 2015/0218276 | A1 | 8/2015 | Chen et al. |

FOREIGN PATENT DOCUMENTS

| | | |
|---|---|---|
| EP | 0 425 235 A2 | 5/1991 |
| WO | WO 87/00195 A1 | 1/1987 |
| WO | WO 90/03430 A1 | 4/1990 |
| WO | WO 91/00360 A1 | 1/1991 |
| WO | WO 92/00373 A1 | 1/1992 |
| WO | WO 92/09690 A2 | 6/1992 |
| WO | WO 93/06213 A1 | 4/1993 |
| WO | WO 93/08829 A1 | 5/1993 |
| WO | WO 93/11161 A1 | 6/1993 |
| WO | WO 93/16185 A2 | 8/1993 |
| WO | WO 93/21232 A1 | 10/1993 |
| WO | WO 94/04690 A1 | 3/1994 |
| WO | WO 94/11026 A2 | 5/1994 |
| WO | WO 94/29351 A2 | 12/1994 |
| WO | WO 96/07321 A1 | 3/1996 |
| WO | WO 96/07754 A1 | 3/1996 |
| WO | WO 97/30087 A1 | 8/1997 |
| WO | WO 98/45479 A1 | 10/1998 |
| WO | WO 98/58964 A1 | 12/1998 |
| WO | WO 99/22764 A1 | 5/1999 |
| WO | WO 99/51642 A1 | 10/1999 |
| WO | WO 00/42072 A2 | 7/2000 |
| WO | WO 00/61739 A1 | 10/2000 |
| WO | WO 01/29246 A1 | 4/2001 |
| WO | WO 01/45746 A2 | 6/2001 |
| WO | WO 02/060919 A2 | 8/2002 |
| WO | WO 02/088172 A2 | 11/2002 |
| WO | WO 2003/011878 A2 | 2/2003 |
| WO | WO 03/084570 A1 | 10/2003 |
| WO | WO 03/085119 A1 | 10/2003 |
| WO | WO 2004/056312 A2 | 7/2004 |
| WO | WO 2005/035586 A1 | 4/2005 |
| WO | WO 2005/035778 A1 | 4/2005 |
| WO | WO 2005/053742 A1 | 6/2005 |
| WO | WO 2006/015371 A2 | 2/2006 |
| WO | WO 2006/048877 A2 | 5/2006 |
| WO | WO 2007/001851 A2 | 1/2007 |
| WO | WO 2007/144893 A2 | 12/2007 |
| WO | WO 2010/002862 A2 | 1/2010 |
| WO | WO 2010/111367 A1 | 9/2010 |

OTHER PUBLICATIONS

Trudel et al., "The inhibitory anti-FGFR3 antibody, PRO-001, is cytotoxic to t(4;14) multiple myeloma cells", Blood 107(10):4039-4046 (May 15, 2006).

Yin Y. et al., "Redesigning a monospecific anti-FGFR3 antibody to add selectivity for FGFR2 and expand antitumor activity" Molecular Cancer Therapeutics 14(10):2270-2278 (Oct. 2015).

Abrahmsen et al., "Analysis of signals for secretion in the staphylococcal protein A gene," EMBO J., 4(13B):3901-3906 (1985).

Adams et al., "Phenix: a comprehensive Python-based system for macromolecular structure solution," Acta Cryst. D66:213-221 (2010).

Agazie et al., "The phosphotyrosine phosphatase SHP2 is a critical mediator of transformation induced by the oncogenic fibroblast growth factor receptor 3," Oncogene 22:6909-6918 (2003).

Antibodies, A Laboratory Manual, Cold Spring Harbor Laboratory, Ed Harlow and David Lane (1988).

Arie et al., "Chaperone function of FkpA, a heat shock prolyl isomerase, in the periplasm of *Escherichia coli*," Mol. Microbiol. 39(1):199-210 (2001).

Bai et al., "GP369, an FGFR2-IIIb-specific antibody, exhibits potent antitumor activity against human cancers driven by activated FGFR2 signaling," Cancer Research 70(19):7630-7639 (2010).

Baldwin et al., Monoclonal Antibodies in Cancer Treatment, Lancet pp. 603-605 (1986).

Barbas III et al., "Assembly of combinatorial antibody libraries on phage surfaces: The gene III site," PNAS (USA) 88:7978-7982 (1991).

Barbas III et al., "In vitro evolution of a neutralizing human antibody to human immunodeficiency virus type 1 to enhance affinity and broaden strain cross-reactivity," PNAS (USA) 91:3809-3813 (1994).

Barbas III et al., "Semisynthetic combinatorial antibody libraries: A chemical solution to the diversity problem," PNAS (USA) 89:4457-4461 (1992).

Barnes et al., "Methods for Growth of Cultured Cells in Serum-Free Medium," Anal. Biochem 102:255-270 (1980).

Bass et al., "Hormone Phage: An Enrichment Method for Variant Proteins With Altered Binding Properties," Proteins 8:309-314 (1990).

Beenken et al., "The FGF family: biology, pathophysiology and therapy," Nat Rev Drug Discov 8:235-253 (2009).

Bernard-Pierrot et al., "Oncogenic properties of the mutated forms of fibroblast growth factor receptor 3b," Carcinogenesis 27(4):740-747 (2006).

Bothmann et al., "The Periplasmic *Escherichia coli* Peptidylprolyl cis,trans-Isomerase FkpA," J. Biol. Chem. 275(22):17100-17105 (2000).

Brennan et al., "Preparation of Bispecific Antibodies by Chemical Recombination of Monoclonal Immunoglobulin G1 Fragments," Science 229:81-83 (1985).

(56) References Cited

OTHER PUBLICATIONS

Brodeur et al., "Mouse-Human Myeloma Partners for the Production of Heterohybridomas," Monoclonal Antibody Production Techniques and Applications, pp. 51-63 (Marcel Dekker, Inc., New York, 1987).
Bruggemann et al., "Designer Mice: The Production of Human Antibody Repertoires in Transgenic Animals," Year Immunol., 7:33-40 (1993).
Capel et al., "Heterogeneity of Human IgG Fc Receptors," Immunomethods 4:25-34 (1994).
Cariello et al., "Resolution of a Missense Mutant in Human Genomic DNA by Denaturing Gradient Gel Electrophoresis and Direct Sequencing Using In Vitro DNA Amplification: HPRT Munich," Am. J. Hum. Genet. 42:726-734 (1988).
Carlsson et al., "Protein Thiolation and Reversible Protein-Protein Conjugation," Biochem. J. 173:723-737 (1978).
Carter et al., "High Level *Escherichia coli* Expression and Production of a Bivalent Humanized Antibody Fragment," Bio/Technology 10:163-167 (1992).
Carter et al., "Humanization of an anti-p185HER2 antibody for human cancer therapy," PNAS (USA) 89:4285-4289 (1992).
Chang et al., "Immunohistochemistry accurately predicts FGFR3 aberrant expression and t(4;14) in multiple myeloma," Blood 106:353-355 (2005).
Chari et al., "Immunoconjugates Containing Novel Maytansinoids: Promising Anticancer Drugs," Cancer Research 52:127-131 (1992).
Chen et al., "Chaperone Activity of DsbC," J. Biol. Chem. 274(28):19601-19605 (1999).
Chen et al., "Constitutively activated FGFR3 mutants signal through PLCγ-dependent and -independent pathways for hematopoietic transformation," Blood 106:328-337 (2005).
Chen et al., "FGFR3 as a therapeutic target of the small molecule inhibitor PKC412 in hematopoietic malignancies," Oncogene 24:8259-8267 (2005).
Chen et al., "*MolProbity*: all-atom structure validation for macromolecular crystallography," Biol Crystallogr D66:12-21 (2010).
Chen et al., "Selection and Analysis of an Optimized Anti-VEGF Antibody: Crystal Structure of an Affinity-matured Fab in Complex with Antigen," J. Mol. Biol. 293:865-881 (1999).
Chesi et al., "Activated fibroblast growth factor receptor 3 is an oncogene that contributes to tumor progression in multiple myeloma," Blood 97:729-736 (2001).
Chesi et al., "Frequent translocation t(4;14)(p16.3;q32.3) in multiple myeloma is associated with increased expression and activating mutations of fibroblast growth factor receptor 3," Nat Genet 16:260-264 (1997).
Chothia et al., "Canonical Structures for the Hypervariable Regions of Immunoglobulins," J. Mol. Biol. 196:901-917 (1987).
Clackson et al., "Making antibody fragments using phage display libraries," Nature 352: 624-628 (1991).
Clynes et al., "FC receptors are required in passive and active immunity to melanoma," PNAS (USA) 95:652-656 (1998).
Cotton et al., "Reactivity of cytosine and thymine in single-base-pair mismatches with hydroxylamine and osmium tetroxide and its application to the study of mutations," PNAS (USA) 85:4397-4401 (1988).
Crooks et al., "WebLogo: a sequence logo generator," Genome Res 14:1188-1190 (2004).
Cunningham et al., "High-Resolution Epitope Mapping of hGH-Receptor Interactions by Alanine-Scanning Mutagenesis," Science 244:1081-1085 (1989).
Daëron, "Fc Receptor Biology," Annu. Rev. Immunol. 15:203-234 (1997).
Dailey et al., "Mechanisms underlying differential responses to FGF signaling," Cytokine & Growth Factor Reviews 16:233-247 (2005).
de Haas et al., "Fcγ receptors of phagocytes," J Lab. Clin. Med. 126(4):330-341 (1995).
Del Tito, Jr. et al, "Automated fluorescent analysis procedure for enzymatic mutation detection," Clinical Chemistry 44(4):731-739 (1998).
Dennis et al., "Albumin Binding as a General Strategy for Improving the Pharmacokinetics of Proteins," J Biol. Chem. 277(38):35035-35043 (2002).
Direnzo et al., "Neutralizing antibody against FGFR3 shows antitumor effects in multiple tumor models in vivo," Proceedings of AACR Annual Meeting, Abstract No. 2080 (2007).
Doronina et al., "Development of potent monoclonal antibody auristatin conjugates for cancer therapy," Nat. Biotechnol. 21(7):778-784 (2003).
Duncan et al., "The binding site for Clq on IgG," Nature 332:738-40 (1988).
Embleton et al., "In-cell PCR from mRNA: amplifying and linking the rearranged immunoglobulin heavy and light chain V-genes within single cells," Nucl. Acids Res., 20(15):3831-3837 (1992).
Emsley et al., "Features and development of Coot," Acta Cryst. D66:486-501 (2010).
Engels et al., "Gene Synthesis," Angew. Chem. Int. Ed. Engl., 28:716-734 (1989).
Eswarakumar et al., "Cellular signaling by fibroblast growth factor receptors," Cytokine Growth Factor Reviews 16:139-149 (2005).
Fonseca et al., "Clinical and biologic implications of recurrent genomic aberrations in myeloma," Blood 101(11):4569-4575 (2003).
Fraker et al., "Protein and Cell Membrane Iodinations with a Sparingly Soluble Chloroamide, 1,3,4,6-TetraChloro-3a, 6a-Diphenylglycoluril," Biochem. Biophys. Res. Commun. 80(4):849-857 (1978).
Gazzano-Santoro et al., "A non-radioactive complement-dependent cytotoxicity assay for anti-CD20 monoclonal antibody," J Immunol. Methods 202:163-171 (1997).
Geoghegan et al., "Site-Directed Conjugation of Nonpeptide Groups to Peptides and Proteins VIA Periodate Oxidation of a 2-Amino Alcohol. Application to Modification at N-Terminal Serine," Bioconjugate Chem. 3:138-146 (1992).
Ghetie et al., "FcRn: the MHC class I-related receptor that is more than an IgG transporter," Immunology Today (1997).
Ghetie et al., "Multiple Roles for the Major Histocompatibility Complex Class I-Related Receptor FcRn," Ann. Rev. Immunol. 18:739-766 (2000).
Godfrey et al., "Quantitative mRNA Expression Analysis from Formalin-Fixed, Paraffin-Embedded Tissues Using 5' Nuclease Quantitative Reverse Transcription-Polymerase Chain Reaction," J. Molecular Diagnostics 2(2):84-91 (2000).
Goding, Monoclonal Antibodies: Principles and Practice, pp. 56-103 (Academic Press, 1986).
Goetz et al., "Exploring mechanisms of FGF signalling through the lens of structural biology," Nat Rev Mol Cell Biol 14(3):166-180 (2013).
Gomez-Roman et al., "Fibroblast Growth Factor Receptor 3 is Overexpressed in Urinary Tract Carcinomas and Modulates the Neoplastic Cell Growth," Clin Cancer Res 11:459-465 (2005).
Graham et al., "Characteristics of a Human Cell Line Transformed by DNA from Human Adenovirus Type 5," J. Gen. Virol. 36:59-72 (1977).
Gram et al., "In vitro selection and affinity maturation of antibodies from a naive combinatorial immunoglobulin library," PNAS (USA) 89:3576-3580 (1992).
Grand et al., "Targeting FGFR3 in multiple myeloma: inhibition of t(4;14)-positive cells by SU5402 and PD173074," Leukemia 18:962-966 (2004).
Griffiths et al., "Human anti-self antibodies with high specificity from phage display libraries," EMBO J. 12(2):725-734 (1993).
Grose et al., "Fibroblast growth factor signaling in tumorigenesis," Cytokine Growth Factor Reviews 16:179-186 (2005).
Gruber et al., "Efficient Tumor Cell Lysis Mediated by a Bispecific Single Chain Antibody Expressed in *Escherichia coli*," J. Immunol., 152:5368-5374 (1994).
Guss et al., "Structure of the IgG-binding regions of streptococcal protein G," EMBO J. 5(7):1567-1575 (1986).
Guyer et al., "Immunoglobulin Binding by Mouse Intestinal Epithelial Cell Receptors," J Immunol. 117(2):587-593 (1976).
Ham et al., "Media and Growth Requirements," Meth. Enz. 58:44-93 (1979).

(56) References Cited

OTHER PUBLICATIONS

Hara et al., "Overproduction of Penicillin-Binding Protein 7 Suppresses Thermosensitive Growth Defect at Low Osmolarity due to an spr Mutation of *Escherichia coli*," Microbial Drug Resistance 2(1):63-72 (1996).
Harlow and Lane, eds. (1988) Antibodies, A Laboratory Manual.
Harris, "Therapeutic Monoclonals, Production of humanized monoclonal antibodies for in vivo imaging and therapy," Biochem. Soc. Transactions 23:1035-1038 (1995).
Hawkins et al., "Selection of Phage Antibodies by Binding Affinity, Mimicking Affinity Maturation," J. Mol. Biol., 226:889-896 (1992).
Hinman et al., "Preparation and Characterization of Monoclonal Antibody Conjugates of the Calicheamicins: A Novel and Potent Family of Antitumor Antibiotics," Cancer Res. 53:3336-3342 (1993).
Hinton et al., "Engineered Human IgG Antibodies with Longer Serum Half-lives in Primates," J Biol. Chem. 279(8):6213-6216 (2004).
Hogrefe et al., "A bacteriophage lambda vector for the cloning and expression of immunoglobulin Fab fragments on the surface of filamentous phage," Gene 128:119-126 (1993).
Holliger et al., ""Diabodies": Small bivalent and bispecific antibody fragments," PNAS (USA) 90:6444-6448 (1993).
Hoogenboom et al., "By-passing Immunisation, Human Antibodies from Synthetic Repertoires of Germline Vh Gene Segments Rearranged in Vitro," J. Mol. Biol., 227: 381-388 (1992).
Hoogenboom et al., "Multi-subunit proteins on the surface of filamentous phage: methodologies for displaying antibody (Fab) heavy and light chains," Nucl. Acids Res., 19(15):4133-4137 (1991).
Hurle et al., "Protein engineering techniques for antibody humanization," Curr. Op. Biotech. 5:428-433 (1994).
Idusogie et al., "Mapping of the C1q Binding Site on Rituxan, a Chimeric Antibody with a Human IgG1 Fc," J Immunol. 164:4178-4184 (2000).
Jackson et al., "In Vitro Antibody Maturation, Improvement of a High Affinity, Neutralizing Antibody Against IL-1β" J. Immunol. 154:3310-3319 (1995).
Jakobovits et al., "Analysis of homozygous mutant chimeric mice: Deletion of the immunoglobulin heavy-chain joining region blocks B-cell development and antibody production," PNAS (USA) 90:2551-2555 (1993).
Jakobovits et al., "Germ-line transmission and expression of a human-derived yeast artificial chromosome," Nature, 362:255-258 (1993).
Jones et al., "Rapid PCR-Cloning of Full-Length Mouse Immunoglobulin Variable Regions," Biotechnol., 9:88-89 (1991).
Jones et al., "Replacing the complementarity-determining regions in a human antibody with those from a mouse," Nature 321:522-525 (1986).
Kabat et al., Sequences of Proteins of Immunological Interest, 5th Ed. Public Health Service, National Institutes of Health, Bethesda, MD. (1991) vols. 1-3.
Keler et al., "Bispecific Antibody-dependent Cellular Cytotoxicity of HER2/neu-overexpressing Tumor Cells by Fcγ Receptor Type I-expressing Effector Cells," Cancer Res. 57:4008-4014 (1997).
Kim et al., "Localization of the site of the murine IgG1 molecule that is involved in binding to the murine intestinal Fc receptor," J Immunol. 24:2429-2434 (1994).
Köhler et al., "Continuous cultures of fused cells secreting antibody of predefined specificity," Nature 256:495-497 (1975).
Kostelny et al., "Formation of a Bispecific Antibody by the Use of Leucine Zippers," J Immunol., 148(5):1547-1553 (1992).
Kozbor et al., "A Human Hybrid Myeloma for Production of Human Monoclonal Antibodies," J Immunol., 133(6):3001-3005 (1984).
Kunii et al., "FGFR2-amplified gastric cancer cell lines require FGFR2 and Erbb3 signaling for growth and survival," Cancer research 68(7):2340-2348 (2008).
Kunkel et al., "Efficient site-directed mutagenesis using Uracil-Containing DNA," Methods Enzymol 204:125-139 (1991).

L'Hôte et al., "Cell responses to FGFR3 signalling: growth, differentiation and apoptosis," Experimental Cell Research 304:417-431 (2005).
Lee et al., "High-affinity Human Antibodies from Phage-displayed Synthetic Fab Libraries with a Single Framework Scaffold," J. Mol. Biol., 340:1073-1093 (2004).
Li et al., "The myeloma-associated oncogene fibroblast growth factor receptor 3 is transforming in hematopoietic cells," Blood 97(8):2413-2419 (2001).
Lindmark et al., "Binding of Immunoglobulins to Protein A and Immunoglobulin Levels in Mammalian Sera," J. Immunol. Meth. 62:1-13 (1983).
Liu et al., "Eradication of large colon tumor xenografts by targeted delivery of maytansinoids," PNAS (USA) 93:8618-8623 (1996).
Lode et al., "Targeted Therapy with a Novel Enediyene Antibiotic Calicheamicin θ1 Effectively Suppresses Growth and Dissemination of Liver Metastases in a Syngeneic Model of Murine Neuroblastoma," Cancer Research 58:2925-2928 (1998).
Mandler et al., "Immunoconjugates of Geldanamycin and Anti-HER2 Monoclonal Antibodies: Antiproliferative Activity on Human Breast Carcinoma Cell Lines," Jour. of the Nat. Cancer Inst. 92(19):1573-1581 (2000).
Mandler et al., "Modifications in Synthesis Strategy Improve the Yield and Efficacy of Geldanamycin-Herceptin Immunoconjugates," Bioconjugate Chem. 13:786-791 (2002).
Mandler et al., "Synthesis and Evaluation of Antiproliferative Activity of a Geldanamycin-Herceptin Immunoconjugate," Bioorganic & Med. Chem. Letters 10.1025-1028 (2000).
Marks et al., "By-Passing Immunization, Human Antibodies from V-gene Libraries Displayed on Phage," J Mol. Biol., 222:581-597 (1991).
Marks et al., "By-Passing Immunization: Building High Affinity Human Antibodies by Chain Shuffling," Bio/Technology 10:779-783 (1992).
Martinez-Torrecuadrada et al., "Antitumor activity of fibroblast growth factor receptor 3-specific immunotoxins in a xenograft mouse model of bladder carcinoma is mediated by apoptosis," Mol Cancer Ther 7(4):862-873 (2008).
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res 11(17):6280-6290 (2005).
Mather et al., "Culture of Testicular Cells in Hormone-Supplemented Serum-Free Medium," Annals N.Y. Acad. Sci. 383:44-68 (1982).
Mather, "Establishment and Characterization of Two Distinct Mouse Testicular Epithelial Cell Lines," Biol. Reprod. 23:243-252 (1980).
Matsuda et al., "Structure and physical map of 64 variable segments in the 3' 0.8-megabase region of the human immunoglobulin heavy-chain locus," Nature Genet., 3:88-94 (1993).
McCoy et al., "Phaser crystallographic software," J Applied Crystallography 40:658-674 (2007).
Meyers et al., "Detection of Single Base Substitutions by Ribonuclease Cleavage at Mismatches in RNA: DNA Duplexes," Science 230:1242-1246 (1985).
Milstein et al., "Hybrid hybridomas and their use in immunohistochemistry," Nature, 305:537-540 (1983).
Mohammadi et al., "Structural basis for fibroblast growth factor receptor activation," Cytokine & Growth Factor Reviews 16:107-137 (2005).
Moreau et al., "Recurrent 14q32 translocations determine the prognosis of multiple myeloma, especially in patients receiving intensive chemotherapy," Blood 100(5):1579-1583 (2002).
Morimoto et al., "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods 24:107-117 (1992).
Morrison et al., "Chimeric human antibody molecules: Mouse antigen-binding domains with human constant region domains," PNAS (USA) 81:6851-6855 (1984).

(56) References Cited

OTHER PUBLICATIONS

Munson et al., "Ligand: A Versatile Computerized Approach for Characterization of Ligand-Binding Systems," Anal. Biochem., 107:220-239 (1980).
Newton et al., "Analysis of any point mutation in DNA. The amplification refractory mutation system (ARMS)," Nucleic Acids Research vol. 17(7):2503-2516 (1989).
Nicolaou et al., "Calicheamicin θ: A Rationally Designed Molecule with Extremely Potent and Selective DNA Cleaving Properties and Apoptosis Inducing Activity," Agnew. Chem. Intl. Ed. Engl., 33(2):183-186 (1994).
Niculescu-Duvaz et al., "Antibody-directed enzyme prodrug therapy (ADEPT): a review," Adv. Drug Del. Rev. 26:151-172 (1997).
Novack et al., "Detection of single base-pair mismatches in DNA by chemical modification followed by electrophoresis in 15% polyacrylamide gel," PNAS (USA) 83:586-590 (1986).
Okazaki et al., "Fucose Depletion from Human IgG1 Oligosaccharide Enhances Binding Enthalpy and Association Rate Between IgG1 and FcγRIIIa," J. Mol. Biol. 336:1239-1249 (2004).
Orita et al., "Detection of polymorphisms of human DNA by gel electrophoresis as single-strand conformation polymorphisms," PNAS (USA) 86:2766-2770 (1989).
Orita et al., "Rapid and Sensitive Detection of Point Mutations and DNA Polymorphisms Using the Polymerase Chain Reaction," Genomics 5:874-879 (1989).
Orlandi et al., "Cloning immunoglobulin variable domains for expression by the polymerase chain reaction," PNAS (USA) 86:3833-3837 (1989).
Orum et al., "Efficient method for constructing comprehensive murine Fab antibody libraries displayed on phage," Nucleic Acids Res., 21(19):4491-4498 (1993).
Otwinowski et al., "Processing of X-Ray Diffraction Data Collected in Oscillation Mode," Methods in Enzymology 276:307-326 (1997).
Pai et al., "Antibody-Mediated Inhibition of Fibroblast Growth Factor 19 Results in Increased Bile Acids Synthesis and Ileal Malabsorption of Bile Acids in Cynomolgus Monkeys," Toxicol Sci 126(2):446-456 (2012).
Paterson et al., "Preclinical studies of fibroblast growth factor receptor 3 as a therapeutic target in multiple myeloma," Br J Haematol 124:595-603 (2004).
Pettit et al., "Antineoplastic agents 365. Dolastatin 10 SAR probes," Anti-Cancer Drug Design 13:243-277 (1998).
Pettit et al., "Dolastatins 24. Synthesis of (−)-dolastatin 10.1 X-Ray molecular structure of N,N-dimethylvalyl-valyl-dolaisoleuine tert-butyl ester," J. Chem. Soc. Perkin Trans. 1:859-863 (1996).
Pettit et al., "Specific Activities of Dolastatin 10 and Peptide Derivatives against *Cryptococcus neoformans*," Antimicrob. Agents Chemother. 42(11):2961-2965 (1998).
Pettit et al., "The Dolastatins; 18: Stereospecific Synthesis of Dolaproine1," Synthesis 719-725 (1996).
Plowright et al., "Ectopic expression of fibroblast growth factor receptor 3 promotes myeloma cell proliferation and prevents apoptosis," Blood 95(3):992-998 (2000).
Pluckthun, "Mono- and Bivalent Antibody Fragments Produced in *Escherichia coli*: Engineering, Folding and Antigen Binding," Immunol. Revs, 130:151-188 (1992).
Pollett et al., "Overexpression of the myeloma-associated oncogene fibroblast growth factor receptor 3 confers dexamethasone resistance," Blood 100(10):3819-3821 (2002).
Presta et al., "Humanization of an Antibody Directed Against IgE," J Immunol. 151(5):2623-2632 (1993).
Presta et al., "Humanization of an Anti-Vascular Endothelial Growth Factor Monoclonal Antibody for the Therapy of Solid Tumors and Other Disorders," Cancer Res. 57:4593-4599 (1997).
Presta, "Antibody engineering," Curr. Op. Struct. Biol. 2:593-596 (1992).
Proba et al., "Functional antibody single-chain fragments from the cytoplasm of *Escherichia coli*: influence of thioredoxin reductase (TrxB)," Gene, 159:203-207 (1995).

Qing et al., "Antibody-based targeting of FGFR3 in bladder carcinoma and t(4;14)-positive multiple myeloma in mice," The Journal of Clinical Investigation 119(5):1216-1229 (2009).
Ramm et al., "The Periplasmic *Escherichia coli* Peptidylprolyl cis, trans-Isomerase FkpA," J. Biol. Chem. 275(22):17106-17113 (2000).
Rauchenberger et al., "Human Combinatorial Fab Library Yielding Specific and Functional Antibodies against the Human Fibroblast Growth Factor Receptor 3*," J Biol Chem 278(40):38194-38205 (2003).
Ravetch et al., "Fc Receptors," Annu. Rev. Immunol 9:457-492 (1991).
Riechmann et al., "Reshaping human antibodies for therapy," Nature 332:323-329 (1988).
Ripka et al., "Two Chinese Hamster Ovary Glycosylation Mutants Affected in the Conversion of GDP-Mannose to GDP-Fucose," Arch. Biochem. Biophys. 249(2):533-545 (1986).
Ronchetti et al., "Deregulated FGFR3 mutants in multiple myeloma cell lines with t(4;14): comparative analysis of Y373C, K650E and the novel G384D mutations," Oncogene 20:3553-3562 (2001).
Rowland et al., Drug localisation and growth inhibition studies of vindesine-monoclonal anti-CEA conjugates in a human tumour xenograft, Cancer Immunol. Immunother., 21:183-187 (1986).
Ruano et al., "Direct haplotyping of cbromosomal segments from multiple heterozygotes via allele-specific PCR amplification," Nucleic Acids Research 17(20):8392 (1989).
Saiki et al., "Primer-Directed Enzymatic Amplification of DNA with a Thermostable DNA Polymerase," Science 239:487-491 (1988).
Sastry et al., "Cloning of the immunological repertoire in *Escherichia coli* for generation of monoclonal catalytic antibodies: Construction of a heavy chain variable region-specific cDNA library," PNAS (USA), 86:5728-5732 (1989).
Schier et al., "Identification of functional and structural amino-acid residues by parsimonious mutagenesis," Gene 169:147-155 (1996).
Shalaby et al., "Development of Humanized Bispecific Antibodies Reactive with Cytotoxic Lymphocytes and Tumor Cells Overexpressing the HER2 Protooncogene," J Exp. Med., 175:217-225 (1992).
Shenk et al., "Biochemical Method for Mapping Mutational Alterations in DNA with S1 Nuclease: The Location of Deletions and Temperature-Sensitive Mutations in Simian Virus 40," PNAS (USA) 72(3):989-993 (1975).
Shields et al., "High Resolution Mapping of the Binding Site on Human IgG1 for FcγRI, FcγRII, FcγRIII, and FcRn and Design of IgG1 Variants with Improved Binding to the FcγR," J Biol. Chem. 276(9):6591-6604 (2001).
Siebenlist et al., "*E. coli* RNA Polymerase Interacts Homologously with Two Different Promoters," Cell 20:269-281 (1980).
Simmons et al., "Expression of full-length immunoglobulins in *Escherichia coli*: rapid and efficient production of aglycosylated antibodies," J. Immunol. Method, 263:133-147 (2002).
Sims et al., "A Humanized CD18 Antibody Can Block Function without Cell Destruction," J. Immunol. 151(4):2296-2308 (1993).
Skerra et al., "Bacterial expression of immunoglobin fragments," Curr. Opinion in Immunol., 5:256-262 (1993).
Somasundaram et al., "Development of a trispecific antibody conjugate that directs two distinct tumor-associated antigens to CD64 on myeloid effector cells," Hum. Antibodies 9:47-54 (1999).
Specht et al., "Quantitative Gene Expression Analysis in Microdissected Archival Formalin-Fixed and Paraffin-Embedded Tumor Tissue," Am. J. Pathol. 158(2):419-429 (2001).
Suresh et al., "Bispecific Monoclonal Antibodies from Hybrid Hybridomas," Methods in Enzymology, 121:210-228 (1986).
Syrigos et al., "Antibody Directed Enzyme Prodrug Therapy (ADEPT): A Review of the Experimental and Clinical Considerations," Anticancer Research 19:605-614 (1999).
Thorpe, "Antibody Carriers of Cytotoxic Agents in Cancer Therapy: A Review," Monoclonal Antibodies '84: Biological and Clinical Applications, pp. 475-506 (1985).
Tomlinson et al. "Knockdown by shRNA identifies S249C mutant FGFR3 as a potential therapeutic target in bladder cancer," Oncogene 26:5889-5899 (2007).
Tomlinson et al., "FGFR3 protein expression and its relationship to mutation status and prognostic variables in bladder cancer," J Pathol 213:91-98 (2007).

(56) References Cited

OTHER PUBLICATIONS

Tomlinson et al., "The Repertoire of Human Germline VH Sequences Reveals about Fifty Groups of VH Segments with Different Hypervariable Loops," J Mol. Biol., 227:776-798 (1992).
Traunecker et al., "Bispecific single chain molecules (Janusins) target cytotoxic lymphocytes on HIV infected cells," EMBO J, 10(12):3655-3659 (1991).
Trudel et al. "CHIR-258, a novel, multitargeted tyrosine kinase inhibitor for the potential treatment of t(4;14) multiple myeloma," Blood 105(7):2941-2948 (2005).
Trudel et al., "Inhibition of fibroblast growth factor receptor 3 induces differentiation and apoptosis in t(4;14) myeloma," Blood 103(9):3521-3528 (2004).
Trudel et al., The inhibitory anti-FGFR3 antibody, PRO-001, is cytotoxic to t(4;14) multiple myeloma cells, Blood 107(10):4039-4046 (2006).
Turner et al., "Fibroblast growth factor signalling: from development to cancer," Nat Rev Cancer 10:116-129 (2010).
Tutt et al., "Trispecific F(ab')3 Derivatives That Use Cooperative Signaling Via the TCR/CD3 Complex and CD2 to Activate and Redirect Resting Cytotoxic T Cells," J Immunol. 147:60-69 (1991).
Urlaub et al., "Isolation of Chinese hamster cell mutants deficient in dihydrofolate reductase activity," PNAS USA 77(7):4216-4220 (1980).
van Rhijn et al., "Frequent FGFR3 mutations in urothelial papilloma," J Pathol 198:245-251 (2002).
Vaswani et al., "Humanized antibodies as potential therapeutic drugs," Annals of Allergy, Asthma & Immunol. 81:105-115 (1998).
Verhoeyen et al., "Reshaping Human Antibodies: Grafting an Antilysozyme Activity," Science 239:1534-1536 (1988).
Vitetta et al., "Redesigning Nature's Poisons to Create Anti-Tumor Reagents," Science 238:1098-1104 (1987).
Ward et al., "Binding activities of a repertoire of single immunoglobulin variable domains secreted from *Escherichia coli*," Nature 341:544-546 (1989).
Waterhouse et al., "Combinatorial infection and in vivo recombination: a strategy for making large phage antibody repertoires," Nucl. Acids Res., 21(9):2265-2266 (1993).
Wesche et al., "Fibroblast growth factors and their receptors in cancer," Biochem J. 437:199-213 (2011).
Williams et al., "Cloning and sequencing of human immunoglobulin Vγ, gene segments," Eur. J. Immunol., 23:1456-1461 (1993).
Wilman, "Prodrugs in Cancer Chemotherapy," Biochemical Society Transactions 14:375-382, 615th Meeting Belfast (1986).
Winn et al., "Overview of the CCP4 suite and current developments," Biol. Crystallogr D67:235-242 (2011).
Winter et al., "A method to detect and characterize point mutations in transcribed genes: Amplification and overexpression of the mutant c-Ki-ras allele in human tumor cells," PNAS (USA) 82:7575-7579 (1985).
Winter et al., "Making Antibodies by Phage Display Technology," Ann. Rev. Immunol., 12:433-455 (1994).
Wiseman et al., "Ibritumomab tiuxetan radioimmunotherapy for patients with relapsed or refractory non-Hodgkin lymphoma and mild thrombocytopenia: a phase II multicenter trial," Blood 99(12):4336-4342 (2002).
Wiseman et al., "Phase I/II 90Y-Zevalin (yttrium-90 ibritumomab tiuxetan, IDEC-Y2B8) radioimmunotherapy dosimetry results in relapsed or refractory non-Hodgkin's lymphoma," Eur. Jour. Nucl. Med. 27:766-777 (2000).
Witzig et al., "Randomized Controlled Trial of Yttrium-90-Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma," J. Clin. Oncol 20:2453-2463 (2002).
Witzig et al., "Treatment With Ibritumomab Tiuxetan Radioimmunotherapy in Patients With Rituximab-Refractory Follicular Non-Hodgkin's Lymphoma," J. Clin. Oncol. 20:3262-3269 (2002).
Woyke et al., "In Vitro Activities and Postantifungal Effects of the Potent Dolastatin 10 Derivative Auristatin PHE," Antimicrob. Agents and Chemother. 45(12):3580-3584 (2001).
Wu et al., "The Ligation Amplification Reaction (LAR)-Amplification of Specific DNA Sequences Using Sequential Rounds of Template-Dependent Ligation," Genomics 4:560-569 (1989).
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotech. Bioeng. 87(5):614-622 (2004).
Yaniv, "Enhancing elements for activation of eukaryotic promoters," Nature 297:17-18 (1982).
Yelton et al., "Affinity Maturation of the BR96 Anti-Carcinoma Antibody by Codon-Based Mutagenesis," J. Immunol. 155:1994-2004 (1995).
Zeilder et al., "Simultaneous Activation of T Cells and Accessory Cells by a New Class of Intact Bispecific Antibody Results in Efficient Tumor Cell Killing," J. Immunol. 163:1246-1252 (1999).

* cited by examiner

FIG. 2A
FIG. 2B
FIG. 2C
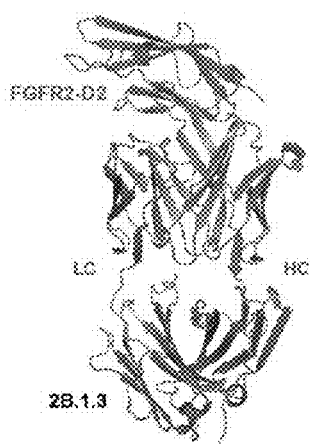
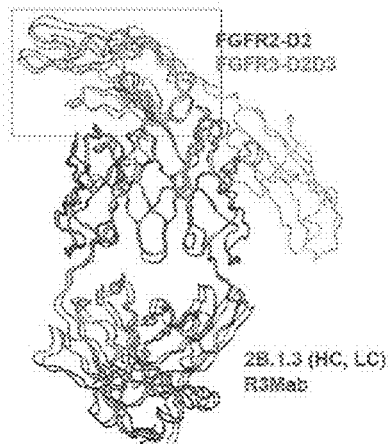
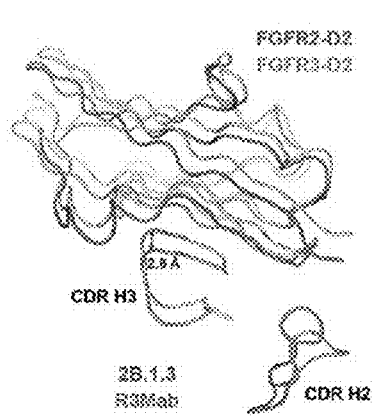

FIG. 9A

FGFR2-IIIb

SEQ ID NO: 52

MVSWGRFICLVVVTMATLSLARPSFSLVEDTTLEPEEPPTKYQISQPEVYVAAPGESLE

VRCLLKDAAVISWTKDGVHLGPNNRTVLIGEYLQIKGATPRDSGLYACTASRTVDSET

WYFMVNVTDAISSGDDEDDTDGAEDFVSENSNNKRAPYWTNTEKMEKRLHAVPAAN
                                          SEQ ID NO:91
TVKFRCPAGGNPMPTMRWLKNGKEFKQEHRIGGYKVRNQHWSLIMESVVPSDKGNY
                                        SEQ ID NO:92
TCVVENEYGSINHTYHLDVVERSPHRPILQAGLPANASTVVGGDVEFVCKVYSDAQPH

IQWIKHVEKNGSKYGPDGLPYLKVLKHSGINSSNAEVLALFNVTEADAGEYICKVSNYI

GQANQSAWLTVLPKQQAPGREKEITASPDYLEIAIYCIGVFLIACMVVTVILCRMKNTTK

KPDFSSQPAVHKLTKRIPLRRQVTVSAESSSSMNSNTPLVRITTRLSSTADTPMLAGVS

EYELPEDPKWEFPRDKLTLGKPLGEGCFGQVVMAEAVGIDKDKPKEAVTVAVKMLKD

DATEKDLSDLVSEMEMMKMIGKHKNIINLLGACTQDGPLYVIVEYASKGNLREYLRARR

PPGMEYSYDINRVPEEQMTFKDLVSCTYQLARGMEYLASQKCIHRDLAARNVLVTENN

VMKIADFGLARDINNIDYYKKTTNGRLPVKWMAPEALFDRVYTHQSDVWSFGVLMWEI

FTLGGSPYPGIPVEELFKLLKEGHRMDKPANCTNELYMMMRDCWHAVPSQRPTFKQL

VEDLDRILTLTTNEEYLDLSQPLEQYSPSYPDTRSSCSSGDDSVFSPDPMPYEPCLPQ

YPHINGSVKT

FIG. 9B

FGFR2-IIIc

SEQ ID NO: 54

MVSWGRFICLVVVTMATLSLARPSFSLVEDTTLEPEEPPTKYQISQPEVYVAAPGESLE

VRCLLKDAAVISWTKDGVHLGPNNRTVLIGEYLQIKGATPRDSGLYACTASRTVDSET

WYFMVNVTDAISSGDDEDDTDGAEDFVSENSNNKRAPYWTNTEKMEKRLHAVPAAN
<u>SEQ ID NO:91</u>
TVKFRCPAGGNPMPTMRWLKNGKEFKQEHRIGGYKVRNQHWSLIMESVVPSDKGNY
<u>SEQ ID NO:92</u>
TCVVENEYGSINHTYHLDVVERSPHRPILQAGLPANASTVVGGDVEFVCKVYSDAQPH

IQWIKHVEKNGSKYGPDGLPYLKVLKAAGVNTTDKEIEVLYIRNVTFEDAGEYTCLAGN

SIGISFHSAWLTVLPAPGREKEITASPDYLEIAIYCIGVFLIACMVVTVILCRMKNTTKKPD

FSSQPAVHKLTKRIPLRRQVTVSAESSSSMNSNTPLVRITTRLSSTADTPMLAGVSEYE

LPEDPKWEFPRDKLTLGKPLGEGCFGQVVMAEAVGIDKDKPKEAVTVAVKMLKDDAT

EKDLSDLVSEMEMMKMIGKHKNIINLLGACTQDGPLYVIVEYASKGNLREYLRARRPPG

MEYSYDINRVPEEQMTFKDLVSCTYQLARGMEYLASQKCIHRDLAARNVLVTENNVM

KIADFGLARDINNIDYYKKTTNGRLPVKWMAPEALFDRVYTHQSDVWSFGVLMWEIFT

LGGSPYPGIPVEELFKLLKEGHRMDKPANCTNELYMMMRDCWHAVPSQRPTFKQLVE

DLDRILTLTTNEEYLDLSQPLEQYSPSYPDTRSSCSSGDDSVFSPDPMPYEPCLPQYP

HINGSVKT

FIG. 9C

FGFR3-IIIb

SEQ ID NO: 56

MGAPACALALCVAVAIVAGASSESLGTEQRVVGRAAEVPGPEPGQQEQLVFGSGDAV

ELSCPPPGGGPMGPTVWVKDGTGLVPSERVLVGPQRLQVLNASHEDSGAYSCRQRL

TQRVLCHFSVRVTDAPSSGDDEDGEDEAEDTGVDTGAPYWTRPERMDKKLLAVPAA
SEQ ID NO:93
NTVRFRCPAAGNPTPSISWLKNGREFRGEHRIGGIKLRHQQWSLVMESVVPSDRGNY
SEQ ID NO:94
TCVVENKFGSIRQTYTLDVLERSPHRPILQAGLPANQTAVLGSDVEFHCKVYSDAQPHI

QWLKHVEVNGSKVGPDGTPYVTVLKSWISESVEADVRLRLANVSERDGGEYLCRATN

FIGVAEKAFWLSVHGPRAAEEELVEADEAGSVYAGILSYGVGFFLFILVVAAVTLCRLR

SPPKKGLGSPTVHKISRFPLKRQVSLESNASMSSNTPLVRIARLSSGEGPTLANVSELE

LPADPKWELSRARLTLGKPLGEGCFGQVVMAEAIGIDKDRAAKPVTVAVKMLKDDATD

KDLSDLVSEMEMMKMIGKHKNIINLLGACTQGGPLYVLVEYAAKGNLREFLRARRPPG

LDYSFDTCKPPEEQLTFKDLVSCAYQVARGMEYLASQKCIHRDLAARNVLVTEDNVMK

IADFGLARDVHNLDYYKKTTNGRLPVKWMAPEALFDRVYTHQSDVWSFGVLLWEIFTL

GGSPYPGIPVEELFKLLKEGHRMDKPANCTHDLYMIMRECWHAAPSQRPTFKQLVED

LDRVLTVTSTDEYLDLSAPFEQYSPGGQDTPSSSSSGDDSVFAHDLLPPAPPSSGGS

FGFR3-IIIc

SEQ ID NO: 58

MGAPACALALCVAVAIVAGASSESLGTEQRVVGRAAEVPGPEPGQQEQLVFGSGDAV

ELSCPPPGGGPMGPTVWVKDGTGLVPSERVLVGPQRLQVLNASHEDSGAYSCRQRL

TQRVLCHFSVRVTDAPSSGDDEDGEDEAEDTGVDTGAPYWTRPERMDKKLLAVPAA
                                        SEQ ID NO:93
NTVRFRCPAAGNPTPSISWLKNGREFRGEHRIGGIKLRHQQWSLVMESVVPSDRGNY
                                     SEQ ID NO:94
TCVVENKFGSIRQTYTLDVLERSPHRPILQAGLPANQTAVLGSDVEFHCKVYSDAQPHI

QWLKHVEVNGSKVGPDGTPYVTVLKTAGANTTDKELEVLSLHNVTFEDAGEYTCLAG

NSIGFSHHSAWLVVLPAEEELVEADEAGSVYAGILSYGVGFFLFILVVAAVTLCRLSPP

KKGLGSPTVHKISRFPLKRQVSLESNASMSSNTPLVRIARLSSGEGPTLANVSELELPA

DPKWELSRARLTLGKPLGEGCFGQVVMAEAIGIDKDRAAKPVTVAVKMLKDDATDKDL

SDLVSEMEMMKMIGKHKNIINLLGACTQGGPLYVLVEYAAKGNLREFLRARRPPGLDY

SFDTCKPPEEQLTFKDLVSCAYQVARGMEYLASQKCIHRDLAARNVLVTEDNVMKIAD

FGLARDVHNLDYYKKTTNGRLPVKWMAPEALFDRVYTHQSDVWSFGVLLWEIFTLGG

SPYPGIPVEELFKLLKEGHRMDKPANCTHDLYMIMRECWHAAPSQRPTFKQLVEDLD

RVLTVTSTDEYLDLSAPFEQYSPGGQDTPSSSSSGDDSVFAHDLLPPAPPSSGGSRT

FIG. 10

|          | SEQ ID NO. | | | |
| Antibody | Nucleic Acid (light chain) | Nucleic Acid (heavy chain) | Amino Acid (light chain) | Amino Acid (heavy chain) |
|---|---|---|---|---|
| 1.3 | 67 | 83 | 59 | 75 |
| 1.95 | 68 | 84 | 60 | 76 |
| 1.73 | 69 | 85 | 61 | 77 |
| 1.32 | 70 | 86 | 62 | 78 |
| 1.88 | 71 | 87 | 63 | 79 |
| 1.1 | 72 | 88 | 64 | 80 |
| 1.3.10 | 73 | 89 | 65 | 81 |
| 1.3.12 | 74 | 90 | 66 | 82 |

FIG. 11A

CDR sequences according to Kabat definition are underlined

Light chain variable region

| Kabat number | | | | CDR L1 - Contact / CDR L1 - Kabat | |
|---|---|---|---|---|---|
| 11F1 | DIQMTQTTSSLSASLGDRVTIICSASQ | . . . . . . | VISNYLNWY |
| 6D12 | ENVLTQSPAIMSASPGEKVTMTCSAS | . . . . . . | SSGRYTFWY |
| 11D4 | DIQMTQTPSSLSASLGDRVTINCRASQ | . . . . . | DISNYFRWY |
| 8E1 | DIQMTQSSSYLSVSLGGSVTITCKASD | . . . . . | HINNWLAWY |
| 48C3 | AVLMTQTPLSLPVSLGDQASISCRSSQNIVHS | . | DGNTYLEWY |
| 8H7 | DIVMTQSQKFMSTSVGDRVSITCKASQ | . . . . . | FVSDAVAWY |
| 21H3 | DIVMTQSQKFMSTSVGDRVSITCKASQ | . . . . . | FVSDAVAWY |
| 25F7 | DIQMTQSSSYLSVSLGGRVTITCKASD | . . . . . | HINNWLAWY |
| 14E6 | DIQMTQSPSSLSASLGERVSLTCRASQ | . . . . . | EISGYLSWL |
| 14C6 | QIVLTQSPAIMSASPGERVTLTCSAGSS | . . . . | LSSSYLYWY |
| 24A1 | DIVMTQSPSSLPMSVGQKVTMSCKSSQSLLNSGNQKNSLAWY | | |
| 5F8 | ESVLTQSPALMSASLGEKVTMTCRAS | . . . . . | SSVNHMYWY |
| 8C1 | DIVMTQSQKFMSTSVGDRVSVTCKASQ | . . . . . | NVDSYVAWY |
| 12A11 | DIVMTQSPATLSVTPGDRVSLSCRASQ | . . . . . | SISDYVYWY |
| 12B8 | DIQMTQSSSFSVSLGDRVTITCKASE | . . . . . | DIYNRLAWY |
| 14C10 | DIVLTQSPASLAVSLGQRATISCRASESVDS | . . | YGNSFMHWY |
| 8C5 | DIVLTQSPTSLAVSLGQRATISCRASESVES | . . | YGNRYMTWY |

| Kabat number | | CDR L2 - Contact / CDR L2 - Kabat |
|---|---|---|
| 11F1 | QQKPDGTVKLLIYFTSSLRSGVPSRFSGSGSGTDYSLTISNL |
| 6D12 | QQKSNTAPKLWIYDTSKLASGVPGRFSGSGSGNSYSLTISSM |
| 11D4 | QQKPNGTIKLLIYYTSRLQSGVPSRFSGSGSGTDYSLTISNL |
| 8E1 | QQKPGNAPRLLIYGTTNLETGVPSRFSGSGSGRDYILSITSL |
| 48C3 | LQKPGQSPKLLIYKVSNRFSGVPDRFSGSGSGRDFTLKISRV |
| 8H7 | QQKPGQSPKLLICSASYRYTGVPDRFTGSGSGTDFTFTISSV |
| 21H3 | QQKPGQSPKLLICSASYRYTGVPDRFTGSGSGTDFTFTISSV |
| 25F7 | QQKPGNAPRLLISGASNLETGIPSRFSGSGSGKDYTLTITSL |
| 14E6 | QQKPDGTIKRLIYAASTLDSGVPRRFSGSRSGSDYSLTISSL |
| 14C6 | QQKPGSSPKLWIYGASNLASGVPGRFSGSGSGTSYSLTISSM |
| 24A1 | QQKPGQSPKLLVYLASTRESGVPDRFIGSGSGTDFTLTISSV |
| 5F8 | QQKSDASPKLWIYYTSTLAPGVPARFSGSGSGNSYSLTISSM |
| 8C1 | QQKAGQSPKPLIYSASYRFSGVPDRFTGSGSGTEFTLTISNV |
| 12A11 | QQKSHESPRLLIIYASQSISGIPSRFSGSGSGSDFTLSINSV |
| 12B8 | QQKPGSAPRLLISAATSLETGVPSRFSGSGSGKDYTLSITSL |
| 14C10 | QQKPGQPPKLLIYRASNLESGIPARFSGSGSRTDFTLTINPV |
| 8C5 | QQKPGQPPKLLIYRAANLQSGIPARFSGSGSRTDFTLTIDPV |

| Kabat number | | CDR L3 - Contact / CDR L3 - Kabat | |
|---|---|---|---|
| 11F1 | EPEDVATYFCQQYSKLP | . . . | WTFGGGTKLELK |
| 6D12 | EAEDVATYYCFQGTGYP | . . | LTFGAGTKLELK |
| 11D4 | EQEDKATYFCHQVRTLP | . . | WTFGGGTKLEIK |
| 8E1 | QSEDVASYYCQQYWNTP | . . | FTFGSGTKLEIK |
| 48C3 | EAGDLGVYYCFQGSHV | . | LTFGAGTRLELK |
| 8H7 | RTEDLAVYYCQQHYIVP | . . | YTFGGGTTLEIE |
| 21H3 | RTEDLAVYYCQQHYIVP | . . | YTFGGGTTLEIE |
| 25F7 | QTEDVATYYCQQYWNTP | . . | FTFGSGTKLEIK |
| 14E6 | ESEDFADYYCLQYGSYP | . . | WTFGGGTKLELK |
| 14C6 | EAEDAASYFCHQWSSYP | . . | LTFGSGTKLELK |
| 24A1 | QAEDLADYFCQQHHSTP | . . | YTFGGGTKLELK |
| 5F8 | EGEDAATYYCQQFTISPSMYTFGGGTKLEIK | | |
| 8C1 | QSEDLAEYFCQQYNISP | . . | YTFGGGTKLEIK |
| 12A11 | EPEDVGVYYCQNGHNFP | . . | YTFGGGTKLEIK |
| 12B8 | QTEDVATYYCQQYWSNP | . . | LTFGAGTKLEIK |
| 14C10 | EADDVANYYCQQSNED | . . . | YTFGGGTKLEIK |
| 8C5 | EADDVATYYCQQSNEDP | . . | WTFGGGTKVEIK |

FIG. 11B

Heavy chain variable region

```
                                                              CDR H1 - Contact
                                                            CDR H1 - Kabat
Kabat number
     11F1   E V Q L V E S G G G L V K P G G S L K L S C A P S G F T F S S Y G I S . . W V R Q T
     6D12   E V Q L Q Q S G A E L V R P G A L V N L S C K A S G F N I K D Y Y M N . . W V K Q R
     11D4   Q V Q V K E S G P G L V A P S Q S L S I T C T V S G F S L T N Y G V S . . W I R Q P
      8E1   E V Q L Q Q S G A E L V K P G A S V K L S C T A A D F N I K D T Y M H . . W V K Q R
     46C3   E V Q L Q Q S G A E L V K P G A S V K L S C T A A D F N I I D T Y I H . . W V K Q R
      8H7   Q V Q L Q Q P G A E I V K P G A S V R L S C K A S G Y S F T S Y W I H . . W V K Q R
     21H3   Q V Q L Q Q P G A E I V K P G A S V R L S C K A S G Y S F T S Y W I H . . W V K Q R
     25F7   E V Q L Q Q S G A E L L K P G A S V R L S C T A S G F N I Q D T F T H . . W V R Q R
     14E6   E V P L Q Q S G P E L V K P G A T V K I S C K P S G D T F T E Y Y M N . . W V R Q S
     14C8   Q I Q L Q Q S G A E L M K P G A S V R M S C K A S G Y T F S S Y W I E . . W V K Q R
     24A1   Q V Q L K Q S G A E L V R P G T S V T L S C K A S G Y T F T D Y E M H . . W M K Q T
      5F8   E V Q L Q Q S G T E L V R P G A S V K L S C T A S D F N I K D T Y I H . . W V K Q R
      8C1   Q V Q L Q Q S G D E L M K P G A S V K I S C K V T G N T F S S Y W I E . . W V K Q R
     12A11  E V K F L E S G G G L V Q P G G S L R L S C A V S G I D F S R Y W M S . . W V R Q A
     12B8   Q I Q L V Q S G P E L K K P G E T A K I S C K A S G Y A F S N Y G M N . . W V K Q A
     14C10  Q V T L K E S G P G I L Q P S Q T L S L T C S F S G F S L S T S A M G I G W I R Q P
      8C5   Q V Q L K Q S G P G L V Q P S Q S L S V A C T V S D F S L T T Y G V H . . W V R Q S CDR H2 - Contact
                              CDR H2 - Kabat
Kabat number
     11F1   P E K R L E W V A T V S S G G R Y T Y Y P D S V K G R F T I S R D N A E N T L Y L Q
     6D12   P E Q G L E W T G W I D P E N D D T I Y A D K F Q G K A T I T A D T S S N T V Y L Q
     11D4   P G K G L E W L G V I W . G D G S I N Y H S A L I S R L T I T K D N S K S Q V F L K
      8E1   P E Q G L E W I G R I D P S N G N A K Y D P K F Q G K A S I T A D S S S N T A Y L H
     46C3   P E Q G L E W I G R I D P A N G N T K Y D P K F Q D K A A L T S D T G S N T A Y L L
      8H7   P G Q G L E W I G E I D P S V S N S N Y N Q K F K G K A T L T A D K S S S T A Y M Q
     21H3   P G Q G L E W I G E I D P S V S N S N Y N Q K F K G K A T L T A D K S S S T A Y M Q
     25F7   P E Q G L E W I G R I D P S N G N T K Y D P K F Q G K A K I L A D T S S N T A Y L Q
     14E6   H G K S L E W I G G I N P N N G E T S Y N Q K F K G K A T L T V D K S S S T A F M Q
     14C8   S G H G L E W I G E I F P G G G S T I Y N E N F R D K A T F T A D T S S N T A Y M Q
     24A1   P V Y G L E W I G A I W P E N A D S V Y N Q K F K G K V T L T A D K S S S T A Y M D
      5F8   P E Q G L D W L G R I D P A N G N T K Y D P K F Q G K A A M T S D T S S N T A Y L R
      8C1   P G H G L E W I G E I L P G S D S T K Y V E K F K V K A T F T A D T S S N T A Y M Q
     12A11  P G K G L E W I G E I S P D S S T I N Y T P S L K D K F V I S R D N A K N T L Y L Q
     12B8   P G K D L K W M G W I D T D T G E A T Y T D D F K G R F V F S L E T S A S T A Y L Q
     14C10  S G K G L E W L A H I W . W D D D K R Y N P A L K S R L T I S K D T S R N Q V F L K
      8C5   P G K G L E W L G V I W . S G G S T D Y N A A F I S R L T I S K D N S K S Q V F F K CDR H3 - Contact
                                     CDR H3 - Kabat
Kabat number
     11F1   M S S L R S E D T A M Y Y C T R G D D G Y A L . . . . . . D Y W G Q G T S V T V S S
     6D12   L T S L T S E D T A V Y Y C A A F T T V F . . . . . . . A Y W G H Q T M V T V S A
     11D4   L N S L E A D D T A T Y Y C A K T H D W F . . . . . . . D Y W G Q G T L V T V S S
      8E1   L S S L T S E D T A V Y Y C A S R A L G N G Y A L . . . G Y W G Q G T S V T V S S
     46C3   F N S L T S E D T A V Y Y C A R Q T S Y S W F . . . . . A Y W G Q G T L V S V S A
      8H7   L S G L T S E D S A V Y F C V R L G V M V Y G S S P F W F A Y W G Q G T L V T V S A
     21H3   L S G L T S E D S A V Y F C V R L G V M V Y G S S P F W F A Y W G Q G T L V T V S A
     25F7   L I G L T S E D T A V Y Y C A S R A L G N G Y A M . . . D Y W G Q G T S V T V S S
     14E6   L R I L T S E D S A V Y F C A R K T T . . . . . . . . N Y W G Q G T T L I V S S
     14C8   L S S L T S E D S A V Y F C A R K G Y Y D A A W F . . . D Y W G Q G T L V T V S S
     24A1   L R S L T S E D S A V Y Y C T R E G G . . . . . . . . N Y W G Q G T T L T V S S
      5F8   L S S L T S E D T A V Y Y C A S S G N Y G A M . . . . D Y W G Q G T S V T V S S
      8C1   L S G L T S E D S A V Y Y C A R G G Y H Y P G W L . . . V Y W G Q G T L V T V S A
     12A11  M S K V R S A D T A L Y Y C A R P S P A L . . . . . . D Y W G Q G T L V T V S A
     12B8   I N N L K N E D M A T Y F C A R E E Y G L F G F . . . . P Y W G H G T L V T V S A
     14C10  I A S V D T A D T A T Y Y F C A R I D G I Y D G S F Y A M . D Y W G Q G T S V T V S S
      8C5   M N S L Q T T D T A I Y Y C A R D Y G S T Y V D A I . . D Y W G Q G T S V T V S S
```

FIG. 14A
wt: FSGDGKAIWDKKQYVSP...
ko: FSETGKQIGIKHST*
FIG. 14B
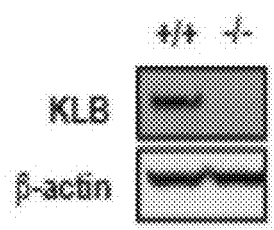
FIG. 14C
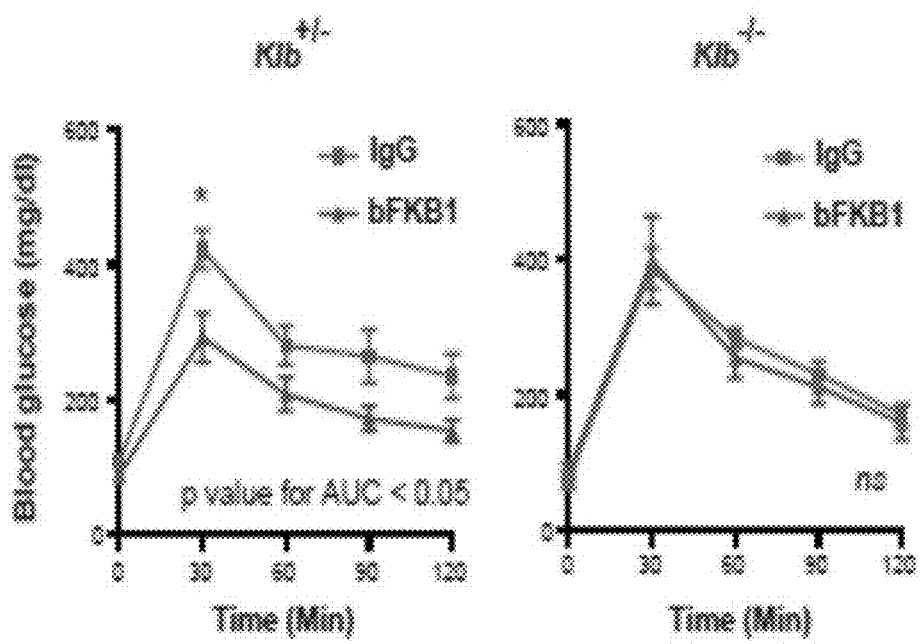

FIG. 16A
| Clone | CDR H1 | CDR H2 | CDR H3 | FGFR3.hk KD (M) | BV ELISA |
|---|---|---|---|---|---|
| 2B.1.1 | TFTST | YWAWD | LYVD | 6.63E-11 | 0.22 |
| 2B.1.1.2 | TFTST | YWAWD | TYDN | 9.08E-11 | 0.13 |
| 2B.1.1.4 | TFTST | YWAWD | IYGG | 1.53E-10 | 0.23 |
| 2B.1.1.6 | TFTST | YWAWD | TYDE | 7.96E-11 | 0.14 |
| 2B.1.1.8 | PFTSL | YWAWD | IYEK | 1.12E-10 | 0.16 |
| 2B.1.1.10 | PFTSQ | YWAWD | TYDK | 1.98E-10 | 0.12 |
| 2B.1.1.12 | PFTST | YWAWD | TYDN | 1.42E-10 | 0.20 |
| 2B.1.3 | TFTST | THLGD | LYVD | 8.34E-11 | 0.15 |
| 2B.1.3.12 | PFTST | THLGD | TYDK | 2.80E-10 | 0.14 |
FIG. 16B
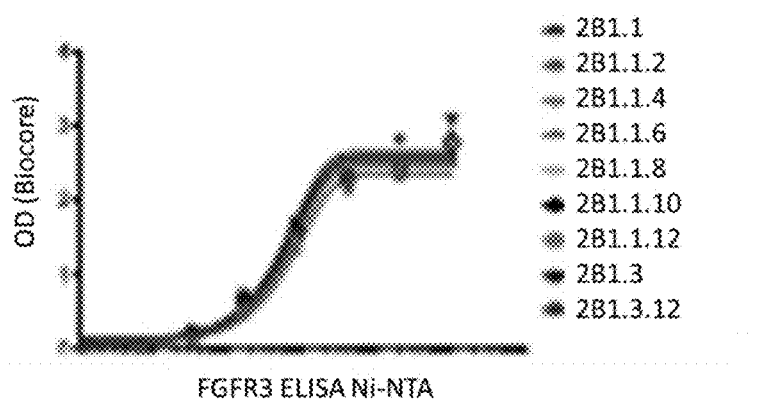
FIG. 16C
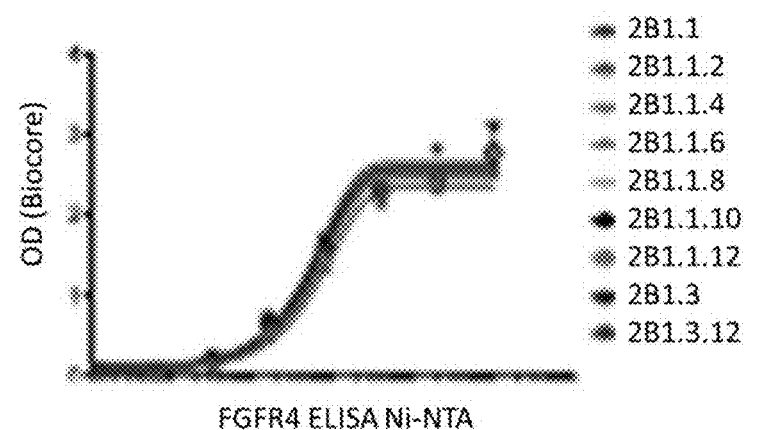

FIG. 18

| Variant | FGFR1c | FGFR2(ECD)/R1t kD | FGFR3c | FGFR4 | FGFR4 Binding affinity(nm) | Notes: |
|---|---|---|---|---|---|---|
| YW182-2 | 14.2 | 1 | 1 | 1 | | R1c Specific Ab |
| YW756-1 | ND | 24.7 | 1 | 1 | | Raised against R2 |
| 2B1.3 | 2.1 | 26 | 12.1 | 1 | 32 | Blocks growth in MCF-7/FGF7 assay,FGF19 Blocking |
| 2B1.3.12 | 1.3 | 27.7 | 11.2 | 1 | <1000 | Blocks Tumor Progression |
| 2B1.1.2 | 1.6 | 35.3 | 17.5 | 1.2 | | |
| 2B1.1.4 | 2.3 | 33.1 | 16.3 | 1.1 | | |
| 2B1.1.6 | 1.8 | 42.3 | 19.3 | 1.5 | | |
| 2B1.1.8 | 2.0 | 40.8 | 16.1 | 1.3 | | |
| 2B1.1.10 | 2.3 | 38.7 | 18.9 | 1 | | |
| 2B1.1 | 3 | 31.6 | 22.1 | 1.5 | 2.8 | Growth agonist in MCF-7/FGF7 assay |
| 2B1.1.12 | 2.6 | 30.3 | 24.9 | 1.5 | | ? |

SEQUENCE LISTING

<160> NUMBER OF SEQ ID NOS: 315

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Asp Val Asp Thr Ser Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Ser Thr Gly His Pro Gln Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Pro Phe Thr Ser Gln Gly Ile Ser
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Thr His Leu Gly Asp Gly Ser Thr Asn Tyr Ala Asp Ser Val Lys
1               5                   10                  15

Gly

<210> SEQ ID NO 6
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Ala Arg Thr Tyr Gly Ile Tyr Asp Thr Tyr Asp Lys Tyr Thr Glu Tyr
1               5                   10                  15

Val Met Asp Tyr
            20

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Pro Phe Thr Ser Thr Gly Ile Ser
1               5                   10

<210> SEQ ID NO 11

<400> SEQUENCE: 11

000

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Arg Thr Tyr Gly Ile Tyr Asp Thr Tyr Asp Met Tyr Thr Glu Tyr
1               5                   10                  15

Val Met Asp Tyr
            20

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 13

Tyr Trp Ala Trp Asp
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Trp Met Phe Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Trp Ala Tyr Asp
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Asp Val Phe Trp
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Val Gly Phe Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Ser Phe Phe Ser
1               5

<210> SEQ ID NO 19
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ser Phe Trp Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr His Pro Tyr Leu
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Ile Phe Tyr Asn
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr His Pro Phe Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Trp Tyr Phe Asp
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Trp Met Phe Asp
```

```
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Trp Ala Trp Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Ile Phe Phe Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Asn Phe Tyr Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Asn Asn Phe Tyr
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp His Pro Trp Met
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 30

Thr His Leu Gly Asp
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Asn Ala Tyr Thr
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Val Phe Phe Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Ser Phe Tyr Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val His Pro Phe Glu
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Trp Ser Trp Gly
1               5

<210> SEQ ID NO 36

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Ser Leu Gly Asp
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ser Phe Phe Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Asn Phe Phe Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Asp Asn Tyr Trp
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Asp Val Phe Trp
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Trp His Pro Phe Arg
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr His Pro Phe His
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Trp Ala Phe Ser
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Val Ala Phe Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr His Leu Gly Asp
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Ile Phe Phe Thr
1               5

<210> SEQ ID NO 47
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 47

Met Ile Phe Tyr Asn
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Val Gly Phe Thr
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Trp Met Phe Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Trp Ala Trp Asp
1               5

<210> SEQ ID NO 51
<211> LENGTH: 2469
<212> TYPE: DNA
<213> ORGANISM: Homo sapiens

<400> SEQUENCE: 51
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc aggggagtc gctagaggtg      180 cgctgcctgt tgaaagatgc cgccgtgatc agttggacta aggatggggt gcacttgggg     240
cccaacaata ggacagtgct tattggggag tacttgcaga taaagggcgc cacgcctaga     300
gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac aacacagaa     480 aagatggaaa agcggctcca tgctgtgcct gcggccaaca ctgtcaagtt tcgctgccca     540
gccgggggga acccaatgcc aaccatgcgg tggctgaaaa acgggaagga gtttaagcag     600
gagcatcgca ttggaggcta caaggtacga aaccagcact ggagcctcat tatggaaagt     660

| | | |
|---|---|---|
| gtggtcccat ctgacaaggg aaattatacc tgtgtagtgg agaatgaata cgggtccatc | 720 | |
| aatcacacgt accacctgga tgttgtggag cgatcgcctc accggcccat cctccaagcc | 780 | |
| ggactgccgg caaatgcctc cacagtggtc ggaggagacg tagagtttgt ctgcaaggtt | 840 | |
| tacagtgatg cccagcccca catccagtgg atcaagcacg tggaaaagaa cggcagtaaa | 900 | |
| tacgggcccg acgggctgcc ctacctcaag gttctcaagc actcggggat aaatagttcc | 960 | |
| aatgcagaag tgctggctct gttcaatgtg accgaggcgg atgctgggga atatatatgt | 1020 | |
| aaggtctcca attatatagg gcaggccaac cagtctgcct ggctcactgt cctgccaaaa | 1080 | |
| cagcaagcgc ctggaagaga aaaggagatt acagcttccc cagactacct ggagatagcc | 1140 | |
| atttactgca tagggtctt cttaatcgcc tgtatggtgg taacagtcat cctgtgccga | 1200 | |
| atgaagaaca cgaccaagaa gccagacttc agcagccagc cggctgtgca caagctgacc | 1260 | |
| aaacgtatcc ccctgcggag acaggtaaca gtttcggctg agtccagctc ctccatgaac | 1320 | |
| tccaacaccc cgctggtgag gataacaaca cgcctctctt caacggcaga cacccccatg | 1380 | |
| ctggcagggg tctccgagta tgaacttcca gaggacccaa atgggagtt tccaagagat | 1440 | |
| aagctgacac tgggcaagcc cctgggagaa ggttgctttg gcaagtggt catggcggaa | 1500 | |
| gcagtgggaa ttgacaaaga caagcccaag gaggcggtca ccgtggccgt gaagatgttg | 1560 | |
| aaagatgatg ccacagagaa agacctttct gatctggtgt cagagatgga gatgatgaag | 1620 | |
| atgattggga acacaagaa tatcataaat cttcttggag cctgcacaca ggatgggcct | 1680 | |
| ctctatgtca tagttgagta tgcctctaaa ggcaacctcc gagaatacct ccgagcccgg | 1740 | |
| aggccacccg ggatggagta ctcctatgac attaaccgtg ttcctgagga gcagatgacc | 1800 | |
| ttcaaggact tggtgtcatg cacctaccag ctggccagag gcatggagta cttggcttcc | 1860 | |
| caaaaatgta ttcatcgaga tttagcagcc agaaatgttt tggtaacaga aaacaatgtg | 1920 | |
| atgaaaatag cagactttgg actcgccaga gatatcaaca atatagacta ttacaaaaag | 1980 | |
| accaccaatg gcggcttcc agtcaagtgg atggctccag aagccctgtt tgatagagta | 2040 | |
| tacactcatc agagtgatgt ctggtccttc ggggtgttaa tgtgggagat cttcactta | 2100 | |
| gggggctcgc cctacccagg gattcccgtg gaggaacttt ttaagctgct gaaggaagga | 2160 | |
| cacagaatgg ataagccagc caactgcacc aacgaactgt acatgatgat gagggactgt | 2220 | |
| tggcatgcag tgccctccca gagaccaacg ttcaagcagt ggtagaaga cttggatcga | 2280 | |
| attctcactc tcacaaccaa tgaggaatac ttggacctca gccaacctct cgaacagtat | 2340 | |
| tcacctagtt accctgacac aagaagttct tgttcttcag gagatgattc tgttttttct | 2400 | |
| ccagaccca tgccttacga accatgcctt cctcagtatc cacacataaa cggcagtgtt | 2460 | |
| aaaacatga | 2469 | |

<210> SEQ ID NO 52
<211> LENGTH: 822
<212> TYPE: PRT
<213> ORGANISM: Homo sapiens

<400> SEQUENCE: 52

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

```
Val Tyr Val Ala Ala Pro Gly Glu Ser Leu Glu Val Arg Cys Leu Leu
 50                  55                  60
Lys Asp Ala Ala Val Ile Ser Trp Thr Lys Asp Gly Val His Leu Gly
 65                  70                  75                  80
Pro Asn Asn Arg Thr Val Leu Ile Gly Glu Tyr Leu Gln Ile Lys Gly
                 85                  90                  95
Ala Thr Pro Arg Asp Ser Gly Leu Tyr Ala Cys Thr Ala Ser Arg Thr
             100                 105                 110
Val Asp Ser Glu Thr Trp Tyr Phe Met Val Asn Val Thr Asp Ala Ile
             115                 120                 125
Ser Ser Gly Asp Asp Glu Asp Asp Thr Asp Gly Ala Glu Asp Phe Val
130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
            195                 200                 205
Val Arg Asn Gln His Trp Ser Leu Ile Met Glu Ser Val Val Pro Ser
210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
            275                 280                 285
Gln Trp Ile Lys His Val Glu Lys Asn Gly Ser Lys Tyr Gly Pro Asp
290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
            340                 345                 350
Ala Trp Leu Thr Val Leu Pro Lys Gln Gln Ala Pro Gly Arg Glu Lys
            355                 360                 365
Glu Ile Thr Ala Ser Pro Asp Tyr Leu Glu Ile Ala Ile Tyr Cys Ile
370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
            420                 425                 430
Ala Glu Ser Ser Ser Ser Met Asn Ser Asn Thr Pro Leu Val Arg Ile
            435                 440                 445
Thr Thr Arg Leu Ser Ser Thr Ala Asp Thr Pro Met Leu Ala Gly Val
450                 455                 460
```

-continued

```
Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
        500                 505                 510

Val Thr Val Ala Val Lys Met Leu Lys Asp Asp Ala Thr Glu Lys Asp
    515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
            565                 570                 575

Leu Arg Ala Arg Arg Pro Pro Gly Met Glu Tyr Ser Tyr Asp Ile Asn
        580                 585                 590

Arg Val Pro Glu Glu Gln Met Thr Phe Lys Asp Leu Val Ser Cys Thr
    595                 600                 605

Tyr Gln Leu Ala Arg Gly Met Glu Tyr Leu Ala Ser Gln Lys Cys Ile
610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
            645                 650                 655

Tyr Tyr Lys Lys Thr Thr Asn Gly Arg Leu Pro Val Lys Trp Met Ala
        660                 665                 670

Pro Glu Ala Leu Phe Asp Arg Val Tyr Thr His Gln Ser Asp Val Trp
    675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
        740                 745                 750

Gln Leu Val Glu Asp Leu Asp Arg Ile Leu Thr Leu Thr Thr Asn Glu
    755                 760                 765

Glu Tyr Leu Asp Leu Ser Gln Pro Leu Glu Gln Tyr Ser Pro Ser Tyr
770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
            805                 810                 815

Asn Gly Ser Val Lys Thr
            820
```

<210> SEQ ID NO 53
<211> LENGTH: 2466
<212> TYPE: DNA
<213> ORGANISM: Homo sapiens

<400> SEQUENCE: 53
atggtcagct gggtcgttt catctgcctg gtcgtggtca ccatggcaac cttgtccctg    60

```
gcccggccct ccttcagttt agttgaggat accacattag agccagaaga gccaccaacc      120
aaataccaaa tctctcaacc agaagtgtac gtggctgcgc caggggagtc gctagaggtg      180
cgctgcctgt tgaaagatgc cgccgtgatc agttggacta aggatggggt gcacttgggg      240
cccaacaata ggacagtgct tattggggag tacttgcaga taaagggcgc cacgcctaga      300
gactccggcc tctatgcttg tactgccagt aggactgtag acagtgaaac ttggtacttc      360
atggtgaatg tcacagatgc catctcatcc ggagatgatg aggatgacac cgatggtgcg      420
gaagattttg tcagtgagaa cagtaacaac aagagagcac catactggac caacacagaa      480
aagatggaaa agcggctcca tgctgtgcct gcggccaaca ctgtcaagtt tcgctgccca      540
gccgggggga acccaatgcc aaccatgcgg tggctgaaaa cgggaagga gtttaagcag      600 gagcatcgca ttggaggcta caaggtacga aaccagcact ggagcctcat tatggaaagt      660
gtggtcccat ctgacaaggg aaattatacc tgtgtagtgg agaatgaata cgggtccatc      720
aatcacacgt accacctgga tgttgtggag cgatcgcctc accggcccat cctccaagcc      780
ggactgccgg caaatgcctc cacagtggtc ggaggagacg tagagtttgt ctgcaaggtt      840
tacagtgatg cccagcccca catccagtgg atcaagcacg tggaaaagaa cggcagtaaa      900
tacgggcccg acgggctgcc ctacctcaag gttctcaagg ccgccggtgt taacaccacg      960
gacaaagaga ttgaggttct ctatattcgg aatgtaactt ttgaggacgc tggggaatat     1020
acgtgcttgg cgggtaattc tattgggata tcctttcact ctgcatggtt gacagttctg     1080
ccagcgcctg aagagaaaaa ggagattaca gcttccccag actacctgga gatagccatt     1140
tactgcatag gggtcttctt aatcgcctgt atggtggtaa cagtcatcct gtgccgaatg     1200
aagaacacga ccaagaagcc agacttcagc agccagccgg ctgtgcacaa gctgaccaaa     1260
cgtatccccc tgcggagaca ggtaacagtt tcggctgagt ccagctcctc catgaactcc     1320 aacacccgc tggtgaggat aacaacacgc ctctcttcaa cggcagacac ccccatgctg     1380 gcagggtct ccgagtatga acttccagag acccaaaat gggagtttcc aagagataag     1440
ctgacactgg gcaagcccct gggagaaggt tgctttgggc aagtggtcat ggcggaagca     1500
gtgggaattg acaaagacaa gcccaaggag gcggtcaccg tggccgtgaa gatgttgaaa     1560
gatgatgcca cagagaaaga cctttctgat ctggtgtcag agatggagat gatgaagatg     1620
attgggaaac acaagaatat cataaatctt cttggagcct gcacacagga tgggcctctc     1680
tatgtcatag ttgagtatgc ctctaaaggc aacctccgag aatacctccg agcccggagg     1740
ccacccggga tggagtactc ctatgacatt aaccgtgttc ctgaggagca gatgaccttc     1800
aaggacttgg tgtcatgcac ctaccagctg gccagaggca tggagtactt ggcttcccaa     1860
aaatgtattc atcgagattt agcagccaga aatgttttgg taacagaaaa caatgtgatg     1920
aaaatagcag actttggact cgccagagat atcaacaata tagactatta caaaaagacc     1980
accaatgggc ggcttccagt caagtggatg gctccagaag ccctgtttga tagagtatac     2040
actcatcaga gtgatgtctg gtccttcggg gtgttaatgt gggagatctt cactttaggg     2100
ggctcgccct acccagggat tcccgtggag gaacttttta gctgctgaa ggaaggacac     2160 agaatggata agccagccaa ctgcaccaac gaactgtaca tgatgatgag ggactgttgg     2220
catgcagtgc cctcccagag accaacgttc aagcagttgg tagaagactt ggatcgaatt     2280
ctcactctca caaccaatga ggaatacttg gacctcagcc aacctctcga acagtattca     2340
cctagttacc ctgacacaag aagttcttgt tcttcaggag atgattctgt tttttctcca     2400
gaccccatgc cttacgaacc atgccttcct cagtatccac acataaacgg cagtgttaaa     2460
``` acatga                                                             2466

<210> SEQ ID NO 54
<211> LENGTH: 821
<212> TYPE: PRT
<213> ORGANISM: Homo sapiens

<400> SEQUENCE: 54

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
            355                 360                 365

```
Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
    515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
    595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
    675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
    755                 760                 765

Tyr Leu Asp Leu Ser Gln Pro Leu Glu Gln Tyr Ser Pro Ser Tyr Pro
770                 775                 780
```

| Asp | Thr | Arg | Ser | Ser | Cys | Ser | Ser | Gly | Asp | Asp | Ser | Val | Phe | Ser | Pro |
|---|---|---|---|---|---|---|---|---|---|---|---|---|---|---|---|
| 785 | | | | 790 | | | | | 795 | | | | | | 800 |

| Asp | Pro | Met | Pro | Tyr | Glu | Pro | Cys | Leu | Pro | Gln | Tyr | Pro | His | Ile | Asn |
|---|---|---|---|---|---|---|---|---|---|---|---|---|---|---|---|
| | | | | 805 | | | | | 810 | | | | | 815 | |

| Gly | Ser | Val | Lys | Thr |
|---|---|---|---|---|
| | | | | 820 |

<210> SEQ ID NO 55
<211> LENGTH: 2427
<212> TYPE: DNA
<213> ORGANISM: Homo sapiens

<400> SEQUENCE: 55

```
atgggcgccc ctgcctgcgc cctcgcgctc tgcgtggccg tggccatcgt ggccggcgcc    60
tcctcggagt ccttggggac ggagcagcgc gtcgtgggc gagcggcaga agtcccgggc    120
ccagagcccg ccagcagga gcagttggtc ttcggcagcg gggatgctgt ggagctgagc    180
tgtcccccgc cgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg cgagtacct ctgtcgagcc    1020
accaatttca taggcgtggc cgagaaggcc ttttggctga cgttcacgg gccccgagca    1080
gccgaggagg agctggtgga ggctgacgag gcgggcagtg tgtatgcagg catcctcagc    1140
tacgggtgg gcttcttcct gttcatcctg gtggtggcgg ctgtgacgct ctgccgcctg    1200
cgcagccccc ccaagaaagg cctgggctcc cccaccgtgc acaagatctc ccgcttcccg    1260
ctcaagcgac aggtgtccct ggagtccaac gcgtccatga gctccaacac accactggtg    1320
cgcatcgcaa ggctgtcctc aggggagggc cccacgctgg ccaatgtctc cgagctcgag    1380
ctgcctgccg accccaaatg ggagctgtct cgggccggc tgaccctggg caagcccctt    1440
ggggagggct gcttcggcca ggtggtcatg gcggaggcca tcggcattga caaggaccgg    1500
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgg gcgcggcggc cccgggcct ggactactcc    1740
ttcgacacct gcaagccgcc cgaggagcag ctcaccttca aggacctggt gtcctgtgcc    1800
taccaggtgg cccggggcat ggagtacttg gcctcccaga gtgcatcca cagggacctg    1860
```

-continued

```
gctgcccgca atgtgctggt gaccgaggac aacgtgatga agatcgcaga cttcgggctg    1920
gcccgggacg tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg gctccccgta ccccggcatc    2100
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca agcagctggt ggaggacctg gaccgtgtcc ttaccgtgac gtccaccgac    2280
gagtacctgg acctgtcggc gcctttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga                                        2427
```

<210> SEQ ID NO 56
<211> LENGTH: 808
<212> TYPE: PRT
<213> ORGANISM: Homo sapiens

<400> SEQUENCE: 56

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270
```

```
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
290                 295                 300
Tyr Val Thr Val Leu Lys Ser Trp Ile Ser Glu Ser Val Glu Ala Asp
305                 310                 315                 320
Val Arg Leu Arg Leu Ala Asn Val Ser Glu Arg Asp Gly Gly Glu Tyr
                325                 330                 335
Leu Cys Arg Ala Thr Asn Phe Ile Gly Val Ala Glu Lys Ala Phe Trp
                340                 345                 350
Leu Ser Val His Gly Pro Arg Ala Ala Glu Glu Glu Leu Val Glu Ala
                355                 360                 365
Asp Glu Ala Gly Ser Val Tyr Ala Gly Ile Leu Ser Tyr Gly Val Gly
370                 375                 380
Phe Phe Leu Phe Ile Leu Val Val Ala Ala Val Thr Leu Cys Arg Leu
385                 390                 395                 400
Arg Ser Pro Pro Lys Lys Gly Leu Gly Ser Pro Thr Val His Lys Ile
                405                 410                 415
Ser Arg Phe Pro Leu Lys Arg Gln Val Ser Leu Glu Ser Asn Ala Ser
                420                 425                 430
Met Ser Ser Asn Thr Pro Leu Val Arg Ile Ala Arg Leu Ser Ser Gly
                435                 440                 445
Glu Gly Pro Thr Leu Ala Asn Val Ser Glu Leu Glu Leu Pro Ala Asp
                450                 455                 460
Pro Lys Trp Glu Leu Ser Arg Ala Arg Leu Thr Leu Gly Lys Pro Leu
465                 470                 475                 480
Gly Glu Gly Cys Phe Gly Gln Val Val Met Ala Glu Ala Ile Gly Ile
                485                 490                 495
Asp Lys Asp Arg Ala Ala Lys Pro Val Thr Val Ala Val Lys Met Leu
                500                 505                 510
Lys Asp Asp Ala Thr Asp Lys Asp Leu Ser Asp Leu Val Ser Glu Met
                515                 520                 525
Glu Met Met Lys Met Ile Gly Lys His Lys Asn Ile Ile Asn Leu Leu
530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Pro Gly
                565                 570                 575
Leu Asp Tyr Ser Phe Asp Thr Cys Lys Pro Pro Glu Glu Gln Leu Thr
                580                 585                 590
Phe Lys Asp Leu Val Ser Cys Ala Tyr Gln Val Ala Arg Gly Met Glu
                595                 600                 605
Tyr Leu Ala Ser Gln Lys Cys Ile His Arg Asp Leu Ala Ala Arg Asn
                610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
                660                 665                 670
Tyr Thr His Gln Ser Asp Val Trp Ser Phe Gly Val Leu Leu Trp Glu
                675                 680                 685
Ile Phe Thr Leu Gly Gly Ser Pro Tyr Pro Gly Ile Pro Val Glu Glu
```

```
                 690            695            700
Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
        770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 57
<211> LENGTH: 2421
<212> TYPE: DNA
<213> ORGANISM: Homo sapiens

<400> SEQUENCE: 57
```

| | | | | | |
|---|---|---|---|---|---|
| atgggcgccc | ctgcctgcgc | cctcgcgctc | tgcgtggccg | tggccatcgt | ggccggcgcc | 60 |
| tcctcggagt | ccttggggac | ggagcagcgc | gtcgtggggc | gagcggcaga | agtcccgggc | 120 |
| ccagagcccg | ccagcagga | gcagttggtc | ttcggcagcg | gggatgctgt | ggagctgagc | 180 |
| tgtcccccgc | ccgggggtgg | tcccatgggg | cccactgtct | gggtcaagga | tggcacaggg | 240 |
| ctggtgccct | cggagcgtgt | cctggtgggg | cccccagcggc | tgcaggtgct | gaatgcctcc | 300 |
| cacgaggact | ccggggccta | cagctgccgg | cagcggctca | cgcagcgcgt | actgtgccac | 360 |
| ttcagtgtgc | gggtgacaga | cgctccatcc | tcgggagatg | acgaagacgg | ggaggacgag | 420 |
| gctgaggaca | caggtgtgga | cacaggggcc | ccttactgga | cacggcccga | gcggatggac | 480 |
| aagaagctgc | tggccgtgcc | ggccgccaac | accgtccgct | tccgctgccc | agccgctggc | 540 |
| aaccccactc | cctccatctc | ctggctgaag | aacggcaggg | agttccgcgg | cgagcaccgc | 600 |
| attggaggca | tcaagctgcg | gcatcagcag | tggagcctgg | tcatggaaag | cgtggtgccc | 660 |
| tcggaccgcg | gcaactacac | ctgcgtcgtg | gagaacaagt | ttggcagcat | ccggcagacg | 720 |
| tacacgctgg | acgtgctgga | cgctccccg | caccggccca | tcctgcaggc | ggggctgccg | 780 |
| gccaaccaga | cggcggtgct | gggcagcgac | gtggagttcc | actgcaaggt | gtacagtgac | 840 |
| gcacagcccc | acatccagtg | gctcaagcac | gtggaggtga | atggcagcaa | ggtgggcccg | 900 |
| gacggcacac | cctacgttac | cgtgctcaag | acggcgggcg | ctaacaccac | cgacaaggag | 960 |
| ctagaggttc | tctccttgca | aacgtcacc | tttgaggacg | ccggggagta | cacctgcctg | 1020 |
| gcgggcaatt | ctattgggtt | ttctcatcac | tctgcgtggc | tggtggtgct | gccagccgag | 1080 |
| gaggagctgg | tggaggctga | cgaggcgggc | agtgtgtatg | caggcatcct | cagctacggg | 1140 |
| gtgggcttct | tcctgttcat | cctggtggtg | gcggctgtga | cgctctgccg | cctgcgcagc | 1200 |
| ccccccaaga | aaggcctggg | ctcccccacc | gtgcacaaga | tctcccgctt | ccgctcaag | 1260 |
| cgacaggtgt | ccctggagtc | caacgcgtcc | atgagctcca | acacaccact | ggtgcgcatc | 1320 |
| gcaaggctgt | cctcagggga | gggcccacg | ctggccaatg | tctccgagct | cgagctgcct | 1380 |
| gccgaccca | aatgggagct | gtctcgggcc | cggctgaccc | tgggcaagcc | ccttgggag | 1440 |

```
ggctgcttcg gccaggtggt catggcggag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggccccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acaaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg gggggctccc cgtaccccgg catccctgtg    2100
gaggagctct tcaagctgct gaaggagggc accgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgccccggc cccacccagc    2400 agtgggggct cgcggacgtg a                                              2421
```

<210> SEQ ID NO 58
<211> LENGTH: 806
<212> TYPE: PRT
<213> ORGANISM: Homo sapiens

<400> SEQUENCE: 58

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
```

```
              195                 200                 205
Gln Gln Trp Ser Leu Val Met Glu Ser Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620
```

-continued

```
Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
        660                 665                 670

His Gln Ser Asp Val Trp Ser Phe Gly Val Leu Leu Trp Glu Ile Phe
    675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 59
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser

```
                    20                  25                  30
Leu Ala Trp Tyr Lys Gln Lys Pro Gly Lys Ala Pro Lys Leu Leu Ile
                35                  40                  45
Tyr Ser Ala Ser Phe Leu Tyr Ser Gly Val Pro Ser Arg Phe Ser Gly
             50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Thr Gly His Pro Gln
                 85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
        210

<210> SEQ ID NO 62
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Val Asp Thr Ser
                20                  25                  30
Leu Ala Trp Tyr Lys Gln Lys Pro Gly Lys Ala Pro Lys Leu Leu Ile
                35                  40                  45
Tyr Ser Ala Ser Phe Leu Tyr Ser Gly Val Pro Ser Arg Phe Ser Gly
             50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Thr Gly His Pro Gln
                 85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 63
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gatatccaga tgacccagtc cccgagctcc ctgtccgcct ctgtgggcga tagggtcacc    60

```
atcacctgcc gtgccagtca ggatgttgat acttctctgg cctggtataa acagaaacca    120
ggaaaagctc cgaagcttct gatttactcg gcatccttcc tctactctgg agtcccttct    180
cgcttctctg gtagcggttc cgggacggat ttcactctga ccatcagcag tctgcagccg    240
gaagacttcg caacttatta ctgtcagcaa tctaccggtc atcctcagac gttcggacag    300
ggtaccaagg tggagatcaa acgaactgtg gctgcaccat ctgtcttcat cttcccgcca    360
tctgatgagc agttgaaatc tggaactgct tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 68
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gatatccaga tgacccagtc cccgagctcc ctgtccgcct ctgtgggcga tagggtcacc     60
atcacctgcc gtgccagtca ggatgttgat acttctctgg cctggtataa acagaaacca    120
ggaaaagctc cgaagcttct gatttactcg gcatccttcc tctactctgg agtcccttct    180
cgcttctctg gtagcggttc cgggacggat ttcactctga ccatcagcag tctgcagccg    240
gaagacttcg caacttatta ctgtcagcaa tctaccggtc atcctcagac gttcggacag    300
ggtaccaagg tggagatcaa acgaactgtg gctgcaccat ctgtcttcat cttcccgcca    360
tctgatgagc agttgaaatc tggaactgct tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 69
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gatatccaga tgacccagtc cccgagctcc ctgtccgcct ctgtgggcga tagggtcacc     60
atcacctgcc gtgccagtca ggatgttgat acttctctgg cctggtataa acagaaacca    120
ggaaaagctc cgaagcttct gatttactcg gcatccttcc tctactctgg agtcccttct    180
cgcttctctg gtagcggttc cgggacggat ttcactctga ccatcagcag tctgcagccg    240
gaagacttcg caacttatta ctgtcagcaa tctaccggtc atcctcagac gttcggacag    300
ggtaccaagg tggagatcaa acgaactgtg gctgcaccat ctgtcttcat cttcccgcca    360
tctgatgagc agttgaaatc tggaactgct tctgttgtgt gcctgctgaa taacttctat    420
cccagagagg ccaaagtaca gtggaaggtg gataacgccc tccaatcggg taactcccag    480
```

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 70
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
gatatccaga tgacccagtc cccgagctcc ctgtccgcct ctgtgggcga tagggtcacc     60
atcacctgcc gtgccagtca ggatgttgat acttctctgg cctggtataa acagaaacca    120
ggaaaagctc cgaagcttct gatttactcg gcatccttcc tctactctgg agtcccttct    180
cgcttctctg gtagcggttc cgggacggat ttcactctga ccatcagcag tctgcagccg    240
gaagacttcg caacttatta ctgtcagcaa tctaccggtc atcctcagac gttcggacag    300
ggtaccaagg tggagatcaa acgaactgtg gctgcaccat ctgtcttcat cttcccgcca    360
tctgatgagc agttgaaatc tggaactgct tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 71
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
gatatccaga tgacccagtc cccgagctcc ctgtccgcct ctgtgggcga tagggtcacc     60
atcacctgcc gtgccagtca ggatgttgat acttctctgg cctggtataa acagaaacca    120
ggaaaagctc cgaagcttct gatttactcg gcatccttcc tctactctgg agtcccttct    180
cgcttctctg gtagcggttc cgggacggat ttcactctga ccatcagcag tctgcagccg    240
gaagacttcg caacttatta ctgtcagcaa tctaccggtc atcctcagac gttcggacag    300
ggtaccaagg tggagatcaa acgaactgtg gctgcaccat ctgtcttcat cttcccgcca    360
tctgatgagc agttgaaatc tggaactgct tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 72
<211> LENGTH: 642
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 72

```
gatatccaga tgacccagtc cccgagctcc ctgtccgcct ctgtgggcga tagggtcacc    60
atcacctgcc gtgccagtca ggatgttgat acttctctgg cctggtataa acagaaacca   120
ggaaaagctc cgaagcttct gatttactcg gcatccttcc tctactctgg agtcccttct   180
cgcttctctg gtagcggttc cgggacggat ttcactctga ccatcagcag tctgcagccg   240
gaagacttcg caacttatta ctgtcagcaa tctaccggtc atcctcagac gttcggacag   300
ggtaccaagg tggagatcaa acgaactgtg gctgcaccat ctgtcttcat cttcccgcca   360
tctgatgagc agttgaaatc tggaactgct tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 73
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
gatatccaga tgacccagtc cccgagctcc ctgtccgcct ctgtgggcga tagggtcacc    60
atcacctgcc gtgccagtca ggatgttgat acttctctgg cctggtataa acagaaacca   120
ggaaaagctc cgaagcttct gatttactcg gcatccttcc tctactctgg agtcccttct   180
cgcttctctg gtagcggttc cgggacggat ttcactctga ccatcagcag tctgcagccg   240
gaagacttcg caacttatta ctgtcagcaa tctaccggtc atcctcagac gttcggacag   300
ggtaccaagg tggagatcaa acgaactgtg gctgcaccat ctgtcttcat cttcccgcca   360
tctgatgagc agttgaaatc tggaactgct tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 74
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gatatccaga tgacccagtc cccgagctcc ctgtccgcct ctgtgggcga tagggtcacc    60
atcacctgcc gtgccagtca ggatgttgat acttctctgg cctggtataa acagaaacca   120
ggaaaagctc cgaagcttct gatttactcg gcatccttcc tctactctgg agtcccttct   180
cgcttctctg gtagcggttc cgggacggat ttcactctga ccatcagcag tctgcagccg   240
```

```
gaagacttcg caacttatta ctgtcagcaa tctaccggtc atcctcagac gttcggacag    300
ggtaccaagg tggagatcaa acgaactgtg gctgcaccat ctgtcttcat cttcccgcca    360
tctgatgagc agttgaaatc tggaactgct tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 75
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Thr His Leu Gly Asp Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ile Tyr Asp Leu Tyr Val Asp Tyr Thr Glu Tyr
            100                 105                 110

Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
    195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285
```

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455

<210> SEQ ID NO 76
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Leu Ile Phe Phe Thr Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ile Tyr Asp Leu Tyr Val Asp Tyr Thr Glu Tyr
            100                 105                 110

Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

```
Ser Ser Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 77
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Met Ile Phe Tyr Asn Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ala Arg Thr Tyr Gly Ile Tyr Asp Leu Tyr Val Asp Tyr Thr Glu Tyr
                100                 105                 110

Val Met Asp Tyr Trp Gly Gln Gly Thr Leu Val Thr Val Ser Ser Ala
                115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
                195                 200                 205

Ile Cys Asn Val Asn His Lys Pro Ser Asn Thr Lys Val Asp Lys Lys
        210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Lys Phe Asn Trp Tyr
                275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
                450                 455
```

<210> SEQ ID NO 78
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Trp Val Gly Phe Thr Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ile Tyr Asp Leu Tyr Val Asp Tyr Thr Glu Tyr
            100                 105                 110

Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu

```
                      405                 410                 415
Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
            450                 455

<210> SEQ ID NO 79
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Ile Trp Met Phe Thr Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ile Tyr Asp Leu Tyr Val Asp Tyr Thr Glu Tyr
            100                 105                 110

Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300
```

```
Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 80
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Tyr Trp Ala Trp Asp Gly Ser Thr Asn Tyr Ala Asp Ser Val
    50                  55                  60

Lys Gly Arg Phe Thr Ile Ser Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Thr Tyr Gly Ile Tyr Asp Leu Tyr Val Asp Tyr Thr Glu Tyr
        100                 105                 110

Val Met Asp Tyr Trp Gly Gln Gly Thr Leu Val Thr Val Ser Ser Ala
    115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Gln Thr Tyr
    195                 200                 205
```

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
    450                 455

<210> SEQ ID NO 81
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Thr Ser Gln
            20                  25                  30

Gly Ile Ser Trp Val Arg Gln Ala Pro Gly Lys Gly Leu Glu Trp Val
        35                  40                  45

Gly Arg Thr His Leu Gly Asp Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Thr Tyr Gly Ile Tyr Asp Thr Tyr Asp Lys Tyr Thr Glu Tyr

```
            100                 105                 110
Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 82
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82
```

-continued

Glu Val Gln Leu Val Glu Ser Gly Gly Leu Val Gln Pro Gly Gly
1               5                   10                  15

Ser Leu Arg Leu Ser Cys Ala Ala Ser Gly Phe Pro Phe Thr Ser Thr
            20                  25                  30

Gly Ile Ser Trp Val Arg Gln Ala Pro Gly Lys Gly Leu Glu Trp Val
        35                  40                  45

Gly Arg Thr His Leu Gly Asp Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ile Tyr Asp Thr Tyr Asp Met Tyr Thr Glu Tyr
            100                 105                 110

Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val

```
                420             425             430
Phe Ser Cys Ser Val Met His Glu Ala Leu His Asn His Tyr Thr Gln
            435                 440                 445
Lys Ser Leu Ser Leu Ser Pro Gly Lys
    450                 455
```

<210> SEQ ID NO 83
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
gaggttcagc tggtggagtc tggcggtggc ctggtgcagc caggggggctc actccgtttg    60
tcctgtgcag cttctggctt caccttcact agtactggga ttagctgggt gcgtcaggcc   120
ccgggtaagg gcctggaatg ggttggtagg acgcatttgg gtgatggttc tactaactat   180
gccgatagcg tcaagggccg tttcactata agcgcagaca catccaaaaa cacagcctac   240
ctacaaatga acagcttaag agctgaggac actgccgtct attattgtgc tcgtacctac   300
ggcatctacg acctgtacgt ggactacacg gagtacgtta tggactactg gggtcaagga   360
accctggtca ccgtctcctc ggcctccacc aagggcccat cggtcttccc cctggcaccc   420
tcctccaaga gcacctctgg gggcacagcg gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac tgtgccctct   600
agcagcttgg gcacccagac ctacatctgc aacgtgaatc acaagcccag caacaccaag   660
gtggacaaga agttgagccc aaatcttgtg acaaaactca cacatgccca ccgtgccca   720
gcacctgaac tcctgggggg accgtcagtc ttcctcttcc ccccaaaacc caaggacacc   780
ctcatgatct cccggacccc tgaggtcaca tgcgtggtgg tggacgtgag ccacgaagac   840
cctgaggtca agttcaactg gtacgtggac ggcgtggagg tgcataatgc caagacaaag   900
ccgcgggagg agcagtacaa cagcacgtac cgggtggtca gcgtcctcac cgtcctgcac   960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggaaga gatgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca gagcaggtg gcagcagggg aacgtcttct catgctccgt gatgcatgag  1320
gctctgcaca accactacac gcagaagagc ctctccctgt ctccgggtaa a            1371
```

<210> SEQ ID NO 84
<211> LENGTH: 1370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
gaggttcagc tggtggagtc tggcggtggc ctggtgcagc caggggggctc actccgtttg    60
tcctgtgcag cttctggctt caccttcact agtactggga ttagctgggt gcgtcaggcc   120
```

```
ccgggtaagg gcctggaatg ggttggtagg ttaattttt ttacaggttc tactaactat    180
gccgatagcg tcaagggccg tttcactata agcgcagaca catccaaaaa cacagcctac    240
ctacaaatga acagcttaag agctgaggac actgccgtct attattgtgc tcgtacctac    300
ggcatctacg acctgtacgt ggactacacg gagtacgtta tggactactg ggtcaaggaa    360
ccctggtcac cgtctcctcg gcctccacca agggcccatc ggtcttcccc ctggcaccct    420
cctccaagag cacctctggg ggcacagcgg ccctgggctg cctggtcaag gactacttcc    480
ccgaaccggt gacggtgtcg tggaactcag gcgccctgac cagcggcgtg cacaccttcc    540
cggctgtcct acagtcctca ggactctact ccctcagcag cgtggtgact gtgccctcta    600
gcagcttggg cacccagacc tacatctgca acgtgaatca caagcccagc aacaccaagg    660
tggacaagaa agttgagccc aaatcttgtg acaaaactca cacatgccca ccgtgcccag    720
cacctgaact cctggggggga ccgtcagtct tcctcttccc cccaaaaccc aaggacaccc    780
tcatgatctc ccggaccccct gaggtcacat gcgtggtggt ggacgtgagc cacgaagacc    840
ctgaggtcaa gttcaactgg tacgtggacg gcgtggaggt gcataatgcc aagacaaagc    900
cgcgggagga gcagtacaac agcacgtacc gggtggtcag cgtcctcacc gtcctgcacc    960
aggactggct gaatggcaag gagtacaagt gcaaggtctc caacaaagcc ctcccagccc    1020
ccatcgagaa aaccatctcc aaagccaaag gcagccccg agaaccacag gtgtacaccc    1080
tgcccccatc ccgggaagag atgaccaaga accaggtcag cctgacctgc ctggtcaaag    1140
gcttctatcc cagcgacatc gccgtggagt gggagagcaa tgggcagccg gagaacaact    1200
acaagaccac gcctcccgtg ctggactccg acggctcctt cttcctctac agcaagctca    1260
ccgtggacaa gagcaggtgg cagcagggga acgtcttctc atgctccgtg atgcatgagg    1320
ctctgcacaa ccactacacg cagaagagcc tctccctgtc tccgggtaaa             1370

<210> SEQ ID NO 85
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gaggttcagc tggtggagtc tggcggtggc ctggtgcagc caggggggctc actccgtttg    60 tcctgtgcag cttctggctt caccttcact agtactggga ttagctgggt gcgtcaggcc    120
ccgggtaagg gcctggaatg ggttggtagg atgattttt ataatggttc tactaactat    180
gccgatagcg tcaagggccg tttcactata agcgcagaca catccaaaaa cacagcctac    240
ctacaaatga acagcttaag agctgaggac actgccgtct attattgtgc tcgtacctac    300
ggcatctacg acctgtacgt ggactacacg gagtacgtta tggactactg ggtcaagga    360 accctggtca ccgtctcctc ggcctccacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac tgtgccctct    600
agcagcttgg gcacccagac ctacatctgc aacgtgaatc acaagccag caacaccaag    660 gtggacaaga agttgagcc caaatcttgt gacaaaactc acacatgccc accgtgccca    720
gcacctgaac tcctgggggg accgtcagtc ttcctcttcc ccccaaaacc caaggacacc    780
```

```
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgggtggtca gcgtcctcac cgtcctgcac      960
caggactggc tgaatggcaa ggagtacaag tgcaaggtct ccaacaaagc cctcccagcc     1020
cccatcgaga aaaccatctc caaagccaaa gggcagcccc gagaaccaca ggtgtacacc     1080
ctgcccccat cccgggaaga gatgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca agagcaggtg gcagcagggg aacgtcttct catgctccgt gatgcatgag     1320
gctctgcaca accactacac gcagaagagc ctctccctgt ctccgggtaa a              1371
```

<210> SEQ ID NO 86
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
gaggttcagc tggtggagtc tggcggtggc ctggtgcagc caggggggctc actccgtttg       60 tcctgtgcag cttctggctt caccttcact agtactggga ttagctgggt gcgtcaggcc      120
ccgggtaagg gcctggaatg ggttggtagg tgggtcggat ttacaggttc tactaactat      180
gccgatagcg tcaagggccg tttcactata agcgcagaca catccaaaaa cacagcctac      240
ctacaaatga acagcttaag agctgaggac actgccgtct attattgtgc tcgtacctac      300
ggcatctacg acctgtacgt ggactacacg gagtacgtta tggactactg gggtcaagga      360
accctggtca ccgtctcctc ggcctccacc aagggcccat cggtcttccc cctggcaccc      420
tcctccaaga gcacctctgg gggcacagcg gccctgggct gcctggtcaa ggactacttc      480
cccgaaccgg tgacggtgtc gtggaactca ggcgccctga ccagcggcgt gcacaccttc      540
ccggctgtcc tacagtcctc aggactctac tccctcagca gcgtggtgac tgtgccctct      600
agcagcttgg gcacccagac ctacatctgc aacgtgaatc acaagcccag caacaccaag      660
gtggacaaga aagttgagcc caaatcttgt gacaaaactc acacatgccc accgtgccca      720
gcacctgaac tcctgggggg accgtcagtc ttcctcttcc ccccaaaacc caaggacacc      780
ctcatgatct cccggacccc tgaggtcaca tgcgtggtgg tggacgtgag ccacgaagac      840
cctgaggtca agttcaactg gtacgtggac ggcgtggagg tgcataatgc caagacaaag      900
ccgcgggagg agcagtacaa cagcacgtac cgggtggtca gcgtcctcac cgtcctgcac      960
caggactggc tgaatggcaa ggagtacaag tgcaaggtct ccaacaaagc cctcccagcc     1020
cccatcgaga aaaccatctc caaagccaaa gggcagcccc gagaaccaca ggtgtacacc     1080
ctgcccccat cccgggaaga gatgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca agagcaggtg gcagcagggg aacgtcttct catgctccgt gatgcatgag     1320
gctctgcaca accactacac gcagaagagc ctctccctgt ctccgggtaa a              1371
```

```
<210> SEQ ID NO 87
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gaggttcagc tggtggagtc tggcggtggc ctggtgcagc caggggggctc actccgtttg      60 tcctgtgcag cttctggctt caccttcact agtactggga ttagctgggt gcgtcaggcc     120
ccgggtaagg gcctggaatg ggttggtagg atttggatgt ttacaggttc tactaactat     180
gccgatagcg tcaagggccg tttcactata agcgcagaca catccaaaaa cacagcctac     240
ctacaaatga acagcttaag agctgaggac actgccgtct attattgtgc tcgtacctac     300
ggcatctacg acctgtacgt ggactacacg gagtacgtta tggactactg ggtcaagga      360 accctggtca ccgtctcctc ggcctccacc aagggcccat cggtcttccc cctggcaccc     420
tcctccaaga gcacctctgg gggcacagcg gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctct     600
agcagcttgg gcacccagac ctacatctgc aacgtgaatc acaagcccag caacaccaag     660
gtggacaaga agttgagccc aaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgggtggtca gcgtcctcac cgtcctgcac     960
caggactggc tgaatggcaa ggagtacaag tgcaaggtct ccaacaaagc cctcccagcc    1020
cccatcgaga aaaccatctc caaagccaaa gggcagcccc gagaaccaca ggtgtacacc    1080 ctgccccat cccgggaaga gatgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca gagcaggtg gcagcagggg aacgtcttct catgctccgt gatgcatgag    1320
gctctgcaca accactacac gcagaagagc ctctccctgt ctccgggtaa a             1371

<210> SEQ ID NO 88
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gaggttcagc tggtggagtc tggcggtggc ctggtgcagc caggggggctc actccgtttg      60 tcctgtgcag cttctggctt cccgttcact agtcagggga ttagctgggt gcgtcaggcc     120
ccgggtaagg gcctggaatg ggttggtagg acgcatttgg gtgatggttc tactaactat     180
gccgatagcg tcaagggccg tttcactata agcgcagaca catccaaaaa cacagcctac     240
ctacaaatga acagcttaag agctgaggac actgccgtct attattgtgc tcgtacctac     300
ggcatctacg acacgtatga taagtacacg gagtacgtta tggactactg ggtcaagga      360
```

| | |
|---|---|
| accctggtca ccgtctcctc ggcctccacc aagggcccat cggtcttccc cctggcaccc | 420 |
| tcctccaaga gcacctctgg gggcacagcg ccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac tgtgccctct | 600 |
| agcagcttgg gcacccagac ctacatctgc aacgtgaatc acaagcccag caacaccaag | 660 |
| gtggacaaga aagttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgggtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggaaga gatgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca agagcaggtg gcagcagggg aacgtcttct catgctccgt gatgcatgag | 1320 |
| gctctgcaca accactacac gcagaagagc ctctccctgt ctccgggtaa a | 1371 |

<210> SEQ ID NO 89
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

| | |
|---|---|
| gaggttcagc tggtggagtc tggcggtggc ctggtgcagc caggggggctc actccgtttg | 60 |
| tcctgtgcag cttctggctt cccgttcact agtcagggga ttagctgggt gcgtcaggcc | 120 |
| ccgggtaagg gcctggaatg ggttggtagg acgcatttgg gtgatggttc tactaactat | 180 |
| gccgatagcg tcaagggccg tttcactata agcgcagaca catccaaaaa cacagcctac | 240 |
| ctacaaatga acagcttaag agctgaggac actgccgtct attattgtgc tcgtacctac | 300 |
| ggcatctacg acacgtatga taagtacacg gagtacgtta tggactactg gggtcaagga | 360 |
| accctggtca ccgtctcctc ggcctccacc aagggcccat cggtcttccc cctggcaccc | 420 |
| tcctccaaga gcacctctgg gggcacagcg ccctgggct gcctggtcaa ggactacttc | 480 |
| cccgaaccgg tgacggtgtc gtggaactca ggcgccctga ccagcggcgt gcacaccttc | 540 |
| ccggctgtcc tacagtcctc aggactctac tccctcagca gcgtggtgac tgtgccctct | 600 |
| agcagcttgg gcacccagac ctacatctgc aacgtgaatc acaagcccag caacaccaag | 660 |
| gtggacaaga aagttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgggtggtca gcgtcctcac cgtcctgcac | 960 |
| caggactggc tgaatggcaa ggagtacaag tgcaaggtct ccaacaaagc cctcccagcc | 1020 |

```
cccatcgaga aaaccatctc caaagccaaa gggcagcccc gagaaccaca ggtgtacacc    1080
ctgcccccat cccgggaaga gatgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gatgcatgag    1320
gctctgcaca accactacac gcagaagagc ctctccctgt ctccgggtaa a             1371
```

<210> SEQ ID NO 90
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
gaggttcagc tggtggagtc tggcggtggc ctggtgcagc caggggggctc actccgtttg      60 tcctgtgcag cttctggctt cccgttcact agtacgggga ttagctgggt gcgtcaggcc     120
ccgggtaagg gcctggaatg ggttggtagg acgcatttgg gtgatggttc tactaactat     180
gccgatagcg tcaagggccg tttcactata agcgcagaca catccaaaaa cacagcctac     240
ctacaaatga acagcttaag agctgaggac actgccgtct attattgtgc tcgtacctac     300
ggcatctacg acacgtatga tatgtacacg gagtacgtta tggactactg gggtcaagga     360
accctggtca ccgtctcctc ggcctccacc aagggcccat cggtcttccc cctggcaccc     420
tcctccaaga gcacctctgg gggcacagcg gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac tgtgccctct     600
agcagcttgg gcacccagac ctacatctgc aacgtgaatc acaagcccag caacaccaag     660
gtggacaaga aagttgagcc caaatcttgt gacaaaactc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgggtggtca gcgtcctcac cgtcctgcac     960
caggactggc tgaatggcaa ggagtacaag tgcaaggtct ccaacaaagc cctcccagcc    1020
cccatcgaga aaccatctc caaagccaaa gggcagcccc gagaaccaca ggtgtacacc     1080
ctgcccccat cccgggaaga gatgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta cagcaagctc    1260
accgtggaca agagcaggtg gcagcagggg aacgtcttct catgctccgt gatgcatgag    1320
gctctgcaca accactacac gcagaagagc ctctccctgt ctccgggtaa a             1371
```

<210> SEQ ID NO 91
<211> LENGTH: 25
<212> TYPE: PRT
<213> ORGANISM: Homo sapiens

<400> SEQUENCE: 91

```
Thr Asn Thr Glu Lys Met Glu Lys Arg Leu His Ala Val Pro Ala Ala
1               5                   10                  15
```

```
Asn Thr Val Lys Phe Arg Cys Pro Ala
            20                  25

<210> SEQ ID NO 92
<211> LENGTH: 14
<212> TYPE: PRT
<213> ORGANISM: Homo sapiens

<400> SEQUENCE: 92

Tyr Lys Val Arg Asn Gln His Trp Ser Leu Ile Met Glu Ser
1               5                   10

<210> SEQ ID NO 93
<211> LENGTH: 25
<212> TYPE: PRT
<213> ORGANISM: Homo sapiens

<400> SEQUENCE: 93

Thr Arg Pro Glu Arg Met Asp Lys Lys Leu Leu Ala Val Pro Ala Ala
1               5                   10                  15

Asn Thr Val Arg Phe Arg Cys Pro Ala
            20                  25

<210> SEQ ID NO 94
<211> LENGTH: 14
<212> TYPE: PRT
<213> ORGANISM: Homo sapiens

<400> SEQUENCE: 94

Ile Lys Leu Arg His Gln Gln Trp Ser Leu Val Met Glu Ser
1               5                   10

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Trp Val Arg Gln Ala Pro Gly Lys Gly Leu Glu Trp Val
1               5                   10

<210> SEQ ID NO 97
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 97

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Gly Gln Gly Thr Leu Val Thr Val Ser Ser
1               5                   10

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Tyr Gln Gln Lys Pro Gly Lys Ala Pro Lys Leu Leu Ile Tyr
1               5                   10                  15

<210> SEQ ID NO 101
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 102

Phe Gly Gln Gly Thr Lys Val Glu Ile Lys
1               5                   10

<210> SEQ ID NO 103
<211> LENGTH: 34
<212> TYPE: PRT
<213> ORGANISM: Homo sapiens

<400> SEQUENCE: 103

Ser Ser Pro Thr Arg Leu Ala Val Ile Pro Trp Gly Val Arg Lys Leu
1               5                   10                  15

Leu Arg Trp Val Arg Arg Asn Tyr Gly Asp Met Asp Ile Tyr Ile Thr
            20                  25                  30

Ala Ser

<210> SEQ ID NO 104
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Asp Phe Ser Leu Thr Thr Tyr
            20                  25                  30

Gly Val His Trp Val Arg Gln Ala Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Tyr Gly Ser Thr Tyr Val Asp Ala Ile Asp Tyr Trp Gly Gln
            100                 105                 110

Gly Thr Leu Val Thr Val Ser Ser
        115                 120

<210> SEQ ID NO 105
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Ser Tyr
            20                  25                  30

Gly Asn Arg Tyr Met Thr Trp Tyr Gln Gln Lys Pro Gly Gln Pro Pro
        35                  40                  45

Lys Leu Leu Ile Tyr Arg Ala Ala Asn Leu Gln Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110

<210> SEQ ID NO 106
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Asp Phe Ser Leu Thr Thr Tyr
            20                  25                  30

Gly Val His Trp Val Arg Gln Ala Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Tyr Gly Ser Thr Tyr Val Asp Ala Ile Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
    290                 295                 300

Val Val Ser Val Leu Thr Val Leu His Gln Asp Trp Leu Asn Gly Lys

```
                305                 310                 315                 320
            Glu Tyr Lys Cys Lys Val Ser Asn Lys Ala Leu Pro Ala Pro Ile Glu
                            325                 330                 335

Lys Thr Ile Ser Lys Ala Lys Gly Gln Pro Arg Glu Pro Gln Val Tyr
                            340                 345                 350

Thr Leu Pro Pro Ser Arg Glu Glu Met Thr Lys Asn Gln Val Ser Leu
                            355                 360                 365

Ser Cys Ala Val Lys Gly Phe Tyr Pro Ser Asp Ile Ala Val Glu Trp
                            370                 375                 380

Glu Ser Asn Gly Gln Pro Glu Asn Asn Tyr Lys Thr Thr Pro Pro Val
            385                 390                 395                 400

Leu Asp Ser Asp Gly Ser Phe Phe Leu Val Ser Lys Leu Thr Val Asp
                            405                 410                 415

Lys Ser Arg Trp Gln Gln Gly Asn Val Phe Ser Cys Ser Val Met His
                            420                 425                 430

Glu Ala Leu His Asn His Tyr Thr Gln Lys Ser Leu Ser Leu Ser Pro
                            435                 440                 445

Gly Lys
                450

<210> SEQ ID NO 107
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Val Leu Thr Gln Ser Pro Asp Ser Leu Ala Val Ser Leu Gly
            1               5                   10                  15

Glu Arg Ala Thr Ile Asn Cys Arg Ala Ser Glu Ser Val Glu Ser Tyr
                            20                  25                  30

Gly Asn Arg Tyr Met Thr Trp Tyr Gln Gln Lys Pro Gly Gln Pro Pro
                        35                  40                  45

Lys Leu Leu Ile Tyr Arg Ala Ala Asn Leu Gln Ser Gly Val Pro Asp
            50                  55                  60

Arg Phe Ser Gly Ser Gly Ser Gly Thr Asp Phe Thr Leu Thr Ile Ser
            65                  70                  75                  80

Ser Leu Gln Ala Glu Asp Val Ala Val Tyr Tyr Cys Gln Gln Ser Asn
                            85                  90                  95

Glu Asp Pro Trp Thr Phe Gly Gln Gly Thr Lys Val Glu Ile Lys Arg
                        100                 105                 110

Thr Val Ala Ala Pro Ser Val Phe Ile Phe Pro Pro Ser Asp Glu Gln
                        115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
            145                 150                 155                 160

Gly Asn Ser Gln Glu Ser Val Thr Glu Gln Asp Ser Lys Asp Ser Thr
                            165                 170                 175

Tyr Ser Leu Ser Ser Thr Leu Thr Leu Ser Lys Ala Asp Tyr Glu Lys
                        180                 185                 190

His Lys Val Tyr Ala Cys Glu Val Thr His Gln Gly Leu Ser Ser Pro
                        195                 200                 205
```

```
Val Thr Lys Ser Phe Asn Arg Gly Glu Cys
    210                 215
```

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Ser Tyr Gly Ile Ser
1               5
```

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Asp Tyr Tyr Met Asn
1               5
```

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Asn Tyr Gly Val Ser
1               5
```

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
Asp Thr Tyr Met His
1               5
```

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Asp Thr Tyr Ile His
1               5
```

<210> SEQ ID NO 113
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 113

Ser Tyr Trp Ile His
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Thr Phe Thr His
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Glu Tyr Thr Met Asn
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Tyr Trp Ile Glu
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Tyr Glu Met His
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Thr Tyr Ile His
1               5

```
<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Tyr Trp Met Ser
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asn Tyr Gly Met Asn
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Thr Ser Ala Met Gly Ile Gly
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Tyr Gly Val His
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Gln Tyr Ser Lys Leu Pro Trp Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124
```

```
Phe Gln Gly Thr Gly Tyr Pro Leu Thr
1               5
```

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
His Gln Val Arg Thr Leu Pro Trp Thr
1               5
```

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Gln Gln Tyr Trp Asn Thr Pro Phe Thr
1               5
```

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Phe Gln Gly Ser His Val Leu Thr
1               5
```

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Gln Gln His Tyr Ile Val Pro Tyr Thr
1               5
```

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Leu Gln Tyr Gly Ser Tyr Pro Trp Thr
1               5
```

<210> SEQ ID NO 130
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 130

His Gln Trp Ser Ser Tyr Pro Leu Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Gln His His Ser Thr Pro Tyr Thr
1               5

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gln Phe Thr Ile Ser Pro Ser Met Tyr Thr
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Gln Tyr Asn Ile Ser Pro Tyr Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Asn Gly His Asn Phe Pro Tyr Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Gln Tyr Trp Ser Asn Pro Leu Thr
1               5
```

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Ser Asn Glu Asp Tyr Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Gln Ser Asn Glu Asp Pro Trp Thr
1               5

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Val Ser Ser Gly Gly Arg Tyr Thr Tyr Tyr Pro Asp Ser Val Lys
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Ile Asp Pro Glu Asn Asp Asp Thr Ile Tyr Asp Pro Lys Phe Gln
1               5                   10                  15

Gly

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Val Ile Trp Gly Asp Gly Ser Ile Asn Tyr His Ser Ala Leu Ile Ser
1               5                   10                  15

<210> SEQ ID NO 141
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 141

Arg Ile Asp Pro Ser Asn Gly Asn Ala Lys Tyr Asp Pro Lys Phe Gln
1               5                   10                  15

Gly

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Ile Asp Pro Ala Asn Gly Asn Thr Lys Tyr Asp Pro Lys Phe Gln
1               5                   10                  15

Asp

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Ile Asp Pro Ser Val Ser Asn Ser Asn Tyr Asn Gln Lys Phe Lys
1               5                   10                  15

Gly

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Ile Asp Pro Ser Asn Gly Asn Thr Lys Tyr Asp Pro Lys Phe Gln
1               5                   10                  15

Gly

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Ile Asn Pro Asn Asn Gly Glu Thr Ser Tyr Asn Gln Lys Phe Lys
1               5                   10                  15

Gly

<210> SEQ ID NO 146
<211> LENGTH: 17
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 146

Glu Ile Phe Pro Gly Gly Gly Ser Thr Ile Tyr Asn Glu Asn Phe Arg
1               5                   10                  15

Asp

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ile Trp Pro Glu Asn Ala Asp Ser Val Tyr Asn Gln Lys Phe Lys
1               5                   10                  15

Gly

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ile Asp Pro Ala Asn Gly Asn Thr Lys Tyr Asp Pro Lys Phe Gln
1               5                   10                  15

Gly

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Glu Ile Leu Pro Gly Ser Asp Ser Thr Lys Tyr Val Glu Lys Phe Lys
1               5                   10                  15

Val

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Glu Ile Ser Pro Asp Ser Ser Thr Ile Asn Tyr Thr Pro Ser Leu Lys
1               5                   10                  15

Asp

<210> SEQ ID NO 151
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Trp Ile Asp Thr Asp Thr Gly Glu Ala Thr Tyr Thr Asp Asp Phe Lys
1               5                   10                  15

Gly

<210> SEQ ID NO 152
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

His Ile Trp Trp Asp Asp Asp Lys Arg Tyr Asn Pro Ala Leu Lys Ser
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Val Ile Trp Ser Gly Gly Ser Thr Asp Tyr Asn Ala Ala Phe Ile Ser
1               5                   10                  15

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Gly Asp Gly Tyr Ala Leu Asp Tyr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Thr Thr Val Phe Ala Tyr
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156
```

```
Thr His Asp Trp Phe Asp Tyr
1               5

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Ala Leu Gly Asn Gly Tyr Ala Leu Gly Tyr
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Thr Ser Tyr Ser Trp Phe Ala Tyr
1               5

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Gly Val Met Val Tyr Gly Ser Ser Pro Phe Trp Phe Ala Tyr
1               5                   10                  15

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ala Leu Gly Asn Gly Tyr Ala Met Asp Tyr
1               5                   10

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Lys Thr Thr Asn Tyr
1               5

<210> SEQ ID NO 162
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 162

Arg Gly Tyr Tyr Asp Ala Ala Trp Phe Asp Tyr
1               5                   10

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Gly Gly Asn Tyr
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Gly Asn Tyr Gly Ala Met Asp Tyr
1               5

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Gly Tyr His Tyr Pro Gly Trp Leu Val Tyr
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Ser Pro Ala Leu Asp Tyr
1               5

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Glu Glu Tyr Gly Leu Phe Gly Phe Pro Tyr
1               5                   10
```

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ile Asp Gly Ile Tyr Asp Gly Ser Phe Tyr Ala Met Asp Tyr
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Tyr Gly Ser Thr Tyr Val Asp Ala Ile Asp Tyr
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Ala Ser Gln Val Ile Ser Asn Tyr Leu Asn
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Ala Ser Ser Ser Gly Arg Tyr Thr Phe
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Ala Ser Gln Asp Ile Ser Asn Tyr Phe Asn
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 173

Lys Ala Ser Asp His Ile Asn Asn Trp Leu Ala
1               5                   10

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Ser Ser Gln Asn Ile Val His Ser Asp Gly Asn Thr Tyr Leu Glu
1               5                   10                  15

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Ala Ser Gln Phe Val Ser Asp Ala Val Ala
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Ala Ser Gln Glu Ile Ser Gly Tyr Leu Ser
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Ala Ser Ser Ser Leu Ser Ser Ser Tyr Leu Tyr
1               5                   10

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Lys Ser Ser Gln Ser Leu Leu Asn Ser Gly Asn Gln Lys Asn Ser Leu
1               5                   10                  15
Ala

<210> SEQ ID NO 179
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Ala Ser Ser Ser Val Asn His Met Tyr
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Lys Ala Ser Gln Asn Val Asp Ser Tyr Val Ala
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Ala Ser Gln Ser Ile Ser Asp Tyr Val Tyr
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Ala Ser Glu Asp Ile Tyr Asn Arg Leu Ala
1               5                   10

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ala Ser Glu Ser Val Asp Ser Tyr Gly Asn Ser Phe Met His
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184
```

Arg Ala Ser Glu Ser Val Glu Ser Tyr Gly Asn Arg Tyr Met Thr
1               5                   10                  15

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Phe Thr Ser Ser Leu Arg Ser
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Thr Ser Lys Leu Ala Ser
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Tyr Thr Ser Arg Leu Gln Ser
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Thr Thr Asn Leu Glu Thr
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Lys Val Ser Asn Arg Phe Ser
1               5

<210> SEQ ID NO 190
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 190

Ser Ala Ser Tyr Arg Tyr Thr
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Ala Ser Asn Leu Glu Thr
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Ala Ser Thr Leu Asp Ser
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Ala Ser Asn Leu Ala Ser
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Leu Ala Ser Thr Arg Glu Ser
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Tyr Thr Ser Thr Leu Ala Pro
1               5

```
<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ser Ala Ser Tyr Arg Phe Ser
1               5

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Tyr Ala Ser Gln Ser Ile Ser
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Ala Thr Ser Leu Glu Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ala Ser Asn Leu Glu Ser
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ala Ala Asn Leu Gln Ser
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201
```

```
Gln Gln Tyr Ser Lys Leu Pro Trp Thr
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Phe Gln Gly Thr Gly Tyr Pro Leu Thr
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

His Gln Val Arg Thr Leu Pro Trp Thr
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Gln Tyr Trp Asn Thr Pro Phe Thr
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Phe Gln Gly Ser His Val Leu Thr
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Gln His Tyr Ile Val Pro Tyr Thr
1               5

<210> SEQ ID NO 207
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 207

Leu Gln Tyr Gly Ser Tyr Pro Trp Thr
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

His Gln Trp Ser Ser Tyr Pro Leu Thr
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Gln His His Ser Thr Pro Tyr Thr
1               5

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Gln Phe Thr Ile Ser Pro Ser Met Tyr Thr
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Gln Tyr Asn Ile Ser Pro Tyr Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Asn Gly His Asn Phe Pro Tyr Thr
1               5
```

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

Gln Gln Tyr Trp Ser Asn Pro Leu Thr
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

Gln Gln Ser Asn Glu Asp Tyr Thr
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Gln Gln Ser Asn Glu Asp Pro Trp Thr
1               5

<210> SEQ ID NO 216
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Glu Val Gln Leu Val Glu Ser Gly Gly Gly Leu Val Lys Pro Gly Gly
1               5                   10                  15

Ser Leu Lys Leu Ser Cys Ala Pro Ser Gly Phe Thr Phe Ser Ser Tyr
            20                  25                  30

Gly Ile Ser Trp Val Arg Gln Thr Pro Glu Lys Arg Leu Glu Trp Val
        35                  40                  45

Ala Thr Val Ser Ser Gly Gly Arg Tyr Thr Tyr Tyr Pro Asp Ser Val
    50                  55                  60

Lys Gly Arg Phe Thr Ile Ser Arg Asp Asn Ala Glu Asn Thr Leu Tyr
65                  70                  75                  80

Leu Gln Met Ser Ser Leu Arg Ser Glu Asp Thr Ala Met Tyr Tyr Cys
                85                  90                  95

Thr Arg Gly Gly Asp Gly Tyr Ala Leu Asp Tyr Trp Gly Gln Gly Thr
            100                 105                 110

Ser Val Thr Val Ser Ser
        115

<210> SEQ ID NO 217

```
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Gln Gln Ser Gly Ala Glu Leu Val Arg Pro Gly Ala
1               5                   10                  15

Leu Val Asn Leu Ser Cys Lys Ala Ser Gly Phe Asn Ile Lys Asp Tyr
            20                  25                  30

Tyr Met Asn Trp Val Lys Gln Arg Pro Glu Gln Gly Leu Glu Trp Thr
        35                  40                  45

Gly Trp Ile Asp Pro Glu Asn Asp Asp Thr Ile Tyr Asp Pro Lys Phe
    50                  55                  60

Gln Gly Lys Ala Thr Ile Thr Ala Asp Thr Ser Ser Asn Thr Val Tyr
65                  70                  75                  80

Leu Gln Leu Thr Ser Leu Thr Ser Glu Asp Thr Ala Val Tyr Tyr Cys
                85                  90                  95

Ala Ala Phe Thr Thr Val Phe Ala Tyr Trp Gly His Gln Thr Met Val
            100                 105                 110

Thr Val Ser Ala
        115

<210> SEQ ID NO 218
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Ser Trp Ile Arg Gln Pro Pro Gly Lys Gly Leu Glu Trp Leu
        35                  40                  45

Gly Val Ile Trp Gly Asp Gly Ser Ile Asn Tyr His Ser Ala Leu Ile
    50                  55                  60

Ser Arg Leu Thr Ile Thr Lys Asp Asn Ser Lys Ser Gln Val Phe Leu
65                  70                  75                  80

Lys Leu Asn Ser Leu Glu Ala Asp Asp Thr Ala Thr Tyr Tyr Cys Ala
                85                  90                  95

Lys Thr His Asp Trp Phe Asp Tyr Trp Gly Gln Gly Thr Leu Val Thr
            100                 105                 110

Val Ser Ala
        115

<210> SEQ ID NO 219
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219
```

Glu Val Gln Leu Gln Gln Ser Gly Ala Glu Leu Val Lys Pro Gly Ala
1               5                   10                  15

Ser Val Lys Leu Ser Cys Thr Ala Ala Asp Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ser Asn Gly Asn Ala Lys Tyr Asp Pro Lys Phe
    50                  55                  60

Gln Gly Lys Ala Ser Ile Thr Ala Asp Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Ser Arg Ala Leu Gly Asn Gly Tyr Ala Leu Gly Tyr Trp Gly Gln
            100                 105                 110

Gly Thr Ser Val Thr Val Ser Ser
            115                 120

<210> SEQ ID NO 220
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Ile Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Asp Lys Ala Ala Leu Thr Ser Asp Thr Asp Ser Asn Thr Ala Tyr
65                  70                  75                  80

Leu Leu Phe Asn Ser Leu Thr Ser Glu Asp Thr Ala Val Tyr Tyr Cys
                85                  90                  95

Ala Arg Gly Thr Ser Tyr Ser Trp Phe Ala Tyr Trp Gly Gln Gly Thr
            100                 105                 110

Leu Val Ser Val Ser Ala
        115

<210> SEQ ID NO 221
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Gln Gln Pro Gly Ala Glu Ile Val Lys Pro Gly Ala
1               5                   10                  15

Ser Val Arg Leu Ser Cys Lys Ala Ser Gly Tyr Ser Phe Thr Ser Tyr
            20                  25                  30

Trp Ile His Trp Val Lys Gln Arg Pro Gly Gln Gly Leu Glu Trp Ile
        35                  40                  45

```
Gly Glu Ile Asp Pro Ser Val Ser Asn Ser Asn Tyr Asn Gln Lys Phe
        50                  55                  60

Lys Gly Lys Ala Thr Leu Thr Ala Asp Lys Ser Ser Thr Ala Tyr
 65                  70                  75                  80

Met Gln Leu Ser Gly Leu Thr Ser Glu Asp Ser Ala Val Tyr Phe Cys
                 85                  90                  95

Val Arg Leu Gly Val Met Val Tyr Gly Ser Ser Pro Phe Trp Phe Ala
                100                 105                 110

Tyr Trp Gly Gln Gly Thr Leu Val Thr Val Ser Ala
            115                 120

<210> SEQ ID NO 222
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Gln Gln Pro Gly Ala Glu Ile Val Lys Pro Gly Ala
 1               5                  10                  15

Ser Val Arg Leu Ser Cys Lys Ala Ser Gly Tyr Ser Phe Thr Ser Tyr
                20                  25                  30

Trp Ile His Trp Val Lys Gln Arg Pro Gly Gln Gly Leu Glu Trp Ile
            35                  40                  45

Gly Glu Ile Asp Pro Ser Val Ser Asn Ser Asn Tyr Asn Gln Lys Phe
        50                  55                  60

Lys Gly Lys Ala Thr Leu Thr Ala Asp Lys Ser Ser Thr Ala Tyr
 65                  70                  75                  80

Met Gln Leu Ser Gly Leu Thr Ser Glu Asp Ser Ala Val Tyr Phe Cys
                 85                  90                  95

Val Arg Leu Gly Val Met Val Tyr Gly Ser Ser Pro Phe Trp Phe Ala
                100                 105                 110

Tyr Trp Gly Gln Gly Thr Leu Val Thr Val Ser Ala
            115                 120

<210> SEQ ID NO 223
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Glu Val Gln Leu Gln Gln Ser Gly Ala Glu Leu Leu Lys Pro Gly Ala
 1               5                  10                  15

Ser Val Arg Leu Ser Cys Thr Ala Ser Gly Phe Asn Ile Gln Asp Thr
                20                  25                  30

Phe Thr His Trp Val Arg Gln Arg Pro Glu Gln Gly Leu Glu Trp Ile
            35                  40                  45

Gly Arg Ile Asp Pro Ser Asn Gly Asn Thr Lys Tyr Asp Pro Lys Phe
        50                  55                  60

Gln Gly Lys Ala Lys Ile Leu Ala Asp Thr Ser Ser Asn Thr Ala Tyr
 65                  70                  75                  80

Leu Gln Leu Ile Gly Leu Thr Ser Glu Asp Thr Ala Val Tyr Tyr Cys
                 85                  90                  95
```

Ala Ser Arg Ala Leu Gly Asn Gly Tyr Ala Met Asp Tyr Trp Gly Gln
            100                 105                 110

Gly Thr Ser Val Thr Val Ser Ser
        115                 120

<210> SEQ ID NO 224
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Pro Leu Gln Gln Ser Gly Pro Glu Leu Val Lys Pro Gly Ala
1               5                   10                  15

Thr Val Lys Ile Ser Cys Lys Pro Ser Gly Asp Thr Phe Thr Glu Tyr
            20                  25                  30

Thr Met Asn Trp Val Arg Gln Ser His Gly Lys Ser Leu Glu Trp Ile
        35                  40                  45

Gly Gly Ile Asn Pro Asn Asn Gly Glu Thr Ser Tyr Asn Gln Lys Phe
    50                  55                  60

Lys Gly Lys Ala Thr Leu Thr Val Asp Lys Ser Ser Ser Thr Ala Phe
65                  70                  75                  80

Met Asp Leu Arg Ile Leu Thr Ser Glu Asp Ser Ala Val Tyr Phe Cys
                85                  90                  95

Ala Arg Lys Thr Thr Asn Tyr Trp Gly Gln Gly Thr Thr Leu Ile Val
            100                 105                 110

Ser Ser

<210> SEQ ID NO 225
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Ile Gln Leu Gln Gln Ser Gly Ala Glu Leu Met Lys Pro Gly Ala
1               5                   10                  15

Ser Val Arg Met Ser Cys Lys Ala Ser Gly Tyr Thr Phe Ser Ser Tyr
            20                  25                  30

Trp Ile Glu Trp Val Lys Gln Arg Ser Gly His Gly Leu Glu Trp Ile
        35                  40                  45

Gly Glu Ile Phe Pro Gly Gly Gly Ser Thr Ile Tyr Asn Glu Asn Phe
    50                  55                  60

Arg Asp Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Tyr Tyr Asp Ala Ala Trp Phe Asp Tyr Trp Gly Gln
            100                 105                 110

Gly Thr Leu Val Thr Val Ser Ala
        115                 120

<210> SEQ ID NO 226
<211> LENGTH: 114
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Lys Gln Ser Gly Ala Glu Leu Val Arg Pro Gly Thr
1               5                   10                  15

Ser Val Thr Leu Ser Cys Lys Ala Ser Gly Tyr Thr Phe Thr Asp Tyr
                20                  25                  30

Glu Met His Trp Met Lys Gln Thr Pro Val Tyr Gly Leu Glu Trp Ile
            35                  40                  45

Gly Ala Ile Trp Pro Glu Asn Ala Asp Ser Val Tyr Asn Gln Lys Phe
        50                  55                  60

Lys Gly Lys Val Thr Leu Thr Ala Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Thr Arg Glu Gly Gly Asn Tyr Trp Gly Gln Gly Thr Thr Leu Thr Val
            100                 105                 110

Ser Ser

<210> SEQ ID NO 227
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Gln Gln Ser Gly Thr Glu Leu Val Arg Pro Gly Ala
1               5                   10                  15

Ser Val Lys Leu Ser Cys Thr Ser Ser Asp Phe Asn Ile Lys Asp Thr
                20                  25                  30

Tyr Ile His Trp Val Lys Gln Arg Pro Glu Gln Gly Leu Asp Trp Leu
            35                  40                  45

Gly Arg Ile Asp Pro Ala Asn Gly Asn Thr Lys Tyr Asp Pro Lys Phe
        50                  55                  60

Gln Gly Lys Ala Ala Met Thr Ser Asp Thr Ser Ser Asn Thr Ala Tyr
65                  70                  75                  80

Leu Arg Leu Ser Ser Leu Thr Ser Glu Asp Thr Ala Val Tyr Tyr Cys
                85                  90                  95

Ala Ser Ser Gly Asn Tyr Gly Ala Met Asp Tyr Trp Gly Gln Gly Thr
            100                 105                 110

Ser Val Thr Val Ser Ser
        115

<210> SEQ ID NO 228
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Gln Gln Ser Gly Asp Glu Leu Met Lys Pro Gly Ala
1               5                   10                  15

```
Ser Val Lys Ile Ser Cys Lys Val Thr Gly Asn Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Ser Thr Lys Tyr Val Glu Lys Phe
    50                  55                  60

Lys Val Lys Ala Thr Phe Thr Ala Asp Thr Ser Ser Asn Thr Ala Tyr
65              70                  75                  80

Met Gln Leu Ser Ser Leu Thr Ser Glu Asp Ser Ala Val Tyr Tyr Cys
                85                  90                  95

Ala Arg Gly Gly Tyr His Tyr Pro Gly Trp Leu Val Tyr Trp Gly Gln
            100                 105                 110

Gly Thr Leu Val Thr Val Ser Ala
        115                 120

<210> SEQ ID NO 229
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Lys Phe Leu Glu Ser Gly Gly Gly Leu Val Gln Pro Gly Gly
1               5                   10                  15

Ser Leu Arg Leu Ser Cys Ala Val Ser Gly Ile Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Ser Pro Asp Ser Ser Thr Ile Asn Tyr Thr Pro Ser Leu
    50                  55                  60

Lys Asp Lys Phe Val Ile Ser Arg Asp Asn Ala Lys Asn Thr Leu Tyr
65              70                  75                  80

Leu Gln Met Ser Lys Val Arg Ser Ala Asp Thr Ala Leu Tyr Tyr Cys
                85                  90                  95

Ala Arg Pro Ser Pro Ala Leu Asp Tyr Trp Gly Gln Gly Thr Leu Val
            100                 105                 110

Thr Val Ser Ala
        115

<210> SEQ ID NO 230
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Ile Gln Leu Val Gln Ser Gly Pro Glu Leu Lys Lys Pro Gly Glu
1               5                   10                  15

Thr Ala Lys Ile Ser Cys Lys Ala Ser Gly Tyr Ala Phe Ser Asn Tyr
            20                  25                  30

Gly Met Asn Trp Val Lys Gln Ala Pro Gly Lys Asp Leu Lys Trp Met
        35                  40                  45

Gly Trp Ile Asp Thr Asp Thr Gly Glu Ala Thr Tyr Thr Asp Asp Phe
    50                  55                  60
```

```
Lys Gly Arg Phe Val Phe Ser Leu Glu Thr Ser Ala Ser Thr Ala Tyr
 65                  70                  75                  80

Leu Gln Ile Asn Asn Leu Lys Asn Glu Asp Met Ala Thr Tyr Phe Cys
                 85                  90                  95

Ala Arg Glu Glu Tyr Gly Leu Phe Gly Phe Pro Tyr Trp Gly His Gly
            100                 105                 110

Thr Leu Val Thr Val Ser Ala
        115

<210> SEQ ID NO 231
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
             20                  25                  30

Ala Met Gly Ile Gly Trp Ile Arg Gln Pro Ser Gly Lys Gly Leu Glu
         35                  40                  45

Trp Leu Ala His Ile Trp Trp Asp Asp Lys Arg Tyr Asn Pro Ala
     50                  55                  60

Leu Lys Ser Arg Leu Thr Ile Ser Lys Asp Thr Ser Arg Asn Gln Val
 65                  70                  75                  80

Phe Leu Lys Ile Ala Ser Val Asp Thr Ala Asp Thr Ala Thr Tyr Phe
                 85                  90                  95

Cys Ala Arg Ile Asp Gly Ile Tyr Asp Gly Ser Phe Tyr Ala Met Asp
            100                 105                 110

Tyr Trp Gly Gln Gly Thr Ser Val Thr Val Ser Ser
        115                 120

<210> SEQ ID NO 232
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Lys Gln Ser Gly Pro Gly Leu Val Gln Pro Ser Gln
 1               5                  10                  15

Ser Leu Ser Val Ala Cys Thr Val Ser Asp Phe Ser Leu Thr Thr Tyr
             20                  25                  30

Gly Val His Trp Val Arg Gln Ser Pro Gly Lys Gly Leu Glu Trp Leu
         35                  40                  45

Gly Val Ile Trp Ser Gly Gly Ser Thr Asp Tyr Asn Ala Ala Phe Ile
     50                  55                  60

Ser Arg Leu Thr Ile Ser Lys Asp Asn Ser Lys Ser Gln Val Phe Phe
 65                  70                  75                  80

Lys Met Asn Ser Leu Gln Thr Thr Asp Thr Ala Ile Tyr Tyr Cys Ala
                 85                  90                  95

Arg Asp Tyr Gly Ser Thr Tyr Val Asp Ala Ile Asp Tyr Trp Gly Gln
            100                 105                 110
```

```
Gly Thr Ser Val Thr Val Ser Ser
        115             120
```

<210> SEQ ID NO 233
<211> LENGTH: 992
<212> TYPE: PRT
<213> ORGANISM: Homo sapiens

<400> SEQUENCE: 233

```
Phe Ser Gly Asp Gly Arg Ala Ile Trp Ser Lys Asn Pro Asn Phe Thr
1               5                   10                  15

Pro Val Asn Glu Ser Gln Leu Phe Leu Tyr Asp Thr Phe Pro Lys Asn
            20                  25                  30

Phe Phe Trp Gly Ile Gly Thr Gly Ala Leu Gln Val Glu Gly Ser Trp
        35                  40                  45

Lys Lys Asp Gly Lys Gly Pro Ser Ile Trp Asp His Phe Ile His Thr
50                  55                  60

His Leu Lys Asn Val Ser Ser Thr Asn Gly Ser Ser Asp Ser Tyr Ile
65                  70                  75                  80

Phe Leu Glu Lys Asp Leu Ser Ala Leu Asp Phe Ile Gly Val Ser Phe
                85                  90                  95

Tyr Gln Phe Ser Ile Ser Trp Pro Arg Leu Phe Pro Asp Gly Ile Val
            100                 105                 110

Thr Val Ala Asn Ala Lys Gly Leu Gln Tyr Tyr Ser Thr Leu Leu Asp
        115                 120                 125

Ala Leu Val Leu Arg Asn Ile Glu Pro Ile Val Thr Leu Tyr His Trp
130                 135                 140

Asp Leu Pro Leu Ala Leu Gln Glu Lys Tyr Gly Gly Trp Lys Asn Asp
145                 150                 155                 160

Thr Ile Ile Asp Ile Phe Asn Asp Tyr Ala Thr Tyr Cys Phe Gln Met
                165                 170                 175

Phe Gly Asp Arg Val Lys Tyr Trp Ile Thr Ile His Asn Pro Tyr Leu
            180                 185                 190

Val Ala Trp His Gly Tyr Gly Thr Gly Met His Ala Pro Gly Glu Lys
        195                 200                 205

Gly Asn Leu Ala Ala Val Tyr Thr Val Gly His Asn Leu Ile Lys Ala
210                 215                 220

His Ser Lys Val Trp His Asn Tyr Asn Thr His Phe Arg Pro His Gln
225                 230                 235                 240

Lys Gly Trp Leu Ser Ile Thr Leu Gly Ser His Trp Ile Glu Pro Asn
                245                 250                 255

Arg Ser Glu Asn Thr Met Asp Ile Phe Lys Cys Gln Gln Ser Met Val
            260                 265                 270

Ser Val Leu Gly Trp Phe Ala Asn Pro Ile His Gly Asp Gly Asp Tyr
        275                 280                 285

Pro Glu Gly Met Arg Lys Lys Leu Phe Ser Val Leu Pro Ile Phe Ser
290                 295                 300

Glu Ala Glu Lys His Glu Met Arg Gly Thr Ala Asp Phe Phe Ala Phe
305                 310                 315                 320

Ser Phe Gly Pro Asn Asn Phe Lys Pro Leu Asn Thr Met Ala Lys Met
                325                 330                 335

Gly Gln Asn Val Ser Leu Asn Leu Arg Glu Ala Leu Asn Trp Ile Lys
            340                 345                 350

Leu Glu Tyr Asn Asn Pro Arg Ile Leu Ile Ala Glu Asn Gly Trp Phe
        355                 360                 365
```

-continued

Thr Asp Ser Arg Val Lys Thr Glu Asp Thr Ala Ile Tyr Met Met
    370             375             380

Lys Asn Phe Leu Ser Gln Val Leu Gln Ala Ile Arg Leu Asp Glu Ile
385             390             395             400

Arg Val Phe Gly Tyr Thr Ala Trp Ser Leu Leu Asp Gly Phe Glu Trp
            405             410             415

Gln Asp Ala Tyr Thr Ile Arg Arg Gly Leu Phe Tyr Val Asp Phe Asn
            420             425             430

Ser Lys Gln Lys Glu Arg Lys Pro Lys Ser Ser Ala His Tyr Tyr Lys
        435             440             445

Gln Ile Ile Arg Glu Asn Gly Phe Ser Leu Lys Glu Ser Thr Pro Asp
    450             455             460

Val Gln Gly Gln Phe Pro Cys Asp Phe Ser Trp Gly Val Thr Glu Ser
465             470             475             480

Val Leu Lys Pro Glu Ser Val Ala Ser Ser Pro Gln Phe Ser Asp Pro
            485             490             495

His Leu Tyr Val Trp Asn Ala Thr Gly Asn Arg Leu Leu His Arg Val
            500             505             510

Glu Gly Val Arg Leu Lys Thr Arg Pro Ala Gln Cys Thr Asp Phe Val
        515             520             525

Asn Ile Lys Lys Gln Leu Glu Met Leu Ala Arg Met Lys Val Thr His
    530             535             540

Tyr Arg Phe Ala Leu Asp Trp Ala Ser Val Leu Pro Thr Gly Asn Leu
545             550             555             560

Ser Ala Val Asn Arg Gln Ala Leu Arg Tyr Tyr Arg Cys Val Val Ser
            565             570             575

Glu Gly Leu Lys Leu Gly Ile Ser Ala Met Val Thr Leu Tyr Tyr Pro
        580             585             590

Thr His Ala His Leu Gly Leu Pro Glu Pro Leu Leu His Ala Asp Gly
        595             600             605

Trp Leu Asn Pro Ser Thr Ala Glu Ala Phe Gln Ala Tyr Ala Gly Leu
    610             615             620

Cys Phe Gln Glu Leu Gly Asp Leu Val Lys Leu Trp Ile Thr Ile Asn
625             630             635             640

Glu Pro Asn Arg Leu Ser Asp Ile Tyr Asn Arg Ser Gly Asn Asp Thr
            645             650             655

Tyr Gly Ala Ala His Asn Leu Leu Val Ala His Ala Leu Ala Trp Arg
            660             665             670

Leu Tyr Asp Arg Gln Phe Arg Pro Ser Gln Arg Gly Ala Val Ser Leu
        675             680             685

Ser Leu His Ala Asp Trp Ala Glu Pro Ala Asn Pro Tyr Ala Asp Ser
    690             695             700

His Trp Arg Ala Ala Glu Arg Phe Leu Gln Phe Glu Ile Ala Trp Phe
705             710             715             720

Ala Glu Pro Leu Phe Lys Thr Gly Asp Tyr Pro Ala Ala Met Arg Glu
            725             730             735

Tyr Ile Ala Ser Lys His Arg Arg Gly Leu Ser Ser Ser Ala Leu Pro
            740             745             750

Arg Leu Thr Glu Ala Glu Arg Arg Leu Leu Lys Gly Thr Val Asp Phe
        755             760             765

Cys Ala Leu Asn His Phe Thr Thr Arg Phe Val Met His Glu Gln Leu
    770             775             780

```
Ala Gly Ser Arg Tyr Asp Ser Asp Arg Asp Ile Gln Phe Leu Gln Asp
            785                 790                 795                 800

Ile Thr Arg Leu Ser Ser Pro Thr Arg Leu Ala Val Ile Pro Trp Gly
                805                 810                 815

Val Arg Lys Leu Leu Arg Trp Val Arg Arg Asn Tyr Gly Asp Met Asp
            820                 825                 830

Ile Tyr Ile Thr Ala Ser Gly Ile Asp Asp Gln Ala Leu Glu Asp Asp
            835                 840                 845

Arg Leu Arg Lys Tyr Tyr Leu Gly Lys Tyr Leu Gln Glu Val Leu Lys
            850                 855                 860

Ala Tyr Leu Ile Asp Lys Val Arg Ile Lys Gly Tyr Tyr Ala Phe Lys
865                 870                 875                 880

Leu Ala Glu Glu Lys Ser Lys Pro Arg Phe Gly Phe Phe Thr Ser Asp
                885                 890                 895

Phe Lys Ala Lys Ser Ser Ile Gln Phe Tyr Asn Lys Val Ile Ser Ser
                900                 905                 910

Arg Gly Phe Pro Phe Glu Asn Ser Ser Arg Cys Ser Gln Thr Gln
            915                 920                 925

Glu Asn Thr Glu Cys Thr Val Cys Leu Phe Leu Val Gln Lys Lys Pro
930                 935                 940

Leu Ile Phe Leu Gly Cys Cys Phe Phe Ser Thr Leu Val Leu Leu Leu
945                 950                 955                 960

Ser Ile Ala Ile Phe Gln Arg Gln Lys Arg Arg Lys Phe Trp Lys Ala
                965                 970                 975

Lys Asn Leu Gln His Ile Pro Leu Lys Lys Gly Lys Arg Val Val Ser
                980                 985                 990

<210> SEQ ID NO 234
<211> LENGTH: 52
<212> TYPE: PRT
<213> ORGANISM: Homo sapiens

<400> SEQUENCE: 234

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly
        50

<210> SEQ ID NO 235
<211> LENGTH: 455
<212> TYPE: PRT
<213> ORGANISM: Homo sapiens

<400> SEQUENCE: 235

Phe Pro Cys Asp Phe Ser Trp Gly Val Thr Glu Ser Val Leu Lys Pro
1               5                   10                  15

Glu Ser Val Ala Ser Ser Pro Gln Phe Ser Asp Pro His Leu Tyr Val
                20                  25                  30

Trp Asn Ala Thr Gly Asn Arg Leu Leu His Arg Val Glu Gly Val Arg
            35                  40                  45

Leu Lys Thr Arg Pro Ala Gln Cys Thr Asp Phe Val Asn Ile Lys Lys
        50                  55                  60
```

```
Gln Leu Glu Met Leu Ala Arg Met Lys Val Thr His Tyr Arg Phe Ala
 65                  70                  75                  80

Leu Asp Trp Ala Ser Val Leu Pro Thr Gly Asn Leu Ser Ala Val Asn
                 85                  90                  95

Arg Gln Ala Leu Arg Tyr Tyr Arg Cys Val Val Ser Glu Gly Leu Lys
            100                 105                 110

Leu Gly Ile Ser Ala Met Val Thr Leu Tyr Tyr Pro Thr His Ala His
        115                 120                 125

Leu Gly Leu Pro Glu Pro Leu Leu His Ala Asp Gly Trp Leu Asn Pro
    130                 135                 140

Ser Thr Ala Glu Ala Phe Gln Ala Tyr Ala Gly Leu Cys Phe Gln Glu
145                 150                 155                 160

Leu Gly Asp Leu Val Lys Leu Trp Ile Thr Ile Asn Glu Pro Asn Arg
                165                 170                 175

Leu Ser Asp Ile Tyr Asn Arg Ser Gly Asn Asp Thr Tyr Gly Ala Ala
            180                 185                 190

His Asn Leu Leu Val Ala His Ala Leu Ala Trp Arg Leu Tyr Asp Arg
        195                 200                 205

Gln Phe Arg Pro Ser Gln Arg Gly Ala Val Ser Leu Ser Leu His Ala
    210                 215                 220

Asp Trp Ala Glu Pro Ala Asn Pro Tyr Ala Asp Ser His Trp Arg Ala
225                 230                 235                 240

Ala Glu Arg Phe Leu Gln Phe Glu Ile Ala Trp Phe Ala Glu Pro Leu
                245                 250                 255

Phe Lys Thr Gly Asp Tyr Pro Ala Ala Met Arg Glu Tyr Ile Ala Ser
            260                 265                 270

Lys His Arg Arg Gly Leu Ser Ser Ala Leu Pro Arg Leu Thr Glu
        275                 280                 285

Ala Glu Arg Arg Leu Leu Lys Gly Thr Val Asp Phe Cys Ala Leu Asn
    290                 295                 300

His Phe Thr Thr Arg Phe Val Met His Glu Gln Leu Ala Gly Ser Arg
305                 310                 315                 320

Tyr Asp Ser Asp Arg Asp Ile Gln Phe Leu Gln Asp Ile Thr Arg Leu
                325                 330                 335

Ser Ser Pro Thr Arg Leu Ala Val Ile Pro Trp Gly Val Arg Lys Leu
            340                 345                 350

Leu Arg Trp Val Arg Arg Asn Tyr Gly Asp Met Asp Ile Tyr Ile Thr
        355                 360                 365

Ala Ser Gly Ile Asp Asp Gln Ala Leu Glu Asp Arg Leu Arg Lys
    370                 375                 380

Tyr Tyr Leu Gly Lys Tyr Leu Gln Glu Val Leu Lys Ala Tyr Leu Ile
385                 390                 395                 400

Asp Lys Val Arg Ile Lys Gly Tyr Tyr Ala Phe Lys Leu Ala Glu Glu
                405                 410                 415

Lys Ser Lys Pro Arg Phe Gly Phe Phe Thr Ser Asp Phe Lys Ala Lys
            420                 425                 430

Ser Ser Ile Gln Phe Tyr Asn Lys Val Ile Ser Ser Arg Gly Phe Pro
        435                 440                 445

Phe Glu Asn Ser Ser Ser Arg
    450                 455

<210> SEQ ID NO 236
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 236

Asp Ile Gln Met Thr Gln Thr Thr Ser Ser Leu Ser Ala Ser Leu Gly
1               5                   10                  15

Asp Arg Val Thr Ile Ile Cys Ser Ala Ser Gln Val Ile Ser Asn Tyr
            20                  25                  30

Leu Asn Trp Tyr Gln Gln Lys Pro Asp Gly Thr Val Lys Leu Leu Ile
        35                  40                  45

Tyr Phe Thr Ser Ser Leu Arg Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Val Ala Thr Tyr Phe Cys Gln Gln Tyr Ser Lys Leu Pro Trp
                85                  90                  95

Thr Phe Gly Gly Gly Thr Lys Leu Glu Leu Lys
            100                 105

<210> SEQ ID NO 237
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Gly Arg Tyr Thr
            20                  25                  30

Phe Trp Tyr Gln Gln Lys Ser Asn Thr Ala Pro Lys Leu Trp Ile Tyr
        35                  40                  45

Asp Thr Ser Lys Leu Ala Ser Gly Val Pro Gly Arg Phe Ser Gly Ser
50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Thr Gly Tyr Pro Leu Thr
                85                  90                  95

Phe Gly Ala Gly Thr Lys Leu Glu Leu Lys
            100                 105

<210> SEQ ID NO 238
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asp Ile Gln Met Thr Gln Thr Pro Ser Ser Leu Ser Ala Ser Leu Gly
1               5                   10                  15

Asp Arg Val Thr Ile Asn Cys Arg Ala Ser Gln Asp Ile Ser Asn Tyr
            20                  25                  30

Phe Asn Trp Tyr Gln Gln Lys Pro Asn Gly Thr Ile Lys Leu Leu Ile
        35                  40                  45

Tyr Tyr Thr Ser Arg Leu Gln Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Lys Ala Thr Tyr Phe Cys His Gln Val Arg Thr Leu Pro Trp
                 85                  90                  95

Thr Phe Gly Gly Gly Thr Lys Leu Glu Ile Lys
                100                 105

<210> SEQ ID NO 239
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asp Ile Gln Met Thr Gln Ser Ser Ser Tyr Leu Ser Val Ser Leu Gly
 1               5                  10                  15

Gly Ser Val Thr Ile Thr Cys Lys Ala Ser Asp His Ile Asn Asn Trp
                 20                  25                  30

Leu Ala Trp Tyr Gln Gln Lys Pro Gly Asn Ala Pro Arg Leu Leu Ile
             35                  40                  45

Tyr Gly Thr Thr Asn Leu Glu Thr Gly Val Pro Ser Arg Phe Ser Gly
 50                  55                  60

Ser Gly Ser Gly Arg Asp Tyr Ile Leu Ser Ile Thr Ser Leu Gln Ser
 65                  70                  75                  80

Glu Asp Val Ala Ser Tyr Tyr Cys Gln Gln Tyr Trp Asn Thr Pro Phe
                 85                  90                  95

Thr Phe Gly Ser Gly Thr Lys Leu Glu Ile Lys
                100                 105

<210> SEQ ID NO 240
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Ala Val Leu Met Thr Gln Thr Pro Leu Ser Leu Pro Val Ser Leu Gly
 1               5                  10                  15

Asp Gln Ala Ser Ile Ser Cys Arg Ser Ser Gln Asn Ile Val His Ser
                 20                  25                  30

Asp Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Arg Asp Phe Thr Leu Lys Ile
 65                  70                  75                  80

Ser Arg Val Glu Ala Gly Asp Leu Gly Val Tyr Tyr Cys Phe Gln Gly
                 85                  90                  95

Ser His Val Leu Thr Phe Gly Ala Gly Thr Arg Leu Glu Leu Lys
                100                 105                 110

<210> SEQ ID NO 241

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Asp Ile Val Met Thr Gln Ser Gln Lys Phe Met Ser Thr Ser Val Gly
1               5                   10                  15

Asp Arg Val Ser Ile Thr Cys Lys Ala Ser Gln Phe Val Ser Asp Ala
            20                  25                  30

Val Ala Trp Tyr Gln Gln Lys Pro Gly Gln Ser Pro Lys Leu Leu Ile
        35                  40                  45

Cys Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Arg Thr
65                  70                  75                  80

Glu Asp Leu Ala Val Tyr Tyr Cys Gln Gln His Tyr Ile Val Pro Tyr
                85                  90                  95

Thr Phe Gly Gly Gly Thr Thr Leu Glu Ile Glu
            100                 105

<210> SEQ ID NO 242
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Asp Ile Val Met Thr Gln Ser Gln Lys Phe Met Ser Thr Ser Val Gly
1               5                   10                  15

Asp Arg Val Ser Ile Thr Cys Lys Ala Ser Gln Phe Val Ser Asp Ala
            20                  25                  30

Val Ala Trp Tyr Gln Gln Lys Pro Gly Gln Ser Pro Lys Leu Leu Ile
        35                  40                  45

Cys Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Arg Thr
65                  70                  75                  80

Glu Asp Leu Ala Val Tyr Tyr Cys Gln Gln His Tyr Ile Val Pro Tyr
                85                  90                  95

Thr Phe Gly Gly Gly Thr Thr Leu Glu Ile Glu
            100                 105

<210> SEQ ID NO 243
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

```
Leu Ala Trp Tyr Gln Gln Lys Pro Gly Asn Ala Pro Arg Leu Leu Ile
            35                  40                  45

Ser Gly Ala Ser Asn Leu Glu Thr Gly Ile Pro Ser Arg Phe Ser Gly
 50                  55                  60

Ser Gly Ser Gly Lys Asp Tyr Thr Leu Thr Ile Thr Ser Leu Gln Thr
 65                  70                  75                  80

Glu Asp Val Ala Thr Tyr Tyr Cys Gln Gln Tyr Trp Asn Thr Pro Phe
                 85                  90                  95

Thr Phe Gly Ser Gly Thr Lys Leu Glu Ile Lys
            100                 105

<210> SEQ ID NO 244
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Glu Ile Ser Gly Tyr
                 20                  25                  30

Leu Ser Trp Leu Gln Gln Lys Pro Asp Gly Thr Ile Lys Arg Leu Ile
            35                  40                  45

Tyr Ala Ala Ser Thr Leu Asp Ser Gly Val Pro Arg Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Gly Ser Tyr Pro Trp
                 85                  90                  95

Thr Phe Gly Gly Gly Thr Lys Leu Glu Leu Lys
            100                 105

<210> SEQ ID NO 245
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Ile Val Leu Thr Gln Ser Pro Ala Ile Met Ser Ala Ser Pro Gly
 1               5                  10                  15

Glu Arg Val Thr Leu Thr Cys Ser Ala Ser Ser Ser Leu Ser Ser Ser
                 20                  25                  30

Tyr Leu Tyr Trp Tyr Gln Gln Lys Pro Gly Ser Ser Pro Lys Leu Trp
            35                  40                  45

Ile Tyr Gly Ala Ser Asn Leu Ala Ser Gly Val Pro Gly Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                 85                  90                  95

Leu Thr Phe Gly Ser Gly Thr Lys Leu Glu Leu Lys
            100                 105
```

<210> SEQ ID NO 246
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Asp Ile Val Met Thr Gln Ser Pro Ser Ser Leu Pro Met Ser Val Gly
1               5                   10                  15

Gln Lys Val Thr Met Ser Cys Lys Ser Ser Gln Ser Leu Leu Asn Ser
            20                  25                  30

Gly Asn Gln Lys Asn Ser Leu Ala Trp Tyr Gln Gln Lys Pro Gly Gln
        35                  40                  45

Ser Pro Lys Leu Leu Val Tyr Leu Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His His Ser Thr Pro Tyr Thr Phe Gly Gly Gly Thr Lys Leu Glu Leu
            100                 105                 110

Lys

<210> SEQ ID NO 247
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Ser Val Leu Thr Gln Ser Pro Ala Leu Met Ser Ala Ser Leu Gly
1               5                   10                  15

Glu Lys Val Thr Met Thr Cys Arg Ala Ser Ser Ser Val Asn His Met
            20                  25                  30

Tyr Trp Tyr Gln Gln Lys Ser Asp Ala Ser Pro Lys Leu Trp Ile Tyr
        35                  40                  45

Tyr Thr Ser Thr Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ile Ser Pro Ser Met
                85                  90                  95

Tyr Thr Phe Gly Gly Gly Thr Lys Leu Glu Ile Lys
            100                 105

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Thr Asp Val Met Asp Tyr
1               5

```
<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Arg Ala Ser Gln Asp Val Ser Thr Ala Val Ala
1               5                   10

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Ala Ser Phe Leu Tyr Ser
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Gln Ser Tyr Thr Thr Pro Pro Thr
1               5

<210> SEQ ID NO 252
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Lys Leu His Ala Val Pro Ala Ala Lys Thr Val Lys Phe Lys Cys Pro
1               5                   10                  15

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Phe Lys Pro Asp His Arg Ile Gly Gly Tyr Lys Val Arg Tyr
1               5                   10

<210> SEQ ID NO 254
<211> LENGTH: 992
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 254

| | | | | | | | | | | | | | | |
|---|---|---|---|---|---|---|---|---|---|---|---|---|---|---|
|Phe|Ser|Gly|Asp|Gly|Arg|Ala|Ile|Trp|Ser|Lys|Asn|Pro|Asn|Phe|Thr|
|1| | | |5| | | | |10| | | | |15| |

Pro Val Asn Glu Ser Gln Leu Phe Leu Tyr Asp Thr Phe Pro Lys Asn
               20                   25                   30

Phe Phe Trp Gly Ile Gly Thr Gly Ala Leu Gln Val Glu Gly Ser Trp
            35                   40                   45

Lys Lys Asp Gly Lys Gly Pro Ser Ile Trp Asp His Phe Ile His Thr
50                    55                   60

His Leu Lys Asn Val Ser Ser Thr Asn Gly Ser Ser Asp Ser Tyr Ile
65                    70                 75                   80

Phe Leu Glu Lys Asp Leu Ser Ala Leu Asp Phe Ile Gly Val Ser Phe
            85                   90                   95

Tyr Gln Phe Ser Ile Ser Trp Pro Arg Leu Phe Pro Asp Gly Ile Val
           100                   105                 110

Thr Val Ala Asn Ala Lys Gly Leu Gln Tyr Tyr Ser Thr Leu Leu Asp
           115                   120               125

Ala Leu Val Leu Arg Asn Ile Glu Pro Ile Val Thr Leu Tyr His Trp
130                  135                 140

Asp Leu Pro Leu Ala Leu Gln Glu Lys Tyr Gly Gly Trp Lys Asn Asp
145                  150                 155            160

Thr Ile Ile Asp Ile Phe Asn Asp Tyr Ala Thr Tyr Cys Phe Gln Met
           165                   170               175

Phe Gly Asp Arg Val Lys Tyr Trp Ile Thr Ile His Asn Pro Tyr Leu
           180                   185               190

Val Ala Trp His Gly Tyr Gly Thr Gly Met His Ala Pro Gly Glu Lys
           195                   200               205

Gly Asn Leu Ala Ala Val Tyr Thr Val Gly His Asn Leu Ile Lys Ala
           210                   215               220

His Ser Lys Val Trp His Asn Tyr Asn Thr His Phe Arg Pro His Gln
225                  230                 235            240

Lys Gly Trp Leu Ser Ile Thr Leu Gly Ser His Trp Ile Glu Pro Asn
           245                   250               255

Arg Ser Glu Asn Thr Met Asp Ile Phe Lys Cys Gln Gln Ser Met Val
           260                   265               270

Ser Val Leu Gly Trp Phe Ala Asn Pro Ile His Gly Asp Gly Asp Tyr
           275                   280               285

Pro Glu Gly Met Arg Lys Lys Leu Phe Ser Val Leu Pro Ile Phe Ser
290                  295                 300

Glu Ala Glu Lys His Glu Met Arg Gly Thr Ala Asp Phe Phe Ala Phe
305                  310                 315            320

Ser Phe Gly Pro Asn Asn Phe Lys Pro Leu Asn Thr Met Ala Lys Met
           325                   330               335

Gly Gln Asn Val Ser Leu Asn Leu Arg Glu Ala Leu Asn Trp Ile Lys
           340                   345               350

Leu Glu Tyr Asn Asn Pro Arg Ile Leu Ile Ala Glu Asn Gly Trp Phe
           355                   360               365

Thr Asp Ser Arg Val Lys Thr Glu Asp Thr Thr Ala Ile Tyr Met Met
           370                   375               380

Lys Asn Phe Leu Ser Gln Val Leu Gln Ala Ile Arg Leu Asp Glu Ile
385                  390                 395            400

Arg Val Phe Gly Tyr Thr Ala Trp Ser Leu Leu Asp Gly Phe Glu Trp

```
                    405                 410                 415
Gln Asp Ala Tyr Thr Ile Arg Arg Gly Leu Phe Tyr Val Asp Phe Asn
                420                 425                 430

Ser Lys Gln Lys Glu Arg Lys Pro Lys Ser Ser Ala His Tyr Tyr Lys
            435                 440                 445

Gln Ile Ile Arg Glu Asn Gly Phe Ser Leu Lys Glu Ser Thr Pro Asp
        450                 455                 460

Val Gln Gly Gln Phe Pro Cys Asp Phe Ser Trp Gly Val Thr Glu Ser
465                 470                 475                 480

Val Leu Lys Pro Glu Ser Val Ala Ser Ser Pro Gln Phe Ser Asp Pro
                485                 490                 495

His Leu Tyr Val Trp Asn Ala Thr Gly Asn Arg Leu Leu His Arg Val
                500                 505                 510

Glu Gly Val Arg Leu Lys Thr Arg Pro Ala Gln Cys Thr Asp Phe Val
            515                 520                 525

Asn Ile Lys Lys Gln Leu Glu Met Leu Ala Arg Met Lys Val Thr His
        530                 535                 540

Tyr Arg Phe Ala Leu Asp Trp Ala Ser Val Leu Pro Thr Gly Asn Leu
545                 550                 555                 560

Ser Ala Val Asn Arg Gln Ala Leu Arg Tyr Tyr Arg Cys Val Val Ser
                565                 570                 575

Glu Gly Leu Lys Leu Gly Ile Ser Ala Met Val Thr Leu Tyr Tyr Pro
            580                 585                 590

Thr His Ala His Leu Gly Leu Pro Glu Pro Leu Leu His Ala Asp Gly
        595                 600                 605

Trp Leu Asn Pro Ser Thr Ala Glu Ala Phe Gln Ala Tyr Ala Gly Leu
    610                 615                 620

Cys Phe Gln Glu Leu Gly Asp Leu Val Lys Leu Trp Ile Thr Ile Asn
625                 630                 635                 640

Glu Pro Asn Arg Leu Ser Asp Ile Tyr Asn Arg Ser Gly Asn Asp Thr
                645                 650                 655

Tyr Gly Ala Ala His Asn Leu Leu Val Ala His Ala Leu Ala Trp Arg
            660                 665                 670

Leu Tyr Asp Arg Gln Phe Arg Pro Ser Gln Arg Gly Ala Val Ser Leu
        675                 680                 685

Ser Leu His Ala Asp Trp Ala Glu Pro Ala Asn Pro Tyr Ala Asp Ser
    690                 695                 700

His Trp Arg Ala Ala Glu Arg Phe Leu Gln Phe Glu Ile Ala Trp Phe
705                 710                 715                 720

Ala Glu Pro Leu Phe Lys Thr Gly Asp Tyr Pro Ala Ala Met Arg Glu
                725                 730                 735

Tyr Ile Ala Ser Lys His Arg Arg Gly Leu Ser Ser Ser Ala Leu Pro
            740                 745                 750

Arg Leu Thr Glu Ala Glu Arg Arg Leu Leu Lys Gly Thr Val Asp Phe
        755                 760                 765

Cys Ala Leu Asn His Phe Thr Thr Arg Phe Val Met His Glu Gln Leu
    770                 775                 780

Ala Gly Ser Arg Tyr Asp Ser Asp Arg Asp Ile Gln Phe Leu Gln Asp
785                 790                 795                 800

Ile Thr Arg Leu Ser Ser Pro Thr Arg Leu Ala Val Ile Pro Trp Gly
                805                 810                 815

Val Arg Lys Leu Leu Arg Trp Val Arg Arg Asn Tyr Gly Asp Met Asp
            820                 825                 830
```

```
Ile Tyr Ile Thr Ala Ser Gly Ile Asp Asp Gln Ala Leu Glu Asp Asp
            835                 840                 845

Arg Leu Arg Lys Tyr Tyr Leu Gly Lys Tyr Leu Gln Glu Val Leu Lys
850                 855                 860

Ala Tyr Leu Ile Asp Lys Val Arg Ile Lys Gly Tyr Tyr Ala Phe Lys
865                 870                 875                 880

Leu Ala Glu Glu Lys Ser Lys Pro Arg Phe Gly Phe Thr Ser Asp
                885                 890                 895

Phe Lys Ala Lys Ser Ser Ile Gln Phe Tyr Asn Lys Val Ile Ser Ser
                900                 905                 910

Arg Gly Phe Pro Phe Glu Asn Ser Ser Arg Cys Ser Gln Thr Gln
                915                 920                 925

Glu Asn Thr Glu Cys Thr Val Cys Leu Phe Leu Val Gln Lys Lys Pro
930                 935                 940

Leu Ile Phe Leu Gly Cys Cys Phe Ser Thr Leu Val Leu Leu Leu
945                 950                 955                 960

Ser Ile Ala Ile Phe Gln Arg Gln Lys Arg Arg Lys Phe Trp Lys Ala
                965                 970                 975

Lys Asn Leu Gln His Ile Pro Leu Lys Lys Gly Lys Arg Val Val Ser
                980                 985                 990

<210> SEQ ID NO 255
<211> LENGTH: 820
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
```

-continued

```
                195                 200                 205
Ala Thr Trp Ser Ile Ile Met Asp Ser Val Val Pro Ser Asp Lys Gly
210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
                260                 265                 270

Phe Met Cys Lys Val Tyr Ser Asp Pro Gln Pro His Ile Gln Trp Leu
                275                 280                 285

Lys His Ile Glu Val Asn Gly Ser Lys Ile Gly Pro Asp Asn Leu Pro
290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Glu Arg Pro Ala Val Met Thr
                355                 360                 365

Ser Pro Leu Tyr Leu Glu Ile Ile Ile Tyr Cys Thr Gly Ala Phe Leu
370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
                420                 425                 430

Ala Ser Met Asn Ser Gly Val Leu Leu Val Arg Pro Ser Arg Leu Ser
                435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
                500                 505                 510

Met Leu Lys Ser Asp Ala Thr Glu Lys Asp Leu Ser Asp Leu Ile Ser
                515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
                580                 585                 590

Leu Ser Ser Lys Asp Leu Val Ser Cys Ala Tyr Gln Val Ala Arg Gly
                595                 600                 605

Met Glu Tyr Leu Ala Ser Lys Lys Cys Ile His Arg Asp Leu Ala Ala
610                 615                 620
```

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
            645                 650                 655

Asn Gly Arg Leu Pro Val Lys Trp Met Ala Pro Glu Ala Leu Phe Asp
        660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
            725                 730                 735

Ala Val Pro Ser Gln Arg Pro Thr Phe Lys Gln Leu Val Glu Asp Leu
        740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
            805                 810                 815

Leu Lys Arg Arg
        820

<210> SEQ ID NO 256
<211> LENGTH: 948
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Asp Tyr Lys Asp Asp Asp Asp Lys Leu Glu Phe Ser Gly Asp Gly Lys
1               5                   10                  15

Ala Ile Trp Asp Lys Lys Gln Tyr Val Ser Pro Val Asn Pro Gly Gln
            20                  25                  30

Leu Phe Leu Tyr Asp Thr Phe Pro Lys Asn Phe Ser Trp Gly Val Gly
        35                  40                  45

Thr Gly Ala Phe Gln Val Glu Gly Ser Trp Lys Ala Asp Gly Arg Gly
    50                  55                  60

Pro Ser Ile Trp Asp Arg Tyr Val Asp Ser His Leu Arg Gly Val Asn
65                  70                  75                  80

Ser Thr Asp Arg Ser Thr Asp Ser Tyr Val Phe Leu Glu Lys Asp Leu
            85                  90                  95

Leu Ala Leu Asp Phe Leu Gly Val Ser Phe Tyr Gln Phe Ser Ile Ser
        100                 105                 110

Trp Pro Arg Leu Phe Pro Asn Gly Thr Val Ala Ala Val Asn Ala Lys
    115                 120                 125

Gly Leu Gln Tyr Tyr Arg Ala Leu Leu Asp Ser Leu Val Leu Arg Asn
130                 135                 140

Ile Glu Pro Ile Val Thr Leu Tyr His Trp Asp Leu Pro Leu Thr Leu

-continued

```
            145                 150                 155                 160
        Gln Glu Glu Tyr Gly Gly Trp Lys Asn Ala Thr Met Ile Asp Leu Phe
                        165                 170                 175
        Asn Asp Tyr Ala Thr Tyr Cys Phe Gln Thr Phe Gly Asp Arg Val Lys
                        180                 185                 190
        Tyr Trp Ile Thr Ile His Asn Pro Tyr Leu Val Ala Trp His Gly Phe
                        195                 200                 205
        Gly Thr Gly Met His Ala Pro Gly Glu Lys Gly Asn Leu Thr Ala Val
                        210                 215                 220
        Tyr Thr Val Gly His Asn Leu Ile Lys Ala His Ser Lys Val Trp His
        225                 230                 235                 240
        Asn Tyr Asp Lys Asn Phe Arg Pro His Gln Lys Gly Trp Leu Ser Ile
                        245                 250                 255
        Thr Leu Gly Ser His Trp Ile Glu Pro Asn Arg Thr Glu Asn Met Glu
                        260                 265                 270
        Asp Val Ile Asn Cys Gln His Ser Met Ser Ser Val Leu Gly Trp Phe
                        275                 280                 285
        Ala Asn Pro Ile His Gly Asp Gly Asp Tyr Pro Glu Phe Met Lys Thr
                        290                 295                 300
        Ser Ser Val Ile Pro Glu Phe Ser Glu Ala Glu Lys Glu Val Arg
        305                 310                 315                 320
        Gly Thr Ala Asp Phe Phe Ala Phe Ser Phe Gly Pro Asn Asn Phe Arg
                        325                 330                 335
        Pro Ser Asn Thr Val Val Lys Met Gly Gln Asn Val Ser Leu Asn Leu
                        340                 345                 350
        Arg Gln Val Leu Asn Trp Ile Lys Leu Glu Tyr Asp Asn Pro Arg Ile
                        355                 360                 365
        Leu Ile Ser Glu Asn Gly Trp Phe Thr Asp Ser Tyr Ile Lys Thr Glu
                        370                 375                 380
        Asp Thr Thr Ala Ile Tyr Met Met Lys Asn Phe Leu Asn Gln Val Leu
        385                 390                 395                 400
        Gln Ala Ile Lys Phe Asp Glu Ile Gln Val Phe Gly Tyr Thr Ala Trp
                        405                 410                 415
        Thr Leu Leu Asp Gly Phe Glu Trp Gln Asp Ala Tyr Thr Thr Arg Arg
                        420                 425                 430
        Gly Leu Phe Tyr Val Asp Phe Asn Ser Glu Gln Lys Glu Arg Lys Pro
                        435                 440                 445
        Lys Ser Ser Ala His Tyr Tyr Lys Gln Ile Ile Gln Asp Asn Gly Phe
        450                 455                 460
        Pro Leu Gln Glu Ser Thr Pro Asp Met Lys Gly Gln Phe Pro Cys Asp
        465                 470                 475                 480
        Phe Ser Trp Gly Val Thr Glu Ser Val Leu Lys Pro Glu Phe Thr Val
                        485                 490                 495
        Ser Ser Pro Gln Phe Thr Asp Pro His Leu Tyr Val Trp Asn Val Thr
                        500                 505                 510
        Gly Asn Arg Leu Leu Tyr Arg Val Glu Gly Val Arg Leu Lys Thr Arg
                        515                 520                 525
        Pro Ser Gln Cys Thr Asp Tyr Val Ser Ile Lys Lys Arg Val Glu Met
                        530                 535                 540
        Leu Ala Lys Met Lys Val Thr His Tyr Gln Phe Ala Leu Asp Trp Thr
        545                 550                 555                 560
        Ser Ile Leu Pro Thr Gly Asn Leu Ser Lys Ile Asn Arg Gln Val Leu
                        565                 570                 575
```

```
Arg Tyr Tyr Arg Cys Val Val Ser Glu Gly Leu Lys Leu Gly Ile Ser
            580                 585                 590

Pro Met Val Thr Leu Tyr His Pro Thr His Ser His Leu Gly Leu Pro
        595                 600                 605

Met Pro Leu Leu Ser Ser Gly Gly Trp Leu Asn Thr Asn Thr Ala Lys
610                 615                 620

Ala Phe Gln Asp Tyr Ala Gly Leu Cys Phe Lys Glu Leu Gly Asp Leu
625                 630                 635                 640

Val Lys Leu Trp Ile Thr Ile Asn Glu Pro Asn Arg Leu Ser Asp Met
                645                 650                 655

Tyr Asn Arg Thr Ser Asn Asp Thr Tyr Arg Ala Ala His Asn Leu Met
            660                 665                 670

Ile Ala His Ala Gln Val Trp His Leu Tyr Asp Arg Gln Tyr Arg Pro
        675                 680                 685

Val Gln His Gly Ala Val Ser Leu Ser Leu His Ser Asp Trp Ala Glu
    690                 695                 700

Pro Ala Asn Pro Tyr Val Glu Ser His Trp Lys Ala Ala Glu Arg Phe
705                 710                 715                 720

Leu Gln Phe Glu Ile Ala Trp Phe Ala Asp Pro Leu Phe Lys Thr Gly
                725                 730                 735

Asp Tyr Pro Leu Ala Met Lys Glu Tyr Ile Ala Ser Lys Lys Gln Arg
            740                 745                 750

Gly Leu Ser Ser Val Leu Pro Arg Phe Thr Leu Lys Glu Ser Arg
        755                 760                 765

Leu Val Lys Gly Thr Ile Asp Phe Tyr Ala Leu Asn His Phe Thr Thr
770                 775                 780

Arg Phe Val Ile His Lys Gln Leu Asn Thr Asn Cys Ser Val Ala Asp
785                 790                 795                 800

Arg Asp Val Gln Phe Leu Gln Asp Ile Thr Arg Leu Ser Ser Pro Ser
            805                 810                 815

Arg Leu Ala Val Thr Pro Trp Gly Met Arg Lys Leu Leu Gly Trp Ile
        820                 825                 830

Arg Arg Asn Tyr Arg Asp Met Asp Ile Tyr Val Thr Ala Asn Gly Ile
    835                 840                 845

Asp Asp Leu Ala Leu Glu Asp Asp Gln Ile Arg Lys Tyr Tyr Leu Glu
850                 855                 860

Lys Tyr Val Gln Glu Ala Leu Lys Ala Tyr Leu Ile Asp Lys Val Lys
865                 870                 875                 880

Ile Lys Gly Tyr Tyr Ala Phe Lys Leu Thr Glu Glu Lys Ser Lys Pro
            885                 890                 895

Arg Phe Gly Phe Phe Thr Ser Asp Phe Lys Ala Lys Ser Ser Val Gln
        900                 905                 910

Phe Tyr Ser Lys Leu Ile Ser Ser Gly Phe Ser Ser Glu Asn Arg
    915                 920                 925

Ser Pro Ala Cys Gly Gln Pro Pro Glu Asp Thr Glu Cys Ala Ile Cys
930                 935                 940

Ser Phe Leu Thr
945

<210> SEQ ID NO 257
<211> LENGTH: 949
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 257

```
Asp Tyr Lys Asp Asp Asp Lys Leu Asp Phe Pro Gly Asp Gly Arg
1               5                   10                  15

Ala Val Trp Ser Gln Asn Pro Asn Leu Ser Pro Val Asn Glu Ser Gln
            20                  25                  30

Leu Phe Leu Tyr Asp Thr Phe Pro Lys Asn Phe Phe Trp Gly Val Gly
            35                  40                  45

Thr Gly Ala Phe Gln Val Glu Gly Ser Trp Lys Lys Asp Gly Lys Gly
50                  55                  60

Leu Ser Val Trp Asp His Phe Ile Ala Thr His Leu Asn Val Ser Ser
65                  70                  75                  80

Arg Asp Gly Ser Ser Asp Ser Tyr Ile Phe Leu Glu Lys Asp Leu Ser
                85                  90                  95

Ala Leu Asp Phe Leu Gly Val Ser Phe Tyr Gln Phe Ser Ile Ser Trp
            100                 105                 110

Pro Arg Leu Phe Pro Asp Gly Thr Val Ala Val Ala Asn Ala Lys Gly
        115                 120                 125

Leu Gln Tyr Tyr Asn Arg Leu Leu Asp Ser Leu Leu Leu Arg Asn Ile
    130                 135                 140

Glu Pro Val Val Thr Leu Tyr His Trp Asp Leu Pro Trp Ala Leu Gln
145                 150                 155                 160

Glu Lys Tyr Gly Gly Trp Lys Asn Glu Thr Leu Ile Asp Leu Phe Asn
                165                 170                 175

Asp Tyr Ala Thr Tyr Cys Phe Gln Thr Phe Gly Asp Arg Val Lys Tyr
            180                 185                 190

Trp Ile Thr Ile His Asn Pro Tyr Leu Val Ala Trp His Gly Tyr Gly
        195                 200                 205

Thr Gly Leu His Ala Pro Gly Glu Lys Gly Asn Val Ala Ala Val Tyr
    210                 215                 220

Thr Val Gly His Asn Leu Leu Lys Ala His Ser Lys Val Trp His Asn
225                 230                 235                 240

Tyr Asn Arg Asn Phe Arg Pro His Gln Lys Gly Trp Leu Ser Ile Thr
                245                 250                 255

Leu Gly Ser His Trp Ile Glu Pro Asn Arg Ala Glu Ser Ile Val Asp
            260                 265                 270

Ile Leu Lys Cys Gln Gln Ser Met Val Ser Val Leu Gly Trp Phe Ala
        275                 280                 285

Asn Pro Ile His Gly Asp Gly Asp Tyr Pro Glu Val Met Thr Lys Lys
    290                 295                 300

Leu Leu Ser Val Leu Pro Ala Phe Ser Glu Ala Glu Lys Asn Glu Val
305                 310                 315                 320

Arg Gly Thr Ala Asp Phe Phe Ala Phe Ser Phe Gly Pro Asn Asn Phe
                325                 330                 335

Lys Pro Leu Asn Thr Met Ala Lys Met Gly Gln Asn Val Ser Leu Asn
            340                 345                 350

Leu Arg Gln Val Leu Asn Trp Ile Lys Leu Glu Tyr Gly Asn Pro Arg
        355                 360                 365

Ile Leu Ile Ala Glu Asn Gly Trp Phe Thr Asp Ser Tyr Val Gln Thr
    370                 375                 380

Glu Asp Thr Thr Ala Ile Tyr Met Met Lys Asn Phe Leu Asn Gln Val
385                 390                 395                 400
```

-continued

```
Leu Gln Ala Ile Arg Leu Asp Gly Val Arg Val Phe Gly Tyr Thr Ala
            405                 410                 415

Trp Ser Leu Leu Asp Gly Phe Glu Trp Gln Asp Ala Tyr Asn Thr Arg
            420                 425                 430

Arg Gly Leu Phe Tyr Val Asp Phe Asn Ser Glu Gln Arg Glu Arg Arg
            435                 440                 445

Pro Lys Ser Ser Ala His Tyr Tyr Lys Gln Val Ile Gly Glu Asn Gly
            450                 455                 460

Phe Thr Leu Arg Glu Ala Thr Pro Asp Leu Gln Gly Gln Phe Pro Cys
465                 470                 475                 480

Asp Phe Ser Trp Gly Val Thr Glu Ser Val Leu Lys Pro Glu Ser Val
            485                 490                 495

Ala Ser Ser Pro Gln Phe Ser Asp Pro His Leu Tyr Val Trp Asn Ala
            500                 505                 510

Thr Gly Asn Arg Met Leu His Arg Val Glu Gly Val Arg Leu Lys Thr
            515                 520                 525

Arg Pro Ala Gln Cys Thr Asp Phe Ile Thr Ile Lys Lys Gln Leu Glu
            530                 535                 540

Met Leu Ala Arg Met Lys Val Thr His Phe Arg Phe Ala Leu Asp Trp
545                 550                 555                 560

Ala Ser Val Leu Pro Thr Gly Asn Leu Ser Glu Val Asn Arg Gln Ala
            565                 570                 575

Leu Arg Tyr Tyr Arg Cys Val Val Thr Glu Gly Leu Lys Leu Asn Ile
            580                 585                 590

Ser Pro Met Val Thr Leu Tyr Tyr Pro Thr His Ala His Leu Gly Leu
            595                 600                 605

Pro Ala Pro Leu Leu His Ser Gly Gly Trp Leu Asp Pro Ser Thr Ala
            610                 615                 620

Lys Ala Phe Arg Asp Tyr Ala Gly Leu Cys Phe Arg Glu Leu Gly Asp
625                 630                 635                 640

Leu Val Lys Leu Trp Ile Thr Ile Asn Glu Pro Asn Arg Leu Ser Asp
            645                 650                 655

Val Tyr Asn Arg Thr Ser Asn Asp Thr Tyr Gln Ala Ala His Asn Leu
            660                 665                 670

Leu Ile Ala His Ala Ile Val Trp His Leu Tyr Asp Arg Gln Tyr Arg
            675                 680                 685

Pro Ser Gln Arg Gly Ala Leu Ser Leu Ser Leu His Ser Asp Trp Ala
            690                 695                 700

Glu Pro Ala Asn Pro Tyr Val Ala Ser His Trp Gln Ala Ala Glu Arg
705                 710                 715                 720

Phe Leu Gln Phe Glu Ile Ala Trp Phe Ala Glu Pro Leu Phe Lys Thr
            725                 730                 735

Gly Asp Tyr Pro Val Ala Met Arg Glu Tyr Ile Ala Ser Lys Thr Arg
            740                 745                 750

Arg Gly Leu Ser Ser Ser Val Leu Pro Arg Phe Ser Asp Ala Glu Arg
            755                 760                 765

Arg Leu Val Lys Gly Ala Ala Asp Phe Tyr Ala Leu Asn His Phe Thr
            770                 775                 780

Thr Arg Phe Val Met His Glu Gln Gln Asn Gly Ser Arg Tyr Asp Ser
785                 790                 795                 800

Asp Arg Asp Val Gln Phe Leu Gln Asp Ile Thr Arg Leu Ala Ser Pro
            805                 810                 815
```

```
Ser Arg Leu Ala Val Met Pro Trp Gly Glu Gly Lys Leu Leu Arg Trp
                820                 825                 830

Met Arg Asn Asn Tyr Gly Asp Leu Asp Val Tyr Ile Thr Ala Asn Gly
            835                 840                 845

Ile Asp Asp Gln Ala Leu Gln Asn Asp Gln Leu Arg Gln Tyr Tyr Leu
        850                 855                 860

Glu Lys Tyr Val Gln Glu Ala Leu Lys Ala Tyr Leu Ile Asp Lys Ile
865                 870                 875                 880

Lys Ile Lys Gly Tyr Tyr Ala Phe Lys Leu Thr Glu Glu Lys Ser Lys
                885                 890                 895

Pro Arg Phe Gly Phe Phe Thr Ser Asp Phe Lys Ala Lys Ser Ser Ile
            900                 905                 910

Gln Phe Tyr Asn Lys Leu Ile Thr Ser Asn Gly Phe Pro Ser Glu Asn
        915                 920                 925

Gly Gly Pro Arg Cys Asn Gln Thr Gln Gly Asn Pro Glu Cys Thr Val
        930                 935                 940

Cys Leu Leu Leu Leu
945

<210> SEQ ID NO 258
<211> LENGTH: 950
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Asp Tyr Lys Asp Asp Asp Lys Leu Glu Phe Ser Gly Asp Gly Arg
1               5                   10                  15

Ala Val Trp Ser Lys Asn Pro Asn Phe Thr Pro Val Asn Glu Ser Gln
            20                  25                  30

Leu Phe Leu Tyr Asp Thr Phe Pro Lys Asn Phe Phe Trp Gly Val Gly
        35                  40                  45

Thr Gly Ala Leu Gln Val Glu Gly Ser Trp Lys Lys Asp Gly Lys Gly
    50                  55                  60

Pro Ser Ile Trp Asp His Phe Val His Thr His Leu Lys Asn Val Ser
65                  70                  75                  80

Ser Thr Asn Gly Ser Ser Asp Ser Tyr Ile Phe Leu Glu Lys Asp Leu
                85                  90                  95

Ser Ala Leu Asp Phe Ile Gly Val Ser Phe Tyr Gln Phe Ser Ile Ser
            100                 105                 110

Trp Pro Arg Leu Phe Pro Asp Gly Ile Val Thr Val Ala Asn Ala Lys
        115                 120                 125

Gly Leu Gln Tyr Tyr Asn Thr Leu Leu Asp Ser Leu Val Leu Arg Asn
    130                 135                 140

Ile Glu Pro Ile Val Thr Leu Tyr His Trp Asp Leu Pro Leu Ala Leu
145                 150                 155                 160

Gln Glu Lys Tyr Gly Gly Trp Lys Asn Asp Thr Ile Ile Asp Ile Phe
                165                 170                 175

Asn Asp Tyr Ala Thr Tyr Cys Phe Gln Thr Phe Gly Asp Arg Val Lys
            180                 185                 190

Tyr Trp Ile Thr Ile His Asn Pro Tyr Leu Val Ala Trp His Gly Tyr
        195                 200                 205

Gly Thr Gly Met His Ala Pro Gly Glu Lys Gly Asn Leu Ala Ala Val
    210                 215                 220
```

```
Tyr Thr Val Gly His Asn Leu Ile Lys Ala His Ser Lys Val Trp His
225                 230                 235                 240

Asn Tyr Asn Thr His Phe Arg Pro His Gln Lys Gly Trp Leu Ser Ile
            245                 250                 255

Thr Leu Gly Ser His Trp Ile Glu Pro Asn Arg Ser Glu Asn Thr Met
        260                 265                 270

Asp Ile Leu Lys Cys Gln Gln Ser Met Val Ser Val Leu Gly Trp Phe
    275                 280                 285

Ala Ser Pro Ile His Gly Asp Gly Asp Tyr Pro Glu Gly Met Lys Lys
290                 295                 300

Lys Leu Leu Ser Ile Leu Pro Leu Phe Ser Glu Ala Lys Asn Glu
305                 310                 315                 320

Val Arg Gly Thr Ala Asp Phe Phe Ala Phe Ser Phe Gly Pro Asn Asn
                325                 330                 335

Phe Lys Pro Leu Asn Thr Met Ala Lys Met Gly Gln Asn Val Ser Leu
            340                 345                 350

Asn Leu Arg Glu Ala Leu Asn Trp Ile Lys Leu Glu Tyr Asn Asn Pro
        355                 360                 365

Arg Ile Leu Ile Ala Glu Asn Gly Trp Phe Thr Asp Ser His Val Lys
    370                 375                 380

Thr Glu Asp Thr Thr Ala Ile Tyr Met Met Lys Asn Phe Leu Ser Gln
385                 390                 395                 400

Val Leu Gln Ala Ile Arg Leu Asp Glu Ile Arg Val Phe Gly Tyr Thr
                405                 410                 415

Ala Trp Ser Leu Leu Asp Gly Phe Glu Trp Gln Asp Ala Tyr Thr Ile
            420                 425                 430

Arg Arg Gly Leu Phe Tyr Val Asp Phe Asn Ser Lys Gln Lys Glu Arg
        435                 440                 445

Lys Pro Lys Ser Ser Ala His Tyr Tyr Lys Gln Ile Ile Arg Glu Asn
    450                 455                 460

Gly Phe Ser Leu Lys Glu Ala Thr Pro Asp Val Gln Gly Gln Phe Pro
465                 470                 475                 480

Cys Asp Phe Ser Trp Gly Val Thr Glu Ser Val Leu Lys Pro Glu Ser
                485                 490                 495

Val Ala Ser Ser Pro Gln Phe Ser Asp Pro Tyr Leu Tyr Val Trp Asn
            500                 505                 510

Ala Thr Gly Asn Arg Leu Leu His Arg Val Glu Gly Val Arg Leu Lys
        515                 520                 525

Thr Arg Pro Ala Gln Cys Thr Asp Phe Val Asn Ile Lys Lys Gln Leu
    530                 535                 540

Glu Met Leu Ala Arg Met Lys Val Thr His Tyr Arg Phe Ala Leu Asp
545                 550                 555                 560

Trp Ala Ser Val Leu Pro Thr Gly Asn Leu Ser Ala Val Asn Arg Gln
                565                 570                 575

Ala Leu Arg Tyr Tyr Arg Cys Val Val Ser Glu Gly Leu Lys Leu Gly
            580                 585                 590

Ile Ser Ala Met Val Thr Leu Tyr Tyr Pro Thr His Ala His Leu Gly
        595                 600                 605

Leu Pro Glu Pro Leu Leu His Ala Gly Gly Trp Leu Asn Pro Ser Thr
    610                 615                 620

Val Glu Ala Phe Gln Ala Tyr Ala Gly Leu Cys Phe Gln Glu Leu Gly
625                 630                 635                 640
```

```
Asp Leu Val Lys Leu Trp Ile Thr Ile Asn Glu Pro Asn Arg Leu Ser
            645                 650                 655

Asp Ile Tyr Asn Arg Ser Gly Asn Asp Thr Tyr Gly Ala Ala His Asn
        660                 665                 670

Leu Leu Val Ala His Ala Leu Ala Trp Arg Leu Tyr Asp Arg Gln Phe
        675                 680                 685

Arg Pro Ser Gln Arg Gly Ala Val Ser Leu Ser Leu His Ala Asp Trp
690                 695                 700

Ala Glu Pro Ala Asn Pro Tyr Ala Asp Ser His Trp Arg Ala Ala Glu
705                 710                 715                 720

Arg Phe Leu Gln Phe Glu Ile Ala Trp Phe Ala Glu Pro Leu Phe Lys
                725                 730                 735

Thr Gly Asp Tyr Pro Ala Ala Met Arg Glu Tyr Ile Ala Ser Lys His
            740                 745                 750

Arg Arg Gly Leu Ser Ser Ser Ala Leu Pro Arg Leu Thr Glu Ala Glu
        755                 760                 765

Arg Arg Leu Leu Lys Gly Thr Val Asp Phe Cys Ala Leu Asn His Phe
770                 775                 780

Thr Thr Arg Phe Val Met His Glu Gln Leu Ala Gly Ser Arg Tyr Asp
785                 790                 795                 800

Ser Asp Arg Asp Ile Gln Phe Leu Gln Asp Ile Thr Arg Leu Ser Ser
                805                 810                 815

Pro Thr Arg Leu Ala Val Ile Pro Trp Gly Val Arg Lys Leu Leu Arg
            820                 825                 830

Trp Val Arg Arg Asn Tyr Gly Asp Met Asp Ile Tyr Ile Thr Ala Ser
        835                 840                 845

Gly Ile Asp Asp Gln Ala Leu Glu Asp Asp Arg Leu Arg Lys Tyr Tyr
850                 855                 860

Leu Glu Lys Tyr Leu Gln Glu Val Leu Lys Ala Tyr Leu Ile Asp Lys
865                 870                 875                 880

Val Arg Ile Lys Gly Tyr Tyr Ala Phe Lys Leu Ala Glu Glu Lys Ser
                885                 890                 895

Lys Pro Arg Phe Gly Phe Phe Thr Ser Asp Phe Lys Ala Lys Ser Ser
            900                 905                 910

Ile Gln Phe Tyr Asn Lys Met Ile Ser Ser Ser Gly Phe Pro Ser Glu
        915                 920                 925

Asn Ser Ser Arg Cys Ser Gln Thr Gln Lys Asn Thr Glu Cys Thr
930                 935                 940

Val Cys Leu Phe Leu Ala
945                 950

<210> SEQ ID NO 259
<211> LENGTH: 950
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Tyr Lys Asp Asp Asp Lys Leu Glu Phe Ser Gly Asp Gly Arg
1               5                   10                  15

Ala Val Trp Ser Lys Asn Pro Asn Phe Thr Pro Val Asn Glu Ser Gln
            20                  25                  30

Leu Phe Leu Tyr Asp Thr Phe Pro Lys Asn Phe Phe Trp Gly Val Gly
        35                  40                  45
```

-continued

```
Thr Gly Ala Leu Gln Val Glu Gly Ser Trp Lys Lys Asp Gly Lys Gly
 50                  55                  60
Pro Ser Ile Trp Asp His Phe Val His Thr His Leu Lys Asn Val Ser
 65                  70                  75                  80
Ser Thr Asn Gly Ser Ser Asp Ser Tyr Ile Phe Leu Glu Lys Asp Leu
                 85                  90                  95
Ser Ala Leu Asp Phe Ile Gly Val Ser Phe Tyr Gln Phe Ser Ile Ser
            100                 105                 110
Trp Pro Arg Leu Phe Pro Asp Gly Ile Val Thr Val Ala Asn Ala Lys
        115                 120                 125
Gly Leu Gln Tyr Tyr Asn Ala Leu Leu Asp Ser Leu Val Leu Arg Asn
130                 135                 140
Ile Glu Pro Ile Val Thr Leu Tyr His Trp Asp Leu Pro Leu Ala Leu
145                 150                 155                 160
Gln Glu Lys Tyr Gly Gly Trp Lys Asn Asp Thr Ile Ile Asp Ile Phe
                165                 170                 175
Asn Asp Tyr Ala Thr Tyr Cys Phe Gln Thr Phe Gly Asp Arg Val Lys
            180                 185                 190
Tyr Trp Ile Thr Ile His Asn Pro Tyr Leu Val Ala Trp His Gly Tyr
        195                 200                 205
Gly Thr Gly Met His Ala Pro Gly Glu Lys Gly Asn Leu Ala Ala Val
210                 215                 220
Tyr Thr Val Gly His Asn Leu Ile Lys Ala His Ser Lys Val Trp His
225                 230                 235                 240
Asn Tyr Asn Thr His Phe Arg Pro His Gln Lys Gly Trp Leu Ser Ile
                245                 250                 255
Thr Leu Gly Ser His Trp Ile Glu Pro Asn Arg Ser Glu Asn Thr Met
            260                 265                 270
Asp Ile Leu Lys Cys Gln Gln Ser Met Val Ser Val Leu Gly Trp Phe
        275                 280                 285
Ala Asn Pro Ile His Gly Asp Gly Asp Tyr Pro Glu Gly Met Lys Lys
290                 295                 300
Lys Leu Leu Ser Ile Leu Pro Leu Phe Ser Glu Ala Glu Lys Asn Glu
305                 310                 315                 320
Val Arg Gly Thr Ala Asp Phe Phe Ala Phe Ser Phe Gly Pro Asn Asn
                325                 330                 335
Phe Lys Pro Leu Asn Thr Met Ala Lys Met Gly Gln Asn Val Ser Leu
            340                 345                 350
Asn Leu Arg Glu Ala Leu Asn Trp Ile Lys Leu Glu Tyr Asn Asn Pro
        355                 360                 365
Gln Ile Leu Ile Ala Glu Asn Gly Trp Phe Thr Asp Ser His Val Lys
370                 375                 380
Thr Glu Asp Thr Thr Ala Ile Tyr Met Met Lys Asn Phe Leu Ser Gln
385                 390                 395                 400
Val Leu Gln Ala Ile Arg Leu Asp Glu Ile Arg Val Phe Gly Tyr Thr
                405                 410                 415
Ala Trp Ser Leu Leu Asp Gly Phe Glu Trp Gln Asp Ala Tyr Thr Ile
            420                 425                 430
Arg Arg Gly Leu Phe Tyr Val Asp Phe Asn Ser Lys Gln Lys Glu Arg
        435                 440                 445
Lys Pro Lys Ser Ser Ala His Tyr Tyr Lys Gln Ile Ile Arg Glu Asn
450                 455                 460
```

```
Gly Phe Ser Leu Lys Glu Ala Thr Pro Asp Val Gln Gly Gln Phe Pro
465                 470                 475                 480

Cys Asp Phe Ser Trp Gly Val Thr Glu Ser Val Leu Lys Pro Glu Ser
            485                 490                 495

Val Ala Ser Ser Pro Gln Phe Ser Asp Pro Tyr Leu Tyr Val Trp Asn
        500                 505                 510

Ala Thr Gly Asn Arg Leu Leu His Arg Val Glu Gly Val Arg Leu Lys
    515                 520                 525

Thr Arg Pro Ala Gln Cys Thr Asp Phe Val Asn Ile Lys Lys Gln Leu
530                 535                 540

Glu Met Leu Ala Arg Met Lys Val Thr His Tyr Arg Phe Ala Leu Asp
545                 550                 555                 560

Trp Ala Ser Val Leu Pro Thr Gly Asn Leu Ser Ala Val Asn Arg Gln
            565                 570                 575

Ala Leu Arg Tyr Tyr Arg Cys Val Val Ser Glu Gly Leu Lys Leu Gly
        580                 585                 590

Ile Ser Ala Met Val Thr Leu Tyr Tyr Pro Thr His Ala His Leu Gly
    595                 600                 605

Leu Pro Glu Pro Leu Leu His Ala Gly Gly Trp Leu Asn Pro Ser Thr
610                 615                 620

Val Glu Ala Phe Gln Ala Tyr Ala Gly Leu Cys Phe Gln Glu Leu Gly
625                 630                 635                 640

Asp Leu Val Lys Leu Trp Ile Thr Ile Asn Glu Pro Asn Arg Leu Ser
            645                 650                 655

Asp Ile Tyr Asn Arg Ser Gly Asn Asp Thr Tyr Gly Ala Ala His Asn
        660                 665                 670

Leu Leu Val Ala His Ala Leu Ala Trp Arg Leu Tyr Asp Arg Gln Phe
    675                 680                 685

Arg Pro Ser Gln Arg Gly Ala Val Ser Leu Ser Leu His Ala Asp Trp
690                 695                 700

Ala Glu Pro Ala Asn Pro Tyr Ala Asp Ser His Trp Arg Ala Ala Glu
705                 710                 715                 720

Arg Phe Leu Gln Phe Glu Ile Ala Trp Phe Ala Glu Pro Leu Phe Lys
            725                 730                 735

Thr Gly Asp Tyr Pro Ala Ala Met Arg Glu Tyr Ile Ala Ser Lys His
        740                 745                 750

Arg Arg Gly Leu Ser Ser Ser Ala Leu Pro Arg Leu Thr Glu Ala Glu
    755                 760                 765

Arg Arg Leu Leu Lys Gly Thr Val Asp Phe Cys Ala Leu Asn His Phe
770                 775                 780

Thr Thr Arg Phe Val Met His Glu Gln Leu Ala Gly Ser Arg Tyr Asp
785                 790                 795                 800

Ser Asp Arg Asp Ile Gln Phe Leu Gln Asp Ile Thr Arg Leu Ser Ser
            805                 810                 815

Pro Thr Arg Leu Ala Val Ile Pro Trp Gly Val Arg Lys Leu Leu Arg
        820                 825                 830

Trp Val Arg Arg Asn Tyr Gly Asp Met Asp Ile Tyr Ile Thr Ala Ser
    835                 840                 845

Gly Ile Asp Asp Gln Ala Leu Glu Asp Asp Arg Leu Arg Lys Tyr Tyr
850                 855                 860

Leu Glu Lys Tyr Leu Gln Glu Val Leu Lys Ala Tyr Leu Ile Asp Lys
865                 870                 875                 880

Val Arg Ile Lys Gly Tyr Tyr Ala Phe Lys Leu Ala Glu Glu Lys Ser
```

885                 890                 895
Lys Pro Arg Phe Gly Phe Phe Thr Ser Asp Phe Lys Ala Lys Ser Ser
            900                 905                 910

Ile Gln Phe Tyr Asn Lys Met Ile Ser Ser Ser Gly Phe Pro Ser Glu
            915                 920                 925

Asn Ser Ser Ser Arg Cys Ser Gln Thr Gln Lys Asn Thr Glu Cys Thr
        930                 935                 940

Val Cys Leu Phe Leu Val
945                 950

<210> SEQ ID NO 260
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

-continued

```
Phe Val Leu Gly Trp Phe Ala Lys Pro Val Phe Ile Asp Gly Asp Tyr
290                 295                 300
Pro Glu Ser Met Lys Asn Asn Leu Ser Ser Ile Leu Pro Asp Phe Thr
305                 310                 315                 320
Glu Ser Glu Lys Lys Phe Ile Lys Gly Thr Ala Asp Phe Phe Ala Leu
                325                 330                 335
Cys Phe Gly Pro Thr Leu Ser Phe Gln Leu Leu Asp Pro His Met Lys
                340                 345                 350
Phe Arg Gln Leu Glu Ser Pro Asn Leu Arg Gln Leu Leu Ser Trp Ile
                355                 360                 365
Asp Leu Glu Phe Asn His Pro Gln Ile Phe Ile Val Glu Asn Gly Trp
370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                405                 410                 415
Val Asp Val Ile Gly Tyr Thr Ala Trp Ser Leu Met Asp Gly Phe Glu
                420                 425                 430
Trp His Arg Gly Tyr Ser Ile Arg Arg Gly Leu Phe Tyr Val Asp Phe
                435                 440                 445
Leu Ser Gln Asp Lys Met Leu Leu Pro Lys Ser Ser Ala Leu Phe Tyr
450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                485                 490                 495
Asn Tyr Ile Gln Val Asp Thr Thr Leu Ser Gln Phe Thr Asp Leu Asn
                500                 505                 510
Val Tyr Leu Trp Asp Val His Ser Lys Arg Leu Ile Lys Val Asp
                515                 520                 525
Gly Val Val Thr Lys Lys Arg Lys Ser Tyr Cys Val Asp Phe Ala Ala
                530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
                565                 570                 575
Gln Val Asn His Thr Ile Leu Gln Tyr Tyr Arg Cys Met Ala Ser Glu
                580                 585                 590
Leu Val Arg Val Asn Ile Thr Pro Val Val Ala Leu Trp Gln Pro Met
                595                 600                 605
Ala Pro Asn Gln Gly Leu Pro Arg Leu Leu Ala Arg Gln Gly Ala Trp
610                 615                 620
Glu Asn Pro Tyr Thr Ala Leu Ala Phe Ala Glu Tyr Ala Arg Leu Cys
625                 630                 635                 640
Phe Gln Glu Leu Gly His His Val Lys Leu Trp Ile Thr Met Asn Glu
                645                 650                 655
Pro Tyr Thr Arg Asn Met Thr Tyr Ser Ala Gly His Asn Leu Leu Lys
                660                 665                 670
Ala His Ala Leu Ala Trp His Val Tyr Asn Glu Lys Phe Arg His Ala
                675                 680                 685
Gln Asn Gly Lys Ile Ser Ile Ala Leu Gln Ala Asp Trp Ile Glu Pro
690                 695                 700
Ala Cys Pro Phe Ser Gln Lys Asp Lys Glu Val Ala Glu Arg Val Leu
```

```
                705                 710                 715                 720
Glu Phe Asp Ile Gly Trp Leu Ala Glu Pro Ile Phe Gly Ser Gly Asp
                    725                 730                 735
Tyr Pro Trp Val Met Arg Asp Trp Leu Asn Gln Arg Asn Asn Phe Leu
                    740                 745                 750
Leu Pro Tyr Phe Thr Glu Asp Lys Lys Leu Ile Gln Gly Thr Phe
                    755                 760                 765
Asp Phe Leu Ala Leu Ser His Tyr Thr Thr Ile Leu Val Asp Ser Glu
                770                 775                 780
Lys Glu Asp Pro Ile Lys Tyr Asn Asp Tyr Leu Glu Val Gln Glu Met
785                 790                 795                 800
Thr Asp Ile Thr Trp Leu Asn Ser Pro Ser Gln Val Ala Val Val Pro
                    805                 810                 815
Trp Gly Leu Arg Lys Val Leu Asn Trp Leu Lys Phe Lys Tyr Gly Asp
                820                 825                 830
Leu Pro Met Tyr Ile Ile Ser Asn Gly Ile Asp Asp Gly Leu His Ala
                835                 840                 845
Glu Asp Asp Gln Leu Arg Val Tyr Tyr Met Gln Asn Tyr Ile Asn Glu
850                 855                 860
Ala Leu Lys Ala His Ile Leu Asp Gly Ile Asn Leu Cys Gly Tyr Phe
865                 870                 875                 880
Ala Tyr Ser Phe Asn Asp Arg Thr Ala Pro Arg Phe Gly Leu Tyr Arg
                    885                 890                 895
Tyr Ala Ala Asp Gln Phe Glu Pro Lys Ala Ser Met Lys His Tyr Arg
                900                 905                 910
Lys Ile Ile Asp Ser Asn Gly Phe Pro Gly Pro Glu Thr Leu Glu Arg
                915                 920                 925
Phe Cys Pro Glu Glu Phe Thr Val Cys Thr Glu Cys Ser Phe His
                930                 935                 940
Thr Arg Lys Ser Leu Leu Ala Phe Ile Ala Phe Leu Phe Phe Ala Ser
945                 950                 955                 960
Ile Ile Ser Leu Ser Leu Ile Phe Tyr Tyr Ser Lys Lys Gly Arg Arg
                965                 970                 975
Ser Tyr Lys Leu Glu Asp Tyr Lys Asp Asp Asp Lys
                980                 985

<210> SEQ ID NO 261
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ser Thr Tyr Ile Ser
1               5

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Glu Ile Asp Pro Tyr Asp Gly Ala Thr Asp Tyr Ala Asp Ser Val Lys
```

1               5                   10                  15

Gly

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Glu His Phe Asp Ala Trp Val His Tyr Tyr Val Met Asp Tyr
1               5                   10

<210> SEQ ID NO 264
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Phe Pro Cys Asp Phe Ser Trp Gly Val Thr Glu Ser Val Leu Lys Pro
1               5                   10                  15

Glu Ser Val Ala Ser Ser Pro Gln Phe Ser Asp Pro His Leu Tyr Val
            20                  25                  30

Trp Asn Ala Thr Gly Asn Arg Leu Leu His Arg Val Glu Gly Val Arg
        35                  40                  45

Leu Lys Thr Arg Pro Ala Gln Cys Thr Asp Phe Val Asn Ile Lys Lys
    50                  55                  60

Gln Leu Glu Met Leu Ala Arg Met Lys Val Thr His Tyr Arg Phe Ala
65                  70                  75                  80

Leu Asp Trp Ala Ser Val Leu Pro Thr Gly Asn Leu Ser Ala Val Asn
                85                  90                  95

Arg Gln Ala Leu Arg Tyr Tyr Arg Cys Val Val Ser Glu Gly Leu Lys
            100                 105                 110

Leu Gly Ile Ser Ala Met Val Thr Leu Tyr Tyr Pro Thr His Ala His
        115                 120                 125

Leu Gly Leu Pro Glu Pro Leu Leu His Ala Asp Gly Trp Leu Asn Pro
    130                 135                 140

Ser Thr Ala Glu Ala Phe Gln Ala Tyr Ala Gly Leu Cys Phe Gln Glu
145                 150                 155                 160

Leu Gly Asp Leu Val Lys Leu Trp Ile Thr Ile Asn Glu Pro Asn Arg
                165                 170                 175

Leu Ser Asp Ile Tyr Asn Arg Ser Gly Asn Asp Thr Tyr Gly Ala Ala
            180                 185                 190

His Asn Leu Leu Val Ala His Ala Leu Ala Trp Arg Leu Tyr Asp Arg
        195                 200                 205

Gln Phe Arg Pro Ser Gln Arg Gly Ala Val Ser Leu Ser Leu His Ala
    210                 215                 220

Asp Trp Ala Glu Pro Ala Asn Pro Tyr Ala Asp Ser His Trp Arg Ala
225                 230                 235                 240

Ala Glu Arg Phe Leu Gln Phe Glu Ile Ala Trp Phe Ala Glu Pro Leu
                245                 250                 255

Phe Lys Thr Gly Asp Tyr Pro Ala Ala Met Arg Glu Tyr Ile Ala Ser
            260                 265                 270

Lys His Arg Arg Gly Leu Ser Ser Ser Ala Leu Pro Arg Leu Thr Glu
            275                 280                 285

Ala Glu Arg Arg Leu Leu Lys Gly Thr Val Asp Phe Cys Ala Leu Asn
        290                 295                 300

His Phe Thr Thr Arg Phe Val Met His Glu Gln Leu Ala Gly Ser Arg
305                 310                 315                 320

Tyr Asp Ser Asp Arg Asp Ile Gln Phe Leu Gln Asp Ile Thr Arg Leu
                325                 330                 335

Ser Ser Pro Thr Arg Leu Ala Val Ile Pro Trp Gly Val Arg Lys Leu
            340                 345                 350

Leu Arg Trp Val Arg Arg Asn Tyr Gly Asp Met Asp Ile Tyr Ile Thr
        355                 360                 365

Ala Ser Gly Ile Asp Asp Gln Ala Leu Glu Asp Asp Arg Leu Arg Lys
    370                 375                 380

Tyr Tyr Leu Gly Lys Tyr Leu Gln Glu Val Leu Lys Ala Tyr Leu Ile
385                 390                 395                 400

Asp Lys Val Arg Ile Lys Gly Tyr Tyr Ala Phe Lys Leu Ala Glu Glu
                405                 410                 415

Lys Ser Lys Pro Arg Phe Gly Phe Phe Thr Ser Asp Phe Lys Ala Lys
            420                 425                 430

Ser Ser Ile Gln Phe Tyr Asn Lys Val Ile Ser Ser Arg Gly Phe Pro
        435                 440                 445

Phe Glu Asn Ser Ser Ser Arg
    450                 455

<210> SEQ ID NO 265
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gttaccggct tctccggaga cgggaaagca atatgg                                    36

<210> SEQ ID NO 266
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly
    50

<210> SEQ ID NO 267
<211> LENGTH: 938
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 267

```
Phe Ser Gly Asp Gly Lys Ala Ile Trp Asp Lys Lys Gln Tyr Val Ser
1               5                   10                  15

Pro Val Asn Pro Ser Gln Leu Phe Leu Tyr Asp Thr Phe Pro Lys Asn
            20                  25                  30

Phe Ser Trp Gly Val Gly Thr Gly Ala Phe Gln Val Glu Gly Ser Trp
        35                  40                  45

Lys Thr Asp Gly Arg Gly Pro Ser Ile Trp Asp Arg Tyr Val Tyr Ser
    50                  55                  60

His Leu Arg Gly Val Asn Gly Thr Asp Arg Ser Thr Asp Ser Tyr Ile
65                  70                  75                  80

Phe Leu Glu Lys Asp Leu Leu Ala Leu Asp Phe Leu Gly Val Ser Phe
                85                  90                  95

Tyr Gln Phe Ser Ile Ser Trp Pro Arg Leu Phe Pro Asn Gly Thr Val
            100                 105                 110

Ala Ala Val Asn Ala Gln Gly Leu Arg Tyr Tyr Arg Ala Leu Leu Asp
        115                 120                 125

Ser Leu Val Leu Arg Asn Ile Glu Pro Ile Val Thr Leu Tyr His Trp
    130                 135                 140

Asp Leu Pro Leu Thr Leu Gln Glu Glu Tyr Gly Gly Trp Lys Asn Ala
145                 150                 155                 160

Thr Met Ile Asp Leu Phe Asn Asp Tyr Ala Thr Tyr Cys Phe Gln Thr
                165                 170                 175

Phe Gly Asp Arg Val Lys Tyr Trp Ile Thr Ile His Asn Pro Tyr Leu
            180                 185                 190

Val Ala Trp His Gly Phe Gly Thr Gly Met His Ala Pro Gly Glu Lys
        195                 200                 205

Gly Asn Leu Thr Ala Val Tyr Thr Val Gly His Asn Leu Ile Lys Ala
    210                 215                 220

His Ser Lys Val Trp His Asn Tyr Asp Lys Asn Phe Arg Pro His Gln
225                 230                 235                 240

Lys Gly Trp Leu Ser Ile Thr Leu Gly Ser His Trp Ile Glu Pro Asn
                245                 250                 255

Arg Thr Asp Asn Met Glu Asp Val Ile Asn Cys Gln His Ser Met Ser
            260                 265                 270

Ser Val Leu Gly Trp Phe Ala Asn Pro Ile His Gly Asp Gly Asp Tyr
        275                 280                 285

Pro Glu Phe Met Lys Thr Gly Ala Met Ile Pro Glu Phe Ser Glu Ala
    290                 295                 300

Glu Lys Glu Glu Val Arg Gly Thr Ala Asp Phe Phe Ala Phe Ser Phe
305                 310                 315                 320

Gly Pro Asn Asn Phe Arg Pro Ser Asn Thr Val Val Lys Met Gly Gln
                325                 330                 335

Asn Val Ser Leu Asn Leu Arg Gln Val Leu Asn Trp Ile Lys Leu Glu
            340                 345                 350

Tyr Asp Asp Pro Gln Ile Leu Ile Ser Glu Asn Gly Trp Phe Thr Asp
        355                 360                 365

Ser Tyr Ile Lys Thr Glu Asp Thr Thr Ala Ile Tyr Met Met Lys Asn
    370                 375                 380

Phe Leu Asn Gln Val Leu Gln Ala Ile Lys Phe Asp Glu Ile Arg Val
385                 390                 395                 400
```

-continued

```
Phe Gly Tyr Thr Ala Trp Thr Leu Leu Asp Gly Phe Glu Trp Gln Asp
            405                 410                 415
Ala Tyr Thr Thr Arg Arg Gly Leu Phe Tyr Val Asp Phe Asn Ser Glu
            420                 425                 430
Gln Lys Glu Arg Lys Pro Lys Ser Ser Ala His Tyr Tyr Lys Gln Ile
            435                 440                 445
Ile Gln Asp Asn Gly Phe Pro Leu Lys Glu Ser Thr Pro Asp Met Lys
        450                 455                 460
Gly Arg Phe Pro Cys Asp Phe Ser Trp Gly Val Thr Glu Ser Val Leu
465                 470                 475                 480
Lys Pro Glu Phe Thr Val Ser Ser Pro Gln Phe Thr Pro His Leu
                485                 490                 495
Tyr Val Trp Asn Val Thr Gly Asn Arg Leu Leu Tyr Arg Val Glu Gly
                500                 505                 510
Val Arg Leu Lys Thr Arg Pro Ser Gln Cys Thr Asp Tyr Val Ser Ile
            515                 520                 525
Lys Lys Arg Val Glu Met Leu Ala Lys Met Lys Val Thr His Tyr Gln
        530                 535                 540
Phe Ala Leu Asp Trp Thr Ser Ile Leu Pro Thr Gly Asn Leu Ser Lys
545                 550                 555                 560
Val Asn Arg Gln Val Leu Arg Tyr Tyr Arg Cys Val Val Ser Glu Gly
                565                 570                 575
Leu Lys Leu Gly Val Phe Pro Met Val Thr Leu Tyr His Pro Thr His
                580                 585                 590
Ser His Leu Gly Leu Pro Leu Pro Leu Leu Ser Ser Gly Gly Trp Leu
            595                 600                 605
Asn Met Asn Thr Ala Lys Ala Phe Gln Asp Tyr Ala Glu Leu Cys Phe
        610                 615                 620
Arg Glu Leu Gly Asp Leu Val Lys Leu Trp Ile Thr Ile Asn Glu Pro
625                 630                 635                 640
Asn Arg Leu Ser Asp Met Tyr Asn Arg Thr Ser Asn Asp Thr Tyr Arg
                645                 650                 655
Ala Ala His Asn Leu Met Ile Ala His Ala Gln Val Trp His Leu Tyr
                660                 665                 670
Asp Arg Gln Tyr Arg Pro Val Gln His Gly Ala Val Ser Leu Ser Leu
            675                 680                 685
His Cys Asp Trp Ala Glu Pro Ala Asn Pro Phe Val Asp Ser His Trp
        690                 695                 700
Lys Ala Ala Glu Arg Phe Leu Gln Phe Glu Ile Ala Trp Phe Ala Asp
705                 710                 715                 720
Pro Leu Phe Lys Thr Gly Asp Tyr Pro Ser Val Met Lys Glu Tyr Ile
                725                 730                 735
Ala Ser Lys Asn Gln Arg Gly Leu Ser Ser Ser Val Leu Pro Arg Phe
            740                 745                 750
Thr Ala Lys Glu Ser Arg Leu Val Lys Gly Thr Val Asp Phe Tyr Ala
        755                 760                 765
Leu Asn His Phe Thr Thr Arg Phe Val Ile His Lys Gln Leu Asn Thr
770                 775                 780
Asn Arg Ser Val Ala Asp Arg Asp Val Gln Phe Leu Gln Asp Ile Thr
785                 790                 795                 800
Arg Leu Ser Ser Pro Ser Arg Leu Ala Val Thr Pro Trp Gly Val Arg
                805                 810                 815
```

```
Lys Leu Leu Ala Trp Ile Arg Arg Asn Tyr Arg Asp Arg Asp Ile Tyr
            820                 825                 830

Ile Thr Ala Asn Gly Ile Asp Asp Leu Ala Leu Glu Asp Asp Gln Ile
            835                 840                 845

Arg Lys Tyr Tyr Leu Glu Lys Tyr Val Gln Glu Ala Leu Lys Ala Tyr
        850                 855                 860

Leu Ile Asp Lys Val Lys Ile Lys Gly Tyr Tyr Ala Phe Lys Leu Thr
865                 870                 875                 880

Glu Glu Lys Ser Lys Pro Arg Phe Gly Phe Phe Thr Ser Asp Phe Arg
                885                 890                 895

Ala Lys Ser Ser Val Gln Phe Tyr Ser Lys Leu Ile Ser Ser Ser Gly
            900                 905                 910

Leu Pro Ala Glu Asn Arg Ser Pro Ala Cys Gly Gln Pro Ala Glu Asp
        915                 920                 925

Thr Asp Cys Thr Ile Cys Ser Phe Leu Val
    930                 935
```

<210> SEQ ID NO 268
<211> LENGTH: 53
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 268

```
Met Glu Lys Lys Leu His Ala Val Pro Ala Ala Lys Thr Val Lys Phe
1               5                   10                  15

Lys Cys Pro Ser Ser Gly Thr Pro Asn Pro Thr Leu Arg Trp Leu Lys
            20                  25                  30

Asn Gly Lys Glu Phe Lys Pro Asp His Arg Ile Gly Gly Tyr Lys Val
        35                  40                  45

Arg Tyr Ala Thr Trp
    50
```

<210> SEQ ID NO 269
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 269

```
Ser Ser Pro Thr Arg Leu Ala Val Ile Pro Trp Gly Val Arg Lys Leu
1               5                   10                  15

Leu Arg Trp Val Arg Arg Asn Tyr Gly Asp Met Asp Ile Tyr Ile Thr
            20                  25                  30

Ala Ser
```

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 270

```
Ser Ser Pro Thr Arg Leu Ala Val Ile Pro Trp Gly Val Arg Lys Leu
1               5                   10                  15
```

```
Leu Arg Trp Val Arg Arg Asn Tyr Gly Asp Met Asp Ile Tyr Ile Thr
            20                  25                  30

Ala Ser

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Ser Ser Pro Ser Arg Leu Ala Val Thr Pro Trp Gly Met Arg Lys Leu
1               5                   10                  15

Leu Gly Trp Ile Arg Arg Asn Tyr Arg Asp Met Asp Ile Tyr Val Thr
            20                  25                  30

Ala Asn

<210> SEQ ID NO 272
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Ser Ser Pro Ser Arg Leu Ala Val Thr Pro Trp Gly Val Arg Lys Leu
1               5                   10                  15

Leu Ala Trp Ile Arg Arg Asn Tyr Arg Asp Arg Asp Ile Tyr Ile Thr
            20                  25                  30

Ala Asn

<210> SEQ ID NO 273
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Ala Ser Pro Ser Arg Leu Ala Val Met Pro Trp Gly Glu Gly Lys Leu
1               5                   10                  15

Leu Arg Trp Met Arg Asn Asn Tyr Gly Asp Leu Asp Val Tyr Ile Thr
            20                  25                  30

Ala Asn

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Phe Ser Gly Asp Gly Lys Ala Ile Trp Asp Lys Lys Gln Tyr Val Ser
1               5                   10                  15

Pro
```

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Phe Ser Glu Thr Gly Lys Gln Tyr Gly Ile Lys Asn Ser Thr
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Arg Ala Ser Gln Asp Val Asp Thr Ser Leu Ala
1               5                   10

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ser Ala Ser Phe Leu Tyr Ser
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gln Gln Ser Thr Gly His Pro Gln Thr
1               5

<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Phe Thr Phe Thr Ser Thr Gly Ile Ser
1               5                   10

<210> SEQ ID NO 280
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 280

Arg Tyr Trp Ala Trp Asp Gly Ser Thr Asn Tyr Ala Asp Ser Val Lys
1               5                   10                  15

Gly

<210> SEQ ID NO 281
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Arg Thr Tyr Gly Ile Tyr Asp Thr Tyr Asp Glu Tyr Thr Glu Tyr
1               5                   10                  15

Val Met Asp Tyr
            20

<210> SEQ ID NO 282
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Tyr Trp Ala Trp Asp Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Tyr Gly Ile Tyr Asp Thr Tyr Asp Glu Tyr Thr Glu Tyr
            100                 105                 110

Val Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240
```

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 283
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Thr Phe Thr Ser Thr
1               5

<210> SEQ ID NO 285
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Pro Phe Thr Ser Leu
1               5

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Pro Phe Thr Ser Gln
1               5

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Pro Phe Thr Ser Thr
1               5

<210> SEQ ID NO 288
<211> LENGTH: 4
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 288

Leu Tyr Val Asp
1

<210> SEQ ID NO 289
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Thr Tyr Asp Asn
1

<210> SEQ ID NO 290
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ile Tyr Gly Gly
1

<210> SEQ ID NO 291
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Thr Tyr Asp Glu
1

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 292

His His His His His His His His
1               5

<210> SEQ ID NO 293
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Thr Tyr Asp Lys
1

```
<210> SEQ ID NO 294
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Thr Tyr Asp Met
1

<210> SEQ ID NO 295
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ile Tyr Glu Lys
1

<210> SEQ ID NO 296
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Asp Ile Cys Leu Pro Arg Trp Gly Cys Leu Trp
1               5                   10

<210> SEQ ID NO 297
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(27)

<400> SEQUENCE: 297 tct ggc ttc acc ttc act agt act ggg                          27
Ser Gly Phe Thr Phe Thr Ser Thr Gly
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ser Gly Phe Thr Phe Thr Ser Thr Gly
1               5

<210> SEQ ID NO 299
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 299 att tat cct act aac                                                    15
Ile Tyr Pro Thr Asn
1               5

<210> SEQ ID NO 300
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ile Tyr Pro Thr Asn
1               5

<210> SEQ ID NO 301
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(18)

<400> SEQUENCE: 301 tac ggc atc tac gac ctg                                                18
Tyr Gly Ile Tyr Asp Leu
1               5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Tyr Gly Ile Tyr Asp Leu
1               5

<210> SEQ ID NO 303
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 303 acc ttc act agt act                                                    15
Thr Phe Thr Ser Thr
1               5

<210> SEQ ID NO 304
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 304 ctg tac gtg gac                                                         12
Leu Tyr Val Asp
1

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(24)

<400> SEQUENCE: 305 tac tcg gca tcc ttc ctc tac tct                                         24
Tyr Ser Ala Ser Phe Leu Tyr Ser
1               5

<210> SEQ ID NO 306
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Tyr Ser Ala Ser Phe Leu Tyr Ser
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 307

His His His His His His
1               5

<210> SEQ ID NO 308
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Ser Tyr
            20                  25                  30

Val Ala Trp Tyr Gln Gln Lys Ala Gly Gln Ser Pro Lys Pro Leu Ile
```

```
                    35                  40                  45

Tyr Ser Ala Ser Tyr Arg Phe Ser Gly Val Pro Asp Arg Phe Thr Gly
 50                  55                  60

Ser Gly Ser Gly Thr Glu Phe Thr Leu Thr Ile Ser Asn Val Gln Ser
 65                  70                  75                  80

Glu Asp Leu Ala Glu Tyr Phe Cys Gln Gln Tyr Asn Ile Ser Pro Tyr
                 85                  90                  95

Thr Phe Gly Gly Gly Thr Lys Leu Glu Ile Lys
                100                 105

<210> SEQ ID NO 309
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                 20                  25                  30

Val Tyr Trp Tyr Gln Gln Lys Ser His Glu Ser Pro Arg Leu Leu Ile
             35                  40                  45

Ile Tyr Ala Ser Gln Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Asn Phe Pro Tyr
                 85                  90                  95

Thr Phe Gly Gly Gly Thr Lys Leu Glu Ile Lys
                100                 105

<210> SEQ ID NO 310
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Ile Gln Met Thr Gln Ser Ser Ser Ser Phe Ser Val Ser Leu Gly
 1               5                  10                  15

Asp Arg Val Thr Ile Thr Cys Lys Ala Ser Glu Asp Ile Tyr Asn Arg
                 20                  25                  30

Leu Ala Trp Tyr Gln Gln Lys Pro Gly Ser Ala Pro Arg Leu Leu Ile
             35                  40                  45

Ser Ala Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
 65                  70                  75                  80

Glu Asp Val Ala Thr Tyr Tyr Cys Gln Gln Tyr Trp Ser Asn Pro Leu
                 85                  90                  95

Thr Phe Gly Ala Gly Thr Lys Leu Glu Ile Lys
                100                 105
```

```
<210> SEQ ID NO 311
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Asn Tyr Tyr Cys Gln Gln Ser Asn
                85                  90                  95

Glu Asp Tyr Thr Phe Gly Gly Gly Thr Lys Leu Glu Ile Lys
            100                 105                 110

<210> SEQ ID NO 312
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Glu Ser Tyr
            20                  25                  30

Gly Asn Arg Tyr Met Thr Trp Tyr Gln Gln Lys Pro Gly Gln Pro Pro
        35                  40                  45

Lys Leu Leu Ile Tyr Arg Ala Ala Asn Leu Gln Ser Gly Ile Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 313
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Ala Pro Tyr Trp Thr Asn Thr Glu Lys Met Glu Lys Arg Leu His Ala
1               5                   10                  15

Val Pro Ala Ala Asn Thr Val Lys Phe Arg Cys Pro Ala Gly Gly Asn
            20                  25                  30
```

```
Pro Met Pro Thr Met Arg Trp Leu Lys Asn Gly Lys Glu Phe Lys Gln
        35                  40                  45

Glu His Arg Ile Gly Gly Tyr Lys Val Arg Asn Gln His Trp Ser Leu
    50                  55                  60

Ile Met Glu Ser Val Val Pro Ser Asp Lys Gly Asn Tyr Thr Cys Val
65                  70                  75                  80

Val Glu Asn Glu Tyr Gly Ser Ile Asn His Thr Tyr His Leu Asp Val
                85                  90                  95

Val Glu Arg

<210> SEQ ID NO 314
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Ala Pro Tyr Trp Thr Arg Pro Glu Arg Met Asp Lys Lys Leu Leu Ala
1               5                   10                  15

Val Pro Ala Ala Asn Thr Val Arg Phe Arg Cys Pro Ala Ala Gly Asn
                20                  25                  30

Pro Thr Pro Ser Ile Ser Trp Leu Lys Asn Gly Arg Glu Phe Arg Gly
            35                  40                  45

Glu His Arg Ile Gly Gly Ile Lys Leu Arg His Gln Gln Trp Ser Leu
    50                  55                  60

Val Met Glu Ser Val Val Pro Ser Asp Arg Gly Asn Tyr Thr Cys Val
65                  70                  75                  80

Val Glu Asn Lys Phe Gly Ser Ile Arg Gln Thr Tyr Thr Leu Asp Val
                85                  90                  95

Leu Glu Arg

<210> SEQ ID NO 315
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asp Thr Tyr Met Asn
1               5
```

ANTI-FGFR2/3 ANTIBODIES AND METHODS USING SAME

CROSS-REFERENCE TO RELATED APPLICATIONS

This application claims the benefit of priority of provisional U.S. Application No. 62/075,740 filed Nov. 5, 2014, which is herein incorporated by reference in its entirety.

SEQUENCE LISTING

The instant application contains a Sequence Listing which has been submitted electronically in ASCII format and is hereby incorporated by reference in its entirety. Said ASCII copy, created on Nov. 30, 2017, is named 00B206_0208_SL.txt and is 303,387 bytes in size.

FIELD OF THE INVENTION

The present invention relates generally to dual specific anti-FGFR2/3 antibodies, and uses of same.

BACKGROUND OF THE INVENTION

Fibroblast growth factors (FGFs) and their receptors (FGFRs) play critical roles during embryonic development, tissue homeostasis and metabolism (Eswarakumar, V. P., Lax, I., and Schlessinger, J. 2005. Cellular signaling by fibroblast growth factor receptors. Cytokine Growth Factor Rev 16:139-149; L'Hote, C. G., and Knowles, M. A. 2005. Cell responses to FGFR3 signalling: growth, differentiation and apoptosis. Exp Cell Res 304:417-431; Dailey, L., Ambrosetti, D., Mansukhani, A., and Basilico, C. 2005. Mechanisms underlying differential responses to FGF signaling. Cytokine Growth Factor Rev 16:233-247). In humans, there are 22 FGFs (FGF1-14, FGF16-23) and four FGF receptors with tyrosine kinase domain (FGFR1-4). FGFRs consist of an extracellular ligand binding region, with two or three immunoglobulin-like domains (IgD1-3), a single-pass transmembrane region, and a cytoplasmic, split tyrosine kinase domain. FGFR1, 2 and 3 each have two major alternatively spliced isoforms, designated IIIb and IIIc. These isoforms differ by about 50 amino acids in the second half of IgD3, and have distinct tissue distribution and ligand specificity. In general, the IIIb isoform is found in epithelial cells, whereas IIIc is expressed in mesenchymal cells. Upon binding FGF in concert with heparan sulfate proteoglycans, FGFRs dimerize and become phosphorylated at specific tyrosine residues. This facilitates the recruitment of critical adaptor proteins, such as FGFR substrate 2 α (FRS2α), leading to activation of multiple signaling cascades, including the mitogen-activated protein kinase (MAPK) and PI3K-AKT pathways (Eswarakumar, V. P., Lax, I., and Schlessinger, J. 2005. Cellular signaling by fibroblast growth factor receptors. Cytokine Growth Factor Rev 16:139-149; Dailey, L., Ambrosetti, D., Mansukhani, A., and Basilico, C. 2005. Mechanisms underlying differential responses to FGF signaling. Cytokine Growth Factor Rev 16:233-247; Mohammadi, M., Olsen, S. K., and Ibrahimi, O. A. 2005. Structural basis for fibroblast growth factor receptor activation. Cytokine Growth Factor Rev 16:107-137). Consequently, FGFs and their cognate receptors regulate a broad array of cellular processes, including proliferation, differentiation, migration and survival, in a context-dependent manner.

Aberrantly activated FGFRs have been implicated in specific human malignancies (Eswarakumar, V. P., Lax, I., and Schlessinger, J. 2005. Cellular signaling by fibroblast growth factor receptors. Cytokine Growth Factor Rev 16:139-149; Grose, R., and Dickson, C. 2005. Fibroblast growth factor signaling in tumorigenesis. Cytokine Growth Factor Rev 16:179-186). In particular, the t(4;14) (p16.3; q32) chromosomal translocation occurs in about 15-20% of multiple myeloma patients, leading to overexpression of FGFR3 and correlates with shorter overall survival (Chang, H., Stewart, A. K., Qi, X. Y., Li, Z. H., Yi, Q. L., and Trudel, S. 2005. Immunohistochemistry accurately predicts FGFR3 aberrant expression and t(4;14) in multiple myeloma. Blood 106:353-355; Chesi, M., Nardini, E., Brents, L. A., Schrock, E., Ried, T., Kuehl, W. M., and Bergsagel, P. L. 1997. Frequent translocation t(4;14)(p16.3;q32.3) in multiple myeloma is associated with increased expression and activating mutations of fibroblast growth factor receptor 3. Nat Genet 16:260-264; Fonseca, R., Blood, E., Rue, M., Harrington, D., Oken, M. M., Kyle, R. A., Dewald, G. W., Van Ness, B., Van Wier, S. A., Henderson, K. J., et al. 2003. Clinical and biologic implications of recurrent genomic aberrations in myeloma. Blood 101:4569-4575; Moreau, P., Facon, T., Leleu, X., Morineau, N., Huyghe, P., Harousseau, J. L., Bataille, R., and Avet-Loiseau, H. 2002. Recurrent 14q32 translocations determine the prognosis of multiple myeloma, especially in patients receiving intensive chemotherapy. Blood 100:1579-1583). FGFR3 is implicated also in conferring chemoresistance to myeloma cell lines in culture (Pollett, J. B., Trudel, S., Stern, D., Li, Z. H., and Stewart, A. K. 2002. Overexpression of the myeloma-associated oncogene fibroblast growth factor receptor 3 confers dexamethasone resistance. Blood 100:3819-3821), consistent with the poor clinical response of t(4;14)+ patients to conventional chemotherapy (Fonseca, R., Blood, E., Rue, M., Harrington, D., Oken, M. M., Kyle, R. A., Dewald, G. W., Van Ness, B., Van Wier, S. A., Henderson, K. J., et al. 2003. Clinical and biologic implications of recurrent genomic aberrations in myeloma. Blood 101:4569-4575). Overexpression of mutationally activated FGFR3 is sufficient to induce oncogenic transformation in hematopoietic cells and fibroblasts (Bernard-Pierrot, I., Brams, A., Dunois-Larde, C., Caillault, A., Diez de Medina, S. G., Cappellen, D., Graff, G., Thiery, J. P., Chopin, D., Ricol, D., et al. 2006. Oncogenic properties of the mutated forms of fibroblast growth factor receptor 3b. Carcinogenesis 27:740-747; Agazie, Y. M., Movilla, N., Ischenko, I., and Hayman, M. J. 2003. The phosphotyrosine phosphatase SHP2 is a critical mediator of transformation induced by the oncogenic fibroblast growth factor receptor 3. Oncogene 22:6909-6918; Ronchetti, D., Greco, A., Compasso, S., Colombo, G., Dell'Era, P., Otsuki, T., Lombardi, L., and Neri, A. 2001. Deregulated FGFR3 mutants in multiple myeloma cell lines with t(4;14): comparative analysis of Y373C, K650E and the novel G384D mutations. Oncogene 20:3553-3562; Chesi, M., Brents, L. A., Ely, S. A., Bais, C., Robbiani, D. F., Mesri, E. A., Kuehl, W. M., and Bergsagel, P. L. 2001. Activated fibroblast growth factor receptor 3 is an oncogene that contributes to tumor progression in multiple myeloma. Blood 97:729-736; Plowright, E. E., Li, Z., Bergsagel, P. L., Chesi, M., Barber, D. L., Branch, D. R., Hawley, R. G., and Stewart, A. K. 2000. Ectopic expression of fibroblast growth factor receptor 3 promotes myeloma cell proliferation and prevents apoptosis. Blood 95:992-998), and murine bone marrow transplantation models (Chen, J., Williams, I. R., Lee, B. H., Duclos, N., Huntly, B. J., Donoghue, D. J., and Gilliland, D. G. 2005. Constitutively activated FGFR3 mutants signal through PLCgamma-dependent and -independent pathways for hematopoietic transformation. Blood 106:328-337; Li, Z., Zhu, Y. X., Plowright, E. E., Bergsagel, P. L., Chesi, M., Patterson, B., Hawley, T. S., Hawley, R. G., and Stewart, A. K. 2001. The myeloma-associated oncogene fibroblast growth factor receptor 3 is transforming in hematopoietic cells. Blood 97:2413-2419). Accordingly, FGFR3 has been proposed as a potential therapeutic target in multiple myeloma. Indeed, several small-molecule inhibitors targeting FGFRs, although not selective for FGFR3 and having cross-inhibitory activity toward certain other kinases, have demonstrated cytotoxicity against FGFR3-positive myeloma cells in culture and in mouse models (Trudel, S., Ely, S., Farooqi, Y., Affer, M., Robbiani, D. F., Chesi, M., and Bergsagel, P. L. 2004. Inhibition of fibroblast growth factor receptor 3 induces differentiation and apoptosis in t(4;14) myeloma. Blood 103:3521-3528; Trudel, S., Li, Z. H., Wei, E., Wiesmann, M., Chang, H., Chen, C., Reece, D., Heise, C., and Stewart, A. K. 2005. CHIR-258, a novel, multitargeted tyrosine kinase inhibitor for the potential treatment of t(4;14) multiple myeloma. Blood 105:2941-2948; Chen, J., Lee, B. H., Williams, I. R., Kutok, J. L., Mitsiades, C. S., Duclos, N., Cohen, S., Adelsperger, J., Okabe, R., Coburn, A., et al. 2005. FGFR3 as a therapeutic target of the small molecule inhibitor PKC412 in hematopoietic malignancies. Oncogene 24:8259-8267; Paterson, J. L., Li, Z., Wen, X. Y., Masih-Khan, E., Chang, H., Pollett, J. B., Trudel, S., and Stewart, A. K. 2004. Preclinical studies of fibroblast growth factor receptor 3 as a therapeutic target in multiple myeloma. Br J Haematol 124:595-603; Grand, E. K., Chase, A. J., Heath, C., Rahemtulla, A., and Cross, N. C. 2004. Targeting FGFR3 in multiple myeloma: inhibition of t(4;14)-positive cells by SU5402 and PD173074. Leukemia 18:962-966).

FGFR3 overexpression has been documented also in a high fraction of bladder cancers (Gomez-Roman, J. J., Saenz, P., Molina, M., Cuevas Gonzalez, J., Escuredo, K., Santa Cruz, S., Junquera, C., Simon, L., Martinez, A., Gutierrez Banos, J. L., et al. 2005. Fibroblast growth factor receptor 3 is overexpressed in urinary tract carcinomas and modulates the neoplastic cell growth. Clin Cancer Res 11:459-465; Tomlinson, D. C., Baldo, O., Harnden, P., and Knowles, M. A. 2007. FGFR3 protein expression and its relationship to mutation status and prognostic variables in bladder cancer. J Pathol 213:91-98). Furthermore, somatic activating mutations in FGFR3 have been identified in 60-70% of papillary and 16-20% of muscle-invasive bladder carcinomas (Tomlinson, D. C., Baldo, O., Harnden, P., and Knowles, M. A. 2007. FGFR3 protein expression and its relationship to mutation status and prognostic variables in bladder cancer. J Pathol 213:91-98; van Rhijn, B. W., Montironi, R., Zwarthoff, E. C., Jobsis, A. C., and van der Kwast, T. H. 2002. Frequent FGFR3 mutations in urothelial papilloma. J Pathol 198:245-251). In cell culture experiments, RNA interference (Bernard-Pierrot, I., Brams, A., Dunois-Larde, C., Caillault, A., Diez de Medina, S. G., Cappellen, D., Graff, G., Thiery, J. P., Chopin, D., Ricol, D., et al. 2006. Oncogenic properties of the mutated forms of fibroblast growth factor receptor 3b. Carcinogenesis 27:740-747; Tomlinson, D. C., Hurst, C. D., and Knowles, M. A. 2007. Knockdown by shRNA identifies S249C mutant FGFR3 as a potential therapeutic target in bladder cancer. Oncogene 26:5889-5899) or an FGFR3 single-chain Fv antibody fragment inhibited bladder cancer cell proliferation (Martinez-Torrecuadrada, J., Cifuentes, G., Lopez-Serra, P., Saenz, P., Martinez, A., and Casal, J. I. 2005. Targeting the extracellular domain of fibroblast growth factor receptor 3 with human single-chain Fv antibodies inhibits bladder carcinoma cell line proliferation. Clin Cancer Res 11:6280-6290). A recent study demonstrated that an FGFR3 antibody-toxin conjugate attenuates xenograft growth of a bladder cancer cell line through FGFR3-mediated toxin delivery into tumors (Martinez-Torrecuadrada, J. L., Cheung, L. H., Lopez-Serra, P., Barderas, R., Canamero, M., Ferreiro, S., Rosenblum, M. G., and Casal, J. I. 2008. Antitumor activity of fibroblast growth factor receptor 3-specific immunotoxins in a xenograft mouse model of bladder carcinoma is mediated by apoptosis. Mol Cancer Ther 7:862-873). However, it remains unclear whether FGFR3 signaling is indeed an oncogenic driver of in vivo growth of bladder tumors. Moreover, the therapeutic potential for targeting FGFR3 in bladder cancer has not been defined on the basis of in vivo models. Publications relating to FGFR3 and anti-FGFR3 antibodies include U.S. Patent Publication no. 2005/0147612; Rauchenberger et al, J Biol Chem 278 (40):38194-38205 (2003); WO2006/048877; Martinez-Torrecuadrada et al, (2008) Mol Cancer Ther 7(4): 862-873; WO2007/144893; Trudel et al. (2006) 107(10): 4039-4046; Martinez-Torrecuadrada et al (2005) Clin Cancer Res 11 (17): 6280-6290; Gomez-Roman et al (2005) Clin Cancer Res 11:459-465; Direnzo, R et al (2007) Proceedings of AACR Annual Meeting, Abstract No. 2080; WO2010/002862. Crystal structures of FGFR3:anti-FGFR3 antibody are disclosed in U.S. Pat. Pub. No. 20100291114.

While FGFR2 and FGFR3 can be inhibited without disrupting adult-tissue homeostasis, blocking the closely related FGFR1 and FGFR4, which regulate specific metabolic functions, carries a greater safety risk. An anti-FGFR3 antibody disclosed in U.S. patent publication no. 20100291114 was re-engineered here to create function-blocking antibodies that bind with dual specificity to FGFR3 and FGFR2 but spare FGFR1 and FGFR4. Thus a dual-specific antibody was designed and made that blocks FGF binding to FGFR2 and FGFR3 (i.e., FGFR2/3), thereby inhibiting downstream signaling, without blocking FGFR1 or FGFR4.

It is clear that there continues to be a need for agents that have clinical attributes that are optimal for development as therapeutic agents.

As described herein, an antibody that binds monospecifically to FGFR3, was redesigned for binding to other FGFR family members through multiple rounds of engineering, including recruiting binding to FGFR2 and removing binding to FGFR4. The first step of engineering was carried out to gain FGFR2 binding using phage display library. Each phage library constituted mutagenesis of one contacting CDR, and the range of mutagenesis covered as many residues in that CDR as allowed by library size. Choosing multiple consecutive positions for mutagenesis permitted significant freedom in the CDR backbones. Most of the resulting clones that were able to engage FGFR2 harbored all 5 mutations in CDR H2. The crystal structure demonstrated that the full range of mutagenesis was coupled with complete remodeling of the geometry of the CDR loop. The solutions to spatial reorganizations of a CDR are numerous, as evidenced by the identification of diverse H2 mutants that had gained binding to FGFR2. Such a large variety of solutions are not typically seen as outcomes from standard affinity maturation experiments, whereby the recovered sequences usually contain sparse positions on individual CDRs. Therefore, acquiring additional specificity for homologous antigens may require larger mutagenesis freedom than affinity maturation.

The second round of engineering was refinement of specificity to remove FGFR4 binding. Detailed structural analysis of contact residues between the antibody CDR loops and the antigen surface was used to guide the design of phage display libraries. Selected antibody variants showed reduction in FGFR4 binding with retention of binding to FGFR2/3. The sequence solutions to this specificity refinement step were more limited compared to the first round of engineering. The refinement step further demonstrated the ability to differentiate binding specificities among closely related antigens antibody re-engineering.

The dual-specific antibodies generated through the antibody engineering described herein bind to two closely related antigens, namely FGFR2 and FGFR3 (anti-FGFR2/3 antibodies). These anti-FGFR2/3 antibodies (2B.1.3 antibody variants) are regular IgG molecules in that they use identical heavy and light chains. Certain anti-FGFR2/3 antibodies of this invention can bind to two FGFR2 isoforms, two FGFR3 isoforms or one FGFR2 and one FGFR3 isoform in a bivalent or monovalent manner respectively. This contrasts to conventional bispecific IgG, which commonly use two different heavy/light-chain pairs to bind to two different antigens in a monovalent manner. The dual-specific antibodies described share some similarities with "two-in-one" antibodies (Grand, E. K., Chase, A. J., Heath, C., Rahemtulla, A., and Cross, N.C. 2004. Targeting FGFR3 in multiple myeloma: inhibition of t(4;14)-positive cells by SU5402 and PD173074. Leukemia 18:962-966). Bostrom et al. randomized all 3 light-chain CDRs of Herceptin and selected for a second specificity as well as the parental specificity. As expected, the second specificity comes from the dominant contributions of light-chain CDRs (Grand, E. K., Chase, A. J., Heath, C., Rahemtulla, A., and Cross, N.C. 2004. Targeting FGFR3 in multiple myeloma: inhibition of t(4;14)-positive cells by SU5402 and PD173074. Leukemia 18:962-966; Gomez-Roman, J. J., Saenz, P., Molina, M., Cuevas Gonzalez, J., Escuredo, K., Santa Cruz, S., Junquera, C., Simon, L., Martinez, A., Gutierrez Banos, J. L., et al. 2005. Fibroblast growth factor receptor 3 is overexpressed in urinary tract carcinomas and modulates the neoplastic cell growth. Clin Cancer Res 11:459-465). In one case, although EGFR and Her3 are homologous, the binding epitopes by an anti-EGFR/Her3 "two-in-one" antibody are different (Gomez-Roman, J. J., Saenz, P., Molina, M., Cuevas Gonzalez, J., Escuredo, K., Santa Cruz, S., Junquera, C., Simon, L., Martinez, A., Gutierrez Banos, J. L., et al. 2005. Fibroblast growth factor receptor 3 is overexpressed in urinary tract carcinomas and modulates the neoplastic cell growth. Clin Cancer Res 11:459-465). The approach described herein differs from "two-in-one" antibodies in that it appreciates the sequence and structure similarities between the two homologous antigens, and focuses on a more limited set of mutagenesis so as to retain the parental epitope during engineering.

The antibody engineering presented here started from an existing and extensively characterized antibody anti-FGFR antibody that has potential utility for cancer therapy. Since introduction of the first therapeutic monoclonal antibody in the mid-1980s, there have been many clinically and commercially successful antibody drugs in different disease areas, including trastuzumab, cetuximab, adalimumab, bevacizumab, etc. These antibodies displayed exceptional activities in inhibiting their molecular targets. On the other hand, like the FGFR family, multiple homologous proteins are pursued as molecular targets for their various disease associations. Traditional discovery routes to obtain antibodies targeting a functional epitope, either animal immunization or other display-based library selections, are not guaranteed to be successful. Alternatively, as described herein, an antibody can be engineered to acquire specificity towards homologous targets, thereby providing an alternative route for antibody discovery. Moreover, this approach takes advantage of the favorable properties of previously developed antibodies by maintaining the functional epitopes and presumably the biological functions as well. As the clinical antibody repertoire expands, more antibodies could be engineered instead of being discovered ab initio. Potential applications may include protein families that comprise multiple members as disease targets, such as the EGFR family (Tomlinson, D.C., Baldo, O., Harnden, P., and Knowles, M. A. 2007. FGFR3 protein expression and its relationship to mutation status and prognostic variables in bladder cancer. J Pathol 213:91-98), the TNFR family (van Rhijn, B. W., Montironi, R., Zwarthoff, E. C., Jobsis, A. C., and van der Kwast, T. H. 2002. Frequent FGFR3 mutations in urothelial papilloma. J Pathol 198:245-251), the TAM family (Tomlinson, D.C., Hurst, C. D., and Knowles, M. A. 2007. Knockdown by shRNA identifies S249C mutant FGFR3 as a potential therapeutic target in bladder cancer. Oncogene 26:5889-5899; Martinez-Torrecuadrada, J., Cifuentes, G., Lopez-Serra, P., Saenz, P., Martinez, A., and Casal, J. I. 2005. Targeting the extracellular domain of fibroblast growth factor receptor 3 with human single-chain Fv antibodies inhibits bladder carcinoma cell line proliferation. Clin Cancer Res 11:6280-6290), the Ephrin family (Martinez-Torrecuadrada, J. L., Cheung, L. H., Lopez-Serra, P., Barderas, R., Canamero, M., Ferreiro, S., Rosenblum, M. G., and Casal, J. I. 2008. Antitumor activity of fibroblast growth factor receptor 3-specific immunotoxins in a xenograft mouse model of bladder carcinoma is mediated by apoptosis. Mol Cancer Ther 7:862-873). As in the traditional discovery processes, engineered antibodies towards homologs should be considered as new molecules, and still need full characterization of their biochemical, biophysical and biologic properties for any potential therapeutic applications.

All references cited herein, including patent applications and publications, are incorporated by reference in their entirety.

SUMMARY OF THE INVENTION

The invention is based in part on the identification of a variety of FGFR binding agents (such as antibodies, and fragments thereof) that bind FGFR2 and FGFR3 ("FGFR2/3"). FGFR3 presents an important and advantageous therapeutic target, and the invention provides compositions and methods based on binding of the agents to FGFR3, specifically agents that bind FGFR. Specifically, invention provides compositions and methods based on binding of the agents to FGFR2/3 (i.e., binding of the agents that have dual specificity for FGFR2 and FGFR3). FGFR2/3 binding agents of the invention, as described herein, provide important therapeutic and diagnostic agents for use in targeting pathological conditions associated with expression and/or activity of the FGFR3 and/or FGFR2 signaling pathways. Accordingly, the invention provides methods, compositions, kits, and articles of manufacture related to FGFR3 and FGFR2 binding.

The present invention provides antibodies that bind to FGFR2 and FGFR3 (anti-FGFR2/3 antibodies). In one aspect, the invention features an isolated antibody that binds an FGFR3. In some embodiments, the antibody binds a FGFR3 IIIb isoform and/or a FGFR3 IIIc isoform. In some embodiments, the antibody binds a mutated FGFR3 (e.g., one or more of FGFR3 IIIb R248C, S249C, G372C, Y375C, K652E, and/or one or more of FGFR3 IIIc R248C, S249C, G370C, Y373C, K650E). In some embodiments, the antibody binds monomeric FGFR3 (e.g., monomeric FGFR3 IIIb and/or IIIc isoforms). In some embodiments, the antibody promotes formation of monomeric FGFR3, such as by stabilizing the monomeric FGFR3 form relative to the dimeric FGFR3 form. In some embodiments, the antibody binds FGFR2 or a variant thereof. In some embodiments, the antibody binds FGFR2 and any one or more of the FGFR3 variants described herein.

In one aspect, the invention provides an isolated anti-FGFR2/3 antibody, wherein a full length IgG form of the antibody binds human FGFR3 with a Kd of $1 \times 10^{0.7}$ M or higher affinity. In one aspect, the invention provides an isolated anti-FGFR2/3 antibody, wherein a full length IgG form of the antibody binds human FGFR2 with a Kd of $1 \times 10^{0.7}$ M or higher affinity. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore, radioimmunoassay (RIA), and ELISA. In some embodiments, the full length IgG form of the antibody binds human FGFR3 with a Kd of $1 \times 10^{-8}$ M or higher affinity, with a Kd of $1 \times 10^{-9}$ M or higher affinity, or with a Kd of $1 \times 10^{-10}$ M or higher affinity. In some embodiments, the full length IgG form of the antibody binds human FGFR2 with a Kd of $1 \times 10^{-8}$ M or higher affinity, with a Kd of $1 \times 10^{-9}$ M or higher affinity, or with a Kd of $1 \times 10^{-10}$ M or higher affinity. In some embodiments, the full length IgG form of the antibody binds human FGFR2 and FGFR3 with Kds of $1 \times 10^{-8}$ M or higher affinity, with Kds of $1 \times 10^{-9}$ M or higher affinity, or with Kds of $1 \times 10^{-10}$ M or higher affinity.

Generally, the anti-FGFR2/3 antibodies of the present invention are antagonist antibodies. Thus, in one aspect, the anti-FGFR2/3 antibodies inhibit FGFR3 activity (e.g., FGFR3-IIIb and/or FGFR3-IIIc activity). In some embodiments, the anti-FGFR2/3 antibody (generally in bivalent form) does not possess substantial FGFR3 agonist function. In some embodiments, the anti-FGFR2/3 antagonist antibody (generally in bivalent form) possesses little or no FGFR3 agonist function. In one embodiment, an antibody of the invention (generally in bivalent form) does not exhibit an FGFR3 agonist activity level that is above background level that is of statistical significance.

In one aspect, binding of the antibody to a FGFR3 may inhibit dimerization of the receptor with another unit of the receptor, whereby activation of the receptor is inhibited (due, at least in part, to a lack of receptor dimerization). Inhibition can be direct or indirect.

In one aspect, the invention provides anti-FGFR2/3 antibodies that do not possess substantial apoptotic activity (e.g., does not induce apoptosis of a cell, e.g., a transitional cell carcinoma cell or a multiple myeloma cell, such as a multiple myeloma cell comprising a FGFR3 translocation, such as a t(4;14) translocation). In some embodiments, the anti-FGFR2/3 antibody possesses little or no apoptotic function. In some embodiment, the FGFR2/3 antibodies do not exhibit apoptotic function that is above background level that is of statistical significance.

In one aspect, the invention provides anti-FGFR2/3 antibodies that do not induce substantial FGFR3 down-regulation. In some embodiments, the anti-FGFR2/3 antibody induces little or no receptor down-regulation. In some embodiment, the FGFR2/3 antibodies do not induce receptor down-regulation that is above background level that is of statistical significance.

In one aspect, the invention provides anti-FGFR2/3 antibodies that possess effector function. In one embodiment, the effector function comprises antibody-dependent cell-mediated cytotoxicity (ADCC). In one embodiment, the anti-FGFR2/3 antibodies of this invention (in some embodiments, a naked anti-FGFR2/3 antibody) are capable of killing a cell, in some embodiments, a multiple myeloma cells (e.g., multiple myeloma cells comprising a translocation, e.g., a t(4;14) translocation). In some embodiments, the the anti-FGFR2/3 antibodies of this invention are capable of killing a cell that expresses about 10,000 FGFR3 molecules per cell or more (such as about 11,000, about 12,000, about 13,000, about 14,000, about 15,000, about 16,000, about 17,000, about 18,000 or more FGFR3 molecules per cell). In other embodiments, the cell expresses about 2000, about 3000, about 4000, about 5000, about 6000, about 7000, about 8000, or more FGFR3 molecules per cell. In some embodiments, the the anti-FGFR2/3 antibodies of this invention are capable of killing a cell that expresses about 10,000 FGFR2 molecules per cell or more (such as about 11,000, about 12,000, about 13,000, about 14,000, about 15,000, about 16,000, about 17,000, about 18,000 or more FGFR3 molecules per cell). In other embodiments, the cell expresses about 2000, about 3000, about 4000, about 5000, about 6000, about 7000, about 8000, or more FGFR2 molecules per cell.

In one aspect, the anti-FGFR2/3 antibodies of the invention inhibit constitutive FGFR3 activity. In some embodiments, constitutive FGFR3 activity is ligand-dependent FGFR3 constitutive activity. In some embodiments, constitutive FGFR3 activity is ligand-independent constitutive FGFR3 activity. In one aspect, the anti-FGFR2/3 antibodies of the invention inhibit constitutive FGFR2 activity. In one aspect, the anti-FGFR2/3 antibodies of the invention inhibit constitutive FGFR2 and FGFR3 activity.

In one aspect, the anti-FGFR2/3 antibodies of the invention inhibit FGFR3 comprising a mutation corresponding to FGFR3-IIIb$^{R248C}$. As used herein the term "comprising a mutation corresponding to FGFR3-IIIb$^{R248C}$" is understood to encompass FGFR3-IIIb$^{R248C}$ and FGFR3-IIIc$^{R248C}$, as well as additional FGFR3 forms comprising an R to C mutation at a position corresponding to FGFR3-IIIb R248. One of ordinary skill in the art understands how to align FGFR3 sequences in order identify corresponding residues between respective FGFR3 sequences, e.g., aligning a FGFR3-IIIc sequence with a FGFR3-IIIb sequence to identify the position in FGFR3 corresponding R248 position in FGFR3-IIIb. In some embodiments, the anti-FGFR2/3 antibodies of the invention inhibit FGFR3-IIIb$^{R248C}$ and/or FGFR3-IIIc$^{R248C}$.

In one aspect, the anti-FGFR2/3 antibodies of the invention inhibit FGFR3 comprising a mutation corresponding to FGFR3-IIIb$^{K652E}$. For convenience, the term "comprising a mutation corresponding to FGFR3-IIIb$^{K652E}$" is understood to encompass FGFR3-IIIb$^{K652E}$ and FGFR3-IIIc$^{K650E}$, as well as additional FGFR3 forms comprising a K to E mutation at a position corresponding to FGFR3-IIIb K652. One of ordinary skill in the art understands how to align FGFR3 sequences in order identify corresponding residues between respective FGFR3 sequences, e.g., aligning a FGFR3-IIIc sequence with a FGFR3-IIIb sequence to identify the position in FGFR3 corresponding K652 position in FGFR3-IIIb. In some embodiments, the anti-FGFR2/3 antibodies of the invention inhibit FGFR3-IIIb$^{K652E}$ and/or FGFR3-IIIc$^{K650E}$.

In one aspect, the anti-FGFR2/3 antibodies of the invention inhibit FGFR3 comprising a mutation corresponding to FGFR3-IIIb$^{S249C}$. For convenience, the term "comprising a mutation corresponding to FGFR3-IIIb$^{S249C}$" is understood to encompass FGFR3-IIIb$^{S249C}$ and FGFR3-IIIc$^{S249C}$, as well as additional FGFR3 forms comprising an S to C mutation at a position corresponding to FGFR3-IIIb S249. In some embodiments, the anti-FGFR2/3 antibodies of the invention inhibit FGFR3-IIIb$^{S249C}$ and/or FGFR3-IIIc$^{S249C}$.

In one aspect, the anti-FGFR2/3 antibodies of the invention inhibit FGFR3 comprising a mutation corresponding to FGFR3-IIIb$^{G372C}$. For convenience, the term "comprising a mutation corresponding to FGFR3-IIIb$^{G372C}$" is understood to encompass FGFR3-IIIb$^{G372C}$ and FGFR3-IIIc$^{G370C}$, as well as additional FGFR3 forms comprising a G to C mutation at a position corresponding to FGFR3-IIIb G372. In some embodiments, the anti-FGFR2/3 antibodies of the invention inhibit FGFR3-IIIb$^{G372C}$ and/or FGFR3-IIIc$^{G370C}$.

In one aspect, the anti-FGFR2/3 antibodies of the invention inhibit FGFR3 comprising a mutation corresponding to FGFR3-IIIb$^{Y375C}$. For convenience, the term "comprising a mutation corresponding to FGFR3-IIIb$^{Y375C}$" is understood to encompass FGFR3-IIIb$^{Y375C}$ and FGFR3-IIIc$^{Y373C}$, as well as additional FGFR3 forms comprising an S to C mutation at a position corresponding to FGFR3-IIIb S249. In some embodiments, the anti-FGFR2/3 antibodies of the invention inhibit FGFR3-IIIb$^{Y375C}$ and/or FGFR3-IIIc$^{Y373C}$.

In one aspect, the anti-FGFR2/3 antibodies of the invention inhibit (a) FGFR3-IIIb$^{K652E}$ and (b) one or more of FGFR3-IIIb$^{R248C}$, FGFR3-IIIb$^{Y375C}$, FGFR3-IIIb$^{S249C}$, and FGFR3IIIb$^{G372C}$.

In one aspect, the anti-FGFR2/3 antibodies of the invention inhibit (a) FGFR3-IIIc$^{K650E}$ and (b) one or more of FGFR3-IIIc$^{R248C}$, FGFR3-IIIc$^{Y373C}$, FGFR3-IIIc$^{S249C}$, and FGFR3IIIc$^{G370C}$.

In one aspect, the anti-FGFR2/3 antibodies of the invention inhibit (a) FGFR3-IIIb$^{R248C}$ and (b) one or more of FGFR3-IIIb$^{K652E}$, FGFR3-IIIb$^{Y375C}$, FGFR3-IIIb$^{S249C}$, and FGFR3-IIIb$^{G372C}$.

In one aspect, the anti-FGFR2/3 antibodies of the invention inhibit (a) FGFR3-IIIc$^{R248C}$ and (b) one or more of FGFR3-IIIc$^{K65E}$, FGFR3-IIIc$^{Y373C}$, FGFR3-IIIc$^{S249C}$, and FGFR3-IIIc$^{G370C}$.

In one aspect, the anti-FGFR2/3 antibodies of the invention inhibit (a) FGFR3-IIIb$^{G372C}$ and (b) one or more of FGFR3-IIIb$^{K652E}$, FGFR3-IIIb$^{Y375C}$, FGFR3-IIIb$^{S249C}$, and FGFR3-IIIb$^{R248C}$.

In one aspect, the anti-FGFR2/3 antibodies of the invention inhibit (a) FGFR3-IIIc$^{G370C}$ and (b) one or more of FGFR3-IIIc$^{K65E}$, FGFR3-IIIc$^{Y373C}$, FGFR3-IIIc$^{S249C}$, and FGFR3-IIIc$^{R248C}$.

In one aspect, the anti-FGFR2/3 antibodies of the invention inhibit FGFR3-IIIb$^{R248C}$, FGFR3-IIIb$^{K652E}$, FGFR3-IIIb$^{Y375C}$, FGFR3-IIIb$^{S249C}$, and FGFR3-IIIb$^{G372C}$.

In one aspect, the anti-FGFR2/3 antibodies of the invention inhibit FGFR3-IIIc$^{R248C}$, FGFR3-IIIc$^{K65E}$, FGFR3-IIIc$^{Y373C}$, FGFR3-IIIc$^{S249C}$, and FGFR3-IIIc$^{G370C}$.

In one aspect, the invention provides an isolated anti-FGFR2/3 antibody comprising at least one, two, three, four, or five hypervariable region (HVR) sequences selected from: SEQ ID NO 1: RASQDVDTSLA, SEQ ID NO 2: SASFLYS, SEQ ID NO 3: QQSTGHPQT, SEQ ID NO 4: GFPFTSQGIS, SEQ ID NO 5: RTHLGDGSTNYADSVKG, and SEQ ID NO 6: ARTYGIYDTYDKYTEYVMDY. In a specific embodiment, the invention provides the 2B.1.3.10 anti-FGFR2/3 antibody comprising HVR-L1: RASQDVDTSLA (SEQ ID NO: 1), HVR-L2: SASFLYS (SEQ ID NO: 2), HVR-L3: QQSTGHPQT (SEQ ID NO: 3), HVR-H1: GFPFTSQGIS (SEQ ID NO: 4), HVR-H2: RTHLGDGSTNYADSVKG (SEQ ID NO: 5), and HVR-H3: ARTYGIYDTYDKYTEYVMDY (SEQ ID NO: 6).

In one aspect, the invention provides an isolated anti-FGFR2/3 antibody comprising at least one, two, three, four, or five hypervariable region (HVR) sequences selected from: SEQ ID NO 1: RASQDVDTSLA, SEQ ID NO 2: SASFLYS, SEQ ID NO 3: QQSTGHPQT, SEQ ID NO 10: GFPFTSTGIS, SEQ ID NO 5: RTHLGDGSTNYADSVKG, and SEQ ID NO 12: ARTYGIYDTYDMYTEYVMDY. In a specific embodiment, the invention provides the 2B.1.3.12 anti-FGFR2/3 antibody comprising HVR-L1: RASQDVDTSLA (SEQ ID NO: 1), HVR-L2: SASFLYS (SEQ ID NO: 2), HVR-L3: QQSTGHPQT (SEQ ID NO: 3), HVR-H1: GFPFTSTGIS (SEQ ID NO: 10), HVR-H2: RTHLGDGSTNYADSVKG (SEQ ID NO: 5), and HVR-H3: ARTYGIYDTYDMYTEYVMDY (SEQ ID NO: 12).

In certain embodiments, the HVR-H1 of an anti-FGFR2/3 antibody described herein comprises the sequence FTS at positions 4-6 of SEQ ID NO:4.

In certain embodiments, at least one HVR of an anti-FGFR2/3 antibody described herein is a variant HVR, where the variant HVR sequence comprises modification of at least one residue (at least two residues, at least three or more residues) of the sequence depicted in SEQ ID NOs: 1-6. The modification desirably is a substitution, insertion, or deletion. In some embodiments, a HVR-L1 variant comprises 1-6 (1, 2, 3, 4, 5, or 6) substitutions. In some embodiments, a HVR-L2 variant comprises 1-6 (1, 2, 3, 4, 5, or 6) substitutions. In some embodiments, a HVR-L3 variant comprises 1-6 (1, 2, 3, 4, 5, or 6) substitutions. In some embodiments, a HVR-H1 variant comprises 1-6 (1, 2, 3, 4, 5, or 6) substitutions. In some embodiments, a HVR-H2 variant comprises 1-6 (1, 2, 3, 4, 5, or 6) substitutions. In some embodiments, a HVR-H3 variant comprises 1-6 (1, 2, 3, 4, 5, or 6) substitutions.

In certain embodiments, the HVR-H1 of an anti-FGFR2/3 antibody described herein is a variant HVR-H1 wherein the variant HVR-H1 comprises substitutions at amino acids P3 and/or Q7 (SEQ ID NO:4). In specific embodiments, the variant HVR-H1 comprises a P3T substitution. In specific embodiments, the variant HVR-H1 comprises a Q7T or a Q7L substitution. In specific embodiments, the variant HVR-H1 comprises a P3T and a Q7L substitution. In specific embodiments, the variant HVR-H1 comprises a P3T and a Q7T substitution. In certain embodiments, the variant HVR-H1 comprises a sequence selected from the group listed in Table 11: TFTST (SEQ ID NO: 284), PFTSL (SEQ ID NO: 285), PFTSQ (SEQ ID NO: 286), and PFTST (SEQ ID NO: 287).

In certain embodiments, the HVR-H3 of an anti-FGFR2/3 antibody described herein is a variant HVR-H3 wherein the variant HVR-H3 comprises substitutions at amino acids T9, D11, and/or K12 (SEQ ID NO:6). In specific embodiments, the variant HVR-H3 comprises a T9I substitution. In specific embodiments, the variant HVR-H3 comprises a T9L substitution. In specific embodiments, the variant HVR-H3 comprises a D11V substitution. In specific embodiments, the variant HVR-H3 comprises a D11G substitution. In specific embodiments, the variant HVR-H3 comprises a D11E substitution. In specific embodiments, the variant HVR-H3 comprises a K12D substitution. In specific embodiments, the variant HVR-H3 comprises a K12N substitution. In specific embodiments, the variant HVR-H3 comprises a K12G substitution. In specific embodiments, the variant HVR-H3 comprises a K12E substitution. In specific embodiments, the variant HVR-H3 comprises a K12M substitution. In specific embodiments, the variant HVR-H3 comprises a T9L, a D11V, and a K12D substitution. In specific embodiments, the variant HVR-H3 comprises only a K12D substitution. In specific embodiments, the variant HVR-H3 comprises a T9I, a D11G, and a K12G substitution. In specific embodiments, the variant HVR-H3 comprises only a K12E substitution. In specific embodiments, the variant HVR-H3 comprises a T9I and a D11E substitution. In specific embodiments, the variant HVR-H3 comprises only a K12M substitution. In certain embodiments, the variant HVR-H3 comprises a sequence selected from the group listed in Table 11: LYVD (SEQ ID NO: 288), TYDN (SEQ ID NO: 289), IYGG (SEQ ID NO: 290), TYDE (SEQ ID NO: 291), IYEK (SEQ ID NO: 295), TYDK (SEQ ID NO: 293), and TYDM (SEQ ID NO: 294).

In certain embodiments, the HVR-H1 of an anti-FGFR2/3 antibody described herein is a variant HVR-H1 wherein the variant HVR-H1 comprises substitutions at amino acids P3 and/or Q7 (SEQ ID NO:4) and the HVR-H3 of an anti-FGFR2/3 antibody described herein is a variant HVR-H3 wherein the variant HVR-H3 comprises substitutions at amino acids T9, D11, and/or K12 (SEQ ID NO:6). In certain embodiments, the variant HVR-H1 and HVR-H3 of an anti-FGFR2/3 antibody of this invention comprise sequences selected from the group listed in Table 11: TFTST (SEQ ID NO: 284) (HVR-H1) and LYVD (SEQ ID NO: 288) (HVR-H3), TFTST (SEQ ID NO: 284) (HVR-H1) and TYDN (SEQ ID NO: 289) (HVR-H3), TFTST (SEQ ID NO: 284) (HVR-H1) and IYGG (SEQ ID NO: 290) (HVR-H3), TFTST (SEQ ID NO: 284) (HVR-H1) and TYDE (SEQ ID NO: 291) (HVR-H3), PFTSL (SEQ ID NO: 285) (HVR-H1) and IYEK (SEQ ID NO: 295) (HVR-H3), PFTSQ (SEQ ID NO: 286) (HVR-H1) and TYDK (SEQ ID NO: 293) (HVR-H3), PFTST (SEQ ID NO: 287) (HVR-H1) and TYDM (SEQ ID NO: 294) (HVR-H3).

In certain embodiments, the anti-FGFR2/3 antibody of this invention comprises a HVR-H2 sequence selected from the group consisting of the sequences recited in SEQ ID NOs: 13-44. In certain embodiments, the anti-FGFR2/3 antibody of this invention comprises a HVR-H2 sequence selected from the group consisting of the sequences recited in SEQ ID NOs:45-50.

In specific embodiments, the anti-FGFR2/3 antibodies of this invention bind to FGFR2-IIIb (SEQ ID NOs:51 and 52), FGFR2-IIIc (SEQ ID NOs:53 and 54), FGFR3-IIIb (SEQ ID NOs:55 and 56), and/or FGFR3-IIIc (SEQ ID NOs:57 and 58). In certain embodiments, the anti-FGFR2/3 antibodies of this invention bind to FGFR2-IIIb, FGFR2-IIIc, FGFR3-IIIb, and FGFR3-IIIc. In specific embodiments, the anti-FGFR2/3 antibodies of this invention bind to an FGFR selected from the group consisting of FGFR2-IIIb, FGFR2-IIIc, FGFR3-IIIb, and FGFR3-IIIc. In specific embodiments, the anti-FGFR2/3 antibodies of this invention bind to two FGFRs selected from the group consisting of FGFR2-IIIb, FGFR2-IIIc, FGFR3-IIIb, and FGFR3-IIIc. In specific embodiments, the anti-FGFR2/3 antibodies of this invention bind to three FGFRs selected from the group consisting of FGFR2-IIIb, FGFR2-IIIc, FGFR3-IIIb, and FGFR3-IIIc.

Antibodies of the invention can comprise any suitable framework variable domain sequence, provided binding activity to FGFR3 and FGFR2 are substantially retained. For example, in some embodiments, antibodies of the invention comprise a human subgroup III heavy chain framework consensus sequence. In one embodiment of these antibodies, the framework consensus sequence comprises a substitution at position 71, 73, and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093). In one embodiment, these antibodies further comprise a human κI light chain framework consensus sequence. In a particular embodiment, these antibodies comprise light chain HVR sequences of huMAb4D5-8 as described in U.S. Pat. Nos. 6,407,213 & 5,821,337.) In one embodiment, these antibodies comprise light chain variable domain sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093).

In one embodiment, the amino acid sequence of the light chain of an antibody of this invention comprises SEQ ID NO:59.

In one embodiment, the amino acid sequence of the light chain of an antibody of this invention comprises SEQ ID NO:60.

In one embodiment, the amino acid sequence of the light chain of an antibody of this invention comprises SEQ ID NO:61.

In one embodiment, the amino acid sequence of the light chain of an antibody of this invention comprises SEQ ID NO:62.

In one embodiment, the amino acid sequence of the light chain of an antibody of this invention comprises SEQ ID NO:63.

In one embodiment, the amino acid sequence of the light chain of an antibody of this invention comprises SEQ ID NO:64.

In one embodiment, the amino acid sequence of the light chain of an antibody of this invention comprises SEQ ID NO:65.

In one embodiment, the amino acid sequence of the light chain of an antibody of this invention comprises SEQ ID NO:66.

In one embodiment, the amino acid sequence of the heavy chain of an antibody of this invention comprises SEQ ID NO:75.

In one embodiment, the amino acid sequence of the heavy chain of an antibody of this invention comprises SEQ ID NO:76.

In one embodiment, the amino acid sequence of the heavy chain of an antibody of this invention comprises SEQ ID NO:77.

In one embodiment, the amino acid sequence of the heavy chain of an antibody of this invention comprises SEQ ID NO:78.

In one embodiment, the amino acid sequence of the heavy chain of an antibody of this invention comprises SEQ ID NO:79.

In one embodiment, the amino acid sequence of the heavy chain of an antibody of this invention comprises SEQ ID NO:80.

In one embodiment, the amino acid sequence of the heavy chain of an antibody of this invention comprises SEQ ID NO:81.

In one embodiment, the amino acid sequence of the heavy chain of an antibody of this invention comprises SEQ ID NO:82.

In specific embodiments, the antibody of this invention comprises a light chain comprising amino acid SEQ ID NO:59 and a heavy chain amino acid sequence comprising SEQ ID NO:75. In specific embodiments, the antibody of this invention comprises a light chain amino acid sequence comprising SEQ ID NO:60 and a heavy chain amino acid sequence comprising SEQ ID NO:76. In specific embodiments, the antibody of this invention comprises a light chain amino acid sequence comprising SEQ ID NO:61 and a heavy chain amino acid sequence comprising SEQ ID NO:77. In specific embodiments, the antibody of this invention comprises a light chain amino acid sequence comprising SEQ ID NO:62 and a heavy chain amino acid sequence comprising SEQ ID NO:78. In specific embodiments, the antibody of this invention comprises a light chain amino acid sequence comprising SEQ ID NO:63 and a heavy chain amino acid sequence comprising SEQ ID NO:79. In specific embodiments, the antibody of this invention comprises a light chain amino acid sequence comprising SEQ ID NO:64 and a heavy chain amino acid sequence comprising SEQ ID NO:80. In specific embodiments, the antibody of this invention comprises a light chain amino acid sequence comprising SEQ ID NO:65 and a heavy chain amino acid sequence comprising SEQ ID NO:81. In specific embodiments, the antibody of this invention comprises a light chain amino acid sequence comprising SEQ ID NO:66 and a heavy chain amino acid sequence comprising SEQ ID NO:82.

In one embodiment, the nucleic acid sequence of the light chain of an antibody of this invention comprises SEQ ID NO:67.

In one embodiment, the nucleic acid sequence of the light chain of an antibody of this invention comprises SEQ ID NO:68.

In one embodiment, the nucleic acid sequence of the light chain of an antibody of this invention comprises SEQ ID NO:69.

In one embodiment, the nucleic acid sequence of the light chain of an antibody of this invention comprises SEQ ID NO:70.

In one embodiment, the nucleic acid sequence of the light chain of an antibody of this invention comprises SEQ ID NO:71.

In one embodiment, the nucleic acid sequence of the light chain of an antibody of this invention comprises SEQ ID NO:72.

In one embodiment, the nucleic acid sequence of the light chain of an antibody of this invention comprises SEQ ID NO:73.

In one embodiment, the nucleic acid sequence of the light chain of an antibody of this invention comprises SEQ ID NO:74.

In one embodiment, the nucleic acid sequence of the heavy chain of an antibody of this invention comprises SEQ ID NO:83.

In one embodiment, the nucleic acid sequence of the heavy chain of an antibody of this invention comprises SEQ ID NO:84.

In one embodiment, the nucleic acid sequence of the heavy chain of an antibody of this invention comprises SEQ ID NO:85.

In one embodiment, the nucleic acid sequence of the heavy chain of an antibody of this invention comprises SEQ ID NO:86.

In one embodiment, the nucleic acid sequence of the heavy chain of an antibody of this invention comprises SEQ ID NO:87.

In one embodiment, the nucleic acid sequence of the heavy chain of an antibody of this invention comprises SEQ ID NO:88.

In one embodiment, the nucleic acid sequence of the heavy chain of an antibody of this invention comprises SEQ ID NO:89.

In one embodiment, the nucleic acid sequence of the heavy chain of an antibody of this invention comprises SEQ ID NO:90.

In specific embodiments, the antibody of this invention comprises a light chain comprising nucleic acid SEQ ID NO:67 and a heavy chain nucleic acid sequence comprising SEQ ID NO:83. In specific embodiments, the antibody of this invention comprises a light chain nucleic acid sequence comprising SEQ ID NO:68 and a heavy chain nucleic acid sequence comprising SEQ ID NO:84. In specific embodiments, the antibody of this invention comprises a light chain nucleic acid sequence comprising SEQ ID NO:69 and a heavy chain nucleic acid sequence comprising SEQ ID NO:85. In specific embodiments, the antibody of this invention comprises a light chain nucleic acid sequence comprising SEQ ID NO:70 and a heavy chain nucleic acid sequence comprising SEQ ID NO:86. In specific embodiments, the antibody of this invention comprises a light chain nucleic acid sequence comprising SEQ ID NO:71 and a heavy chain nucleic acid sequence comprising SEQ ID NO:87. In specific embodiments, the antibody of this invention comprises a light chain nucleic acid sequence comprising SEQ ID NO:72 and a heavy chain nucleic acid sequence comprising SEQ ID NO:88. In specific embodiments, the antibody of this invention comprises a light chain nucleic acid sequence comprising SEQ ID NO:73 and a heavy chain nucleic acid sequence comprising SEQ ID NO:89. In specific embodiments, the antibody of this invention comprises a light chain nucleic acid sequence comprising SEQ ID NO:74 and a heavy chain nucleic acid sequence comprising SEQ ID NO:90.

In certain embodiments, the anti-FGFR2/3 antibody comprises a light chain amino acid sequence comprising SEQ ID NO:65 and a heavy chain nucleic acid sequence comprising SEQ ID NO:81. In specific embodiments, the anti-FGFR2/3 antibody has the following CDRs:

```
                                      (SEQ ID NO: 1)
         HVR-L1: RASQDVDTSLA (SEQ ID NO: 2)
         HVR-L2: SASFLYS (SEQ ID NO: 3)
         HVR-L3: QQSTGHPQT (SEQ ID NO: 4)
         HVR-H1: GFPFTSQGIS (SEQ ID NO: 5)
         HVR-H2: RTHLGDGSTNYADSVKG (SEQ ID NO: 6)
         HVR-H3: ARTYGIYDTYDKYTEYVMDY
```

In certain embodiments, the anti-FGFR2/3 antibody comprises a light chain amino acid sequence comprising SEQ ID NO:66 and a heavy chain nucleic acid sequence comprising SEQ ID NO:82. In certain embodiments, the anti-FGFR2/3 antibody has the following CDRs:

```
                                               (SEQ ID NO: 1)
HVR-L1: RASQDVDTSLA (SEQ ID NO: 2)
HVR-L2: SASFLYS (SEQ ID NO: 3)
HVR-L3: QQSTGHPQT (SEQ ID NO: 10)
HVR-H1: GFPFTSTGIS (SEQ ID NO: 5)
HVR-H2: RTHLGDGSTNYADSVKG (SEQ ID NO: 12)
HVR-H3: ARTYGIYDTYDMYTEYVMDY
```

In certain embodiments the anti-FGFR2/3 antibody binds to a region within amino acids 153-251 of a FGFR2 (SEQ ID NOs:52 and 54):

```
                                             (SEQ ID NO: 313)
APYWTNTEKMEKRLHAVPAANTVKFRCPAGGNPMPTMRWLKNGKEFKQEH

RIGGYKVRNQHWSLIMESVVPSDKGNYTCVVENEYGSINHTYHLDVVER.
```

In certain embodiments the anti-FGFR2/3 antibody binds to a region within amino acids 150-248 of a FGFR3 (SEQ ID NOs:56 and 58):

```
                                             (SEQ ID NO: 314)
APYWTRPERMDKKLLAVPAANTVRFRCPAAGNPTPSISWLKNGREFRGEH

RIGGIKLRHQQWSLVMESVVPSDRGNYTCVVENKFGSIRQTYTLDVLER.
```

In a preferred embodiment the anti-FGFR2/3 antibody binds to a region within amino acids 153-251 of a FGFR2 (SEQ ID NOs:52 and 54) and to a region within amino acids 150-248 of a FGFR3 (SEQ ID NOs:56 and 58).

In certain embodiments the anti-FGFR2/3 antibody binds to a region within amino acids 157-181 (TNTEKMEKRL-HAVPAANTVKFRCPA (SEQ ID NO:91)) of a FGFR2 (SEQ ID NOs:52 and 54) (FIG. 9). In certain embodiments the anti-FGFR2/3 antibody binds to a region within amino acids 207-220 (YKVRNQHWSLIMES (SEQ ID NO:92)) of a FGFR2 (SEQ ID NOs:52 and 54) (FIG. 9). In specific embodiments, the anti-FGFR2/3 antibody binds to a region of FGFR2-IIIb that aligns with SEQ ID NO:52. In specific embodiments, the anti-FGFR2/3 antibody binds to a region of FGFR2-IIIc that aligns with SEQ ID NO:54.

In certain embodiments, the anti-FGFR2/3 antibody binds to amino acids 157-181 (TNTEKMEKRLHAVPAANTVK-FRCPA (SEQ ID NO:91)) of FGFR2-IIIb (SEQ ID NO:52). In certain embodiments, the anti-FGFR2/3 antibody binds to amino acids 157-181 of FGFR2-IIIc (SEQ ID NO:54). In certain embodiments, the anti-FGFR2/3 antibody binds to amino acids 207-220 (YKVRNQHWSLIMES (SEQ ID NO:92)) of a FGFR2 (SEQ ID NOs:52 and 54) (FIG. 9). In certain embodiments, the anti-FGFR2/3 antibody binds to amino acids 207-220 of FGFR2-IIIb (SEQ ID NO:52). In certain embodiments, the anti-FGFR2/3 antibody binds to amino acids 207-220 of FGFR2-IIIc (SEQ ID NO:54).

In a specific embodiment, the anti-FGFR2/3 antibody binds to a region within amino acids 157-181(TNTEKME-KRLHAVPAANTVKFRCPA (SEQ ID NO:91)) of a FGFR2 (SEQ ID NOs:52 and 54) and to a region within amino acids 207-220 (YKVRNQHWSLIMES (SEQ ID NO:92)) of FGFR2-IIIb (SEQ ID NOs:52 and 54). In a specific embodiment, the anti-FGFR2/3 antibody binds to amino acids 157-181(TNTEKMEKRLHAVPAANTVKFRCPA (SEQ ID NO:91)) of a FGFR2 (SEQ ID NOs:52 and 54) and to amino acids 207-220 (YKVRNQHWSLIMES (SEQ ID NO:92)) of FGFR2-IIIb (SEQ ID NOs:52 and 54).

In certain embodiments the anti-FGFR2/3 antibody binds to a region within amino acids 154-178 (TRPERMDKKL-LAVPAANTVRFRCPA (SEQ ID NO:93)) of FGFR3-IIIb (SEQ ID NO:56). In certain embodiments the anti-FGFR2/3 antibody binds to a region within amino acids 154-178 (TRPERMDKKLLAVPAANTVRFRCPA (SEQ ID NO:93)) of FGFR3-IIIc (SEQ ID NO:58). In certain embodiments the anti-FGFR2/3 antibody binds to a region within amino acids 204-217 (IKLRHQQWSLVMES (SEQ ID NO:94)) of FGFR3-IIIb (SEQ ID NO:56). In certain embodiments the anti-FGFR2/3 antibody binds to a region within amino acids 204-217 (IKLRHQQWSLVMES (SEQ ID NO:94)) of FGFR3-IIIc (SEQ ID NO:58). In specific embodiments, the anti-FGFR2/3 antibody binds to a region of FGFR3-IIIb that aligns with SEQ ID NO:56. In specific embodiments, the anti-FGFR2/3 antibody binds to a region of FGFR3-IIIb that aligns with SEQ ID NO:58.

In specific embodiments, the anti-FGFR2/3 antibody binds to amino acids 154-178 (TRPERMDKKLLAV-PAANTVRFRCPA (SEQ ID NO:93)) of FGFR3-IIIb (SEQ ID NO:56). In specific embodiments, the anti-FGFR2/3 antibody binds to amino acids 154-178 (TRPERMDKKL-LAVPAANTVRFRCPA (SEQ ID NO:93)) of FGFR3-IIIc (SEQ ID NO:58). In specific embodiments, the anti-FGFR2/3 antibody binds to amino acids 204-217 (IKL-RHQQWSLVMES (SEQ ID NO:94)) of FGFR3-IIIb (SEQ ID NO:56). In specific embodiments, the anti-FGFR2/3 antibody binds to amino acids 204-217 (IKLRHQQWS-LVMES (SEQ ID NO:94)) of FGFR3-IIIc (SEQ ID NO:58).

In a preferred embodiment, the anti-FGFR2/3 antibody binds to the following epitopes of an FGFR2: TNTEKME-KRLHAVPAANTVKFRCPA (SEQ ID NO:91) and YKVRNQHWSLIMES (SEQ ID NO:92). In a preferred embodiment, the anti-FGFR2/3 antibody binds to the following epitopes of an FGFR3: TRPERMDKKLLAV-PAANTVRFRCPA (SEQ ID NO:93) and IKLRHQQWS-LVMES (SEQ ID NO:94). In preferred embodiments, the anti-FGFR2/3 antibody binds to following epitopes:

```
FGFR2:
                                             (SEQ ID NO: 91)
    TNTEKMEKRLHAVPAANTVKFRCPA
    and (SEQ ID NO: 92)
    YKVRNQHWSLIIVIES,
    and FGFR3:
                                             (SEQ ID NO: 93)
    TRPERMDKKLLAVPAANTVRFRCPA
    and (SEQ ID NO: 94)
    IKLRHQQWSLVMES.
```

In certain embodiments, the anti-FGFR2/3 antibody binds to SEQ ID NOs:91-94. In certain embodiments, the anti-FGFR2/3 antibody binds to SEQ ID NOs:91 and 92. In certain embodiments, the anti-FGFR2/3 antibody binds to SEQ ID NOs:91-93. In certain embodiments, the anti- FGFR2/3 antibody binds to SEQ ID NOs:91, 93, and 94. In certain embodiments, the anti-FGFR2/3 antibody binds to SEQ ID NOs:91 and 94. In certain embodiments, the anti-FGFR2/3 antibody binds to SEQ ID NOs:92-94. In certain embodiments, the anti-FGFR2/3 antibody binds to SEQ ID NOs:92 and 93. In certain embodiments, the anti-FGFR2/3 antibody binds to SEQ ID NOs:92 and 94. In certain embodiments, the anti-FGFR2/3 antibody binds to SEQ ID NOs:93 and 91. In certain embodiments, the anti-FGFR2/3 antibody binds to SEQ ID NOs:91, 92, and 94. In certain embodiments, the anti-FGFR2/3 antibody binds to a combination of any two or more epitopes provided in SEQ ID NOs:91-94.

In certain embodiments, the anti-FGFR2/3 antibody binds to a region within amino acids 153-251 of FGFR2-IIIb (SEQ ID NO:52). In certain embodiments, the anti-FGFR2/3 antibody binds to a region within amino acids 153-251 of FGFR2-IIIc (SEQ ID NO:54). In preferred embodiments, the anti-FGFR2/3 antibody binds to a region within amino acids 153-251 of FGFR2-IIIb (SEQ ID NO:52) and FGFR2-IIIc (SEQ ID NO:54). In certain embodiments, the anti-FGFR2/3 antibody binds to a region within amino acids 150-248 of FGFR3-IIIb (SEQ ID NO:56). In certain embodiments, the anti-FGFR2/3 antibody binds to a region within amino acids 150-248 of FGFR3-IIIb (SEQ ID NO:58). In preferred embodiments, the anti-FGFR2/3 antibody binds to a region within amino acids 150-248 of FGFR3-IIIb (SEQ ID NO:56) and FGFR3-IIIc (SEQ ID NO:58).

In a preferred embodiment, the anti-FGFR2/3 antibody binds to a region within amino acids 153-251 of FGFR2-IIIb (SEQ ID NO:52) and/or FGFR2-IIIc (SEQ ID NO:54) and to a region within amino acids 150-248 of FGFR3-IIIb (SEQ ID NO:56) and/or FGFR3-IIIc (SEQ ID NO:58).

In some embodiments, the anti-FGFR2/3 antibody binds to an epitope comprising one or more amino acids selected from T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody binds to an epitope comprising amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 4 angstroms or less from one or more amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 4 angstroms or less from amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 3.5 angstroms or less from one or more amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 3.5 angstroms or less from amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 3.0 angstroms or less from one or more amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 3.0 angstroms or less from amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 4.0, 3.75, 3.5, 3.25, or 3.0 angstroms or less from one or more amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the anti-FGFR2/3 antibody when bound to FGFR2 is positioned 4.0, 3.75, 3.5, 3.25, or 3.0 angstroms or less from amino acids T157, N158, T159, E160, K161, M162, E163, K164, R165, L166, H167, A168, V169, P170, A171, A172, N173, T174, V175, K176, F177, R178, C179, P180, and A181 of FGFR2 (e.g., SEQ ID NOs:52 and 54). In some embodiments, the one or more amino acids and/or the one or more amino acid residues is about any of 1, 2, 3, 4, 5, 6, 7, 8, 9, 10, 11, and/or 12 amino acids and/or amino acid residues. In some embodiments, the epitope is determined by crystallography (e.g., crystallography methods described in the Examples). In preferred embodiments, the anti-FGFR2/3 antibody binds to human FGFR2 (hFGFR2) (e.g., SEQ ID NOs:52 and 54).

In some embodiments, the anti-FGFR2/3 antibody binds to an epitope comprising one or more amino acids selected from Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody binds to an epitope comprising amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 4 angstroms or less from one or more amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 4 angstroms or less from amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 3.5 angstroms or less from one or more amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 3.5 angstroms or less from amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 3.0 angstroms or less from one or more amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 3.0 angstroms or less from amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 4.0, 3.75, 3.5, 3.25, or 3.0 angstroms or less from one or more amino acids Y207, K208, V209, R210, N211, Q212, H213, W214, S215, L216, I217, M218, E219, and S220 of FGFR2 (e.g., SEQ ID NOs:52 and 54). In some embodiments, the anti-FGFR2/3 antibody when bound to FGFR2 is positioned 4.0, 3.75, 3.5, 3.25, or 3.0 angstroms or less from amino acids Y207, K208, V209, R210, N211, Q212, H213, W214, S215, L216, I217, M218, E219, and S220 of FGFR2 (e.g., SEQ ID NOs:52 and 54). In some embodiments, the one or more amino acids and/or the one or more amino acid residues is about any of 1, 2, 3, 4, 5, 6, 7, 8, 9, 10, 11, and/or 12 amino acids and/or amino acid residues. In some embodiments, the epitope is determined by crystallography (e.g., crystallography methods described in the Examples). In preferred embodiments, the anti-FGFR2/3 antibody binds to human FGFR2 (hFGFR2) (e.g., SEQ ID NOs:52 and 54).

In some embodiments, the anti-FGFR2/3 antibody binds to an epitope comprising one or more amino acids selected from T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody binds to an epitope comprising amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 4 angstroms or less from one or more amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 4 angstroms or less from amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 3.5 angstroms or less from one or more amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 3.5 angstroms or less from amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 3.0 angstroms or less from one or more amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 3.0 angstroms or less from amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 4.0, 3.75, 3.5, 3.25, or 3.0 angstroms or less from one or more amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the anti-FGFR2/3 antibody when bound to FGFR3 is positioned 4.0, 3.75, 3.5, 3.25, or 3.0 angstroms or less from amino acids T154, R155, P156, E157, R158, M159, D160, K161, K162, L163, L164, A165, V166, P167, A168, A169, N170, T171, V172, R173, F174, R175, C176, P177, and A178 of FGFR3 (e.g., SEQ ID NOs:56 and 58). In some embodiments, the one or more amino acids and/or the one or more amino acid residues is about any of 1, 2, 3, 4, 5, 6, 7, 8, 9, 10, 11, and/or 12 amino acids and/or amino acid residues. In some embodiments, the epitope is determined by crystallography (e.g., crystallography methods described in the Examples). In preferred embodiments, the anti-FGFR2/3 antibody binds to human FGFR3 (hFGFR3) (e.g., SEQ ID NOs:56 and 58).

In some embodiments, the anti-FGFR2/3 antibody binds to an epitope comprising one or more amino acids selected from I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody binds to an epitope comprising amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 4 angstroms or less from one or more amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 4 angstroms or less from amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 3.5 angstroms or less from one or more amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 3.5 angstroms or less from amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 3.0 angstroms or less from one or more amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 3.0 angstroms or less from amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 4.0, 3.75, 3.5, 3.25, or 3.0 angstroms or less from one or more amino acids I204, K205, L206, R207, H208, Q209, Q210, W211, S212, L213, V214, M215, E216, and S217 of FGFR3 (e.g., SEQ ID NOs:56 and 58). In some embodiments, the anti-FGFR2/3 antibody when bound to FGFR3 is positioned 4.0, 3.75, 3.5, 3.25, or 3.0 angstroms or less from amino acids I204, K205, L206, R207, H208, Q209, Q210, W211, S212, L213, V214, M215, E216, and S217 of FGFR3 (e.g., SEQ ID NOs:56 and 58). In some embodiments, the one or more amino acids and/or the one or more amino acid residues is about any of 1, 2, 3, 4, 5, 6, 7, 8, 9, 10, 11, and/or 12 amino acids and/or amino acid residues. In some embodiments, the epitope is determined by crystallography (e.g., crystallography methods described in the Examples). In preferred embodiments, the anti-FGFR2/3 antibody binds to human FGFR3 (hFGFR3) (e.g., SEQ ID NOs:56 and 58).

In specific embodiments, the anti-FGFR2/3 antibody binds to one epitope on FGFR2 selected from SEQ ID NOs: 91 and 92 and one epitope on FGFR3 selected from SEQ ID NOs: 93 and 94. In certain embodiments, the anti-FGFR2/3 antibody binds to two epitopes on FGFR2 comprising SEQ ID NOs: 91 and 92 and one epitope on FGFR3 selected from SEQ ID NOs: 93 and 94. In certain embodiments, the anti-FGFR2/3 antibody binds to one epitope on FGFR2 selected from SEQ ID NOs: 91 and 92 and two epitopes on FGFR3 comprising SEQ ID NOs: 93 and 94. In a preferred embodiment, the anti-FGFR2/3 antibody binds to two epitopes on FGFR2 comprising SEQ ID NOs: 91 and 92 and two epitopes on FGFR3 comprising SEQ ID NOs: 93 and 94 (FIG. 9).

In one aspect, the invention provides an anti-FGFR2/3 antibody that binds a polypeptide comprising, consisting essentially of or consisting of the following amino acid sequence: TNTEKMEKRLHAVPAANTVKFRCPA (SEQ ID NO:91) and/or YKVRNQHWSLIMES (SEQ ID NO:92).

In one aspect, the invention provides an anti-FGFR2/3 antibody that binds a polypeptide comprising, consisting essentially of or consisting of the following amino acid sequence: TRPERMDKKLLAVPAANTVRFRCPA (SEQ ID NO:93) and/or IKLRHQQWSLVMES (SEQ ID NO:94).

In one aspect, the invention provides an anti-FGFR2/3 antibody that binds a polypeptide comprising, consisting essentially of or consisting of the following amino acid sequence: TNTEKMEKRLHAVPAANTVKFRCPA (SEQ ID NO:91) or YKVRNQHWSLIMES (SEQ ID NO:92) and TRPERMDKKLLAVPAANTVRFRCPA (SEQ ID NO:93) or IKLRHQQWSLVMES (SEQ ID NO:94).

In one embodiment, an anti-FGFR2/3 antibody of the invention specifically binds an amino acid sequence having at least 50%, 60%, 70%, 80%, 90%, 95%, 96%, 97%, 98%, or 99% sequence identity or similarity with the sequence TNTEKMEKRLHAVPAANTVKFRCPA (SEQ ID NO:91) and/or YKVRNQHWSLIMES (SEQ ID NO:92). In one embodiment, an anti-FGFR2/3 antibody of the invention specifically binds an amino acid sequence having at least 50%, 60%, 70%, 80%, 90%, 95%, 96%, 97%, 98%, or 99% sequence identity or similarity with the sequence TRPERMDKKLLAVPAANTVRFRCPA (SEQ ID NO:93) and/or IKLRHQQWSLVMES (SEQ ID NO:94).

In one embodiment, an anti-FGFR2/3 antibody of the invention specifically binds an amino acid sequence having at least 50%, 60%, 70%, 80%, 90%, 95%, 96%, 97%, 98%, or 99% sequence identity or similarity with the sequence TNTEKMEKRLHAVPAANTVKFRCPA (SEQ ID NO:91) or YKVRNQHWSLIMES (SEQ ID NO:92) and an amino acid sequence having at least 50%, 60%, 70%, 80%, 90%, 95%, 96%, 97%, 98%, or 99% sequence identity or similarity with the sequence TRPERMDKKLLAVPAANTVRFRCPA (SEQ ID NO:93) or IKLRHQQWSLVMES (SEQ ID NO:94).

One of ordinary skill in the art understands how to align FGFR3 sequences in order identify corresponding residues between respective FGFR3 sequences. Similarly, one of ordinary skill in the art understands how to align FGFR2 sequences in order identify corresponding residues between respective FGFR2 sequences.

In one aspect, the invention provides an anti-FGFR2/3 antibody that competes with any of the above-mentioned antibodies for binding to FGFR3 and/or FGFR2. In one aspect, the invention provides an anti-FGFR2/3 antibody that binds to the same or a similar epitope on FGFR3 and/or FGFR2 as any of the above-mentioned antibodies.

As is known in the art, and as described in greater detail herein, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below).

In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is an antibody fragment. In some embodiments, the antibody is a Fab, Fab', Fab'-SH, F(ab')$_2$, or scFv.

In some embodiment, the FGFR2/3 antibody is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex and form a Fc region that increases stability of said antibody fragment compared to a Fab molecule comprising said antigen binding arm. See, e.g., WO2006/015371.

In one embodiment, the antibody is a chimeric antibody, for example, an antibody comprising antigen binding sequences from a non-human donor grafted to a heterologous non-human, human, or humanized sequence (e.g., framework and/or constant domain sequences). In one embodiment, the non-human donor is a mouse. In a further embodiment, an antigen binding sequence is synthetic, e.g., obtained by mutagenesis (e.g., phage display screening, etc.). In a particular embodiment, a chimeric antibody of the invention has murine V regions and a human C region. In one embodiment, the murine light chain V region is fused to a human kappa light chain. In another embodiment, the murine heavy chain V region is fused to a human IgG1 C region.

Humanized antibodies of the invention include those that have amino acid substitutions in the framework region (FR) and affinity maturation variants with changes in the grafted CDRs. The substituted amino acids in the CDR or FR are not limited to those present in the donor or recipient antibody. In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. In other embodiments, the antibodies of the invention comprise changes in amino acid residues in the Fc region that lead to decreased effector function, e.g., decreased CDC and/or ADCC function and/or decreased B-cell killing. In some embodiments, the antibodies of the invention are characterized by decreased binding (such as absence of binding) to human complement factor C1q and/or human Fc receptor on natural killer (NK) cells. In some embodiments, the antibodies of the invention are characterized by decreased binding (such as the absence of binding) to human FcγRI, FcγRIIA, and/or FcγRIIIA. In some embodiments, the antibodies of the invention are of the IgG class (e.g., IgG1 or IgG4) and comprise at least one mutation in E233, L234, G236, D265, D270, N297, E318, K320, K322, A327, A330, P331, and/or P329 (numbering according to the EU index). In some embodiments, the antibodies comprise the mutations L234A/L235A or D265A/N297A.

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108. See also US 2004/0093621. Antibodies with a bisecting N-acetylglucosamine (GlcNAc) in the carbohydrate attached to an Fc region of the antibody are referenced in WO 2003/011878 and U.S. Pat. No. 6,602,684. Antibodies with at least one galactose residue in the oligosaccharide attached to an Fc region of the antibody are reported in WO 1997/30087. See also, WO 1998/58964 and WO 1999/22764 concerning antibodies with altered carbohydrate attached to the Fc region thereof. See also US 2005/0123546 on antigen-binding molecules with modified glycosylation. In one aspect, the invention provides FGFR3 binding polypeptides comprising any of the antigen binding sequences provided herein, wherein the FGFR3 binding polypeptides specifically bind to a FGFR3, e.g., a human and/or cyno and/or mouse FGFR3.

The antibodies of the invention bind (such as specifically bind) FGFR3 (e.g. FGFR3-IIIb and/or FGFR3-IIIc) and FGFR2 (e.g. FGFR2-IIIb and/or FGFR2-IIIc), and in some embodiments, may modulate (e.g. inhibit) one or more aspects of FGFR3 and/or FGFR2 signaling (such as FGFR3 phosphorylation) and/or disruption of any biologically relevant FGFR3 and/or FGFR3 ligand biological pathway and/or disruption of any biologically relevant FGFR2 and/or FGFR2 ligand biological pathway, and/or treatment and/or prevention of a tumor, cell proliferative disorder or a cancer; and/or treatment or prevention of a disorder associated with FGFR3 and/or FGFR2 expression and/or activity (such as increased FGFR3 and/or FGFR2 expression and/or activity). In some embodiments, the FGFR2/3 antibody specifically binds to a polypeptide consisting essentially of or consisting essentially of a FGFR3 (e.g., a human or mouse FGFR3) and/or a FGFR2 (e.g., a human or mouse FGFR3). In some embodiments, the antibody specifically binds FGFR3 with a Kd of $1 \times 10^{-7}$ M or higher affinity. In some embodiments, the antibody specifically binds FGFR2 with a Kd of $1 \times 10^{-7}$ M or higher affinity. In some embodiments, the antibody specifically binds FGFR3 and FGF2 with Kds of $1 \times 10^{-7}$ M or higher affinity.

In some embodiments, the anti-FGFR2/3 antibody of the invention is not an anti-FGFR3 antibody described in U.S. Patent Publication no. 2005/0147612 (e.g., antibody MSPRO2, MSPRO12, MSPRO59, MSPRO11, MSPRO21, MSPRO24, MSPRO26, MSPRO28, MSPRO29, MSPRO43, MSPRO55), antibody described in Rauchenberger et al, J Biol Chem 278 (40):38194-38205 (2003); an antibody described in PCT Publication No. WO2006/048877 (e.g., antibody PRO-001), an antibody described in Martinez-Torrecuadrada et al, Mol Cancer Ther (2008) 7(4): 862-873 (e.g., scFvαFGFR3 3C), an antibody described in Direnzo, R et al (2007) Proceedings of AACR Annual Meeting, Abstract No. 2080 (e.g., D11), or an antibody described in WO 2010/002862 (e.g., antibodies 15D8, 27H2, 4E7, 2G4, 20B4).

In one aspect, the invention provides compositions comprising one or more antibodies of the invention and a carrier. In one embodiment, the carrier is pharmaceutically acceptable.

In another aspect, the invention provides nucleic acids encoding a FGFR2/3 antibody of the invention.

In yet another aspect, the invention provides vectors comprising a nucleic acid of the invention.

In a further aspect, the invention provides compositions comprising one or more nucleic acids of the invention and a carrier. In one embodiment, the carrier is pharmaceutically acceptable.

In one aspect, the invention provides host cells comprising a nucleic acid or a vector of the invention. A vector can be of any type, for example, a recombinant vector such as an expression vector. Any of a variety of host cells can be used. In one embodiment, a host cell is a prokaryotic cell, for example, E. coli. In another embodiment, a host cell is a eukaryotic cell, for example a mammalian cell such as Chinese Hamster Ovary (CHO) cell.

In a further aspect, the invention provides methods of making an antibody of the invention. For example, the invention provides methods of making an anti-FGFR2/3 antibody (which, as defined herein includes full length antibody and fragments thereof), said method comprising expressing in a suitable host cell a recombinant vector of the invention encoding the antibody, and recovering the antibody. In some embodiments, the method comprises culturing a host cell comprising nucleic acid encoding the antibody so that the nucleic acid is expressed. In some embodiments, the method further comprises recovering the antibody from the host cell culture. In some embodiments, the antibody is recovered from the host cell culture medium. In some embodiments, the method further comprises combining the recovered antibody with a pharmaceutically acceptable carrier, excipient, or carrier to prepare a pharmaceutical formulation comprising the humanized antibody.

In one aspect, the invention provides an article of manufacture comprising a container; and a composition contained within the container, wherein the composition comprises one or more FGFR2/3 antibodies of the invention. In one embodiment, the composition comprises a nucleic acid of the invention. In another embodiment, a composition comprising an antibody further comprises a carrier, which in some embodiments is pharmaceutically acceptable. In one embodiment, an article of manufacture of the invention further comprises instructions for administering the composition (e.g., the antibody) to an individual (such as instructions for any of the methods described herein).

In another aspect, the invention provides a kit comprising a first container comprising a composition comprising one or more anti-FGFR2/3 antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In another embodiment, a kit further comprises instructions for administering the composition (e.g., the antibody) to an individual.

In a further aspect, the invention provides an anti-FGFR2/3 antibody of the invention for use as a medicament.

In a further aspect, the invention provides an anti-FGFR2/3 antibody of the invention for use in treating or preventing a disorder, such as a pathological condition associated with FGFR3 activation and/or expression (in some embodiments, over-expression). In a further aspect, the invention provides an anti-FGFR2/3 antibody of the invention for use in treating or preventing a disorder, such as a pathological condition associated with FGFR2 activation and/or expression (in some embodiments, over-expression). In a further aspect, the invention provides an anti-FGFR2/3 antibody of the invention for use in treating or preventing a disorder, such as a pathological condition associated with FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer.

In a further aspect, the invention provides an anti-FGFR2/3 antibody of the invention for use in treating or preventing a disorder such as a skeletal disorder. In some embodiments, the disorder is achondroplasia, hypochondroplasia, dwarfism, thantophoric dysplasia (TD; clinical forms TD1 and TDII), or craniosynostosis syndrome.

In a further aspect, the invention provides an anti-FGFR2/3 antibody of the invention for use in reducing cell proliferation.

In a further aspect, the invention provides an anti-FGFR2/3 antibody of the invention for use in killing a cell. In some embodiments, the cell is a multiple myeloma cell. In some embodiments, the cell is killed by ADCC. In some embodiments, the antibody is a naked antibody. In some embodiments, the cell over-expresses FGFR3. In some embodiments, the cell over-expresses FGFR2. In some embodiments, the cell over-expresses FGFR2 and FGFR3.

In a further aspect, the invention provides an anti-FGFR2/3 antibody of the invention for use in depleting cells, such as multiple myeloma cells. In some embodiments, the cell is killed by ADCC. In some embodiments, the antibody is a naked antibody. In some embodiments, the cell over-expresses FGFR3.

In a further aspect, the invention provides use of an anti-FGFR2/3 antibody of the invention in the preparation of a medicament for the therapeutic and/or prophylactic treatment of a disorder, such as a pathological condition associated with FGFR3, FGFR2, or FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In one aspect, the invention provides use of a nucleic acid of the invention in the preparation of a medicament for the therapeutic and/or prophylactic treatment of a disorder, such as a pathological condition associated with FGFR3, FGFR2, or FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In another aspect, the invention provides use of an expression vector of the invention in the preparation of a medicament for the therapeutic and/or prophylactic treatment of a disorder, such as a pathological condition associated with FGFR3, FGFR2, or FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In yet another aspect, the invention provides use of a host cell of the invention in the preparation of a medicament for the therapeutic and/or prophylactic treatment of a disorder, such as a pathological condition associated with FGFR3, FGFR2, or FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In a further aspect, the invention provides use of an article of manufacture of the invention in the preparation of a medicament for the therapeutic and/or prophylactic treatment of a disorder, such as a pathological condition associated with FGFR3, FGFR2, or FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In one aspect, the invention also provides use of a kit of the invention in the preparation of a medicament for the therapeutic and/or prophylactic treatment of a disorder, such as a pathological condition associated with FGFR3, FGFR2, or FGFR2 and FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In a further aspect, the invention provides use of an anti-FGFR2/3 antibody of the invention in the preparation of a medicament for inhibition of cell proliferation. In a further aspect, the invention provides use of an anti-FGFR2/3 antibody of the invention in the preparation of a medicament for cell killing. In some embodiments, the cell is a multiple myeloma cell. In some embodiments, the cell is killed by ADCC. In some embodiments, the antibody is a naked antibody. In some embodiments, the cell over-expresses FGFR3. In some embodiments, the cell over-expresses FGFR2. In some embodiments, the cell over-expresses FGFR3 and FGFR2.

In a further aspect, the invention provides use of an anti-FGFR2/3 antibody of the invention in the preparation of a medicament for depleting cells, such as multiple myeloma cells. In some embodiments, the cell is killed by ADCC. In some embodiments, the antibody is a naked antibody. In some embodiments, the cell over-expresses FGFR3. In some embodiments, the cell over-expresses FGFR2. In some embodiments, the cell over-expresses FGFR3 and FGFR2.

The invention provides methods and compositions useful for modulating disorders associated with expression and/or signaling of FGFR3, such as increased expression and/or signaling or undesired expression and/or signaling. The invention provides methods and compositions useful for modulating disorders associated with expression and/or signaling of FGFR2, such as increased expression and/or signaling or undesired expression and/or signaling. The invention provides methods and compositions useful for modulating disorders associated with expression and/or signaling of FGFR3 and FGFR2, such as increased expression and/or signaling or undesired expression and/or signaling.

Methods of the invention can be used to affect any suitable pathological state. Exemplary disorders are described herein, and include a cancer selected from the group consisting of non-small cell lung cancer, ovarian cancer, thyroid cancer, testicular cancer, endometrial cancer, head and neck cancer, brain cancer (e.g., neuroblastoma or meningioma), skin cancer (e.g., melanoma, basal cell carcinoma, or squamous cell carcinoma), bladder cancer (e.g., transitional cell carcinoma), breast carcinoma, gastric cancer, colorectal cancer (CRC), hepatocellular carcinoma, cervical cancer, lung cancer, pancreatic cancer, prostate cancer, and hematologic malignancies (e.g., T-cell acute lymphoblastic leukemia (T-ALL), B-cell acute lymphoblastic leukemia (B-ALL), acute myelogenous leukemia (AML), B-cell malignancies, Hodgkin lymphoma, and multiple myeloma). In some embodiments, the disorder is invasive transitional cell carcinoma. In some embodiments, the disorder is multiple myeloma. Additional exemplary disorders include skeletal disorders, such as achondroplasia, hypochondroplasia, dwarfism, thantophoric dysplasia (TD; clinical forms TD1 and TDII), or craniosynostosis syndrome.

In certain embodiments, the cancer expresses FGFR3, amplified FGFR3, translocated FGFR3, and/or mutated FGFR3. In certain embodiments, the cancer expresses activated FGFR3. In certain embodiments, the cancer expresses translocated FGFR3 (e.g., a t(4; 14) translocation). In certain embodiments, the cancer expresses constitutive FGFR3. In some embodiments, the constitutive FGFR3 comprises a mutation in the tyrosine kinase domain and/or the juxtamembrane domain and/or a ligand-binding domain. In certain embodiments, the cancer expresses ligand-independent FGFR3. In some embodiments, the cancer expresses ligand-dependent FGFR3.

In some embodiments, the cancer expresses FGFR3 comprising a mutation corresponding to FGFR3-IIIb$^{S248C}$. In some embodiments, the cancer expressed FGFR3-IIIb$^{S248C}$ and/or FGFR3-IIIc$^{S248C}$.

In some embodiments, the cancer expresses FGFR3 comprising a mutation corresponding to FGFR3-IIIb$^{K652E}$. In some embodiments, the cancer expressed FGFR3-IIIb$^{K652E}$ and/or FGFR3-IIIc$^{K650E}$.

FGFR3 comprising a mutation corresponding to FGFR3-IIIb$^{S249C}$. In some embodiments, the cancer expresses FGFR3-IIIb$^{S249C}$ and/or FGFR3-IIIc$^{S249C}$.

In one aspect, the cancer expresses FGFR3 comprising a mutation corresponding to FGFR3-IIIb$^{G372C}$. In some embodiments, the cancer expresses FGFR3-IIIb$^{G372C}$ and/or FGFR3-IIIc$^{G370C}$.

In one aspect, the cancer expresses FGFR3 comprising a mutation corresponding to FGFR3-IIIb$^{Y375C}$. In some embodiments, the cancer expresses FGFR3-IIIb$^{Y375C}$ and/or FGFR3-IIIc$^{Y373C}$.

In some embodiments, the cancer expresses (a) FGFR3-IIIb$^{K652E}$ and (b) one or more of FGFR3-IIIb$^{R248C}$, FGFR3-IIIb$^{Y375C}$, FGFR3-IIIb$^{S249C}$, and FGFR3IIIb$^{G372C}$.

In some embodiments, the cancer expresses (a) FGFR3-IIIb$^{R248C}$ and (b) one or more of FGFR3-IIIb$^{K652E}$, FGFR3-IIIb$^{Y375C}$, FGFR3-IIIb$^{S249C}$, and FGFR3-IIIb$^{G372C}$.

In some embodiments, the cancer expresses (a) FGFR3-IIIb$^{G372C}$ and (b) one or more of FGFR3-IIIb$^{K652E}$, FGFR3-IIIb$^{Y375C}$, FGFR3-IIIb$^{S249C}$, and FGFR3-IIIb$^{R248C}$.

In some embodiments, the cancer expresses FGFR3-IIIb$^{R248C}$, FGFR3-IIIb$^{K652E}$, FGFR3-IIIb$^{Y375C}$, FGFR3-IIIb$^{S249C}$, and FGFR3-IIIb$^{G372C}$.

In certain embodiments, the cancer expresses increased levels of phospho-FGFR3, phospho-FRS2 and/or phospho-MAPK relative to a control sample (e.g., a sample of normal tissue) or level.

In certain embodiments, the cancer expresses FGFR2, amplified FGFR2, translocated FGFR2, and/or mutated FGFR2. In certain embodiments, the cancer expresses activated FGFR2. In certain embodiments, the cancer expresses translocated FGFR2. In certain embodiments, the cancer expresses constitutive FGFR2. In certain embodiments, the cancer expresses ligand-independent FGFR2. In some embodiments, the cancer expresses ligand-dependent FGFR2.

In some embodiments, the cancer expresses FGFR2 comprising a mutation.

In certain embodiments, the cancer expresses: 1) FGFR3, amplified FGFR3, translocated FGFR3, and/or mutated FGFR3 and 2) FGFR2, amplified FGFR2, translocated FGFR2, and/or mutated FGFR2. In certain embodiments, the cancer expresses activated FGFR3 and a FGFR2 as described above. In certain embodiments, the cancer expresses translocated FGFR3 (e.g., a t(4;14) translocation) and a FGFR2 as described above. In certain embodiments, the cancer expresses constitutive FGFR3 and a FGFR2 as described above. In some embodiments, the constitutive FGFR3 comprises a mutation in the tyrosine kinase domain and/or the juxtamembrane domain and/or a ligand-binding domain. In certain embodiments, the cancer expresses ligand-independent FGFR3 and a FGFR2 as described above. In some embodiments, the cancer expresses ligand-dependent FGFR3 and a FGFR2 as described above.

In some embodiments, the cancer expresses FGFR3 comprising a mutation corresponding to FGFR3-IIIb$^{S248C}$ and a FGFR2 as described above (e.g. FGFR2, amplified FGFR2, translocated FGFR2, and/or mutated FGFR2). In some embodiments, the cancer expresses FGFR3-IIIb$^{S248C}$ and/or FGFR3-IIIc$^{S248C}$ and a FGFR2 as described above (e.g. FGFR2, amplified FGFR2, translocated FGFR2, and/or mutated FGFR2).

In some embodiments, the cancer expresses FGFR3 comprising a mutation corresponding to FGFR3-IIIb$^{K652E}$ and a FGFR2 as described above (e.g. FGFR2, amplified FGFR2, translocated FGFR2, and/or mutated FGFR2). In some embodiments, the cancer expresses FGFR3-IIIb$^{K652E}$ and/or FGFR3-IIIc$^{K650E}$ and a FGFR2 as described above (e.g. FGFR2, amplified FGFR2, translocated FGFR2, and/or mutated FGFR2).

FGFR3 comprising a mutation corresponding to FGFR3-IIIb$^{S249C}$ and a FGFR2 as described above (e.g. FGFR2, amplified FGFR2, translocated FGFR2, and/or mutated FGFR2). In some embodiments, the cancer expresses FGFR3-IIIb$^{S249C}$ and/or FGFR3-IIIc$^{S249C}$ and a FGFR2 as described above (e.g. FGFR2, amplified FGFR2, translocated FGFR2, and/or mutated FGFR2).

In one aspect, the cancer expresses FGFR3 comprising a mutation corresponding to FGFR3-IIIb$^{G372}$c and a FGFR2 as described above (e.g. FGFR2, amplified FGFR2, translocated FGFR2, and/or mutated FGFR2). In some embodiments, the cancer expresses FGFR3-IIIb$^{G372C}$ and/or FGFR3-IIIc$^{G370C}$ and a FGFR2 as described above (e.g. FGFR2, amplified FGFR2, translocated FGFR2, and/or mutated FGFR2).

In one aspect, the cancer expresses FGFR3 comprising a mutation corresponding to FGFR3-IIIb$^{Y375C}$ and a FGFR2 as described above (e.g. FGFR2, amplified FGFR2, translocated FGFR2, and/or mutated FGFR2). In some embodiments, the cancer expresses FGFR3-IIIb$^{G375C}$ and/or FGFR3-IIIc$^{Y373C}$ and a FGFR2 as described above (e.g. FGFR2, amplified FGFR2, translocated FGFR2, and/or mutated FGFR2).

In some embodiments, the cancer expresses (a) FGFR3-IIIb$^{K652E}$ and (b) one or more of FGFR3-IIIb$^{R248C}$, FGFR3-IIIb$^{Y375C}$, FGFR3-IIIb$^{S249C}$, and FGFR3IIIb$^{G372C}$ and (c) a FGFR2 as described above (e.g. FGFR2, amplified FGFR2, translocated FGFR2, and/or mutated FGFR2).

In some embodiments, the cancer expresses (a) FGFR3-IIIb$^{R248C}$ and (b) one or more of FGFR3-IIIb$^{K652E}$, FGFR3-IIIb$^{Y375C}$, FGFR3-IIIb$^{S249C}$, and FGFR3-IIIb$^{G372C}$ and (c) a FGFR2 as described above (e.g. FGFR2, amplified FGFR2, translocated FGFR2, and/or mutated FGFR2).

In some embodiments, the cancer expresses (a) FGFR3-IIIb$^{G372C}$ and (b) one or more of FGFR3-IIIb$^{K652E}$, FGFR3-IIIb$^{Y375C}$, FGFR3-IIIb$^{S249C}$, and FGFR3-IIIb$^{R248C}$ and (c) a FGFR2 as described above (e.g. FGFR2, amplified FGFR2, translocated FGFR2, and/or mutated FGFR2).

In some embodiments, the cancer expresses (a) FGFR3-IIIb$^{R248C}$, FGFR3-IIIb$^{K652E}$, FGFR3-IIIb$^{K375C}$, FGFR3-IIIb$^{S249C}$, and FGFR3-IIIb$^{G372C}$, and (b) a FGFR2 as described above (e.g. FGFR2, amplified FGFR2, translocated FGFR2, and/or mutated FGFR2).

In certain embodiments, the cancer expresses increased levels of phospho-FGFR3, phospho-FRS2 and/or phospho-MAPK relative to a control sample (e.g., a sample of normal tissue) or level and a FGFR2 as described above (e.g. FGFR2, amplified FGFR2, translocated FGFR2, and/or mutated FGFR2).

In some embodiments, the cancer expresses (e.g., on the cell surface) about 10,000 FGFR3 molecules per cell or more (such as 11,000, 12,000, 13,000, 14,000, 15,000, 16,000, 17,000, 18,000 or more FGFR3 receptors). In some embodiments, the cancer expresses about 13000 FGFR3 molecules. In other embodiments, the cancer expresses about 5000, 6000, 7000, 8000, or more FGFR3 molecules. In some embodiments, the cancer expresses less than about 4000, 3000, 2000, 1000, or fewer FGFR3 molecules. In some embodiments, the cancer expresses less than about 1000 FGFR3 molecules. In some embodiments, the cancer expresses (e.g., on the cell surface) about 10,000 FGFR2 molecules per cell or more (such as 11,000, 12,000, 13,000, 14,000, 15,000, 16,000, 17,000, 18,000 or more FGFR2 receptors). In some embodiments, the cancer expresses about 13000 FGFR2 molecules. In other embodiments, the cancer expresses about 5000, 6000, 7000, 8000, or more FGFR2 molecules. In some embodiments, the cancer expresses less than about 4000, 3000, 2000, 1000, or fewer FGFR2 molecules. In some embodiments, the cancer expresses less than about 1000 FGFR2 molecules. In some embodiments, the cancer expresses (e.g., on the cell surface) about 10,000 FGFR3 and 10,000 FGFR2 molecules per cell or more (such as 11,000, 12,000, 13,000, 14,000, 15,000, 16,000, 17,000, 18,000 or more FGFR3 receptors and 11,000, 12,000, 13,000, 14,000, 15,000, 16,000, 17,000, 18,000 or more FGFR2 receptors). In some embodiments, the cancer expresses about 13000 FGFR3 molecules and 13000 FGFR2 molecules. In other embodiments, the cancer expresses about 5000, 6000, 7000, 8000, or more FGFR3 molecules and about 5000, 6000, 7000, 8000, or more FGFR2 molecules. In some embodiments, the cancer expresses less than about 4000, 3000, 2000, 1000, or fewer FGFR3 molecules and less than about 4000, 3000, 2000, 1000, or fewer FGFR2 molecules. In some embodiments, the cancer expresses less than about 1000 FGFR3 molecules and less than about 1000 FGFR2 molecules.

In one embodiment, a cell that is targeted in a method of the invention is a cancer cell. For example, a cancer cell can be one selected from the group consisting of a breast cancer cell, a colorectal cancer cell, a lung cancer cell (e.g., a non-small cell lung cancer cell), a thyroid cancer cell, a multiple myeloma cell, a testicular cancer cell, a papillary carcinoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell (e.g., a transitional cell carcinoma cell), a gastric carcinoma cell, a head and neck squamous carcinoma cell, a melanoma cell, a leukemia cell, a multiple myeloma cell (e.g. a multiple myeloma cell comprising a t(4:14) FGFR3 translocation) and a colon adenoma cell. In one embodiment, a cell that is targeted in a method of the invention is a hyperproliferative and/or hyperplastic cell. In another embodiment, a cell that is targeted in a method of the invention is a dysplastic cell. In yet another embodiment, a cell that is targeted in a method of the invention is a metastatic cell.

In one aspect, the invention provides methods for inhibiting cell proliferation in a subject, the method comprising administering to the subject an effective amount of an anti-FGFR2/3 antibody to reduce cell proliferation.

In one aspect, the invention provides methods for killing a cell in a subject, the method comprising administering to the subject an effective amount of an anti-FGFR2/3 antibody to kill a cell. In some embodiments, the cell is a multiple myeloma cell. In some embodiments, the cell is killed by ADCC. In some embodiments, the antibody is a naked antibody. In some embodiments, the cell over-expresses FGFR3. In some embodiments, the cell over-expresses FGFR2. In some embodiments, the cell over-expresses FGFR3 and FGFR2.

In one aspect, the invention provides methods for depleting cells (such as multiple myeloma cells) in a subject, the method comprising administering to the subject an effective amount of an anti-FGFR2/3 antibody to kill a cell. In some embodiments, the cell is killed by ADCC. In some embodiments, the antibody is a naked antibody. In some embodiments, the cell over-expresses FGFR2/3.

In one aspect, the invention provides methods for treating or preventing a skeletal disorder. In some embodiments, the disorder is achondroplasia, hypochondroplasia, dwarfism, thantophoric dysplasia (TD; clinical forms TD1 and TDII), or craniosynostosis syndrome.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

In one aspect, the invention provides methods comprising administration of an effective amount of an anti-FGFR2/3 antibody in combination with an effective amount of another therapeutic agent (such as an anti-angiogenesis agent, another antibody, a chemotherapeutic agent, a cytotoxic agent, an immunosuppressive agent, a prodrug, a cytokine, cytotoxic radiotherapy, a corticosteroid, an anti-emetic, a cancer vaccine, an analgesic, or a growth inhibitory agent). For example, anti-FGFR2/3 antibodies are used in combinations with an anti-cancer agent or an anti-angiogenic agent to treat various neoplastic or non-neoplastic conditions. In particular examples, the anti-FGFR2/3 antibodies are used in combination with velcade, revlimid, tamoxifen, letrozole, exemestane, anastrozole, irinotecan, cetuximab, fulvestrant, vinorelbine, bevacizumab, vincristine, cisplatin, gemcitabine, methotrexate, vinblastine, carboplatin, paclitaxel, docetaxel, pemetrexed, 5-fluorouracil, doxorubicin, bortezomib, lenalidomide, dexamethasone, melphalin, prednisone, vincristine, and/or thalidomide.

Depending on the specific cancer indication to be treated, the combination therapy of the invention can be combined with additional therapeutic agents, such as chemotherapeutic agents, or additional therapies such as radiotherapy or surgery. Many known chemotherapeutic agents can be used in the combination therapy of the invention. Preferably those chemotherapeutic agents that are standard for the treatment of the specific indications will be used. Dosage or frequency of each therapeutic agent to be used in the combination is preferably the same as, or less than, the dosage or frequency of the corresponding agent when used without the other agent(s).

In another aspect, the invention provides any of the anti-FGFR2/3 antibodies described herein, wherein the anti-FGFR2/3 antibody comprises a detectable label. In another aspect, the invention provides a complex of any of the anti-FGFR2/3 antibodies described herein and FGFR2/3. In some embodiments, the complex is in vivo or in vitro. In some embodiments, the complex comprises a cancer cell. In some embodiments, the anti-FGFR2/3 antibody is detectably labeled.

The present disclosure also provides antibodies that bind to beta-Klotho (KLB) and bispecific antibodies that bind to both KLB and FGFR2 and/or FGFR3 (the "FGFR2/3+KLB bispecific antibody"), and methods of using the same. In specific embodiments, the FGFR2/3+KLB bispecific antibody can be used to treat metabolic diseases and disorders including weight loss and improvement in glucose and lipid metabolism. In certain embodiments, the FGFR2/3+KLB bispecific antibody can be used to treat metabolic disorders or diseases without a significant impact on the liver and without a significant loss in bone mass. In preferred embodiments, the FGFR2/3+KLB bispecific antibody is used to treat non-alcoholic steatohepatitis (NASH).

In certain embodiments, the bispecific antibody is an isolated antibody. In certain embodiments, the bispecific antibody can bind to both KLB and FGFR2, KLB and FGFR3, or all three of KLB, FGFR2, and FGFR3, wherein the antibody binds to the C-terminal domain of KLB. In certain embodiments, the bispecific antibody binds to a fragment of KLB including the amino acid sequence SSPTRLAVIPWGVRKLLRWVRRNYGDMDIYITAS (SEQ ID NO: 103).

In certain embodiments, the bispecific antibody that binds KLB also binds to an epitope within a fragment of FGFR2 including the amino acid sequence TNTEKMEKRLHAVPAANTVKFRCPA (SEQ ID NO: 91) or YKVRNQHWSLIMES (SEQ ID NO:92). In certain embodiments, the bispecific antibody that binds KLB also binds to an epitope within a fragment of FGFR3 including the amino acid sequence TRPERMDKKLLAVPAANTVRFRCPA (SEQ ID NO: 93) and IKLRHQQWSLVMES (SEQ ID NO:94). In certain embodiments, the bispecific antibody that binds KLB also binds to an epitope within a fragment of FGFR2 including the amino acid sequence TNTEKMEKRLHAVPAANTVKFRCPA (SEQ ID NO: 91) or YKVRNQHWSLIMES (SEQ ID NO:92) and binds to an epitope within a fragment of FGFR3 including the amino acid sequence TRPERMDKKLLAVPAANTVRFRCPA (SEQ ID NO: 93) and IKLRHQQWSLVMES (SEQ ID NO:94).

In certain embodiments, the bispecific antibody that binds KLB also binds to an epitope within a fragment of FGFR2 having at least 50%, 60%, 70%, 80%, 90%, 95%, 96%, 97%, 98%, or 99% sequence identity or similarity with amino acid sequence TNTEKMEKRLHAVPAANTVKFRCPA (SEQ ID NO: 91) and/or YKVRNQHWSLIMES (SEQ ID NO:92). In certain embodiments, the bispecific antibody that binds KLB also binds to an epitope within a fragment of FGFR3 having at least 50%, 60%, 70%, 80%, 90%, 95%, 96%, 97%, 98%, or 99% sequence identity or similarity with amino acid sequence TRPERMDKKLLAVPAANTVRFRCPA (SEQ ID NO: 93) and IKLRHQQWSLVMES (SEQ ID NO:94). In certain embodiments, the bispecific antibody that binds KLB also binds to an epitope within a fragment of FGFR2 having at least 50%, 60%, 70%, 80%, 90%, 95%, 96%, 97%, 98%, or 99% sequence identity or similarity with amino acid sequence TNTEKMEKRLHAVPAANTVKFRCPA (SEQ ID NO: 91) and/or YKVRNQHWSLIMES (SEQ ID NO:92) and also binds to an epitope within a fragment of FGFR3 having at least 50%, 60%, 70%, 80%, 90%, 95%, 96%, 97%, 98%, or 99% sequence identity or similarity with amino acid sequence TRPERMDKKLLAVPAANTVRFRCPA (SEQ ID NO: 93) and IKLRHQQWSLVMES (SEQ ID NO:94).

In certain embodiments, the bispecific antibody that binds KLB also binds FGFR2 within the amino acid sequence range of 157 to 181 of SEQ ID NOs: 52 or 54. In certain embodiments, the bispecific antibody that binds KLB also binds FGFR2 within the amino acid sequence range of 207 to 220 of SEQ ID NOs: 52 or 54. In certain embodiments, the bispecific antibody that binds KLB also binds FGFR2 within the amino acid sequence range of 157 to 181 and 207 to 220 of SEQ ID NOs: 52 or 54.

In certain embodiments, the bispecific antibody that binds KLB and FGFR2/3 inhibits constitutive FGFR2 and/or FGFR3 activity. In certain embodiments, the constitutive FGFR2/3 activity is ligand-dependent constitutive FGFR2/3 activity. In certain embodiments, the constitutive FGFR2/3 activity is ligand-independent constitutive FGFR2/3 activity. In certain embodiments, the constitutive FGFR2/3 activity is FGFR2 and FGFR3 activity.

In certain embodiments, an FGFR2/3+KLB bispecific antibody of the present disclosure reduces blood glucose levels in vivo. In certain embodiments, an FGFR2/3+KLB bispecific antibody of the present disclosure does not significantly affect bone density. In certain embodiments, an FGFR2/3+KLB bispecific antibody of the present disclosure does not have a significant impact on the liver. In certain embodiments, an FGFR2/3+KLB bispecific antibody of the present disclosure induces ERK and MEK phosphorylation in the liver at significantly lower levels than FGF21 induces. In certain embodiments, an FGFR2/3+KLB bispecific antibody of the present disclosure binds to KLB with a $K_d$ from $10^{-8}$ M to $10^{-13}$ M. In certain embodiments, an FGFR2/3+KLB bispecific antibody of the present disclosure can bind to a FGFR2 and/or FGFR3 protein with a $K_d$ from $10^{-8}$ M to $10^{-13}$ M. In certain embodiments, an FGFR2/3+KLB bispecific antibody of the present disclosure can bind to FGFR2 and/or FGFR3 with a $K_d$ from $10^{-8}$ M to $10^{-13}$ M.

In certain embodiments, an FGFR2/3+KLB bispecific antibody of the present disclosure binds to an epitope present on KLB. For example, and not by way of limitation, the present disclosure provides an FGFR2/3+KLB bispecific antibody can bind the same epitope on KLB as an antibody shown in FIGS. 11A and 11B. In certain embodiments, an FGFR2/3+KLB bispecific antibody of the present disclosure can bind the same epitope as the 12A11 or the 8C5 antibody. In certain embodiments, an FGFR2/3+KLB bispecific antibody of the present disclosure can bind to an epitope within the C-terminal domain of KLB. In certain embodiments, the an FGFR2/3+KLB bispecific antibody of the present disclosure can bind to a fragment of KLB consisting of the amino acid sequence SSPTRLAVIPWGVRKLLRWVRRNYGD-MDIYITAS (SEQ ID NO: 103).

In certain embodiments, the KLB arm of any of the FGFR2/3+KLB bispecific antibodies of the present disclosure is an arm of any KLB antibody described in US20150218276 which is incorporated herein in its entirety.

In certain embodiments, the FGFR2/3 arm of any of the FGFR2/3+KLB bispecific antibodies of the present disclosure is an arm of any FGFR2/3 antibodies described herein.

In certain embodiments, an FGFR2/3+KLB bispecific antibody of the present disclosure includes a first antibody, or antigen binding portion thereof, that includes a heavy chain variable region and a light chain variable region, where the heavy chain variable region includes amino acids having a sequence that is at least 95% identical to the sequence set forth in SEQ ID NO: 104, and the light chain variable region includes amino acids having a sequence that is at least 95% identical to the sequence set forth in SEQ ID NO: 105. In certain embodiments, the second antibody, or antigen binding portion thereof, includes a heavy chain variable region and a light chain variable region, where the heavy chain variable region includes amino acids having a sequence that is at least 95% identical to a sequence set forth in column 2 of Table 1, and the light chain variable region includes amino acids having a sequence that is at least 95% identical to a sequence set forth in column 3 of Table 1.

TABLE 1

HC and LC sequences of exemplary FGFR2/3 antibodies

| Antibody | HC SEQ ID NO: | LC SEQ ID NO: |
| --- | --- | --- |
| 2B.1.3 | 75 | 59 |
| 2B.1.95 | 76 | 60 |
| 2B.1.73 | 77 | 61 |
| 2B.1.32 | 78 | 62 |
| 2B.1.88 | 79 | 63 |
| 2B.1.1 | 80 | 64 |
| 2B.1.3.10 | 81 | 65 |
| 2B.1.3.12 | 82 | 66 |

In certain embodiments, an anti-KLB/anti-FGFR1 bispecific antibody of the present disclosure includes a first antibody, or antigen binding portion thereof, which includes a heavy chain region and a light chain region, where the heavy chain region includes amino acids having a sequence that is at least 95% identical to the sequence set forth in SEQ ID NO: 106, and the light chain region includes amino acids having a sequence that is at least 95% identical to the sequence set forth in SEQ ID NO: 107. In certain embodiments, the second antibody, or antigen binding portion thereof, includes a heavy chain region and a light chain region, where the heavy chain region includes amino acids having a sequence that is at least 95% identical to a sequence set forth in column 2 of Table 1, and the light chain region includes amino acids having a sequence that is at least 95% identical to a sequence set forth in column 3 of Table 1.

In preferred embodiments, an FGFR2/3+KLB bispecific antibody of the present disclosure includes a first anti-KLB antibody, or antigen binding portion thereof, that includes a heavy chain variable region and a light chain variable region, where the heavy chain variable region includes amino acids having a sequence that is at least 95% identical to the sequence set forth in SEQ ID NO: 104, and the light chain variable region includes amino acids having a sequence that is at least 95% identical to the sequence set forth in SEQ ID NO: 105; and the second anti-FGFR2/3 antibody, or antigen binding portion thereof, includes a heavy chain variable region and a light chain variable region, where the heavy chain variable region includes amino acids having a sequence that is at least 95% identical to a sequence set SEQ ID NO: 82, and the light chain variable region includes amino acids having a sequence that is at least 95% identical to a sequence set forth in SEQ ID NO: 66.

In preferred embodiments, an FGFR2/3+KLB bispecific antibody of the present disclosure includes a first anti-KLB antibody, or antigen binding portion thereof, that includes a heavy chain variable region and a light chain variable region, where the heavy chain variable region includes amino acids having a sequence that is at least 95% identical to the sequence set forth in SEQ ID NO: 104, and the light chain variable region includes amino acids having a sequence that is at least 95% identical to the sequence set forth in SEQ ID NO: 105; and the second anti-FGFR2/3 antibody, or antigen binding portion thereof, includes a heavy chain variable region and a light chain variable region, where the heavy chain variable region includes amino acids having a sequence that is at least 95% identical to a sequence set SEQ ID NO: 82, and the light chain variable region includes amino acids having a sequence that is at least 95% identical to a sequence set forth in SEQ ID NO: 66.

In preferred embodiments, an FGFR2/3+KLB bispecific antibody of the present disclosure includes a first anti-KLB antibody, or antigen binding portion thereof, that includes a heavy chain variable region and a light chain variable region, where the heavy chain variable region includes amino acids having a sequence that is at least 95% identical to the sequence set forth in SEQ ID NO: 104, and the light chain variable region includes amino acids having a sequence that is at least 95% identical to the sequence set forth in SEQ ID NO: 105; and the second anti-FGFR2/3 antibody, or antigen binding portion thereof, includes a heavy chain and a light chain, where the heavy chain includes amino acids having a sequence that is at least 95% identical to a sequence set SEQ ID NO: 282, and the light chain includes amino acids having a sequence that is at least 95% identical to a sequence set forth in SEQ ID NO: 283.

In preferred embodiments, an FGFR2/3+KLB bispecific antibody of the present disclosure includes a first anti-KLB antibody, or antigen binding portion thereof, that includes a heavy chain variable region and a light chain variable region, where the heavy chain variable region includes amino acids having a sequence that is at least 95% identical to the sequence set forth in SEQ ID NO: 104, and the light chain variable region includes amino acids having a sequence that is at least 95% identical to the sequence set forth in SEQ ID NO: 105; and the second anti-FGFR2/3 antibody, or antigen binding portion thereof, wherein the CDRs on the light chain, comprise amino acids having a sequence that are at least 90%, 91%, 92%, 93%, 94%, 95%, 95%, 96%, 97%, 98%, 99%, or 100% identical to a SEQ ID NOs: 1-3 (CDRL1, CDRL2, and CDRL3), and wherein the CDRs on the heavy chain, comprise amino acids having a sequence that are at least 90%, 91%, 92%, 93%, 94%, 95%, 95%, 96%, 97%, 98%, 99%, or 100% identical to SEQ ID NO: 10, 5 and 12 (CDRH1, CDRH2, and CDRH3).

In preferred embodiments, an FGFR2/3+KLB bispecific antibody of the present disclosure includes a first anti-KLB antibody, or antigen binding portion thereof, that includes a heavy chain variable region and a light chain variable region, where the heavy chain variable region includes amino acids having a sequence that is at least 95% identical to the sequence set forth in SEQ ID NO: 104, and the light chain variable region includes amino acids having a sequence that is at least 95% identical to the sequence set forth in SEQ ID NO: 105; and the second anti-FGFR2/3 antibody, or antigen binding portion thereof, wherein the CDRs on the light chain, comprise amino acids having a sequence that are at least 90%, 91%, 92%, 93%, 94%, 95%, 95%, 96%, 97%, 98%, 99%, or 100% identical to a SEQ ID NOs: 276-278 (CDRL1, CDRL2, and CDRL3), and wherein the CDRs on the heavy chain, comprise amino acids having a sequence that are at least 90%, 91%, 92%, 93%, 94%, 95%, 95%, 96%, 97%, 98%, 99%, or 100% identical to SEQ ID NO: 279-281 (CDRH1, CDRH2, and CDRH3).

In certain embodiments, an FGFR2/3+KLB bispecific antibody of the present disclosure includes a first anti-KLB antibody, or antigen binding portion thereof, comprising: (a) HVR-H3 comprising an amino acid sequence selected from the group consisting of SEQ ID NOs: 154-169, (b) HVR-L3 comprising an amino acid sequence selected from the group consisting of SEQ ID NOs: 201-215, and (c) HVR-H2 comprising an amino acid sequence selected from the group consisting of SEQ ID NOs: 138-153.

In certain embodiments, an FGFR2/3+KLB bispecific antibody of the present disclosure includes a first anti-KLB antibody, or antigen binding portion thereof, comprising (a) HVR-H1 comprising an amino acid sequence selected from the group consisting of SEQ ID NOs: 108-122 and 315, (b) HVR-H2 comprising an amino acid sequence selected from the group consisting of SEQ ID NOs: 138-153, and (c) HVR-H3 comprising an amino acid sequence selected from the group consisting of SEQ ID NOs: 154-169.

In certain embodiments, an FGFR2/3+KLB bispecific bispecific antibody of the present disclosure includes a first anti-KLB antibody, or antigen binding portion thereof, comprising (a) HVR-L1 comprising an amino acid sequence selected from the group consisting of SEQ ID NOs: 170-184, (b) HVR-L2 comprising an amino acid sequence selected from the group consisting of SEQ ID NOs: 185-200, and (c) HVR-L3 comprising an amino acid sequence selected from the group consisting of SEQ ID NOs: 201-215.

In certain embodiments, an FGFR2/3+KLB bispecific bispecific antibody of the present disclosure includes a first anti-KLB antibody, or antigen binding portion thereof, comprising (a) HVR-H1 comprising the amino acid sequence of SEQ ID NO: 119, (b) HVR-H2 comprising the amino acid sequence of SEQ ID NO: 150, (c) HVR-H3 comprising the amino acid sequence of SEQ ID NO: 166, (d) HVR-L1 comprising the amino acid sequence of SEQ ID NO: 181, (e) HVR-L2 comprising the amino acid sequence of SEQ ID NO: 197, and (f) HVR-L3 comprising the amino acid sequence of SEQ ID NO: 212.

In certain embodiments, an FGFR2/3+KLB bispecific antibody of the present disclosure includes a first anti-KLB antibody, or antigen binding portion thereof, comprising (a) HVR-H1 comprising the amino acid sequence of SEQ ID NO: 122, (b) HVR-H2 comprising the amino acid sequence of SEQ ID NO: 153, (c) HVR-H3 comprising the amino acid sequence of SEQ ID NO: 169, (d) HVR-L1 comprising the amino acid sequence of SEQ ID NO: 184, (e) HVR-L2 comprising the amino acid sequence of SEQ ID NO: 200, and (f) HVR-L3 comprising the amino acid sequence of SEQ ID NO: 215.

In certain embodiments, an FGFR2/3+KLB bispecific antibody of the present disclosure includes one arm from an anti-KLB antibody, or antigen binding portion thereof, selected from any of the anti-KLB antibodies disclosed herein or in US20150218276 which is incorporated herein in its entirety and one arm of an FGFR2/3 antibody disclosed herein. In specific embodiments the arms of the FGFR2/3+KLB bispecific are selected from the following combinations:

a) One arm from the 8C5.K4.M4L.H3.KNV anti-KLB antibody (comprising SEQ ID NO: 104 (HCVR) and SEQ ID NO: 105 (LCVR)) and one arm from the 2B.1.3.12 anti-FGFR2/3 antibody (comprising SEQ ID NO: 82 (heavy chain) and SEQ ID NO: 66 (light chain));

b) One arm from the 8C5.K4.M4L.H3.KNV anti-KLB antibody (comprising SEQ ID NO: 106 (heavy chain) and SEQ ID NO: 107 (light chain)) and one arm from the 2B.1.3.12 anti-FGFR2/3 antibody (comprising SEQ ID NO: 82 (heavy chain) and SEQ ID NO: 66 (light chain));

c) One arm from the 8C5.K4.M4L.H3.KNV anti-KLB antibody (comprising SEQ ID NO: 104 (HCVR) and SEQ ID NO: 105 (LCVR)) and one arm from the 2B.1.3.12 anti-FGFR2/3 antibody (comprising SEQ ID NOs: 1-3 (CDRL1, CDRL2, and CDRL3) and SEQ ID NO: 10, 5 and 12 (CDRH1, CDRH2, and CDRH3));

d) One arm from the 8C5.K4.M4L.H3.KNV anti-KLB antibody (comprising SEQ ID NO: 106 (heavy chain) and SEQ ID NO: 107 (light chain)) and one arm from the 2B.1.3.12 anti-FGFR2/3 antibody (comprising SEQ ID NOs: 1-3 (CDRL1, CDRL2, and CDRL3) and SEQ ID NO: 10, 5 and 12 (CDRH1, CDRH2, and CDRH3));

e) One arm from the 8C5.K4.M4L.H3.KNV anti-KLB antibody (comprising SEQ ID NO: 104 (HCVR) and SEQ ID NO: 105 (LCVR)) and one arm from the 2B.1.1.6 anti-FGFR2/3 antibody (comprising SEQ ID NO: 282 (heavy chain) and SEQ ID NO: 283 (light chain));

f) One arm from the 8C5.K4.M4L.H3.KNV anti-KLB antibody (comprising SEQ ID NO: 106 (heavy chain) and SEQ ID NO: 107 (light chain)) and one arm from the 2B.1.1.6 anti-FGFR2/3 antibody (comprising SEQ ID NO: 282 (heavy chain) and SEQ ID NO: 283 (light chain));

g) One arm from the 8C5.K4.M4L.H3.KNV anti-KLB antibody (comprising SEQ ID NO: 104 (HCVR) and SEQ ID NO: 105 (LCVR)) and one arm from the 2B.1.1.6 anti-FGFR2/3 antibody (comprising SEQ ID NOs: 276-278 (CDRL1, CDRL2, and CDRL3) and SEQ ID NO: 279-281 (CDRH1, CDRH2, and CDRH3)); and h) One arm from the 8C5.K4.M4L.H3.KNV anti-KLB antibody (comprising SEQ ID NO: 106 (heavy chain) and SEQ ID NO: 107 (light chain)) and one arm from the 2B.1.1.6 anti-FGFR2/3 antibody (comprising SEQ ID NOs: 276-278 (CDRL1, CDRL2, and CDRL3) and SEQ ID NO: 279-281 (CDRH1, CDRH2, and CDRH3)).

In certain embodiments, an FGFR2/3+KLB bispecific antibody of the present disclosure includes a first anti-KLB antibody, or antigen binding portion thereof, comprising (a) a heavy chain variable region comprising the amino acid sequence of SEQ ID NO: 104 and (b) a light chain variable region comprising the amino acid sequence of SEQ ID NO: 105. In certain embodiments, an FGFR2/3+KLB bispecific antibody of the present disclosure includes a first anti-KLB antibody, or antigen binding portion thereof, comprising (a) a heavy chain comprising the amino acid sequence of SEQ ID NO: 106 and (b) a light chain comprising the amino acid sequence of SEQ ID NO: 107.

In another aspect, an FGFR2/3+KLB bispecific antibody of the present disclosure includes a first anti-KLB antibody, or antigen binding portion thereof, comprising (a) a heavy chain variable region having at least 95% sequence identity to the amino acid sequence of SEQ ID NO: 104; (b) a light chain variable region having at least 95% sequence identity to the amino acid sequence of SEQ ID NO: 105; and (c) a heavy chain variable region as in (a) and a light chain variable region as in (b).

In certain embodiments, FGFR2/3+KLB bispecific antibody of the present disclosure is a monoclonal antibody. In certain embodiments, the antibody is a human, humanized, or chimeric antibody. In certain embodiments, the antibody has reduced effector function.

In another aspect, the present disclosure provides an isolated nucleic acid encoding an FGFR2/3+KLB bispecific antibody of the present disclosure. In certain embodiments, the present disclosure provides a host cell comprising a nucleic acid encoding an FGFR2/3+KLB bispecific antibody of the present disclosure. In certain embodiments, the present disclosure provides a method of producing an FGFR2/3+KLB bispecific antibody comprising culturing a host cell of the present disclosure so that the antibody is produced. In certain embodiments, this method further comprises recovering the FGFR2/3+KLB bispecific antibody from the host cell.

The present disclosure further provides a pharmaceutical formulation that includes one or more antibodies of the invention and a pharmaceutically acceptable carrier. Specifically, the present disclosure provides a pharmaceutical formulation that includes an FGFR2/3+KLB bispecific antibody described herein. In certain embodiments, the pharmaceutical formulation comprises an additional therapeutic agent.

In another aspect, the present disclosure provides an FGFR2/3+KLB bispecific antibody of the invention for use as a medicament. In certain embodiments, the an anti-KLB/anti-FGFR1 bispecific antibody is for use in treating metabolic disorders, e.g., polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY). In certain embodiments, an FGFR2/3+KLB bispecific antibody is for use in treating type 2 diabetes. In certain embodiments, an FGFR2/3+KLB bispecific antibody is for use in treating obesity. In certain embodiments, the present disclosure provides an an FGFR2/3+KLB bispecific antibody for use in treating Bardet-Biedl syndrome, Prader-Willi syndrome, Alstrom syndrome, Cohen syndrome, Albright's hereditary osteodystrophy (pseudohypoparathyroidism), Carpenter syndrome, MOMO syndrome, Rubinstein-Taybi syndrome, fragile X syndrome and Börjeson-Forssman-Lehman syndrome. In certain embodiments, the an FGFR2/3+KLB bispecific antibody is for use in treating NASH.

In another aspect, the present disclosure provides the use of an FGFR2/3+KLB bispecific antibody, disclosed herein, in the manufacture of a medicament for treatment of metabolic disorders, e.g., polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY), and aging and related diseases such as Alzheimer's disease, Parkinson's disease and ALS. In certain embodiments, the metabolic disorder is type 2 diabetes. In certain embodiments, the metabolic disorder is NASH.

In another aspect, the present disclosure provides a method of treating an individual having a disease selected from the group consisting of polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY), and aging and related diseases such as Alzheimer's disease, Parkinson's disease and ALS, the method comprising administering to the individual an effective amount of one or more FGFR2/3+KLB bispecific antibodies of the present disclosure. In certain embodiments, the disease is diabetes, e.g., type 2 diabetes. In certain embodiments, the disease is obesity. In certain embodiments, the present disclosure provides a method of treating an individual having a disease and/or disorder selected from the group consisting of Bardet-Biedl syndrome, Prader-Willi syndrome, Alstrom syndrome, Cohen syndrome, Albright's hereditary osteodystrophy (pseudohypoparathyroidism), Carpenter syndrome, MOMO syndrome, Rubinstein-Taybi syndrome, fragile X syndrome and Börjeson-Forssman-Lehman syndrome, the method comprising administering to the individual an effective amount of one or more FGFR2/3+KLB bispecific antibodies of the present disclosure. In certain embodiments, the method further includes administering an additional therapeutic agent to the individual. In certain embodiments, a method using one or more FGFR2/3+KLB bispecific antibodies of the present disclosure does not affect liver function in an individual. In certain embodiments, the present disclosure provides a method for inducing weight loss comprising administering to an individual an effective amount of one or more antibodies of the present disclosure.

In another embodiment, an FGFR2/3+KLB bispecific antibody of the present disclosure can be used as a medicament and includes one arm from an anti-KLB antibody, or antigen binding portion thereof, selected from any of the anti-KLB antibodies disclosed herein or in US20150218276 which is incorporated herein in its entirety and one arm of an FGFR2/3 antibody disclosed herein. In specific embodiments the arms of the FGFR2/3+KLB bispecific antibody that can be used as a medicament are selected from the following combinations:

a) One arm from the 8C5.K4.M4L.H3.KNV anti-KLB antibody (comprising SEQ ID NO: 104 (HCVR) and SEQ ID NO: 105 (LCVR)) and one arm from the 2B.1.3.12 anti-FGFR2/3 antibody (comprising SEQ ID NO: 82 (heavy chain) and SEQ ID NO: 66 (light chain));
b) One arm from the 8C5.K4.M4L.H3.KNV anti-KLB antibody (comprising SEQ ID NO: 106 (heavy chain) and SEQ ID NO: 107 (light chain)) and one arm from the 2B.1.3.12 anti-FGFR2/3 antibody (comprising SEQ ID NO: 82 (heavy chain) and SEQ ID NO: 66 (light chain));
c) One arm from the 8C5.K4.M4L.H3.KNV anti-KLB antibody (comprising SEQ ID NO: 104 (HCVR) and SEQ ID NO: 105 (LCVR)) and one arm from the 2B.1.3.12 anti-FGFR2/3 antibody (comprising SEQ ID NOs: 1-3 (CDRL1, CDRL2, and CDRL3) and SEQ ID NO: 10, 5 and 12 (CDRH1, CDRH2, and CDRH3));
d) One arm from the 8C5.K4.M4L.H3.KNV anti-KLB antibody (comprising SEQ ID NO: 106 (heavy chain) and SEQ ID NO: 107 (light chain)) and one arm from the 2B.1.3.12 anti-FGFR2/3 antibody (comprising SEQ ID NOs: 1-3 (CDRL1, CDRL2, and CDRL3) and SEQ ID NO: 10, 5 and 12 (CDRH1, CDRH2, and CDRH3));
e) One arm from the 8C5.K4.M4L.H3.KNV anti-KLB antibody (comprising SEQ ID NO: 104 (HCVR) and SEQ ID NO: 105 (LCVR)) and one arm from the 2B.1.1.6 anti-FGFR2/3 antibody (comprising SEQ ID NO: 282 (heavy chain) and SEQ ID NO: 283 (light chain));
f) One arm from the 8C5.K4.M4L.H3.KNV anti-KLB antibody (comprising SEQ ID NO: 106 (heavy chain) and SEQ ID NO: 107 (light chain)) and one arm from the 2B.1.1.6 anti-FGFR2/3 antibody (comprising SEQ ID NO: 282 (heavy chain) and SEQ ID NO: 283 (light chain));
g) One arm from the 8C5.K4.M4L.H3.KNV anti-KLB antibody (comprising SEQ ID NO: 104 (HCVR) and SEQ ID NO: 105 (LCVR)) and one arm from the 2B.1.1.6 anti-FGFR2/3 antibody (comprising SEQ ID NOs: 276-278 (CDRL1, CDRL2, and CDRL3) and SEQ ID NO: 279-281 (CDRH1, CDRH2, and CDRH3)); and
h) One arm from the 8C5.K4.M4L.H3.KNV anti-KLB antibody (comprising SEQ ID NO: 106 (heavy chain) and SEQ ID NO: 107 (light chain)) and one arm from the 2B.1.1.6 anti-FGFR2/3 antibody (comprising SEQ ID NOs: 276-278 (CDRL1, CDRL2, and CDRL3) and SEQ ID NO: 279-281 (CDRH1, CDRH2, and CDRH3)).

In another embodiment, an FGFR2/3+KLB bispecific antibody of the present disclosure can be used to treat a metabolic disease (e.g., NASH or a related disease) and includes one arm from an anti-KLB antibody, or antigen binding portion thereof, selected from any of the anti-KLB antibodies disclosed herein or in US20150218276 which is incorporated herein in its entirety and one arm of an FGFR2/3 antibody disclosed herein. In specific embodiments the arms of the FGFR2/3+KLB bispecific antibody that can be used to treat a metabolic disease (e.g., NASH or a related disease) are selected from the following combinations:

a) One arm from the 8C5.K4.M4L.H3.KNV anti-KLB antibody (comprising SEQ ID NO: 104 (HCVR) and SEQ ID NO: 105 (LCVR)) and one arm from the 2B.1.3.12 anti-FGFR2/3 antibody (comprising SEQ ID NO: 82 (heavy chain) and SEQ ID NO: 66 (light chain));
b) One arm from the 8C5.K4.M4L.H3.KNV anti-KLB antibody (comprising SEQ ID NO: 106 (heavy chain) and SEQ ID NO: 107 (light chain)) and one arm from the 2B.1.3.12 anti-FGFR2/3 antibody (comprising SEQ ID NO: 82 (heavy chain) and SEQ ID NO: 66 (light chain));
c) One arm from the 8C5.K4.M4L.H3.KNV anti-KLB antibody (comprising SEQ ID NO: 104 (HCVR) and SEQ ID NO: 105 (LCVR)) and one arm from the 2B.1.3.12 anti-FGFR2/3 antibody (comprising SEQ ID NOs: 1-3 (CDRL1, CDRL2, and CDRL3) and SEQ ID NO: 10, 5 and 12 (CDRH1, CDRH2, and CDRH3));
d) One arm from the 8C5.K4.M4L.H3.KNV anti-KLB antibody (comprising SEQ ID NO: 106 (heavy chain) and SEQ ID NO: 107 (light chain)) and one arm from the 2B.1.3.12 anti-FGFR2/3 antibody (comprising SEQ ID NOs: 1-3 (CDRL1, CDRL2, and CDRL3) and SEQ ID NO: 10, 5 and 12 (CDRH1, CDRH2, and CDRH3));
e) One arm from the 8C5.K4.M4L.H3.KNV anti-KLB antibody (comprising SEQ ID NO: 104 (HCVR) and SEQ ID NO: 105 (LCVR)) and one arm from the 2B.1.1.6 anti-FGFR2/3 antibody (comprising SEQ ID NO: 282 (heavy chain) and SEQ ID NO: 283 (light chain));
f) One arm from the 8C5.K4.M4L.H3.KNV anti-KLB antibody (comprising SEQ ID NO: 106 (heavy chain) and SEQ ID NO: 107 (light chain)) and one arm from the 2B.1.1.6 anti-FGFR2/3 antibody (comprising SEQ ID NO: 282 (heavy chain) and SEQ ID NO: 283 (light chain));
g) One arm from the 8C5.K4.M4L.H3.KNV anti-KLB antibody (comprising SEQ ID NO: 104 (HCVR) and SEQ ID NO: 105 (LCVR)) and one arm from the 2B.1.1.6 anti-FGFR2/3 antibody (comprising SEQ ID NOs: 276-278 (CDRL1, CDRL2, and CDRL3) and SEQ ID NO: 279-281 (CDRH1, CDRH2, and CDRH3)); and
h) One arm from the 8C5.K4.M4L.H3.KNV anti-KLB antibody (comprising SEQ ID NO: 106 (heavy chain) and SEQ ID NO: 107 (light chain)) and one arm from the 2B.1.1.6 anti-FGFR2/3 antibody (comprising SEQ ID NOs: 276-278 (CDRL1, CDRL2, and CDRL3) and SEQ ID NO: 279-281 (CDRH1, CDRH2, and CDRH3)).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2C show the crystal structure of the complex between FGFR2 D2 domain and the Fab fragment of Mab 2B.1.3. FIG. 2A shows the overall structure of the complex. FGFR2-D2 was colored as magenta, the heavy chain of the Fab 2B.1.3 green and the light chain blue. FIG. 2B shows the overlay of the structures of FGFR2-D2:2B.1.3 and FGFR3-D2D3:R3Mab. The former complex was colored the same as in FIG. 2A. FGFR3-D2D3 was colored in yellow, and R3Mab gray. FIG. 2C shows the zoom-in representation of the boxed area in FIG. 2B showing the structural differences between the two complexes. Color scheme is the same as in FIG. 2B.

FIG. 3A shows the blocking of FGF-7 binding to human FGFR2-IIIb. FIG. 3B shows the blocking of FGF-1 binding to human FGFR2-IIIc. FIG. 3C shows the blocking of FGF-1 binding to human FGFR3-IIIb. FIG. 3D shows the blocking of FGF-1 binding to human FGFR3-IIIc. FIG. 3E shows the blocking of FGF-19 binding to human FGFR4.

FIG. 4A shows the blocking of FGF7-stimulated FGFR2 signaling by 2B.1 variants in gastric cancer cell line SNU-16. FIG. 4B shows the effect of 2B.1.3.10 and 2B.1.3.12 on the growth of FGFR2-dependent SNU-16 xenografts compared to control antibody. FIG. 4C shows the effects of 2B.1.3.10 and 2B.1.3.12 on the growth of FGFR3-dependent RT112 bladder cancer xenografts.

FIGS. 9A-9D shows the epitopes of the 2B.1.3.10 (i.e., 1.3.10) and 2B.1.3.12 (i.e., 1.3.12) anti-FGFR2/3 antibodies. FIG. 9A shows the FGFR2-IIIb sequence and the epitopes of the anti-FGFR2/3 1.3.10 and 1.3.12 antibodies are underlined and in bold. FIG. 9B shows the FGFR2-IIIc sequence and the epitopes of the anti-FGFR2/3 1.3.10 and 1.3.12 antibodies are underlined and in bold. FIG. 9C shows the FGFR3-IIIb sequence and the epitopes of the anti-FGFR2/3 1.3.10 and 1.3.12 antibodies are underlined and in bold. FIG. 9D shows the FGFR3-IIIc sequence and the epitopes of the anti-FGFR2/3 1.3.10 and 1.3.12 antibodies are underlined and in bold. Antibody 2B.1.3.10 binds to epitopes on FGFR2 that are composed of two beta-strands with residue numbers of 157-181 and 207-220 according to SEQ ID NOs: 52 and 54 (see also SEQ ID NOs: 91 and 92 for epitope sequences). Antibody 2B.1.3.10 also binds to epitopes on FGFR3 that are composed of two beta-strands with residue numbers of 154-178 and 204-217 according to SEQ ID NOs: 56 and 58 (see also SEQ ID NOs: 93 and 94 for epitope sequences). 2B.1.3.12 binds to the same epitopes as 2B.1.3.10. In particular, 2B.1.3.12 binds to the epitope on FGFR2 that is composed of two beta-strands with residue numbers of 157-181 and 207-220. 2B.1.3.12 also binds to an epitope on FGFR3 that is composed of two beta-strands with residue numbers of 154-178 and 204-217.

FIG. 10 shows a chart of the nucleic acid and amino acid SEQ ID NOs corresponding to anti-FGFR2/3 antibodies 1.3, 1.95, 1.73, 1.32, 1.88, 1.1, 1.3.10, and 1.3.12.

FIG. 11A depicts the light chain variable region sequences for 17 anti-KLB antibodies. The CDR L1 sequences are, in order, SEQ ID NOs: 170-175, 175, 173 and 176-184; the CDR L2 sequences are, in order, SEQ ID NOs: 185-190 and 190-200; and the CDH L3 sequences are, in order, SEQ ID NOs: 201-206, 206, 204 and 207-215. The light chain variable region sequences are, in order, SEQ ID NOs: 236-247 and 308-312. FIG. 11B depicts the heavy chain variable region sequences for 17 anti-KLB antibodies. The CDR H1 sequences for the antibodies are, in order (11F1-8C5), SEQ ID NOs: 108-113, 113-118, 116 and 119-122; the CDR H2 sequences are, in order, SEQ ID NOs: 138-143 and 143-153; the CDR H3 sequences are, in order, SEQ ID NOs: 154-159 and 159-169. The heavy chain variable region sequences for the antibodies are, in order, SEQ ID NOs: 216-232.

FIG. 14A shows the N-terminal amino acid sequence of mouse KLB protein (SEQ ID NO: 274), and the corresponding amino acid sequence encoded by the Klb allele in the KO mice (SEQ ID NO: 275) are shown. A missense mutation in Klb gene results in a frame-shift after the second amino acid in the KO allele, as shown with red letters. FIG. 14B shows KLB protein expression in epididymal white adipose tissue in wildtype (+/+) and KLB knockout (−/−) mice. FIG. 14C shows that KLB is important for BsAb20 to affect glucose metabolism. Glucose tolerance test (GTT) in DIO mice that received four weekly injections of BsAb20 or control IgG at 3 mpk. GTT was conducted on day 23, three days after the last injection. The mice were on HFD for 20 weeks prior to GTT. *$p<0.05$.

FIGS. 16A-16C shows seven 2B1.1 variants that were expressed and tested for agonist activity and FGFR2, FGFR3, and FGFR4 binding. FIG. 16A shows a chart detailing the anti-FGFR2/3 antibody variant, the sequence of the CDR H1-H3 of each variant, and the FGFR3 affinity measured by Biacor assays and ELISA. CDR H1 sequences disclosed as SEQ ID NOS 284, 284, 284, 284-287, 284 and 287, respectively, in order of appearance, CDR H2 sequences disclosed as SEQ ID NOS 13, 13, 13, 13, 13, 13, 13, 30 and 30, respectively, in order of appearance, and CDR H3 sequences disclosed as SEQ ID NOS 288-291, 295, 293-294, 288 and 294, respectively, in order of appearance. FIG. 16B shows binding affinity for FGFR3 of the variants as measured by ELISA. FIG. 16C shows binding affinity for FGFR4 of the variants as measured by ELISA.

FIG. 17A shows FGFR3 and FGFR4 activity. FIG. 17B shows FGFR2 and FGFR1 activity.

FIG. 18 shows the anti-FGFR2/3 antibody variant decision matrix used for selecting which anti-FGFR2/3 antibody should be used for the FGFR2/3+KLB bispecific antibody.

FIG. 19A shows FGFR3 activity. FIG. 19B shows FGFR2 activity. FIG. 19C shows FGFR4 activity.

DETAILED DESCRIPTION OF THE INVENTION

Figure 1:
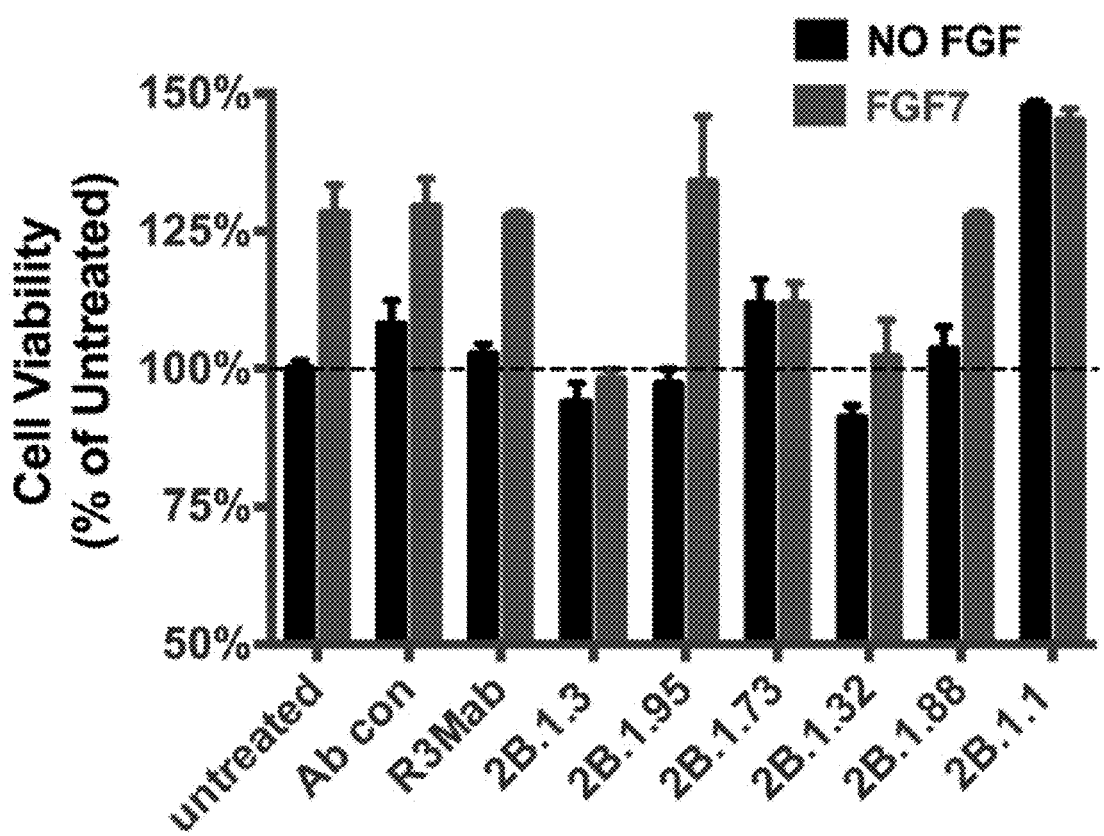
FIG. 1 shows the inhibitory effects of engineered 2B.1 antibodies for FGF7-stimulated MCF-7 cell proliferation. Error bars represent SEM.
Figure 3A:
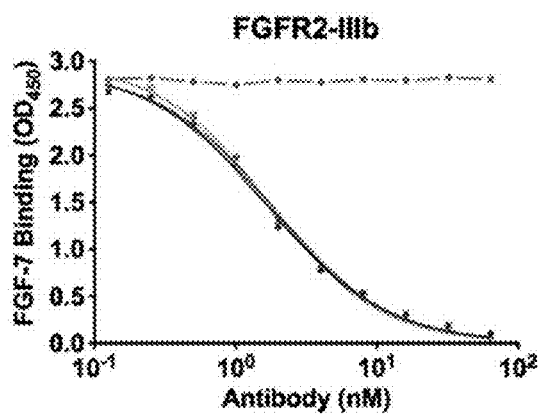
FIGS. 3A-3E show the differential blocking of FGF ligands by R3Mab variants.
Figure 3B:
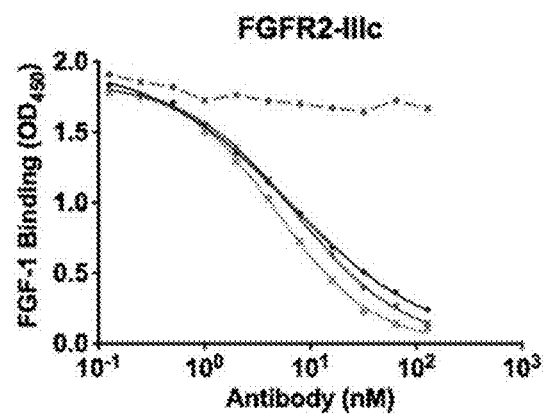
Figure 3C:
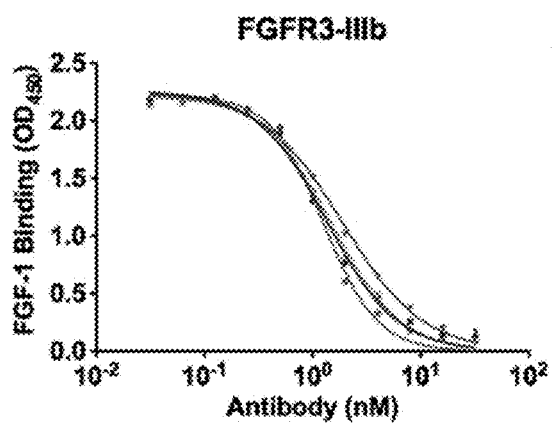
Figure 3D:
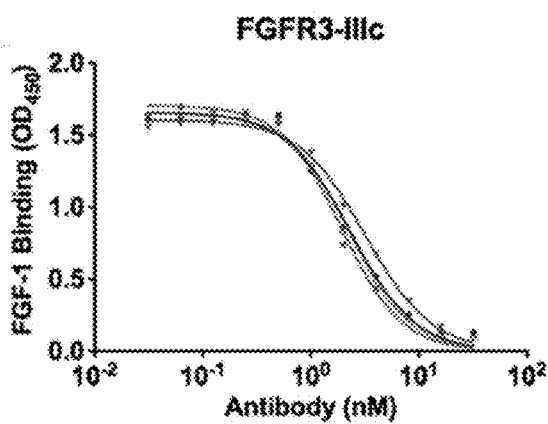
Figure 3E:
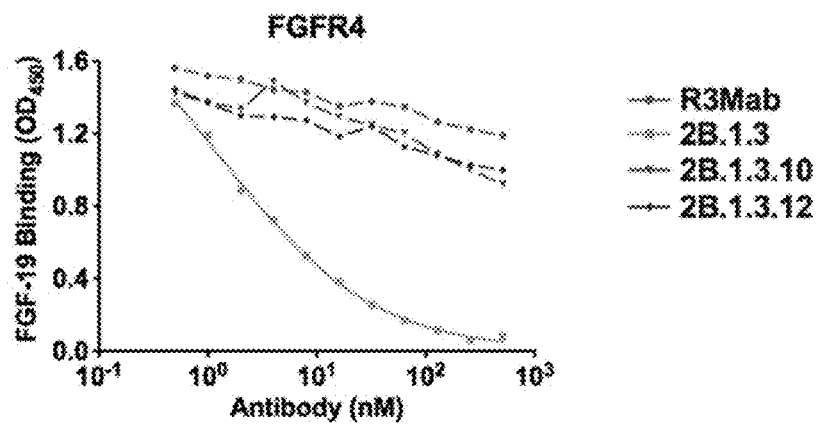

Fibroblast growth factors (FGFs) and their tyrosine kinase receptors (FGFRs) play key roles in regulating specific pathways during embryonic development, as well as homeostasis of diverse tissues, wound healing processes and certain metabolic functions in the adult animal. In humans there are 4 highly homologous FGFRs (FGFR1-4) and 22 FGFs (FGF1-14 and FGF16-23) (Goetz R & Mohammadi M (2013) Exploring mechanisms of FGF signalling through the lens of structural biology. Nat Rev Mol Cell Biol 14(3):166-180; Turner N & Grose R (2010) Fibroblast growth factor signalling: from development to cancer. Nat Rev Cancer 10(2): 116-129; Beenken A & Mohammadi M (2009) The FGF family: biology, pathophysiology and therapy. Nat Rev Drug Discov 8(3):235-253; Wesche J, Haglund K, & Haugsten E M (2011) Fibroblast growth factors and their receptors in cancer. Biochem J 437(2):199-213). The FGFRs comprise an extracellular region with 3 immunoglobulin domains (D1, D2 and D3), a single-pass transmembrane region and a split cytoplasmic kinase moiety (Goetz R & Mohammadi M (2013) Exploring mechanisms of FGF signalling through the lens of structural biology. Nat Rev Mol Cell Biol 14(3):166-180; Mohammadi M, Olsen S K, & Ibrahimi O A (2005) Structural basis for fibroblast growth factor receptor activation. Cytokine Growth Factor Rev 16(2): 107-137). Alternative splicing gives rise to two major variants of FGFRs 1-3, termed isoforms IIIb and IIIc, which differ in the second half of D3 and consequently in ligand-binding specificity (Chang, H., Stewart, A. K., Qi, X. Y., Li, Z. H., Yi, Q. L., and Trudel, S. 2005. Immunohistochemistry accurately predicts FGFR3 aberrant expression and t(4;14) in multiple myeloma. Blood 106:353-355).

Dysregulated signaling by FGFRs 1-4 is associated with pathogenesis in several cancer types (L'Hote, C. G., and Knowles, M. A. 2005. Cell responses to FGFR3 signalling: growth, differentiation and apoptosis. Exp Cell Res 304: 417-431; Dailey, L., Ambrosetti, D., Mansukhani, A., and Basilico, C. 2005. Mechanisms underlying differential responses to FGF signaling. Cytokine Growth Factor Rev 16:233-247). Genomic FGFR alterations, which include gene amplification, chromosomal translocation and activating mutations, can drive aberrant activation of the FGF pathway and promote neoplastic transformation of normal cells. FGFR2 gene amplification occurs in ~10% of gastric and ~4% of triple-negative breast cancers (Chesi, M., Nardini, E., Brents, L. A., Schrock, E., Ried, T., Kuehl, W. M., and Bergsagel, P. L. 1997. Frequent translocation t(4; 14) (p16.3;q32.3) in multiple myeloma is associated with increased expression and activating mutations of fibroblast growth factor receptor 3. Nat Genet 16:260-264; Fonseca, R., Blood, E., Rue, M., Harrington, D., Oken, M. M., Kyle, R. A., Dewald, G. W., Van Ness, B., Van Wier, S. A., Henderson, K. J., et al. 2003. Clinical and biologic implications of recurrent genomic aberrations in myeloma. Blood 101:4569-4575; Moreau, P., Facon, T., Leleu, X., Morineau, N., Huyghe, P., Harousseau, J. L., Bataille, R., and Avet-Loiseau, H. 2002. Recurrent 14q32 translocations determine the prognosis of multiple myeloma, especially in patients receiving intensive chemotherapy. Blood 100:1579-1583), while FGFR3 amplification is associated with specific subsets of bladder cancer (Moreau, P., Facon, T., Leleu, X., Morineau, N., Huyghe, P., Harousseau, J. L., Bataille, R., and Avet-Loiseau, H. 2002. Recurrent 14q32 translocations determine the prognosis of multiple myeloma, especially in patients receiving intensive chemotherapy. Blood 100:1579-1583; Pollett, J. B., Trudel, S., Stern, D., Li, Z. H., and Stewart, A. K. 2002. Overexpression of the myeloma-associated oncogene fibroblast growth factor receptor 3 confers dexamethasone resistance. Blood 100:3819-3821). Missense FGFR mutations are also found in multiple types of cancer (L'Hote, C. G., and Knowles, M. A. 2005. Cell responses to FGFR3 signalling: growth, differentiation and apoptosis. Exp Cell Res 304:417-431; Agazie, Y. M., Movilla, N., Ischenko, I., and Hayman, M. J. 2003. The phosphotyrosine phosphatase SHP2 is a critical mediator of transformation induced by the oncogenic fibroblast growth factor receptor 3. Oncogene 22:6909-6918). Specifically, amino-acid substitutions in the linker region between D2 and D3, e.g. S252W in FGFR2 and S249C in FGFR3, augment FGF-driven signaling and tumor-cell proliferation and represent hot spots for somatic mutation (Agazie, Y. M., Movilla, N., Ischenko, I., and Hayman, M. J. 2003. The phosphotyrosine phosphatase SHP2 is a critical mediator of transformation induced by the oncogenic fibroblast growth factor receptor 3. Oncogene 22:6909-6918; Ronchetti, D., Greco, A., Compasso, S., Colombo, G., Dell'Era, P., Otsuki, T., Lombardi, L., and Neri, A. 2001. Deregulated FGFR3 mutants in multiple myeloma cell lines with t(4; 14): comparative analysis of Y373C, K650E and the novel G384D mutations. Oncogene 20:3553-3562). Activating mutations also occur in the tyrosine kinase region of FGFRs (Chesi, M., Brents, L. A., Ely, S. A., Bais, C., Robbiani, D. F., Mesri, E. A., Kuehl, W. M., and Bergsagel, P. L. 2001. Activated fibroblast growth factor receptor 3 is an oncogene that contributes to tumor progression in multiple myeloma. Blood 97:729-736).

Targeting the FGF-FGFR pathway has been a major area of focus for cancer drug development. This effort has included small-molecule tyrosine kinase inhibitors (TKIs), blocking antibodies, as well as ligand traps (Moreau, P., Facon, T., Leleu, X., Morineau, N., Huyghe, P., Harousseau, J. L., Bataille, R., and Avet-Loiseau, H. 2002. Recurrent 14q32 translocations determine the prognosis of multiple myeloma, especially in patients receiving intensive chemotherapy. Blood 100:1579-1583). Current high-potency FGFR TKIs have limited selectivity for different FGFRs (Moreau, P., Facon, T., Leleu, X., Morineau, N., Huyghe, P., Harousseau, J. L., Bataille, R., and Avet-Loiseau, H. 2002. Recurrent 14q32 translocations determine the prognosis of multiple myeloma, especially in patients receiving intensive chemotherapy. Blood 100:1579-1583), which may impact their therapeutic window. For example, disruption of FGF23 signaling through hetero-complexes of FGFR1 and the co-receptor Klothop can lead to hyperphosphatemia and tissue calcification in patients (Plowright, E. E., Li, Z., Bergsagel, P. L., Chesi, M., Barber, D. L., Branch, D. R., Hawley, R. G., and Stewart, A. K. 2000. Ectopic expression of fibroblast growth factor receptor 3 promotes myeloma cell proliferation and prevents apoptosis. Blood 95:992-998; Chen, J., Williams, I. R., Lee, B. H., Duclos, N., Huntly, B. J., Donoghue, D. J., and Gilliland, D. G. 2005. Constitutively activated FGFR3 mutants signal through PLCgamma-dependent and -independent pathways for hematopoietic transformation. Blood 106:328-337), whereas blockade of FGF19 signaling through FGFR4 hetero-complexes with Klothoβ can disrupt bile acid metabolism (Li, Z., Zhu, Y. X., Plowright, E. E., Bergsagel, P. L., Chesi, M., Patterson, B., Hawley, T. S., Hawley, R. G., and Stewart, A. K. 2001. The myeloma-associated oncogene fibroblast growth factor receptor 3 is transforming in hematopoietic cells. Blood 97:2413-2419). More selective antibodies have been developed to antagonize ligand signaling through individual FGFRs, including FGFR1 (Trudel, S., Ely, S., Farooqi, Y., Affer, M., Robbiani, D. F., Chesi, M., and Bergsagel, P. L. 2004. Inhibition of fibroblast growth factor receptor 3 induces differentiation and apoptosis in t(4; 14) myeloma. Blood 103:3521-3528) FGFR2 (Trudel, S., Li, Z. H., Wei, E., Wiesmann, M., Chang, H., Chen, C., Reece, D., Heise, C., and Stewart, A. K. 2005. CHIR-258, a novel, multitargeted tyrosine kinase inhibitor for the potential treatment of t(4;14) multiple myeloma. Blood 105:2941-2948) and FGFR3 (Chen, J., Lee, B. H., Williams, I. R., Kutok, J. L., Mitsiades, C. S., Duclos, N., Cohen, S., Adelsperger, J., Okabe, R., Coburn, A., et al. 2005. FGFR3 as a therapeutic target of the small molecule inhibitor PKC412 in hematopoietic malignancies. Oncogene 24:8259-8267). However, antibodies recognizing more than one FGFR have not yet been reported.

The previously described monospecific anti-FGFR3 antibody R3Mab effectively blocks binding of FGF1 and FGF9 to both the IIIb and IIIc isoforms of wild-type FGFR3, as well as to certain cancer-associated mutant forms of FGFR3 (Chen, J., Lee, B. H., Williams, I. R., Kutok, J. L., Mitsiades, C. S., Duclos, N., Cohen, S., Adelsperger, J., Okabe, R., Coburn, A., et al. 2005. FGFR3 as a therapeutic target of the small molecule inhibitor PKC412 in hematopoietic malignancies. Oncogene 24:8259-8267; Paterson, J. L., Li, Z., Wen, X. Y., Masih-Khan, E., Chang, H., Pollett, J. B., Trudel, S., and Stewart, A. K. 2004. Preclinical studies of fibroblast growth factor receptor 3 as a therapeutic target in multiple myeloma. Br J Haematol 124:595-603). X-ray structural analysis revealed that R3Mab binds to a specific epitope on FGFR3 that is required for ligand binding. R3Mab displayed potent antitumor activity in mice against human bladder cancer and multiple myeloma tumor xenografts. In the present study, structure-guided phage display was used iteratively to re-engineer R3Mab into derivative antibodies that carry dual specificity for FGFR3 and FGFR2 while sparing FGFR1 and FGFR4. The practical aim of this study was to broaden the potential therapeutic scope beyond that of the parent molecule while avoiding added safety risks. The re-engineered antibodies displayed inhibition of FGF-stimulated tumor-cell growth in vitro and significant efficacy against human cancer xenografts overexpressing FGFR2 or FGFR3 in vivo.

The invention herein provides anti-FGFR2/3 antibodies that are useful for, e.g., treatment or prevention of disease states associated with expression and/or activity of FGFR2 and/or FGFR3, such as increased expression and/or activity or undesired expression and/or activity. In specific embodiments, the invention herein provides anti-FGFR2/3 antibodies that are useful for, e.g., treatment or prevention of disease states associated with expression and/or activity of FGFR2 and FGFR3, such as increased expression and/or activity or undesired expression and/or activity. In some embodiments, the antibodies of the invention are used to treat a tumor, a cancer, and/or a cell proliferative disorder.

In another aspect, the anti-FGFR2/3 antibodies of the invention find utility as reagents for detection and/or isolation of FGFR2 and/or FGFR3, such as detection of FGFR3 in various tissues and cell type. In a specific embodiment, the anti-FGFR2/3 antibodies of the invention find utility as reagents for detection and/or isolation of FGFR2 and FGFR3, such as detection of FGFR2 and FGFR3 in various tissues and cell type.

The invention further provides methods of making and using anti-FGFR2/3 antibodies, and polynucleotides encoding anti-FGFR2/3 antibodies.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "antibody that competes for binding" with a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is described in "Antibodies," Harlow and Lane (Cold Spring Harbor Press, Cold Spring Harbor, N.Y.).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

An "effective amount" of an agent, e.g., a pharmaceutical formulation, refers to an amount effective, at dosages and for periods of time necessary, to achieve the desired therapeutic or prophylactic result. For example, and not by way of limitation, an "effective amount" can refer to an amount of an antibody, disclosed herein, that is able to alleviate, minimize and/or prevent the symptoms of the disease and/or disorder, prolong survival and/or prolong the period until relapse of the disease and/or disorder.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" as used interchangeably herein, refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "individual" or "subject," as used interchangeably herein, is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert," as used herein, refers to instructions customarily included in commercial packages of therapeutic products, that contain information about the indications, usage, dosage, administration, combination therapy, contraindications and/or warnings concerning the use of such therapeutic products.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid (for example, an antibody encoding nucleic acid) where, for example, the nucleic acid molecule is in a chromosomal location different from that of natural cells.

"Isolated nucleic acid encoding an antibody" (including references to a specific antibody, e.g., an anti-KLB antibody) refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is $1\times10^{-7}$, $1\times10^{-8}$, $5\times10^{-8}$, $1\times10^{-9}$, $3\times10^{-9}$, $5\times10^{-9}$, or even $1\times10^{-10}$ or higher affinity. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol. 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 al/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein (e.g., FGFR3-IIIb or -IIIc) (starting from 67 nM) are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 uM) before injection at a flow rate of 5l/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein (e.g., FGFR3-IIIb or -IIIc) (starting from 67 nM) are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/$ $k_{on}$. See, e.g., Chen, Y., et al., (1999) J. Mol. Biol. 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a a spectrometer, such as a stop-flow equipped spectrophotometer (Aviv Instruments) or a 8000-series SLM-Aminco spectrophotometer (ThermoSpectronic) with a stir red cuvette.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in the chart below. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in, e.g., WO2007/001851. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In some embodiments, two or more amino acid sequences are at least 50%, 60%, 70%, 80%, or 90% identical. In some embodiments, two or more amino acid sequences are at least 95%, 97%, 98%, 99%, or even 100% identical. Unless specifically stated otherwise, all % amino acid sequence identity values used herein are obtained as described in the immediately preceding paragraph using the ALIGN-2 computer program.

The term "FGFR3," as used herein, refers, unless specifically or contextually indicated otherwise, to any native or variant (whether native or synthetic) FGFR3 polypeptide (e.g., FGFR3-IIIb isoform or FGFR3-IIIc isoform). The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type FGFR3" generally refers to a polypeptide comprising an amino acid sequence of a naturally occurring FGFR3 protein. The term "wild type FGFR3 sequence" generally refers to an amino acid sequence found in a naturally occurring FGFR3.

The term "FGFR3 ligand," (interchangeably termed "FGF") as used herein, refers, unless specifically or contextually indicated otherwise, to any native or variant (whether native or synthetic) FGFR3 ligand (for example, FGF1, FGF2, FGF4, FGF8, FGF9, FGF17, FGF 18, FGF23) polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type FGFR3 ligand" generally refers to a polypeptide comprising an amino acid sequence of a naturally occurring FGFR3 ligand protein. The term "wild type FGFR3 ligand sequence" generally refers to an amino acid sequence found in a naturally occurring FGFR3 ligand.

The term "FGFR3 activation" refers to activation, or phosphorylation, of the FGFR3 receptor. Generally, FGFR3 activation results in signal transduction (e.g. that caused by an intracellular kinase domain of a FGFR3 receptor phosphorylating tyrosine residues in FGFR3 or a substrate polypeptide). FGFR3 activation may be mediated by FGFR ligand binding to a FGFR3 receptor of interest. FGFR3 ligand (e.g., such as FGF1 or FGF9) binding to FGFR3 may activate a kinase domain of FGFR3 and thereby result in phosphorylation of tyrosine residues in the FGFR3 and/or phosphorylation of tyrosine residues in additional substrate polypeptides(s).

The term "FGFR2," as used herein, refers, unless specifically or contextually indicated otherwise, to any native or variant (whether native or synthetic) FGFR2 polypeptide (e.g., FGFR2-IIIb isoform or FGFR2-IIIc isoform). The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type FGFR2" generally refers to a polypeptide comprising an amino acid sequence of a naturally occurring FGFR2 protein. The term "wild type FGFR2 sequence" generally refers to an amino acid sequence found in a naturally occurring FGFR2.

The term "FGFR2 ligand," (interchangeably termed "FGF2") as used herein, refers, unless specifically or contextually indicated otherwise, to any native or variant (whether native or synthetic) FGFR2 ligand. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type FGFR2 ligand" generally refers to a polypeptide comprising an amino acid sequence of a naturally occurring FGFR2 ligand protein. The term "wild type FGFR2 ligand sequence" generally refers to an amino acid sequence found in a naturally occurring FGFR2 ligand.

The term "FGFR2 activation" refers to activation, or phosphorylation, of the FGFR2 receptor. FGFR2 activation may be mediated by FGFR ligand binding to a FGFR2 receptor of interest. FGFR2 ligand binding to FGFR2 may activate a kinase domain of FGFR2 and thereby result in phosphorylation of tyrosine residues in the FGFR2 and/or phosphorylation of tyrosine residues in additional substrate polypeptides(s).

The term "FGFR2/3 antibody" refers to dual-specific antibodies that bind to FGFR2 and FGFR3. Non-limiting examples of FGFR2/3 antibodies include the dual specific monoclonoal antibodies 2B.1.3.10 and 2B.1.3.12 as described herein. The terms FGFR2/3 and "FGFR 2 and FGFR3" and "FGFR3 and FGFR2" are used interchangeably herein The term "constitutive" as used herein, as for example applied to receptor kinase activity, refers to continuous signaling activity of a receptor that is not dependent on the presence of a ligand or other activating molecules. Depending on the nature of the receptor, all of the activity may be constitutive or the activity of the receptor may be further activated by the binding of other molecules (e. g. ligands). Cellular events that lead to activation of receptors are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The term "ligand-independent" as used herein, as for example applied to receptor signaling activity, refers to signaling activity that is not dependent on the presence of a ligand. A receptor having ligand-independent kinase activity will not necessarily preclude the binding of ligand to that receptor to produce additional activation of the kinase activity.

The term "ligand-dependent" as used herein, as for example applied to receptor signaling activity, refers to signaling activity that is dependent on the presence of a ligand.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

A "tyrosine kinase inhibitor" is a molecule which inhibits to some extent tyrosine kinase activity of a tyrosine kinase such as FGFR2 and FGFR3 receptors.

A cancer or biological sample which "displays FGFR3 expression, amplification, or activation" is one which, in a diagnostic test, expresses (including overexpresses) FGFR3, has amplified FGFR3 gene, and/or otherwise demonstrates activation or phosphorylation of a FGFR3. A cancer or biological sample which "displays FGFR2 expression, amplification, or activation" is one which, in a diagnostic test, expresses (including overexpresses) FGFR2, has amplified FGFR2 gene, and/or otherwise demonstrates activation or phosphorylation of a FGFR2. A cancer or biological sample which "displays FGFR2/3 expression, amplification, or activation" or "displays FGFR2 and FGFR3 expression, amplicification, or activation" is one which, in a diagnostic test, expresses (including overexpresses) FGFR2 and FGFR3, has amplified FGFR2 and FGFR3 genes, and/or otherwise demonstrates activation or phosphorylation of a FGFR2 and a FGFR3.

"Klotho-beta," "KLB" and "beta-Klotho," as used herein, refers to any native beta-Klotho from any vertebrate source, including mammals such as primates (e.g., humans) and rodents (e.g., mice and rats), unless otherwise indicated. The term encompasses "full-length," unprocessed KLB as well as any form of KLB that results from processing in the cell. The term also encompasses naturally occurring variants of KLB, e.g., splice variants or allelic variants. A non-limiting example of a human KLB amino acid sequence targeted by an antibody of the present disclosure, excluding the signal sequence, is as follows:

```
                                          (SEQ ID NO: 233)
FSGDGRAIWSKNPNFTPVNESQLFLYDTFPKNFFWGIGTGALQVEGSWKK

DGKGPSIWDHFIHTHLKNVSSTNGSSDSYIFLEKDLSALDFIGVSFYQFS

ISWPRLFPDGIVTVANAKGLQYYSTLLDALVLRNIEPIVTLYHWDLPLAL

QEKYGGWKNDTIIDIFNDYATYCFQMFGDRVKYWITIHNPYLVAWHGYGT

GMHAPGEKGNLAAVYTVGHNLIKAHSKVWHNYNTHFRPHQKGWLSITLGS

HWIEPNRSENTMDIFKCQQSMVSVLGWFANPIHGDGDYPEGMRKKLFSVL

PIFSEAEKHEMRGTADFFAFSFGPNNFKPLNTMAKMGQNVSLNLREALNW

IKLEYNNPRILIAENGWFTDSRVKTEDTTAIYMMKNFLSQVLQAIRLDEI

RVFGYTAWSLLDGFEWQDAYTIRRGLFYVDFNSKQKERKPKSSAHYYKQI

IRENGFSLKESTPDVQGQFPCDFSWGVTESVLKPESVASSPQFSDPHLYV

WNATGNRLLHRVEGVRLKTRPAQCTDFVNIKKQLEMLARMKVTHYRFALD

WASVLPTGNLSAVNRQALRYYRCVVSEGLKLGISAMVTLYYPTHAHLGLP

EPLLHADGWLNPSTAEAFQAYAGLCFQELGDLVKLWITINEPNRLSDIYN

RSGNDTYGAAHNLLVAHALAWRLYDRQFRPSQRGAVSLSLHADWAEPANP

YADSHWRAAERFLQFEIAWFAEPLFKTGDYPAAMREYIASKHRRGLSSSA

LPRLTEAERRLLKGTVDFCALNHFTTRFVMHEQLAGSRYDSDRDIQFLQD

ITRLSSPTRLAVIPWGVRKLLRWVRRNYGDMDIYITASGIDDQALEDDRL

RKYYLGKYLQEVLKAYLIDKVRIKGYYAFKLAEEKSKPRFGFFTSDFKAK

SSIQFYNKVISSRGFPFENSSSRCSQTQENTECTVCLFLVQKKPLIFLGC

CFFSTLVLLLSIAIFQRQKRRKFWKAKNLQHIPLKKGKRVVS.
```

In certain embodiments, a KLB protein can include a N-terminal signal sequence having the amino acid sequence

```
                                          (SEQ ID NO: 234)
MKPGCAAGSPGNEWIFFSTDEITTRYRNTMSNGGLQRSVILSALILLRAV

TG.
```

The term "C-terminal domain of KLB" refers to the carboxy-terminal glycosidase-like domain of KLB. For example, the C-terminal domain of the exemplary KLB protein shown in SEQ ID NO: 233 comprises the following amino acid sequence:

```
                                          (SEQ ID NO: 235)
FPCDFSWGVTESVLKPESVASSPQFSDPHLYVWNATGNRLLHRVEGVRLK

TRPAQCTDFVNIKKQLEMLARMKVTHYRFALDWASVLPTGNLSAVNRQAL

RYYRCVVSEGLKLGISAMVTLYYPTHAHLGLPEPLLHADGWLNPSTAEAF

QAYAGLCFQELGDLVKLWITINEPNRLSDIYNRSGNDTYGAAHNLLVAHA

LAWRLYDRQFRPSQRGAVSLSLHADWAEPANPYADSHWRAAERFLQFEIA

WFAEPLFKTGDYPAAMREYIASKHRRGLSSSALPRLTEAERRLLKGTVDF

CALNHFTTRFVMHEQLAGSRYDSDRDIQFLQDITRLSSPTRLAVIPWGVR

KLLRWVRRNYGDMDIYITASGIDDQALEDDRLRKYYLGKYLQEVLKAYLI

DKVRIKGYYAFKLAEEKSKPRFGFFTSDFKAKSSIQFYNKVISSRGFPFE

NSSSR.
```

The terms "anti-KLB antibody" and "an antibody that binds to KLB" refer to an antibody that is capable of binding KLB with sufficient affinity such that the antibody is useful as a diagnostic and/or therapeutic agent in targeting KLB. In one embodiment, the extent of binding of an anti-KLB antibody to an unrelated, non-KLB protein is less than about 10% of the binding of the antibody to KLB as measured, e.g., by a radioimmunoassay (RIA). In certain embodiments, an antibody that binds to KLB has a dissociation constant ($K_d$) of ≤1 μM, ≤100 nM, ≤10 nM, ≤1 nM, ≤0.1 nM, ≤0.01 nM, or ≤0.001 nM (e.g., $10^{-8}$ M or less, e.g., from 10 M to $10^{-13}$ M, e.g., from $10^{-9}$ M to $10^{-13}$ M). In certain embodiments, an anti-KLB antibody binds to an epitope of KLB that is conserved among KLB from different species. In certain embodiments, an anti-KLB antibody binds to an epitope on KLB that is in the C-terminal part of the protein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier," as used herein, refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the present disclosure can be used to delay development of a disease or to slow the progression of a disease. "Treatment" refers to both therapeutic treatment and prophylactic or preventative measures. As it relates to the FGFR2/3 antibody, those in need of treatment include those already having a benign, pre-cancerous, or non-metastatic tumor as well as those in which the occurrence or recurrence of cancer is to be prevented.

A cancer or biological sample which "displays FGFR3 activation" is one which, in a diagnostic test, demonstrates activation or phosphorylation of FGFR3. Such activation can be determined directly (e.g. by measuring FGFR3 phosphorylation by ELISA) or indirectly. A cancer or biological sample which "displays FGFR2 activation" is one which, in a diagnostic test, demonstrates activation or phosphorylation of FGFR2. Such activation can be determined directly or indirectly. A cancer or biological sample which "displays FGFR2 and FGFR3 activation" is one which, in a diagnostic test, demonstrates activation or phosphorylation of FGFR2 and FGFR3. Such activation can be determined directly or indirectly.

A cancer or biological sample which "displays constitutive FGFR3 activation" is one which, in a diagnostic test, demonstrates constitutive activation or phosphorylation of a FGFR3. Such activation can be determined directly (e.g. by measuring c-FGFR3 phosphorylation by ELISA) or indirectly. A cancer or biological sample which "displays constitutive FGFR2 activation" is one which, in a diagnostic test, demonstrates constitutive activation or phosphorylation of a FGFR2. Such activation can be determined directly or indirectly. A cancer or biological sample which "displays constitutive FGFR2 and FGFR3 activation" is one which, in a diagnostic test, demonstrates constitutive activation or phosphorylation of a FGFR2 and a FGFR3. Such activation can be determined directly or indirectly.

A cancer or biological sample which "displays FGFR3 amplification" is one which, in a diagnostic test, has amplified FGFR3 gene. A cancer or biological sample which "displays FGFR2 amplification" is one which, in a diagnostic test, has amplified FGFR2 gene. A cancer or biological sample which "displays FGFR2 and FGFR3 amplification" is one which, in a diagnostic test, has amplified FGFR2 and FGFR3 genes.

A cancer or biological sample which "displays FGFR3 translocation" is one which, in a diagnostic test, has translocated FGFR3 gene. An example of a FGFR3 translocation is the t(4; 14) translocation, which occurs in some multiple myeloma tumors. A cancer or biological sample which "displays FGFR2 translocation" is one which, in a diagnostic test, has translocated FGFR2 gene. A cancer or biological sample which "displays FGFR2 and FGFR3 translocation" is one which, in a diagnostic test, has translocated FGFR2 and FGFR3 genes.

A "phospho-ELISA assay" herein is an assay in which phosphorylation of one or more FGFR (e.g. FGFR2 and FGFR3), substrate or downstream signaling molecules is evaluated in an enzyme-linked immunosorbent assay (ELISA) using a reagent, usually an antibody, to detect a phosphorylated FGFR (e.g. FGFR2 and FGFR3), substrate, or downstream signaling molecule. In some embodiments, an antibody which detects phosphorylated FGFR2, FGFR3, or pMAPK is used. In a specific embodiment, an antibody which detects phosphorylated FGFR2 and FGFR3 is used. The assay may be performed on cell lysates, preferably from fresh or frozen biological samples.

A cancer or biological sample which "displays ligand-independent FGFR3 activation" is one which, in a diagnostic test, demonstrates ligand-independent activation or phosphorylation of a FGFR3. Such activation can be determined directly (e.g. by measuring FGFR3 phosphorylation by ELISA) or indirectly. A cancer or biological sample which "displays ligand-independent FGFR2 activation" is one which, in a diagnostic test, demonstrates ligand-independent activation or phosphorylation of a FGFR2. Such activation can be determined directly or indirectly. A cancer or biological sample which "displays ligand-independent FGFR2/3 activation" is one which, in a diagnostic test, demonstrates ligand-independent activation or phosphorylation of a FGFR2 and FGFR3. Such activation can be determined directly or indirectly.

A cancer or biological sample which "displays ligand-dependent FGFR3 activation" is one which, in a diagnostic test, demonstrates ligand-dependent activation or phosphorylation of a FGFR3. Such activation can be determined directly (e.g. by measuring FGFR3 phosphorylation by ELISA) or indirectly. A cancer or biological sample which "displays ligand-dependent FGFR2 activation" is one which, in a diagnostic test, demonstrates ligand-dependent activation or phosphorylation of a FGFR2. Such activation can be determined directly or indirectly. A cancer or biological sample which "displays ligand-dependent FGFR2/3 activation" is one which, in a diagnostic test, demonstrates ligand-dependent activation or phosphorylation of a FGFR2/3. Such activation can be determined directly or indirectly.

A cancer or biological sample which "displays ligand-independent FGFR3 activation" is one which, in a diagnostic test, demonstrates ligand-independent activation or phosphorylation of a FGFR3. Such activation can be determined directly (e.g. by measuring FGFR3 phosphorylation by ELISA) or indirectly. A cancer or biological sample which "displays ligand-independent FGFR2 activation" is one which, in a diagnostic test, demonstrates ligand-independent activation or phosphorylation of a FGFR2. Such activation can be determined directly or indirectly. A cancer or biological sample which "displays ligand-independent FGFR2/3 activation" is one which, in a diagnostic test, demonstrates ligand-independent activation or phosphorylation of a FGFR2/3. Such activation can be determined directly or indirectly.

A cancer cell with "FGFR3 overexpression or amplification" is one which has significantly higher levels of a FGFR3 protein or gene compared to a noncancerous cell of the same tissue type. Such overexpression may be caused by gene amplification or by increased transcription or translation. FGFR3 overexpression or amplification may be determined in a diagnostic or prognostic assay by evaluating increased levels of the FGFR3 protein present on the surface of a cell (e.g. via an immunohistochemistry assay; IHC). Alternatively, or additionally, one may measure levels of FGFR3-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

A cancer cell with "FGFR2 overexpression or amplification" is one which has significantly higher levels of a FGFR2 protein or gene compared to a noncancerous cell of the same tissue type. Such overexpression may be caused by gene amplification or by increased transcription or translation. FGFR2 overexpression or amplification may be determined in a diagnostic or prognostic assay by evaluating increased levels of the FGFR2 protein present on the surface of a cell (e.g. via an immunohistochemistry assay; IHC). Alternatively, or additionally, one may measure levels of FGFR2-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

A cancer cell with "FGFR2/3 overexpression or amplification" is one which has significantly higher levels of FGFR2 and FGFR3 proteins or genes compared to a noncancerous cell of the same tissue type. Such overexpression may be caused by gene amplification or by increased transcription or translation. FGFR2 and FGFR3 overexpression or amplification may be determined in a diagnostic or prognostic assay by evaluating increased levels of the FGFR2 and FGFR3 proteins present on the surface of a cell (e.g. via an immunohistochemistry assay; IHC). Alternatively, or additionally, one may measure levels of FGFR2 and FGFR3-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The term "mutation", as used herein, means a difference in the amino acid or nucleic acid sequence of a particular protein or nucleic acid (gene, RNA) relative to the wild-type protein or nucleic acid, respectively. A mutated protein or nucleic acid can be expressed from or found on one allele (heterozygous) or both alleles (homozygous) of a gene, and may be somatic or germ line. In the instant invention, mutations are generally somatic. Mutations include sequence rearrangements such as insertions, deletions, and point mutations (including single nucleotide/amino acid polymorphisms).

To "inhibit" is to decrease or reduce an activity, function, and/or amount as compared to a reference.

An agent possesses "agonist activity or function" when an agent mimics at least one of the functional activities of a polypeptide of interest (e.g., FGFR ligand, such as FGF1 or FGF9).

An "agonist antibody", as used herein, is an antibody which mimics at least one of the functional activities of a polypeptide of interest (e.g., FGFR ligand, such as FGF 1 or FGF9).

Protein "expression" refers to conversion of the information encoded in a gene into messenger RNA (mRNA) and then to the protein.

Herein, a sample or cell that "expresses" a protein of interest (such as a FGF receptor or FGF receptor ligand) is one in which mRNA encoding the protein, or the protein, including fragments thereof, is determined to be present in the sample or cell.

An "immunoconjugate" (interchangeably referred to as "antibody-drug conjugate," or "ADC") means an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

By "Fc polypeptide" herein is meant one of the polypeptides that make up an Fc region. An Fc polypeptide may be obtained from any suitable immunoglobulin, such as $IgG_1$, $IgG_2$, $IgG_3$, or $IgG_4$ subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

A "blocking" antibody or an antibody "antagonist" is one which inhibits or reduces biological activity of the antigen it binds. Preferred blocking antibodies or antagonist antibodies completely inhibit the biological activity of the antigen.

A "naked antibody" is an antibody that is not conjugated to a heterologous molecule, such as a cytotoxic moiety or radiolabel.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., *Ann. Rev. Immunol.* 18:739-766 (2000), Table 1). Antibodies with substitutions in an Fc region thereof and increased serum half-lives are also described in WO00/42072, WO 02/060919; Shields et al., J. Biol. Chem. 276:6591-6604 (2001); Hinton, *J. Biol. Chem.* 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one preferred embodiment, the serum albumin peptide to be attached comprises an amino acid sequence of DICLPRWGCLW (SEQ ID NO: 296). In another embodiment, the half-life of a Fab is increased by these methods. See also, Dennis et al. *J. Biol. Chem.* 277:35035-35043 (2002) for serum albumin binding peptide sequences.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

The phrase "little to no agonist function" with respect to an antibody of the invention, as used herein, means the antibody does not elicit a biologically meaningful amount of agonist activity, e.g., upon administration to a subject. As would be understood in the art, amount of an activity may be determined quantitatively or qualitatively, so long as a comparison between an antibody of the invention and a reference counterpart can be done. The activity can be measured or detected according to any assay or technique known in the art, including, e.g., those described herein. The amount of activity for an antibody of the invention and its reference counterpart can be determined in parallel or in separate runs. In some embodiments, a bivalent antibody of the invention does not possess substantial agonist function.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured using techniques known in the art, for instance, by cell viability assays, FACS analysis or DNA electrophoresis, and more specifically by binding of annexin V, fragmentation of DNA, cell shrinkage, dilation of endoplasmic reticulum, cell fragmentation, and/or formation of membrane vesicles (called apoptotic bodies).

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized, and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Ilmmunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')₂ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG₁, IgG₂, IgG₃, IgG₄, IgA₁, and IgA₂. The heavy-chain constant domains that correspond to the different classes of immunoglobulins are called α, δ, ε, γ, and μ, respectively. The subunit structures and three-dimensional configurations of different classes of immunoglobulins are well known. "Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |

-continued

| Loop | Kabat | AbM | Chothia | Contact |
|---|---|---|---|---|
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies, vol.* 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins. WO 00/42072 (Presta) describes antibody variants with improved or diminished binding to FcRs. The content of that patent publication is specifically incorporated herein by reference. See, also, Shields et al., *J. Biol. Chem.* 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO 99/51642. The contents of those patent publications are specifically incorporated herein by reference. See, also, Idusogie et al., *J. Immunol.* 164:4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H, and 78H; for instance, the amino acid residues at those positions may be 71A, 73T, and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

```
                              (SEQ ID NO: 95)
EVQLVESGGGLVQPGGSLRLSCAAS- (SEQ ID NO: 96)
H1-WVRQAPGKGLEWV- (SEQ ID NO: 97)
H2-RFTISRDNSKNTLYLQMNSLRAEDTAVYYC- (SEQ ID NO: 98)
H3-WGQGTLVTVSS.
```

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences: DIQMTQSPSSLSAS-VGDRVTITC

```
                              (SEQ ID NO: 99)
DIQMTQSPSSLSASVGDRVTITC- (SEQ ID NO: 100)
L1-WYQQKPGKAPKLLIY- (SEQ ID NO: 101)
L2-GVPSRFSGSGSGTDFTLTISSLQPEDFATYYC- (SEQ ID NO: 102)
L3-FGQGTKVEIK.
```

As used herein, "antibody mutant" or "antibody variant" refers to an amino acid sequence variant of an antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

The term "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer and multiple myeloma.

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

By "dysplasia" is meant any abnormal growth or development of tissue, organ, or cells. Preferably, the dysplasia is high grade or precancerous.

By "metastasis" is meant the spread of http://en.wikipedia.org/wiki/Cancercancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass.

Both stimulatory and inhibitory molecular pathways within the tumor cell regulate this behavior, and interactions between the tumor cell and host cells in the distant site are also significant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

By "primary tumor" or "primary cancer" is meant the original cancer and not a metastatic lesion located in another tissue, organ, or location in the subject's body.

By "benign tumor" or "benign cancer" is meant a tumor that remains localized at the site of origin and does not have the capacity to infiltrate, invade, or metastasize to a distant site.

By "tumor burden" is meant the number of cancer cells, the size of a tumor, or the amount of cancer in the body. Tumor burden is also referred to as tumor load.

By "tumor number" is meant the number of tumors.

By "subject" is meant a mammal, including, but not limited to, a human or non-human mammal, such as a bovine, equine, canine, ovine, or feline. Preferably, the subject is a human.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaI1 and calicheamicin omegaI1 (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil;

amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; VELCADE bortezomib; REVLIMID lenalidomide; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the individual. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g., a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

Anti-FGFR2/3 Antibody Compositions and Methods of Using Anti-FGFR2/3 Antibodies

This invention encompasses compositions, including pharmaceutical compositions, comprising an anti-FGFR2/3 antibody; and polynucleotides comprising sequences encoding an anti-FGFR2/3 antibody. As used herein, compositions comprise one or more antibodies that bind to FGFR2 and FGFR3, and/or one or more polynucleotides comprising sequences encoding one or more antibodies that bind to FGFR2 and FGFR3. These compositions may further comprise suitable carriers, such as pharmaceutically acceptable excipients including buffers, which are well known in the art.

The invention also encompasses isolated antibody and polynucleotide embodiments. The invention also encompasses substantially pure antibody and polynucleotide embodiments.

The invention also encompasses method of treating a disorder, e.g. multiple myeloma or transitional stage carcinoma (e.g., invasive transitional stage carcinoma) using an anti-FGFR2/3 antibody (as described herein or as known in the art).

Anti-FGFR2/3 Antibody Compositions

The anti-FGFR2/3 antibodies of the invention are preferably monoclonal. Also encompassed within the scope of the invention are Fab, Fab', Fab'-SH and F(ab')$_2$ fragments of the anti-FGFR2/3 antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-FGFR2/3 monoclonal antibodies of the invention can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to FGFR2/3 may be raised in animals by multiple subcutaneous (sc) or intraperitoneal (ip) injections of FGFR2/3 and an adjuvant. FGFR2/3 may be prepared using methods well-known in the art, some of which are further described herein. For example, recombinant production of human and mouse FGFR2/3 is described below. In one embodiment, animals are immunized with a FGFR2/3 fused to the Fc portion of an immunoglobulin heavy chain. In a preferred embodiment, animals are immunized with a FGFR2/3-IgG1 fusion protein. Animals ordinarily are immunized against immunogenic conjugates or derivatives of FGFR2/3 with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-FGFR2/3 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against FGFR2/3. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-FGFR2/3 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-FGFR3 antibodies of the invention can be obtained by designing a suitable antigen screening procedure to select for the phage clone of interest followed by construction of a full length anti-FGFR2/3 antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g., as described by Marks et a., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g., as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-FGFR2/3 clones is desired, the individual is immunized with FGFR2/3 to generate an antibody response, and spleen cells and/or circulating B cells other peripheral blood lymphocytes (PBLs) are recovered for library construction. In a preferred embodiment, a human antibody gene fragment library biased in favor of anti-FGFR2/3 clones is obtained by generating an anti-FGFR2/3 antibody response in transgenic mice carrying a functional human immunoglobulin gene array (and lacking a functional endogenous antibody production system) such that FGFR2/3 immunization gives rise to B cells producing human antibodies against FGFR2/3. The generation of human antibody-producing transgenic mice is described below.

Additional enrichment for anti-FGFR2/3 reactive cell populations can be obtained by using a suitable screening procedure to isolate B cells expressing FGFR2/3-specific membrane bound antibody, e.g., by cell separation with FGFR2/3 affinity chromatography or adsorption of cells to fluorochrome-labeled FGFR2/3 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which FGFR2/3 is not antigenic. For libraries incorporating in vitro antibody gene construction, stem cells are harvested from the individual to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (USA), 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128:119-126 (1993), or in vivo by combinatorial infection, e.g., the loxP system described in Waterhouse et al., *Nucl. Acids Res.,* 21:2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g., as described in Barbas et al., *Proc. Natl. Acad. Sci. USA,* 88:7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.,* 20:3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutations can be introduced at random in vitro by using error-prone polymerase (reported in Leung et al., *Technique,* 1:1230-232 and 236-247 (1989)) in the method of Hawkins et al., *J. Mol. Biol.,* 226: 889-896 (1992) or in the method of Gram et al., *Proc. Natl. Acad. Sci USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 96/07754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.,* 10:779-783 (1992). This technique allows the production of antibodies and antibody fragments with affinities in the $10^{-9}$ M range.

FGFR2 and FGFR3 nucleic acid and amino acid sequences are known in the art. Nucleic acid sequence encoding the FGFR2 and FGFR3 can be designed using the amino acid sequence of the desired region of FGFR2 and FGFR3. For example, the FGFR3 can be designed using the amino acid sequence of R3Mab As is well-known in the art, there are two major splice isoforms of FGFR3, FGFR3 IIIb and FGFR3 IIIc. FGFR3 sequences are well-known in the art and may include the sequence of UniProKB/Swiss-Prot accession number P22607 (FGFR3 IIIc) or P22607_2 (FGFR3 IIIb). FGFR2 and FGFR3 mutations have been identified and are well-known in the art and include the following mutations (with reference to the sequences shown in UniProKB/Swiss-Prot accession number P22607 (FGFR3 IIIc) or P22607_2 (FGFR3 IIIb):

| FGFR3-IIIb | FGFR3 IIIc |
|---|---|
| R248C | R248C |
| S249C | S249C |
| G372C | G370C |
| Y375C | Y373C |
| G382R | G380R |
| K652E | K650E |

Nucleic acids encoding FGFR2 and/or FGFR3 can be prepared by a variety of methods known in the art. These methods include, but are not limited to, chemical synthesis by any of the methods described in Engels et al., *Agnew. Chem. Int. Ed. Engl.,* 28: 716-734 (1989), such as the triester, phosphite, phosphoramidite and H-phosphonate methods. In one embodiment, codons preferred by the expression host cell are used in the design of the FGFR2 and/or FGFR3 encoding DNA. Alternatively, DNA encoding FGFR2 and/or FGFR3 can be isolated from a genomic or cDNA library.

Following construction of the DNA molecule encoding the FGFR2 and/or FGFR3, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding the FGFR2 and/or FGFR3 is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.,* 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the FGFR2 and/or FGFR3 can be cultured as described generally in Sambrook et al., supra.

The mammalian host cells used to produce the FGFR2 and/or FGFR3 can be cultured in a variety of media, which is well known in the art and some of which is described herein.

The host cells referred to in this disclosure encompass cells in in vitro culture as well as cells that are within a host animal.

Purification of FGFR2 and/or FGFR3 may be accomplished using art-recognized methods, some of which are described herein.

The purified FGFR2 and/or FGFR3 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the FGFR2 and/or FGFR3 protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, FGFR2 and/or FGFR3 can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized FGFR2 and/or FGFR3 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by FGFR3 antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for FGFR2 and/or FGFR3. However, random mutation of a selected antibody (e.g. as performed in some of the affinity maturation techniques described above) is likely to give rise to many mutants, most binding to antigen, and a few with higher affinity. With limiting FGFR2 and/or FGFR3, rare high affinity phage could be competed out. To retain all the higher affinity mutants, phages can be incubated with excess biotinylated FGFR2 and/or FGFR3, but with the biotinylated FGFR2 and/or FGFR3 at a concentration of lower molarity than the target molar affinity constant for FGFR2 and/or FGFR3. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

FGFR2/3 clones may be activity selected. In one embodiment, the invention provides FGFR2/3 antibodies that block the binding between a FGFR3 receptor and its ligand (such as FGF 1 and/or FGF9) and FGFR2 and its ligand. Fv clones corresponding to such FGFR2/3 antibodies can be selected by (1) isolating FGFR2/3 clones from a phage library as described above, and optionally amplifying the isolated population of phage clones by growing up the population in a suitable bacterial host; (2) selecting FGFR2/3 and a second protein against which blocking and non-blocking activity, respectively, is desired; (3) adsorbing the anti-FGFR2/3 phage clones to immobilized FGFR2/3; (4) using an excess of the second protein to elute any undesired clones that recognize FGFR2/3-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the hybridoma-derived monoclonal antibodies or phage display Fv clones of the invention is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130:151 (1992).

DNA encoding the Fv clones of the invention can be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-FGFR2/3 antibody derived from a hybridoma of the invention can also be modified, for example, by substituting the coding sequence for human heavy- and light-chain constant domains in place of homologous murine sequences derived from the hybridoma clone (e.g., as in the method of Morrison et al., *Proc. Natl. Acad. Sci. USA*, 81:6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Bispecific Antibodies

In one aspect, the invention is based, in part, on the discovery of bispecific antibodies that bind to both KLB and FGFR2/3 ("FGFR2/3+KLB bispecific antibodies"). In certain aspects, the FGFR2/3+KLB bispecific antibodies can be used in the treatment of metabolic diseases and disdorders, such treatment resulting in weight loss and/or improvement in glucose and lipid metabolism without a significant impact on the liver and without significant loss in bone mass. In certain aspects, the FGFR2/3+KLB bispecific antibodies can be used in the treatment of NASH.

In certain embodiments, the FGFR2/3+KLB bispecific antibodies disclosed herein comprise a first arm of any of the anti-FGFR2/3 antibodies disclosed herein and a second arm of any anti-KLB antibody disclosed herein or disclosed in US20150218276 which is incorporated herein in its entirety.

In certain embodiments, an FGFR2/3+KLB bispecific antibody of the present disclosure does not have a significant impact on the liver, e.g., liver function. In certain embodiments, an FGFR2/3+KLB bispecific antibody of the present disclosure does not modulate the activity of an FGFR/KLB receptor complex in the liver as compared to the modulation of an FGFR/KLB receptor complex in the liver by an FGF21 protein. In certain embodiments, an FGFR2/3+KLB bispecific antibody of the present disclosure does not result in the inhibition of the FGFR4/KLB complex and/or does not result in the elevation of liver enzymes such as, but not limited to, ALT, AST, ALP and GLDH. In certain embodiments, an FGFR2/3+KLB bispecific antibody of the present disclosure does not function as an agonist of the FGFR2c/KLB complex and/or the FGFR3c/KLB complex in the liver, which can lead to activated MAPK signaling and/or altered expression of Spry4 and Dusp6 in the liver. In certain embodiments, an FGFR2/3+KLB bispecific antibody of the present disclosure does not result in the activation of MAPK signaling in the liver as compared to the activation of MAPK signaling by an FGF21 protein. In certain embodiments, an FGFR2/3+KLB bispecific antibody of the present disclosure does not function as an agonist of the FGFR4/KLB complex in the liver.

In certain embodiments, an FGFR2/3+KLB bispecific antibody of the present disclosure can be humanized. In certain embodiments, an FGFR2/3+KLB bispecific antibody of the present disclosure comprises an acceptor human framework, e.g., a human immunoglobulin framework or a human consensus framework.

In certain embodiments, an FGFR2/3+KLB bispecific antibody of the present disclosure can be a monoclonal antibody, including a chimeric, humanized or human antibody. In certain embodiments, an FGFR2/3+KLB bispecific antibody of the present disclosure can be an antibody fragment, e.g., a Fv, Fab, Fab', scFv, diabody, or F(ab')$_2$ fragment. In certain embodiments, the FGFR2/3+KLB bispecific antibody is a full length antibody, e.g., an intact IgG1 antibody, or other antibody class or isotype as defined herein. In a certain embodiments, an FGFR2/3+KLB bispecific antibody of the present disclosure can incorporate any of the features, singly or in combination, as described in detailed below.

FGFR2/3+KLB bispecific antibodies of the present disclosure are useful, e.g., for the diagnosis or treatment of metabolic disorders. Non-limiting examples of metabolic disorders include polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), maturity onset diabetes of the young (MODY), and aging and related diseases such as Alzheimer's disease, Parkinson's disease and ALS. In preferred aspects, the metabolic disease is NASH.

In certain embodiments, the FGFR2/3+KLB bispecific antibodies of the present disclosure are can be used, e.g., for the diagnosis or treatment of metabolic disorders. Non-limiting examples of metabolic disorders include polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), maturity onset diabetes of the young (MODY), and aging and related diseases such as Alzheimer's disease, Parkinson's disease and ALS. In preferred aspects, the metabolic disease is NASH.

Exemplary Anti-KLB Antibodies

In one aspect, the present disclosure provides isolated antibodies that bind to a KLB protein. In certain embodiments, an anti-KLB antibody of the present disclosure binds to the C-terminal domain of KLB. In certain embodiments, an anti-KLB antibody of the present disclosure binds to a fragment of KLB that comprises the amino acid sequence SSPTRLAVIPWGVRKLLRWVRRNYGDMDIYITAS (SEQ ID NO: 103). In certain embodiments, the antibody binds to the same epitope as an anti-KLB antibody, e.g., 8C5, described herein.

In certain embodiments, an anti-KLB antibody of the present disclosure comprises at least one, two, three, four, five, or six HVRs selected from (a) HVR-H1 comprising an amino acid sequence of any one of SEQ ID NOs: 108-122 and 315, e.g., 119 or 122; (b) HVR-H2 comprising an amino acid sequence of any one of SEQ ID NOs: 138-153, e.g., 150 or 153; (c) HVR-H3 comprising an amino acid sequence of any one of SEQ ID NOs: 154-169, e.g., 166 or 169; (d)

HVR-L1 comprising an amino acid sequence of any one of SEQ ID NOs: 170-184, e.g., 181 or 184; (e) HVR-L2 comprising an amino acid sequence of any one of SEQ ID NOs: 185-200, e.g., 197 or 200; and (f) HVR-L3 comprising an amino acid sequence of any one of SEQ ID NOs: 201-215, e.g., 212 or 215.

In certain embodiments, the present disclosure provides an anti-KLB antibody comprising at least one, two, three, four, five, or six HVRs selected from (a) HVR-H1 comprising SEQ ID NO: 119; (b) HVR-H2 comprising SEQ ID NO: 150; (c) HVR-H3 comprising SEQ ID NO: 166; (d) HVR-L1 comprising SEQ ID NO: 181; (e) HVR-L2 comprising SEQ ID NO: 197; and (f) HVR-L3 comprising SEQ ID NO: 212. In certain embodiments, the present disclosure provides an anti-KLB antibody comprising at least one, two, three, four, five, or six HVRs selected from (a) HVR-H1 comprising SEQ ID NO: 122; (b) HVR-H2 comprising SEQ ID NO 153; (c) HVR-H3 comprising SEQ ID NO: 169; (d) HVR-L1 comprising SEQ ID NO 184; (e) HVR-L2 comprising SEQ ID NO: 200; and (f) HVR-L3 comprising SEQ ID NO: 215.

The present disclosure further provides an anti-KLB antibody that comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 104. In certain embodiments, a VH sequence having at least 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-KLB antibody comprising that sequence retains the ability to bind to KLB. In certain embodiments, a total of 1 to 10 amino acids have been substituted, inserted and/or deleted in SEQ ID NO: 104. In certain embodiments, substitutions, insertions, or deletions occur in regions outside the HVRs (i.e., in the FRs). Alternatively or additionally, the anti-KLB antibody comprises the VH sequence in SEQ ID NO: 104, including post-translational modifications of that sequence as disclosed below. In certain embodiments, the VH comprises one, two or three HVRs selected from: (a) HVR-H1 comprising the amino acid sequence of SEQ ID NO: 122, (b) HVR-H2 comprising the amino acid sequence of SEQ ID NO: 153, and (c) HVR-H3 comprising the amino acid sequence of SEQ ID NO: 169.

In another aspect, the present disclosure provides an anti-KLB antibody, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 105. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLB antibody comprising that sequence retains the ability to bind to KLB. In certain embodiments, a total of 1 to 10 amino acids have been substituted, inserted and/or deleted in SEQ ID NO: 105. In certain embodiments, the substitutions, insertions, or deletions occur in regions outside the HVRs (i.e., in the FRs). Alternatively or additionally, the anti-KLB antibody comprises the VL sequence in SEQ ID NO: 105, including post-translational modifications of that sequence. In certain embodiments, the VL comprises one, two or three HVRs selected from (a) HVR-L1 comprising the amino acid sequence of SEQ ID NO: 184; (b) HVR-L2 comprising the amino acid sequence of SEQ ID NO: 200; and (c) HVR-L3 comprising the amino acid sequence of SEQ ID NO: 215.

The present disclosure further provides an anti-KLB antibody, wherein the antibody comprises a VH as in any of the embodiments provided above, and a VL as in any of the embodiments provided above. In certain embodiments, the antibody comprises the VH and VL sequences in SEQ ID NO: 104 and SEQ ID NO: 105, respectively, including post-translational modifications of those sequences.

In certain embodiments, an anti-KLB antibody binds to a fragment of KLB consisting of the amino acid sequence SSPTRLAVIPWGVRKLLRWVRRNYGDMDIYITAS (SEQ ID NO: 103).

Bispecific Anti-FGFR2/3 Antibody

The present disclosure further provides bispecific antibodies that bind to both KLB and FGFR2/3 (i.e., FGFR2/3+KLB bispecific antibodies). A bispecific antibody has two different binding specificities, see, e.g., U.S. Pat. Nos. 5,922,845 and 5,837,243; Zeilder (1999) J. Immunol. 163:1246-1252; Somasundaram (1999) Hum. Antibodies 9:47-54; Keler (1997) Cancer Res. 57:4008-4014. For example, and not by way of limitation, the presently disclosed subject matter provides bispecific antibodies having one binding site (e.g., antigen binding site) for a first epitope present on KLB and a second binding site for a second epitope present on FGFR2/3. For example, and not by way of limitation, the present disclosure provides an antibody where one arm binds KLB and comprises any of the anti-KLB antibody sequences described herein and the second arm binds to FGFR2/3 and comprises any of the anti-FGFR2/3 antibody sequences described herein. In certain embodiments, an FGFR2/3+KLB bispecific antibody of the present disclosure has one binding site for a first epitope present on KLB and a second binding site for a second epitope present on FGFR2/3.

In certain embodiments, an FGFR2/3+KLB bispecific antibody, or an antigen-binding portion thereof, includes a heavy chain and a light chain region. In certain embodiments, the full length heavy chain includes amino acids having a sequence that is at least 90%, 91%, 92%, 93%, 94%, 95%, 96%, 97%, 98%, 99%, or 100% identical to the sequence set forth in SEQ ID NO: 106. In certain embodiments, the full length light chain includes amino acids having a sequence that is at least 90%, 91%, 92%, 93%, 94%, 95%, 96%, 97%, 98%, 99%, or 100% identical to the sequence set forth in SEQ ID NO: 107. In certain embodiments, the full length heavy chain includes amino acids having the sequence set forth in SEQ ID NO: 106. In certain embodiments, the full length light chain includes amino acids having the sequence set forth in SEQ ID NO: 107.

In certain embodiments, an FGFR2/3+KLB bispecific antibody, or an antigen-binding portion thereof, includes a heavy chain variable region and a light chain variable region. In certain embodiments, the heavy chain variable region includes amino acids having a sequence that is at least 90%, 91%, 92%, 93%, 94%, 95%, 96%, 97%, 98%, 99%, or 100% identical to the sequence set forth in SEQ ID NO: 104. In certain embodiments, the light chain variable region includes amino acids having a sequence that is at least 90%, 91%, 92%, 93%, 94%, 95%, 96%, 97%, 98%, 99%, or 100% identical to the sequence set forth in SEQ ID NO: 105. In certain embodiments, the heavy chain variable region includes amino acids having the sequence set forth in SEQ ID NO: 104. In certain embodiments, the light chain variable region includes amino acids having the sequence set forth in SEQ ID NO: 105.

In certain embodiments, an FGFR2/3+KLB bispecific antibody comprises at least one, two, three, four, five, or six HVRs selected from (a) HVR-H1 comprising an amino acid sequence of any one of SEQ ID NOs: 108-122 and 315, e.g., 119 or 122; (b) HVR-H2 comprising an amino acid sequence of any one of SEQ ID NOs: 138-153 and, e.g., 150 or 153; (c) HVR-H3 comprising an amino acid sequence of any one of SEQ ID NOs: 154-169, e.g., 166 or 169; (d) HVR-L1 comprising an amino acid sequence of any one of SEQ ID NOs: 170-184, e.g., 181 or 184; (e) HVR-L2 comprising an amino acid sequence of any one of SEQ ID NOs: 185-200, e.g., 197 or 200; and (f) HVR-L3 comprising an amino acid sequence of any one of SEQ ID NOs: 201-215, e.g., 212 or 215.

In certain embodiments, an FGFR2/3+KLB bispecific antibody, comprises at least one, two, three, four, five, or six HVRs selected from (a) HVR-H1 comprising SEQ ID NO: 119; (b) HVR-H2 comprising SEQ ID NO: 150; (c) HVR-H3 comprising SEQ ID NO: 166; (d) HVR-L1 comprising SEQ ID NO: 181; (e) HVR-L2 comprising SEQ ID NO: 197; and (f) HVR-L3 comprising SEQ ID NO: 212. In certain embodiments, the present disclosure provides an anti-KLB antibody comprising at least one, two, three, four, five, or six HVRs selected from (a) HVR-H1 comprising SEQ ID NO: 122; (b) HVR-H2 comprising SEQ ID NO: 153; (c) HVR-H3 comprising SEQ ID NO: 169; (d) HVR-L1 comprising SEQ ID NO: 184; (e) HVR-L2 comprising SEQ ID NO: 200; and (f) HVR-L3 comprising SEQ ID NO: 215.

In certain embodiments, an FGFR2/3+KLB bispecific antibody includes a heavy chain variable region that comprises CDR1, CDR2, and CDR3 domains, and a light chain variable region that comprises CDR1, CDR2, and CDR3 domains. In certain embodiments, the heavy chain variable region CDR1 domain includes an amino acid sequence having a sequence set forth in SEQ ID NO: 108-122 and 315. In certain embodiments, the heavy chain variable region CDR2 domain includes an amino acid sequence a sequence set forth in SEQ ID NO: 138-153. In certain embodiments, the heavy chain variable region CDR3 domain includes an amino acid sequence having a sequence that is at least 90%, 91%, 92%, 93%, 94%, 95%, 96%, 97%, 98%, 99%, or 100% identical to SEQ ID NO: 154-169. In certain embodiments, the light chain variable region CDR1 domain includes an amino acid sequence having a sequence that is at least 90%, 91%, 92%, 93%, 94%, 95%, 96%, 97%, 98%, 99%, or 100% identical to SEQ ID NO: 170-184. In certain embodiments, the light chain variable region CDR2 domain includes an amino acid sequence having a sequence that is at least 90%, 91%, 92%, 93%, 94%, 95%, 96%, 97%, 98%, 99%, or 100% identical to SEQ ID NO: 185-200. In certain embodiments, the light chain variable region CDR3 domain includes an amino acid sequence having a sequence that is at least 90%, 91%, 92%, 93%, 94%, 95%, 96%, 97%, 98%, 99%, or 100% identical to SEQ ID NO: 201-215.

In certain embodiments, an FGFR2/3+KLB bispecific antibody, includes a heavy chain variable region that comprises CDR1, CDR2, and CDR3 domains, and a light chain variable region that comprises CDR1, CDR2, and CDR3 domains. In certain embodiments, the heavy chain variable region CDR1 domain includes an amino acid sequence having a sequence set forth in SEQ ID NO: 108-122 and 315. In certain embodiments, the heavy chain variable region CDR2 domain includes an amino acid sequence having a sequence set forth in SEQ ID NO: 138-153. In certain embodiments, the heavy chain variable region CDR3 domain includes an amino acid sequence having a sequence set forth in SEQ ID NO: 154-169. In certain embodiments, the light chain variable region CDR1 domain includes an amino acid sequence having a sequence set forth in SEQ ID NO: 170-184. In certain embodiments, the light chain variable region CDR2 domain includes an amino acid sequence having a sequence set forth in SEQ ID NO: 185-200. In certain embodiments, the light chain variable region CDR3 domain includes an amino acid sequence having a sequence set forth in SEQ ID NO: 201-215.

In certain embodiments, an FGFR2/3+KLB bispecific antibody, includes a heavy chain variable region CDR1 having the sequence set forth in SEQ ID NO: 122; a heavy chain variable region CDR2 having the sequence set forth in SEQ ID NO: 153; a heavy chain variable region CDR3 having the sequence set forth in SEQ ID NO: 169; a light chain variable region CDR1 having the sequence set forth in SEQ ID NO: 184; a light chain variable region CDR2 having the sequence set forth in SEQ ID NO: 200; and a light chain variable region CDR3 having the sequence set forth in SEQ ID NO: 215.

In certain embodiments, an FGFR2/3+KLB bispecific antibody includes a first antibody, or antigen binding portion thereof, and includes a second antibody, or antigen binding portion thereof, where the first antibody, or antigen binding portion thereof, binds to an epitope present on KLB, and the second antibody, or antigen binding portion thereof, bind to an epitope present on FGFR2/3. For example, and not by way of limitation, the first antibody, or antigen binding portion thereof, can include a heavy chain variable region and a light chain variable region; and the second antibody, or antigen binding portion thereof, can include a heavy chain variable region and a light chain variable region. In certain embodiments, the heavy chain variable region of the first antibody, or antigen binding portion thereof, includes amino acids having a sequence that is at least 90%, 91%, 92%, 93%, 94%, 95%, 96%, 97%, 98%, 99%, or 100% identical to the sequence set forth in SEQ ID NO: 104. In certain embodiments, the light chain variable region of the first antibody, or antigen binding portions thereof, includes amino acids having a sequence that is at least 90%, 91%, 92%, 93%, 94%, 95%, 96%, 97%, 98%, 99%, or 100% identical to the sequence set forth in SEQ ID NO: 105. In certain embodiments, the heavy chain of the second antibody (anti-FGFR2/3 antibody) or antigen binding portion thereof includes amino acids having a sequence that is at least 60%, 70%, 80%, 90%, 91%, 92%, 93%, 94%, 95%, 96%, 97%, 98%, 99%, or 100% identical to the sequence set forth in SEQ ID NO: 282. In certain embodiments, the light chain of the second antibody (anti-FGFR2/3 antibody), or antigen binding portions thereof, includes amino acids having a sequence that is at least 60%, 70%, 80%, 90%, 91%, 92%, 93%, 94%, 95%, 96%, 97%, 98%, 99%, or 100% identical to the sequence set forth in SEQ ID NO: 283.

In certain embodiments, an FGFR2/3+KLB bispecific antibody that binds to the same epitope as an anti-KLB antibody is provided herein. For example, in certain embodiments, an FGFR2/3+KLB bispecific antibody is provided that binds to the same epitope as an anti-KLB antibody comprising the VH sequence of SEQ ID NO: 104 and a VL sequence of SEQ ID NO: 105. In certain embodiments, an FGFR2/3+KLB bispecific antibody is provided that binds to a fragment of KLB consisting of the amino acid sequence SSPTRLAVIPWGVRKLLRWVRRNYGDMDIYITAS (SEQ ID NO: 103).

In certain embodiments, an FGFR2/3+KLB bispecific antibody is provided that binds to a fragment of KLB having an amino acid sequence that is at least 90%, 91%, 92%, 93%, 94%, 95%, 96%, 97%, 98%, 99%, or 100% identical to the sequence set forth in SEQ ID NO: 103.

In certain embodiments, an FGFR2/3+KLB bispecific antibody binds to the same epitope as an anti-KLB antibody is provided herein. For example, in certain embodiments, an FGFR2/3+KLB bispecific antibody is provided that binds to the same epitope as an anti-KLB antibody comprising the full length heavy chain sequence of SEQ ID NO: 106 and a full length light chain sequence of SEQ ID NO: 107.

In certain embodiments, the present disclosure provides an FGFR2/3+KLB bispecific antibody that binds to the same epitope as an anti-FGFR2/3 antibody provided herein. For example, in certain embodiments, an FGFR2/3+KLB bispecific antibody is provided that binds to the same epitope as an anti-FGFR2/3 antibody comprising the VH sequence of SEQ ID NO: 82 and a VL sequence of SEQ ID NO: 66. In certain embodiments, an FGFR2/3+KLB bispecific antibody is provided that binds to an epitope on FGFR2 comprising amino acid sequence TNTEKMEKRLHAVPAANTVK-FRCPA (SEQ ID NO: 91) and/or YKVRNQHWSLIMES (SEQ ID NO: 92) and/or also binds to an epitope on FGFR3 comprising amino acid sequence TRPERMDKKLLAV-PAANTVRFRCPA (SEQ ID NO: 93) and/or IKL-RHQQWSLVMES (SEQ ID NO: 94).

In certain embodiments, the present disclosure provides an FGFR2/3+KLB bispecific antibody that binds to the same epitope as an anti-FGFR2/3 antibody provided herein. For example, in certain embodiments, an FGFR2/3+KLB bispecific antibody is provided that binds to the same epitope as the 2B.1.3.12, 2B.1.3.10, or the 2B.1.1.6 anti-FGFR2/3 antibodies disclosed herein. In certain embodiments, an FGFR2/3+KLB bispecific antibody is provided that binds to the same epitopes as the anti-FGFR2/3 antibodies 2B.1.3.10 and 2B.1.3.12 (i.e., the FGFR2/3+KLB bispecific antibody binds to the same epitope(s) on FGFR2 comprising amino acid sequence TNTEKMEKRLHAVPAANTVKFRCPA (SEQ ID NO: 91) and/or YKVRNQHWSLIMES (SEQ ID NO: 92) and/or also binds to the same epitope(s) on FGFR3 comprising amino acid sequence TRPERMDKKLLAV-PAANTVRFRCPA (SEQ ID NO: 93) and/or IKL-RHQQWSLVMES (SEQ ID NO: 94) as the 2B.1.3.10 and 2B.1.3.12 do).

In certain embodiments, the present disclosure provides an FGFR2/3+KLB bispecific antibody that competes for binding to FGFR2/3 with the 2B.1.3.10 and 2B.1.3.12 antibodies provided herein.

In certain embodiments, an FGFR2/3+KLB bispecific antibody is provided that binds to a fragment of KLB having an amino acid sequence that is at least 90%, 91%, 92%, 93%, 94%, 95%, 96%, 97%, 98%, 99%, or 100% identical to the sequence set forth in SEQ ID NO: 103, and binds to or competes for binding to the FGFR2 epitopes selected from TNTEKMEKRLHAVPAANTVKFRCPA (SEQ ID NO: 91) and YKVRNQHWSLIMES (SEQ ID NO:92) and binds to or competes for biding to the FGFR3 epitopes selected from TRPERMDKKLLAVPAANTVRFRCPA (SEQ ID NO: 93) and IKLRHQQWSLVMES (SEQ ID NO: 94).

In certain embodiments, an anti-KLB/anti-FGFR1 bispecific antibody is provided that binds to a fragment of KLB having the amino acid sequence set forth in SEQ ID NO: 103 and binds to or competes for binding to the FGFR2 epitopes provided in SEQ ID NOs: 91 and 92 and binds to or competes for binding to the FGFR3 epitopes provided in SEQ ID NOs: 93 and 94.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv) (see, e.g., WO 93/16185; U.S. Pat. Nos. 5,571,894 and 5,587,458). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody," e.g., as described, for example, in U.S. Pat. No. 5,641,870. Such linear antibody fragments may be monospecific or bispecific.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-FGFR2/3 antibodies of the invention can be constructed by combining Fv clone variable domain sequence(s) selected from human-derived phage display libraries with known human constant domain sequences(s) as described above. Alternatively, human monoclonal anti-FGFR2/3 antibodies of the invention can be made by the hybridoma method. Human myeloma and mouse-human heteromyeloma cell lines for the production of human monoclonal antibodies have been described, for example, by Kozbor *J. Immunol.,* 133:3001 (1984); Brodeur et al., *Monoclonal Antibody Production Techniques and Applications,* pp. 51-63 (Marcel Dekker, Inc., New York, 1987); and Boerner et al., *J. Immunol.,* 147:86 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA,* 90: 2551 (1993); Jakobovits et al., *Nature,* 362: 255 (1993); Bruggermann et al., *Year in Immunol.,* 7:33 (1993).

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for FGFR3 and the other is for FGFR2. Bispecific antibodies may also be used to localize cytotoxic agents to cells which express FGFR3, FGFR2, or FGFR2/3. Bispecific antibodies can be prepared as full length antibodies or antibody fragments (e.g., F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et a. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fe region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Another type of variant is an amino acid substitution variant. These variants have at least one amino acid (at least two, at least three, at least 4 or more) residue in the antibody molecule replaced by a different residue. The sites of greatest interest for substitutional mutagenesis include the hypervariable regions, but FR alterations are also contemplated. Conservative substitutions are shown in the chart below, under the heading of "preferred substitutions." If such substitutions result in a change in biological activity, then more substantial changes, denominated "exemplary substitutions" in the chart below, or as further described below in reference to amino acid classes, may be introduced and the products screened.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; | Leu |
| Leu (L) | Phe; Norleucine Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: Cys, Ser, Thr, Asn, Gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al., *J. Immunol.* 164: 4178-4184 (2000).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies of the present invention can be characterized for their physical/chemical properties and biological functions by various assays known in the art (some of which are disclosed herein). In some embodiments, antibodies are characterized for any one or more of reduction or blocking of FGF (such as FGF1 and/or FGF9) binding, reduction or blocking of FGFR3 activation, reduction or blocking of FGFR3 downstream molecular signaling, disruption or blocking of FGFR3 binding to a ligand (e.g., FGF1, FGF9), reduction or blocking of FGFR3 dimerization, promotion of formation of monomeric FGFR3, binding to monomeric FGFR3, and/or treatment and/or prevention of a tumor, cell proliferative disorder or a cancer; and/or treatment or prevention of a disorder associated with FGFR3 expression and/or activity (such as increased FGFR3 expression and/or activity). In some embodiments, the antibodies are screened for increased FGFR3 activation, increased FGFR3 downstream molecule signaling, apoptotic activity, FGFR3 down-regulation, and effector function (e.g., ADCC activity). In certain embodiments, antibodies are characterized for any one or more of reduction or blocking of FGFR2 activation, reduction or blocking of FGFR2 downstream molecular signaling, disruption or blocking of FGFR2 binding to a ligand, reduction or blocking of FGFR2 dimerization, promotion of formation of monomeric FGFR2, binding to monomeric FGFR2, and/or treatment and/or prevention of a tumor, cell proliferative disorder or a cancer; and/or treatment or prevention of a disorder associated with FGFR2 expression and/or activity (such as increased FGFR2 expression and/or activity). In some embodiments, the antibodies are screened for increased FGFR2 activation, increased FGFR2 downstream molecule signaling, FGFR2 down-regulation, and effector function (e.g., ADCC activity). In certain embodiments, antibodies are characterized for any one or more of reduction or blocking of FGFR2 and FGFR3 activation, reduction or blocking of FGFR2 and FGFR3 downstream molecular signaling, disruption or blocking of FGFR2 and FGFR3 binding to a ligand (e.g., FGF1, FGF9), reduction or blocking of FGFR2 and FGFR3 dimerization, promotion of formation of monomeric FGFR2 and FGFR3, binding to monomeric FGFR2 and monomeric FGFR3, and/or treatment and/or prevention of a tumor, cell proliferative disorder or a cancer; and/or treatment or prevention of a disorder associated with FGFR2 and FGFR3 expression and/or activity (such as increased FGFR2 and/or FGFR3 expression and/or activity). In some embodiments, the antibodies are screened for increased FGFR2 and FGFR3 activation, increased FGFR2 and FGFR3 downstream molecule signaling, apoptotic activity, FGFR2 and FGFR3 down-regulation, and effector function (e.g., ADCC activity).

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding and other assay are provided below in the Examples section.

If an anti-FGFR2/3 antibody that inhibits cell growth is desired, the candidate antibody can be tested in in vitro and/or in vivo assays that measure inhibition of cell growth. If an anti-FGFR2/3 antibody that does or does not promote apoptosis is desired, the candidate antibody can be tested in assays that measure apoptosis. Methods for examining growth and/or proliferation of a cancer cell, or determining apoptosis of a cancer cell are well known in the art and some are described and exemplified herein. Exemplary methods for determining cell growth and/or proliferation and/or apoptosis include, for example, BrdU incorporation assay, MTT, [3H]-thymidine incorporation (e.g., TopCount assay (PerkinElmer)), cell viability assays (e.g., CellTiter-Glo (Promega)), DNA fragmentation assays, caspase activation assays, tryptan blue exclusion, chromatin morphology assays and the like.

In one embodiment, the present invention contemplates an antibody that possesses effector functions. In certain embodiments, the Fc activities of the antibody are measured. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. An assay to detect ADCC activity is also exemplified herein. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). Clq binding assays may also be carried out to confirm that the antibody is unable to bind Clq and hence lacks CDC activity. To assess complement activation, a CDC assay, e.g., as described in Gazzano-Santoro et al., J. Immunol. Methods 202:163 (1996), may be performed. FcRn binding and in vivo clearance/half life determinations can also be performed using methods known in the art, e.g., those described in the Examples section.

If an anti-FGFR2/3 antibody that binds monomeric FGFR2 and/or FGFR3 is desired, the candidate antibody can be tested in assays (such as in vitro assays) that measure binding to monomeric FGFR2 and/or FGFR3 and promotion of the formation of monomeric FGFR2 and/or FGFR3. Such assays are known in the art and some assays are described and exemplified herein.

If an anti-FGFR2/3 antibody that inhibits FGFR2 and/or FGFR3 dimerization is desired, the candidate antibody can be tested in dimerization assays, e.g., as described herein.

In some embodiments, the FGFR2 and/or FGFR3 agonist function of the candidate antibody is determined. Methods for assessing agonist function or activity of FGFR2 and/or FGFR3 antibodies are known in the art and some are also described herein.

In some embodiments, ability of an FGFR2/3 antibody to promote FGFR2 and/or FGFR3 receptor down-regulation is determined, e.g., using methods described and exemplified herein. In one embodiment, a FGFR2/3 antibody is incubated with suitable test cells, e.g., bladder cancer cell lines (e.g., RT112), and after a suitable period of time, cell lysates are harvested and examined for total FGFR2 and FGFR3 levels. FACS analysis may also be used to examine surface FGFR2 and FGFR3 receptor levels following incubation with candidate FGFR2/3 antibodies Vectors, Host Cells, and Recombinant Methods For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, Pseudomonas species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ (nmpc-fepE) degP41 kanR (U.S. Pat. No. 5,639,635). Other strains and derivatives thereof, such as *E. coli* 294 (ATCC 31,446),

*E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), supra; Georgiou et al., U.S. Pat.

No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and —II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably termed "antibody-drug conjugates" or "ADC"), comprising any of the anti-FGFR2/3 antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al., (2000) Bioorganic & Med. Chem. Letters 10:1025-1028; Mandler et al., (2002) Bioconjugate Chem. 13:786-791), maytansinoids (EP 1391213; Liu et al., (1996) Proc. Natl. Acad. Sci. USA 93:8618-8623), and calicheamicin (Lode et al., (1998) Cancer Res. 58:2928; Hinman et al., (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al., (2000) Eur. Jour. Nucl. Med. 27(7):766-77; Wiseman et al., (2002) Blood 99(12):4336-42; Witzig et al., (2002) J. Clin. Oncol. 20(10): 2453-63; Witzig et al., (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,6937,62; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al., (2003) Nature Biotechnology 21(7):778-784) and are under therapeutic development.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al., (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Libke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., (1989) J. Am. Chem. Soc. 111:5463-5465; Pettit et al., (1998) Anti-Cancer Drug Design 13:243-277; Pettit, G. R., et al., Synthesis, 1996, 719-725; and Pettit et al., (1996) J. Chem. Soc. Perkin Trans. 1 5:859-863. See also Doronina (2003) Nat. Biotechnol. 21(7):778-784; "Monomethylvaline Compounds Capable of Conjugation to Ligands," U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{86}$, $Re^{88}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208, 020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad\qquad\qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i)N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

Methods Using Anti-FGFR2/3 Antibodies

The present invention features the use of an FGFR2/3 antibody as part of a specific treatment regimen intended to provide a beneficial effect from the activity of this therapeutic agent. The present invention is particularly useful in treating cancers of various types at various stages.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from the original site and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade, and cancer cells are described as being well-differentiated (low grade), moderately-differentiated, poorly-differentiated, or undifferentiated (high grade). Well-differentiated cells are quite normal appearing and resemble the normal cells from which they originated. Undifferentiated cells are cells that have become so abnormal that it is no longer possible to determine the origin of the cells.

Cancer staging systems describe how far the cancer has spread anatomically and attempt to put patients with similar prognosis and treatment in the same staging group. Several tests may be performed to help stage cancer including biopsy and certain imaging tests such as a chest x-ray, mammogram, bone scan, CT scan, and MRI scan. Blood tests and a clinical evaluation are also used to evaluate a patient's overall health and detect whether the cancer has spread to certain organs.

To stage cancer, the American Joint Committee on Cancer first places the cancer, particularly solid tumors, in a letter category using the TNM classification system. Cancers are designated the letter T (tumor size), N (palpable nodes), and/or M (metastases). Ti, T2, T3, and T4 describe the increasing size of the primary lesion; N0, N1, N2, N3 indicates progressively advancing node involvement; and M0 and M1 reflect the absence or presence of distant metastases.

In the second staging method, also known as the Overall Stage Grouping or Roman Numeral Staging, cancers are divided into stages 0 to IV, incorporating the size of primary lesions as well as the presence of nodal spread and of distant metastases. In this system, cases are grouped into four stages denoted by Roman numerals I through IV, or are classified as "recurrent." For some cancers, stage 0 is referred to as "in situ" or "Tis," such as ductal carcinoma in situ or lobular carcinoma in situ for breast cancers. High grade adenomas can also be classified as stage 0. In general, stage I cancers are small localized cancers that are usually curable, while stage IV usually represents inoperable or metastatic cancer. Stage II and III cancers are usually locally advanced and/or exhibit involvement of local lymph nodes. In general, the higher stage numbers indicate more extensive disease, including greater tumor size and/or spread of the cancer to nearby lymph nodes and/or organs adjacent to the primary tumor. These stages are defined precisely, but the definition is different for each kind of cancer and is known to the skilled artisan.

Many cancer registries, such as the NCI's Surveillance, Epidemiology, and End Results Program (SEER), use summary staging. This system is used for all types of cancer. It groups cancer cases into five main categories:

In situ is early cancer that is present only in the layer of cells in which it began.

Localized is cancer that is limited to the organ in which it began, without evidence of spread.

Regional is cancer that has spread beyond the original (primary) site to nearby lymph nodes or organs and tissues.

Distant is cancer that has spread from the primary site to distant organs or distant lymph nodes.

Unknown is used to describe cases for which there is not enough information to indicate a stage.

In addition, it is common for cancer to return months or years after the primary tumor has been removed. Cancer that recurs after all visible tumor has been eradicated, is called recurrent disease. Disease that recurs in the area of the primary tumor is locally recurrent, and disease that recurs as metastases is referred to as a distant recurrence.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors. Other examples of tumors are described in the Definitions section.

In some embodiments, the patient herein is subjected to a diagnostic test e.g., prior to and/or during and/or after therapy. Generally, if a diagnostic test is performed, a sample may be obtained from a patient in need of therapy. Where the subject has cancer, the sample may be a tumor sample, or other biological sample, such as a biological fluid, including, without limitation, blood, urine, saliva, ascites fluid, or derivatives such as blood serum and blood plasma, and the like.

The biological sample herein may be a fixed sample, e.g. a formalin fixed, paraffin-embedded (FFPE) sample, or a frozen sample.

Various methods for determining expression of mRNA or protein include, but are not limited to, gene expression profiling, polymerase chain reaction (PCR) including quantitative real time PCR (qRT-PCR), microarray analysis, serial analysis of gene expression (SAGE), MassARRAY, Gene Expression Analysis by Massively Parallel Signature Sequencing (MPSS), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR). In one embodiment, expression of one or more of the above noted genes is deemed positive expression if it is at the median or above, e.g. compared to other samples of the same tumor-type. The median expression level can be determined essentially contemporaneously with measuring gene expression, or may have been determined previously.

The steps of a representative protocol for profiling gene expression using fixed, paraffin-embedded tissues as the RNA source, including mRNA isolation, purification, primer extension and amplification are given in various published journal articles (for example: Godfrey et al. *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR. Finally, the data are analyzed to identify the best treatment option(s) available to the patient on the basis of the characteristic gene expression pattern identified in the tumor sample examined.

Detection of gene or protein expression may be determined directly or indirectly.

One may determine expression or translocation or amplification of FGFR2 and/or FGFR3 in the cancer (directly or indirectly). Various diagnostic/prognostic assays are available for this. In one embodiment, FGFR3 overexpression may be analyzed by IHC. Parafin embedded tissue sections from a tumor biopsy may be subjected to the IHC assay and accorded a FGFR2 and/or FGFR3 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

In some embodiments, those tumors with 0 or 1+ scores for each of FGFR2 and FGFR3 overexpression assessment may be characterized as not overexpressing FGFR2 and FGFR3, whereas those tumors with 2+ or 3+ scores may be characterized as overexpressing each of FGFR2 and FGFR3.

In some embodiments, tumors overexpressing each of FGFR2 and FGFR3 may be rated by immunohistochemical scores corresponding to the number of copies of each of FGFR2 and FGFR3 molecules expressed per cell, and can been determined biochemically:

0=0-90 copies/cell,
1+=at least about 100 copies/cell,
2+=at least about 1000 copies/cell,
3+=at least about 10,000 copies/cell.

Alternatively, or additionally, FISH assays may be carried out on formalin-fixed, paraffin-embedded tumor tissue to determine the presence or and/or extent (if any) of FGFR2 and/or FGFR3 amplification or translocation in the tumor.

FGFR2 and FGFR3 activation may be determined directly (e.g., by phospho-ELISA testing, or other means of detecting phosphorylated receptor) or indirectly (e.g., by detection of activated downstream signaling pathway components, detection of receptor dimers (e.g., homodimers, heterodimers), detection of gene expression profiles and the like.

Similarly, constitutive FGFR2 and FGFR3 and/or ligand-independent or ligand-dependent FGFR2 and FGFR3 may be detected directly or indirectly (e.g., by detection of receptor mutations correlated with constitutive activity, by detection of receptor amplification correlated with constitutive activity and the like).

Methods for detection of nucleic acid mutations are well known in the art. Often, though not necessarily, a target nucleic acid in a sample is amplified to provide the desired amount of material for determination of whether a mutation is present. Amplification techniques are well known in the art. For example, the amplified product may or may not encompass all of the nucleic acid sequence encoding the protein of interest, so long as the amplified product comprises the particular amino acid/nucleic acid sequence position where the mutation is suspected to be.

In one example, presence of a mutation can be determined by contacting nucleic acid from a sample with a nucleic acid probe that is capable of specifically hybridizing to nucleic acid encoding a mutated nucleic acid, and detecting said hybridization. In one embodiment, the probe is detectably labeled, for example with a radioisotope ($^3$H, $^{32}$P, $^{33}$P etc), a fluorescent agent (rhodamine, fluorescene etc.) or a chromogenic agent. In some embodiments, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, nucleic acid probes of the invention are provided in a kit for identifying FGFR2 and/or FGFR3 mutations in a sample, said kit comprising an oligonucleotide that specifically hybridizes to or adjacent to a site of mutation in the nucleic acid encoding FGFR2 and/or FGFR3. The kit may further comprise instructions for treating patients having tumors that contain FGFR2 and/or FGFR3 mutations with a FGFR2 and/or FGFR3 antagonist based on the result of a hybridization test using the kit.

Mutations can also be detected by comparing the electrophoretic mobility of an amplified nucleic acid to the electrophoretic mobility of corresponding nucleic acid encoding wild-type FGFR2 and/or FGFR3. A difference in the mobility indicates the presence of a mutation in the amplified nucleic acid sequence. Electrophoretic mobility may be determined by any appropriate molecular separation technique, for example on a polyacrylamide gel.

Nucleic acids may also be analyzed for detection of mutations using Enzymatic Mutation Detection (EMD) (Del Tito et al, Clinical Chemistry 44:731-739, 1998). EMD uses the bacteriophage resolvase $T_4$ endonuclease VII, which scans along double-stranded DNA until it detects and cleaves structural distortions caused by base pair mismatches resulting from nucleic acid alterations such as point mutations, insertions and deletions. Detection of two short fragments formed by resolvase cleavage, for example by gel eletrophoresis, indicates the presence of a mutation. Benefits of the EMD method are a single protocol to identify point mutations, deletions, and insertions assayed directly from amplification reactions, eliminating the need for sample purification, shortening the hybridization time, and increasing the signal-to-noise ratio. Mixed samples containing up to a 20-fold excess of normal nucleic acids and fragments up to 4 kb in size can been assayed. However, EMD scanning does not identify particular base changes that occur in mutation positive samples, therefore often requiring additional sequencing procedures to identify the specific mutation if necessary. CEL I enzyme can be used similarly to resolvase $T_4$ endonuclease VII, as demonstrated in U.S. Pat. No. 5,869,245.

Another simple kit for detecting mutations is a reverse hybridization test strip similar to Haemochromatosis StripAssay™ (Viennalabs http://www.bamburghmarrsh.com/pdf/4220.pdf) for detection of multiple mutations in HFE, TFR2 and FPN1 genes causing Haemochromatosis. Such an assay is based on sequence specific hybridization following amplification by PCR. For single mutation assays, a microplate-based detection system may be applied, whereas for multi-mutation assays, test strips may be used as "macroarrays". Kits may include ready-to use reagents for sample prep, amplification and mutation detection. Multiplex amplification protocols provide convenience and allow testing of samples with very limited volumes. Using the straightforward StripAssay format, testing for twenty and more mutations may be completed in less than five hours without costly equipment. DNA is isolated from a sample and the target nucleic acid is amplified in vitro (e.g., by PCR) and biotin-labelled, generally in a single ("multiplex") amplification reaction. The amplification products are then selectively hybridized to oligonucleotide probes (wild-type and mutant specific) immobilized on a solid support such as a test strip in which the probes are immobilized as parallel lines or bands. Bound biotinylated amplicons are detected using streptavidin-alkaline phosphatase and color substrates. Such an assay can detect all or any subset of the mutations of the invention. With respect to a particular mutant probe band, one of three signaling patterns are possible: (i) a band only for wild-type probe which indicates normal nucleic acid sequence, (ii) bands for both wild-type and a mutant probe which indicates heterozygous genotype, and (iii) band only for the mutant probe which indicates homozygous mutant genotype. Accordingly, in one aspect, the invention provides a method of detecting mutations of the invention comprising isolating and/or amplifying a target FGFR2 and/or FGFR3 nucleic acid sequence from a sample, such that the amplification product comprises a ligand, contacting the amplification product with a probe which comprises a detectable binding partner to the ligand and the probe is capable of specifically hydribizing to a mutation of the invention, and then detecting the hybridization of said probe to said amplification product. In one embodiment, the ligand is biotin and the binding partner comprises avidin or streptavidin. In one embodiment, the binding partner comprises steptavidin-alkaline which is detectable with color substrates. In one embodiment, the probes are immobilized for example on a test strip wherein probes complementary to different mutations are separated from one another. Alternatively, the amplified nucleic acid is labelled with a radioisotope in which case the probe need not comprise a detectable label.

Alterations of a wild-type gene encompass all forms of mutations such as insertions, inversions, deletions, and/or point mutations. In one embodiment, the mutations are somatic. Somatic mutations are those which occur only in certain tissues, e.g., in the tumor tissue, and are not inherited in the germ line. Germ line mutations can be found in any of a body's tissues.

A sample comprising a target nucleic acid can be obtained by methods well known in the art, and that are appropriate for the particular type and location of the tumor. Tissue biopsy is often used to obtain a representative piece of tumor tissue. Alternatively, tumor cells can be obtained indirectly in the form of tissues/fluids that are known or thought to contain the tumor cells of interest. For instance, samples of lung cancer lesions may be obtained by resection, bronchoscopy, fine needle aspiration, bronchial brushings, or from sputum, pleural fluid or blood. Mutant genes or gene products can be detected from tumor or from other body samples such as urine, sputum or serum. The same techniques discussed above for detection of mutant target genes or gene products in tumor samples can be applied to other body samples. Cancer cells are sloughed off from tumors and appear in such body samples. By screening such body samples, a simple early diagnosis can be achieved for diseases such as cancer. In addition, the progress of therapy can be monitored more easily by testing such body samples for mutant target genes or gene products.

Means for enriching a tissue preparation for tumor cells are known in the art. For example, the tissue may be isolated from paraffin or cryostat sections. Cancer cells may also be separated from normal cells by flow cytometry or laser capture microdissection. These, as well as other techniques for separating tumor from normal cells, are well known in the art. If the tumor tissue is highly contaminated with normal cells, detection of mutations may be more difficult, although techniques for minimizing contamination and/or false positive/negative results are known, some of which are described hereinbelow. For example, a sample may also be assessed for the presence of a biomarker (including a mutation) known to be associated with a tumor cell of interest but not a corresponding normal cell, or vice versa.

Detection of point mutations in target nucleic acids may be accomplished by molecular cloning of the target nucleic acids and sequencing the nucleic acids using techniques well known in the art. Alternatively, amplification techniques such as the polymerase chain reaction (PCR) can be used to amplify target nucleic acid sequences directly from a genomic DNA preparation from the tumor tissue. The nucleic acid sequence of the amplified sequences can then be determined and mutations identified therefrom. Amplification techniques are well known in the art, e.g., polymerase chain reaction as described in Saiki et al., Science 239:487, 1988; U.S. Pat. Nos. 4,683,203 and 4,683,195.

It should be noted that design and selection of appropriate primers are well established techniques in the art.

The ligase chain reaction, which is known in the art, can also be used to amplify target nucleic acid sequences. See, e.g., Wu et al., Genomics, Vol. 4, pp. 560-569 (1989). In addition, a technique known as allele specific PCR can also be used. See, e.g., Ruano and Kidd, Nucleic Acids Research, Vol. 17, p. 8392, 1989. According to this technique, primers are used which hybridize at their 3'ends to a particular target nucleic acid mutation. If the particular mutation is not present, an amplification product is not observed. Amplification Refractory Mutation System (ARMS) can also be used, as disclosed in European Patent Application Publication No. 0332435, and in Newton et al., Nucleic Acids Research, Vol. 17, p. 7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Single stranded conformation polymorphism (SSCP) analysis can also be used to detect base change variants of an allele. See, e.g. Orita et al., Proc. Natl. Acad. Sci. USA Vol. 86, pp. 2766-2770, 1989, and Genomics, Vol. 5, pp. 874-879, 1989. Other techniques for detecting insertions and deletions as known in the art can also be used.

Alteration of wild-type genes can also be detected on the basis of the alteration of a wild-type expression product of the gene. Such expression products include both mRNA as well as the protein product. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR).

Mismatches are hybridized nucleic acid duplexes which are not 100% complementary. The lack of total complementarity may be due to deletions, insertions, inversions, substitutions or frameshift mutations. Mismatch detection can be used to detect point mutations in a target nucleic acid. While these techniques can be less sensitive than sequencing, they are simpler to perform on a large number of tissue samples. An example of a mismatch cleavage technique is the RNase protection method, which is described in detail in Winter et al., Proc. Natl. Acad. Sci. USA, Vol. 82, p. 7575, 1985, and Meyers et al., Science, Vol. 230, p. 1242, 1985. For example, a method of the invention may involve the use of a labeled riboprobe which is complementary to the human wild-type target nucleic acid. The riboprobe and target nucleic acid derived from the tissue sample are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the target nucleic acid mRNA or DNA which might contain a mutation can be amplified before hybridization. Changes in target nucleic acid DNA can also be detected using Southern hybridization, especially if the changes are gross rearrangements, such as deletions and insertions.

Target nucleic acid DNA sequences which have been amplified may also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

Alteration of wild-type target genes can also be detected by screening for alteration of the corresponding wild-type protein. For example, monoclonal antibodies immunoreactive with a target gene product can be used to screen a tissue, for example an antibody that is known to bind to a particular mutated position of the gene product (protein). For example, an antibody that is used may be one that binds to a deleted exon or that binds to a conformational epitope comprising a deleted portion of the target protein. Lack of cognate antigen would indicate a mutation. Antibodies specific for products of mutant alleles could also be used to detect mutant gene product. Antibodies may be identified from phage display libraries. Such immunological assays can be done in any convenient format known in the art. These include Western blots, immunohistochemical assays and ELISA assays. Any means for detecting an altered protein can be used to detect alteration of wild-type target genes.

Primer pairs are useful for determination of the nucleotide sequence of a target nucleic acid using nucleic acid amplification techniques such as the polymerase chain reaction. The pairs of single stranded DNA primers can be annealed to sequences within or surrounding the target nucleic acid sequence in order to prime amplification of the target sequence. Allele-specific primers can also be used. Such primers anneal only to particular mutant target sequence, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques which are well known in the art. Generally, the primers can be made using oligonucleotide synthesizing machines which are commercially available. Design of particular primers is well within the skill of the art.

Nucleic acid probes are useful for a number of purposes. They can be used in Southern hybridization to genomic DNA and in the RNase protection method for detecting point mutations already discussed above. The probes can be used to detect target nucleic acid amplification products. They may also be used to detect mismatches with the wild type gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See Novack et al., Proc. Natl. Acad. Sci. USA, Vol. 83, p. 586, 1986. Generally, the probes are complementary to sequences outside of the kinase domain. An entire battery of nucleic acid probes may be used to compose a kit for detecting mutations in target nucleic acids. The kit allows for hybridization to a large region of a target sequence of interest. The probes may overlap with each other or be contiguous.

If a riboprobe is used to detect mismatches with mRNA, it is generally complementary to the mRNA of the target gene. The riboprobe thus is an antisense probe in that it does not code for the corresponding gene product because it is complementary to the sense strand. The riboprobe generally will be labeled with a radioactive, colorimetric, or fluorometric material, which can be accomplished by any means known in the art. If the riboprobe is used to detect mismatches with DNA it can be of either polarity, sense or anti-sense. Similarly, DNA probes also may be used to detect mismatches.

In some instances, the cancer does or does not overexpress FGFR2 and/or FGFR3. Receptor overexpression may be determined in a diagnostic or prognostic assay by evaluating increased levels of the receptor protein present on the surface of a cell (e.g. via an immunohistochemistry assay; IHC). Alternatively, or additionally, one may measure levels of receptor-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Chemotherapeutic Agents

The combination therapy of the invention can further comprise one or more chemotherapeutic agent(s). The combined administration includes coadministration or concurrent administration, using separate formulations or a single pharmaceutical formulation, and consecutive administration in either order, wherein preferably there is a time period while both (or all) active agents simultaneously exert their biological activities.

The chemotherapeutic agent, if administered, is usually administered at dosages known therefor, or optionally lowered due to combined action of the drugs or negative side effects attributable to administration of the antimetabolite chemotherapeutic agent. Preparation and dosing schedules for such chemotherapeutic agents may be used according to manufacturers' instructions or as determined empirically by the skilled practitioner.

Various chemotherapeutic agents that can be combined are disclosed herein.

In some embodiments, chemotherapeutic agents to be combined are selected from the group consisting of lenalidomide (REVLIMID), proteosome inhibitors (such as bortezomib (VELCADE) and PS342), bora taxoid (including docetaxel and paclitaxel), *vinca* (such as vinorelbine or vinblastine), platinum compound (such as carboplatin or cisplatin), aromatase inhibitor (such as letrozole, anastrazole, or exemestane), anti-estrogen (e.g. fulvestrant or tamoxifen), etoposide, thiotepa, cyclophosphamide, pemetrexed, methotrexate, liposomal doxorubicin, pegylated liposomal doxorubicin, capecitabine, gemcitabine, melthalin, doxorubicin, vincristine, COX-2 inhibitor (for instance, celecoxib), or steroid (e.g., dexamethasone and prednisone). In some embodiments (e.g., embodiments involving treatment of t(4;14)+ multiple myeloma, dexamethasone and lenalidomide, or dexamethasone, or bortezomib, or vincristine, doxorubicin and dexamethason, or thalidomide and dexamethasone, or liposomal doxorubicin, vincristine and dexamethasone, or lenalidomide and dexamethasone, or bortezomib and dexamethasone, or bortezomib, doxorubicin, and dexamethasone are combined. In some embodiments (e.g., embodiments involving bladder cancer), gemcitabine and cisplatin, or a taxane (e.g., paclitaxel, docetaxel), or pemetrexed, or methotrexate, vinblastine, doxorubicin and cisplatin, or carboplatin, or mitomycin C in combination with 5-Fluorouracil, or cisplatin, or cisplatin and 5-Fluorouracil are combined.

Formulations, Dosages and Administrations

The therapeutic agents used in the invention will be formulated, dosed, and administered in a fashion consistent with good medical practice. Factors for consideration in this context include the particular disorder being treated, the particular subject being treated, the clinical condition of the individual patient, the cause of the disorder, the site of delivery of the agent, the method of administration, the scheduling of administration, the drug-drug interaction of the agents to be combined, and other factors known to medical practitioners.

Therapeutic formulations are prepared using standard methods known in the art by mixing the active ingredient having the desired degree of purity with optional physiologically acceptable carriers, excipients or stabilizers (Remington's Pharmaceutical Sciences (20$^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically accepTable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The therapeutic agents of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. An ex vivo strategy can also be used for therapeutic applications. Ex vivo strategies involve transfecting or transducing cells obtained from the subject with a polynucleotide encoding a FGFR2, FGFR3, or FGFR2/3 antagonist. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

For example, if the FGFR2/3 antagonist is an antibody, the antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

In another example, the FGFR2/3 antagonist compound is administered locally, e.g., by direct injections, when the disorder or location of the tumor permits, and the injections can be repeated periodically. The FGFR2/3 antagonist can also be delivered systemically to the subject or directly to the tumor cells, e.g., to a tumor or a tumor bed following surgical excision of the tumor, in order to prevent or reduce local recurrence or metastasis.

Administration of the therapeutic agents in combination typically is carried out over a defined time period (usually minutes, hours, days or weeks depending upon the combination selected). Combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

The therapeutic agent can be administered by the same route or by different routes. For example, the anti-FGFR2/3 antibody in the combination may be administered by intravenous injection while a chemotherapeutic agent in the combination may be administered orally. Alternatively, for example, both of the therapeutic agents may be administered orally, or both therapeutic agents may be administered by intravenous injection, depending on the specific therapeutic agents. The sequence in which the therapeutic agents are administered also varies depending on the specific agents.

Depending on the type and severity of the disease, about 1 μg/kg to 100 mg/kg of each therapeutic agent is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until the cancer is treated, as measured by the methods described above. However, other dosage regimens may be useful.

The present application contemplates administration of the FGFR2/3 antibody by gene therapy. See, for example, WO96/07321 published Mar. 14, 1996 concerning the use of gene therapy to generate intracellular antibodies.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, e.g., cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Example 1. Broadening the Specificity of Anti-FGFR3 Antibodies

Experiments were performed to broaden the binding specificity of an anti-FGFR2/3 antibody. Specifically, experiments were performed to develop antibodies for cancer therapy with dual specificity for FGFR3 and FGFR2 that do not bind the highly related receptors FGFR1 and FGFR4. The starting point was the monospecific antibody R3Mab, which binds to the FGFR3 IIIb and IIIc isoforms with sub-nanomolar affinities (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4;14)-positive multiple myeloma in mice." The Journal of clinical investigation 119(5): 1216-1229). R3Mab shows robust inhibition of FGFR3 signaling and tumor growth in vivo (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4;14)-positive multiple myeloma in mice." The Journal of clinical investigation 119(5): 1216-1229) and has been studied in phase I clinical trials.

Figure 5:
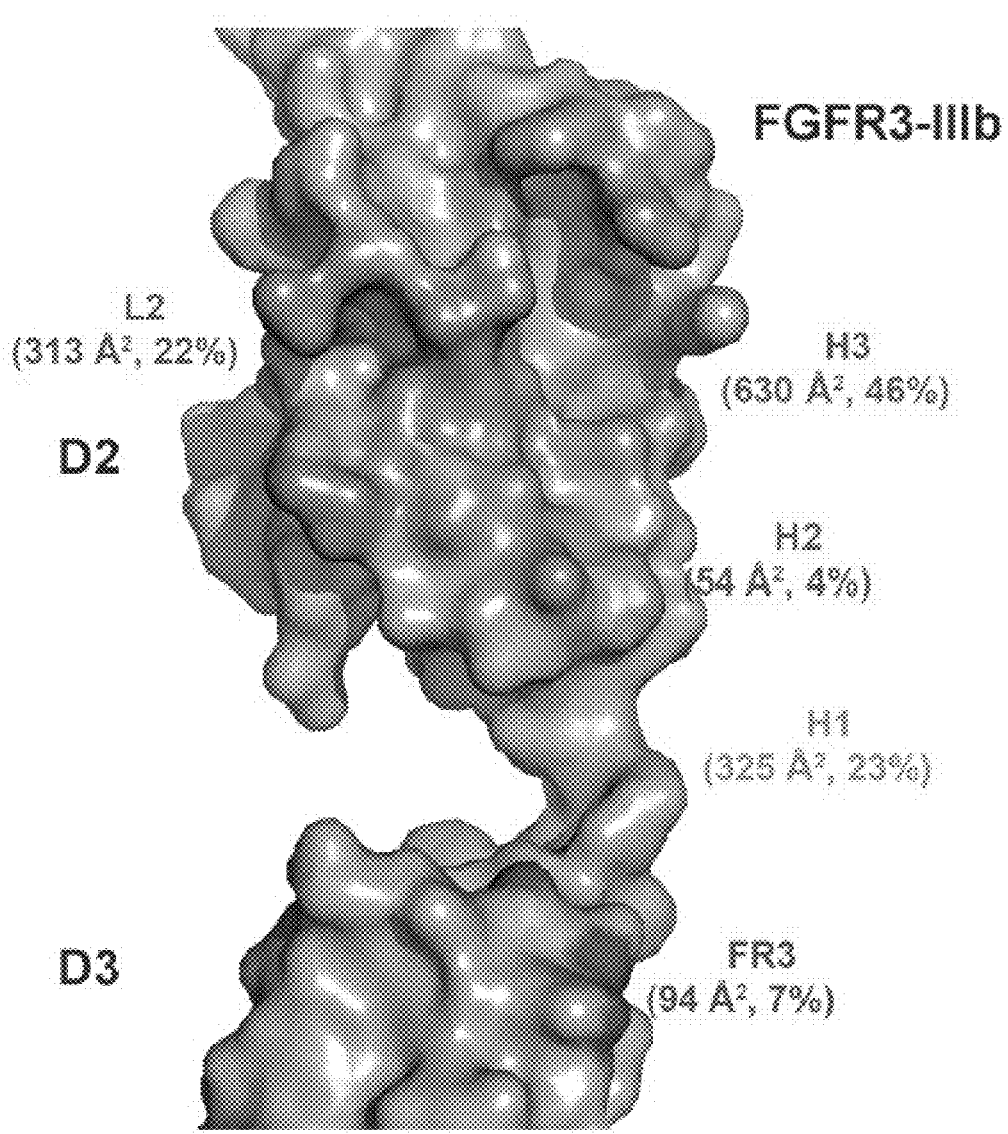
FIG. 5 shows the surface areas on FGFR3-IIIb contacted by R3Mab (PDB 3GRW). The surface of the D2 and D3 domains of FGFR3-IIIb is shown in gray. The contact areas by individual CDR loops of R3Mab are colored. The contact areas by each CDR and their percentages of overall contact areas are labeled as numbers in parentheses.
Figure 6:
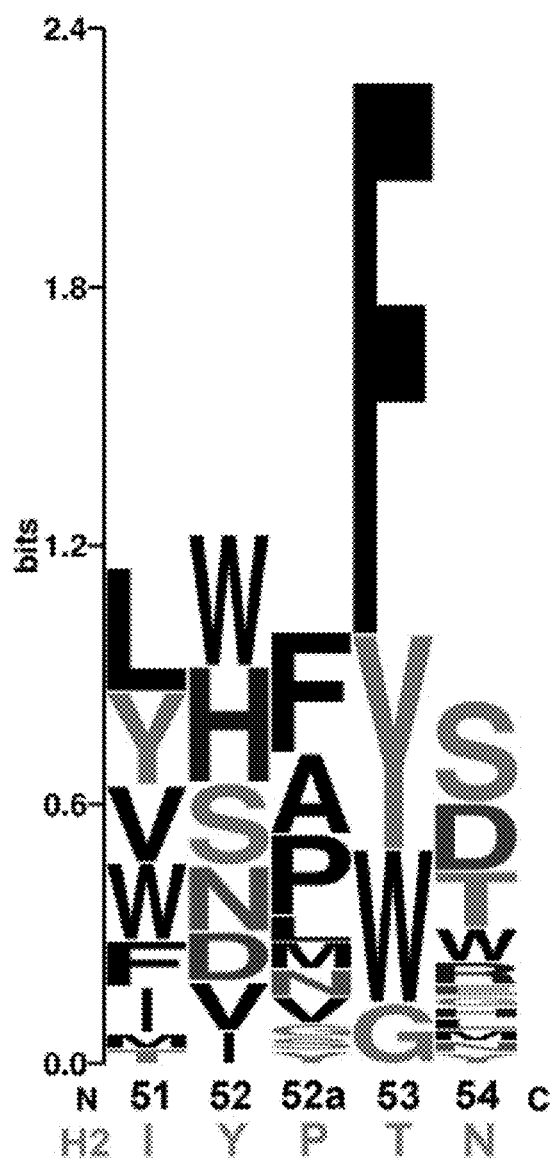
FIG. 6 shows the sequence logo of CDR H2 from phage libraries selected for binding to FGFR2-IIIb prepared using Weblogo 3 (Crooks, G. E., G. Hon, J. M. Chandonia and S. E. Brenner (2004). "WebLogo: a sequence logo generator." Genome Res 14(6): 1188-1190). "IYPTN" disclosed as SEQ ID NO: 300.

The antibody re-design strategy was guided by the previously determined crystallographic structure of an R3Mab Fab fragment in complex with FGFR3-IIIb (PDB 3GRW) (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4;14)-positive multiple myeloma in mice." The Journal of clinical investigation 119(5): 1216-1229). This structure indicates that R3Mab interacts with both the D2 and D3 domains of FGFR3-IIIb. Although D2 was subsequently found here to be sufficient for R3Mab binding, initial analyses were based on the contacts on this original structure. Most of the contact surface on the FGFR3-IIIb antigen was contributed by the antibody complementarity-determining regions (CDRs) H3 (46%), H1 (23%) and L2 (22%), with small contributions from CDR H2 and framework region (FR) residues (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4;14)-positive multiple myeloma in mice." The Journal of clinical investigation 119(5): 1216-1229.) (FIG. 5). The similarity between FGFR3-IIIb and the intended additional FGFR2-IIIb antigen were compared. The D2D3 regions of these two homologs share 68% protein-sequence identity, while their D2 domains share 76% identity (Table 2). Table 2 shows the percentage identities between the two isoforms of the same FGFR (Bold), the complete sequences of the D2D3 domains including the isoform-dependent regions in the D3 (Underline), and the D2D3 domains lacking the isoform-dependent regions (Bold and Underline). Since D3 of the R3Mab-bound FGFR3-IIIb had a different geometry as compared to all other FGFR structures (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4; 14)-positive multiple myeloma in mice." The Journal of clinical investigation 119(5): 1216-1229), the structures of FGFR2-IIIb and FGFR3-IIIb were superimposed on their D2 regions, which yielded a calculated root mean squared deviation (RMSD) of α-carbons of 0.78 Å. Based on this analysis, experiments were designed to re-engineer R3Mab to bind and inhibit FGFR2 as well.

TABLE 2

Sequence identities between FGFR proteins

| | Identity of FGFR (%) | | | | | | |
|---|---|---|---|---|---|---|---|
| | FGFR1-IIIb | FGFR1-IIIc | FGFR2-IIIb | FGFR2-IIIc | FGFG3-IIIb | FGFR3-IIIc | FGFR4 |
| FGFR1-IIIb | 100 | | 77.6 | | | 71.4 | 67.1 |
| FGFR1-IIIc | 88.0 | 100 | | | | | |
| FGFR2-IIIb | 79.1 | 71.6 | 100 | | | 75.8 | 71.4 |
| FGFR2-IIIc | 70.2 | 79.3 | 88.9 | 100 | | | |
| FGFR3-IIIb | 64.7 | 63.5 | 68.1 | 65.9 | 100 | | 78.9 |
| FGFR3-IIIc | 65.9 | 74.5 | 70.2 | 76.9 | 85.1 | 100 | |
| FGFR4 | 64.1 | 68.8 | 68.9 | 71.2 | 70.5 | 75.0 | 100 |

To construct a phage display library, mutations were designed that cover most residues in each of the individual heavy-chain CDRs and a selection of the contact residues on all CDRs (Table 3). In Table 3, N=G, A, T or C; K=G or T. R3Mab variants displayed as Fab fragments on phage particles were selected for binding to FGFR2-IIIb. We did not perform selection on FGFR3 at this stage as we wanted to keep the selection stringency low when bringing in the new FGFR2 specificity. After the first round of panning, the phage outputs from the individual libraries were combined and subjected to 3 further rounds of selection. 95 clones, designated as 2B.1 series, were screened by ELISA. Among these, 81 clones, representing 32 unique sequences, bound to FGFR2-IIIb. All binding clones were apparently derived from the H2 library, because they contained mutations in CDR H2 but not elsewhere (Table 4). Table 4 identifies residues the same as those in R3Mab with underlining. Table 4 identifies residues differing from those in R3Mab with italics. As used in Table 4, "ND" refers to not detectable and "NA" refers to not available due to protein aggregation. All selected antibodies showed substantially improved binding to FGFR2-IIIb relative to R3Mab, with $K_D$ values ranging from 0.3 to 17 nM (Table 4). Remarkably, the mutated H2 sequences contained significant variation, lacking clear consensus and differing from R3Mab at 4 or 5 positions (Table 4, FIG. 6). Thus, there are multiple possible solutions to conferring high-affinity binding of FGFR2-IIIb onto R3Mab.

TABLE 3

Library design for recruiting FGFR2 binding specificity

CDR H1

| Residues | 25 | 26 | 27 | 28 | 29 | 30 | 31 | 32 | 33 |
|---|---|---|---|---|---|---|---|---|---|
| Codons (SEQ ID NO: 297) | TCT | GGC | TTC | ACC | TTC | ACT | AGT | ACT | GGG |
| Amino acids (SEQ ID NO: 298) | S | G | F | T | F | T | S | T | G |
| H1 Lib. | NNK | NNK | | NNK | | NNK | NNK | NNK | NNK |
| H2 Lib. | | | | | | | | | |
| H3 Lib. | | | | | | | | | |
| Combined Lib. | | | | | | | NNT | NNK | NNC |

CDR H2

| Residues | 51 | 52 | 52a | 53 | 54 |
|---|---|---|---|---|---|
| Codons (SEQ ID NO: 299) | ATT | TAT | CCT | ACT | AAC |
| Amino acids (SEQ ID NO: 300) | I | Y | P | T | N |
| H1 Lib. | | | | | |
| H2 Lib. | NNK | NNK | NNK | NNK | NNK |
| H3 Lib. | | | | | |
| Combined Lib. | | NNK | | | |

CDR H3

| Residues | 96 | 97 | 98 | 99 | 100 | 100a |
|---|---|---|---|---|---|---|
| Codons (SEQ ID NO: 301) | TAC | GGC | ATC | TAC | GAC | CTG |

TABLE 3-continued Library design for recruiting FGFR2 binding specificity

| | | | | | | |
|---|---|---|---|---|---|---|
| Amino acids (SEQ ID NO: 302) | Y | G | I | Y | D | L |
| H1 Lib. | | | | | | |
| H2 Lib. | | | | | | |
| H3 Lib. | NNK | NNK | NNK | NNC | NNK | NNK |
| Combined Lib. | | | | NNC | NNK | NNK |

CDR L2

| Residues | 52 | 53 | 54 |
|---|---|---|---|
| Codons | TCC | TTC | CTC |
| Amino acids | S | F | L |
| H1 Lib. | | | |
| H2 Lib. | | | |
| H3 Lib. | | | |
| Combined Lib. | | NNC | |

TABLE 4

Residues differing from those in R3Mab.

| Variant ID | CDR-H2 sequence | SEQ ID NO: | Times found (n) | FGFR2-IIIb $K_D$ (nM) |
|---|---|---|---|---|
| R3Mab | IYPTN | 300 | 0 | ND |
| 2B.1.1 | YWAWD | 13 | 3 | 0.29 |
| 2B.1.88 | IWMFT | 14 | 4 | 0.64 |
| 2B.1.38 | FWAYD | 15 | 1 | 1.1 |
| 2B.1.20 | LDVFW | 16 | 1 | 1.2 |
| 2B.1.32 | WVGFT | 17 | 9 | 1.2 |
| 2B.1.49 | LSFFS | 18 | 1 | 1.3 |
| 2B.1.86 | LSFWT | 19 | 1 | 1.3 |
| 2B.1.9 | YHPYL | 20 | 8 | 1.4 |
| 2B.1.73 | MIFYN | 21 | 1 | 1.4 |
| 2B.1.74 | YHPFR | 22 | 1 | 1.4 |
| 2B.1.14 | LWYFD | 23 | 1 | 1.6 |
| 2B.1.71 | VWMFD | 24 | 1 | 1.6 |
| 2B.1.28 | FWAWS | 25 | 2 | 1.8 |
| 2B.1.95 | LIFFT | 26 | 2 | 1.8 |
| 2B.1.50 | LNFYS | 27 | 2 | 2.0 |
| 2B.1.81 | VNNFY | 28 | 1 | 2.1 |
| 2B.1.25 | WHPWM | 29 | 1 | 2.3 |
| 2B.1.3 | THLGD | 30 | 1 | 2.6 |
| 2B.1.65 | YNAYT | 31 | 1 | 2.7 |
| 2B.1.94 | LVFFS | 32 | 3 | 3.1 |
| 2B.1.78 | LSFYS | 33 | 4 | 3.2 |
| 2B.1.72 | VHPFE | 34 | 1 | 3.5 |
| 2B.1.44 | WWSWG | 35 | 1 | 3.6 |
| 2B.1.52 | FSLGD | 36 | 1 | 3.9 |
| 2B.1.30 | VSFFS | 37 | 1 | 4.1 |
| 2B.1.82 | INFFS | 38 | 1 | 4.9 |
| 2B.1.93 | IDNYW | 39 | 13 | 5.1 |
| 2B.1.55 | VDVFW | 40 | 3 | 5.9 |
| 2B.1.35 | WHPFR | 41 | 5 | 9.4 |
| 2B.1.33 | YHPFH | 42 | 2 | 15 |
| 2B.1.80 | YWAFS | 43 | 2 | 17 |
| 2B.1.92 | WVAFS | 44 | 2 | NA |

Next six variants were selected for measurements of binding to FGFR3 based on their affinities (<3 nM) for FGFR2 and sequence diversity. All the variants showed improved affinities for FGFR3-IIIb (Table 5). To further assess their ability to inhibit receptor-dependent cell growth, proliferation of MCF7 breast carcinoma cells was assayed either with or without FGF7-a specific ligand for FGFR2-IIIb (Goetz, R. and M. Mohammadi (2013). "Exploring mechanisms of FGF signalling through the lens of structural biology." Nat Rev Mol Cell Biol 14(3): 166-180; Bai, A., K. Meetze, N. Y. Vo, S. Kollipara, E. K. Mazsa, W. M. Winston, S. Weiler, L. L. Poling, T. Chen, N. S. Ismail, J. Jiang, L. Lerner, J. Gyuris and Z. Weng (2010). "GP369, an FGFR2-IIIb-specific antibody, exhibits potent antitumor activity against human cancers driven by activated FGFR2 signaling." Cancer research 70(19): 7630-7639). Variant 2B.1.3 exhibited the greatest antagonist activity, as compared to other variants, which showed less or no inhibition, or even displayed stimulatory effect (FIG. 2). Hence, 2B.1.3 was carried over as a functional antibody for further characterizations.

TABLE 5

Binding affinities of selected 2B.1.3 variants for FGFR2-IIIb and FGFR3-IIIb.

| Clone | CDR H2 | SEQ ID NO: | FGFR2-IIIb $K_D$ (nM) | FGFR3-IIIb $K_D$ (nM) |
|---|---|---|---|---|
| R3Mab | IYPTN | 300 | ND | 0.24 |
| 2B.1.3 | THLGD | 30 | 2.6 | 0.09 |
| 2B.1.95 | LIFFT | 46 | 1.8 | 0.19 |
| 2B.1.73 | MIFYN | 47 | 1.4 | 0.09 |
| 2B.1.32 | WVGFT | 48 | 1.2 | 0.06 |
| 2B.1.88 | IWMFT | 49 | 0.64 | 0.05 |
| 2B.1.1 | YWAWD | 50 | 0.29 | 0.09 |

*Residues the same as those in R3Mab are underlined.

Since all FGFR homologs share nearly 70% sequence identity between each other (Table 2), binding of re-engineered variant 2B.1.3 to other FGFRs was evaluated. Mab 2B.1.3 bound FGFR2-IIIc with similar affinity as FGFR2-IIIb (Table 6). Mab 2B.1.3 also showed several-fold higher affinity for FGFR3-IIIb and FGFR3-IIIc than did R3Mab, even though the selection strategy used was based on binding to FGFR2-IIIb. The increased affinity for FGFR3 was consistently exhibited by all the other selected variants tested (data now shown). Moreover, Mab 2B.1.3 also bound to FGFR4, with a $K_D$ value of 32 nM, yet showed no detectable binding to FGFR1 (Table 6). Therefore, variant 2B.1.3 is trispecific, binding to FGFR2, FGFR3 and FGFR4, but not FGFR1.

TABLE 6

Binding affinities of R3Mab and its variants to all FGFR homologs

| | $K_D$ (nM) | | | | | | |
|---|---|---|---|---|---|---|---|
| | FGFR1-IIIb | FGFR1-IIIc | FGFR2-IIIb | FGFR2-IIIc | FGFR3-IIIb | FGFR3-IIIc | FGFR4 |
| R3Mab | ND* | ND | ND | ND | 0.24 | 0.61 | ND |
| 2B.1.3 | ND | ND | 2.6 | 2.0 | 0.09 | 0.07 | 32 |
| 2B.1.3.10 | ND | ND | 2.9 | 1.1 | 0.11 | 0.25 | ND |
| 2B.1.3.12 | ND | ND | 3.0 | 6.1 | 0.50 | 0.72 | ND |

*ND: not detecTable at 500 nM.

Example 2

Figure 7:
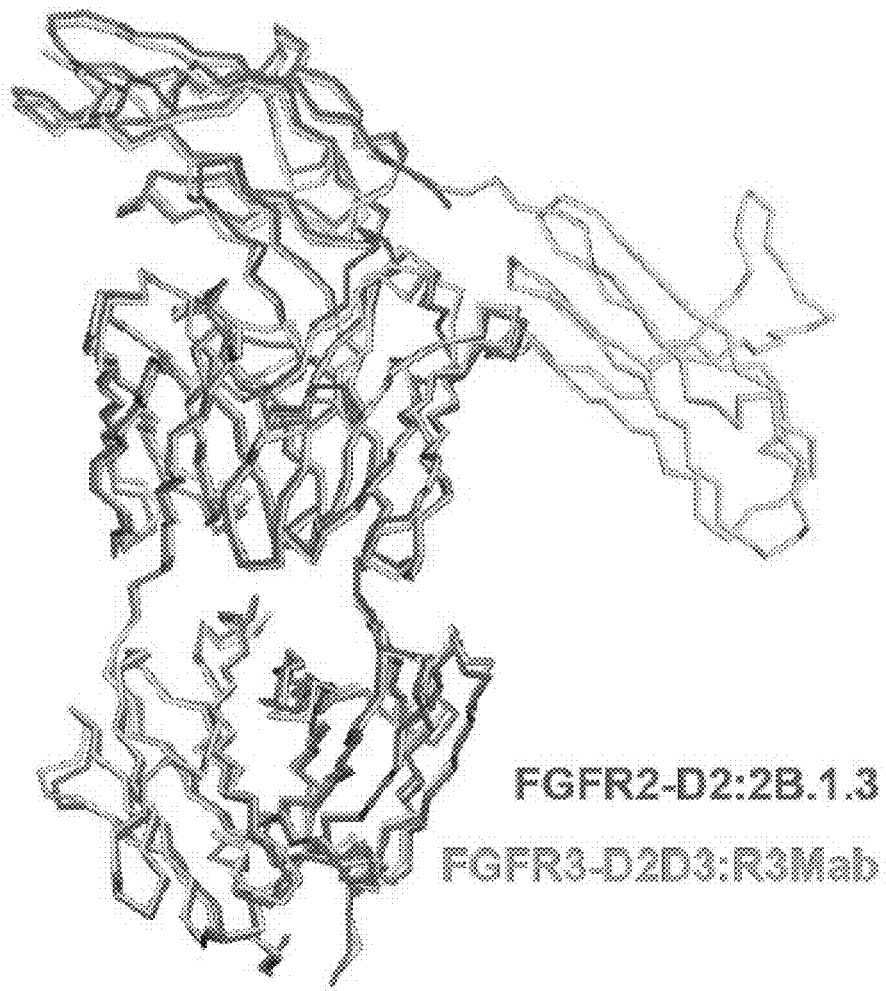
FIG. 7 shows the overall structural alignment of the complexes of FGFR2-D2:2B.1.3 and FGFR3-D2D3: R3Mab.

The structure Mab2B.1 and FGFR2-IIIb complex was determined. Specifically, to obtain direct insight into how the re-engineered variant 2B.1.3 acquired specificity for FGFR2, the crystal structure of its complex with FGFR2 was determined (FIG. 2A, Table 7). FGFR2-IIIb D2D3 was first generated by expression in E. coli and refolding from inclusion bodies and judged to be intact by SDS-PAGE and mass spectrometry. However, in crystals this protein contained only the isoform-independent D2 domain, suggesting proteolysis between D2 and D3 during the crystallization process. The previously determined FGFR3-IIIb:R3Mab complex structure contained both the D2 and D3 domains of FGFR3-IIIb. The whole complex of FGFR2-D2:Mab 2B.1.3 was superimposed closely onto the FGFR3-IIIb:R3Mab structure (FIG. 7), with an overall ca-carbon RMSD of 1.4 Å, indicating that the re-engineering retained the same binding geometry as the original antibody R3Mab. The FGFR3:R3Mab crystal structure suggests considerable interactions between FGFR3 D3 and the CDR H1 loop. Therefore, to investigate the involvement of D3 in binding, proteins of the D2 domains of FGFR2 and FGFR3 were prepared and their binding affinity to R3Mab and Mab 2B.1.3 measured. Only very minor differences in binding affinity between D2 alone and the D2D3 domains were observed for both receptors (Table 8). Thus, D2 is primarily responsible for binding of R3Mab and its derivatives, whereas D3 plays a minimal role.

TABLE 7

Data collection and refinement statistics
of the affinity between 2B.1.3 and FGFR2-D2

| Data collection | |
|---|---|
| Space group | C2 |
| Cell dimensions | |
| a, b, c (Å) | 76.09, 181.24, 94.43 |
| a, b, g (°) | 90.0, 113.7, 90.0 |
| Resolution (Å) | 50.0-2.36 (2.47-2.36) * |
| $R_{sym}$ | 0.094 (0.489) |
| I/σI | 14.4 (1.9) |
| Completeness (%) | 98.3 (99.3) |
| Redundancy | 2.5 (2.5) |
| Refinement | |
| Resolution (Å) | 50.0-2.36 |
| No. reflections | 46,583 |
| $R_{work}/R_{free}$ | 0.198/0.243 |
| No. atoms | |
| Protein | 8298 |
| Water | 152 |

TABLE 7-continued

Data collection and refinement statistics
of the affinity between 2B.1.3 and FGFR2-D2

| B-factors | |
|---|---|
| Protein | 33.6 |
| Water | 25.1 |
| r.m.s. deviations | |
| Bond lengths (Å) | 0.009 |
| Bond angles (°) | 1.2 |

* Values in parentheses are for the highest-resolution shell.

TABLE 8

Comparison of the binding affinities of D2 alone and D2D3
domains of FGFR2 and FGFR3 to R3Mab or Mab 2B.1.3.

| | $K_D$ (nM) | | | |
|---|---|---|---|---|
| | FGFR2-D2 | FGFR2-IIIb (D2D3) | FGFR3-D2 | FGFR3-IIIb (D2D3) |
| R3Mab | ND* | ND* | 0.26 | 0.24 |
| 2B.1.3 | 1.0 | 0.71 | <0.1** | 0.09 |

*ND: not detectable at 200 nM;
**reached the fitting limit of Biacore.

The CDR H2 sequence in Mab 2B.1.3, THLGD (SEQ ID NO: 30), is completely different from the parental H2 sequence in R3Mab, IYPTN (SEQ ID NO: 300). As expected, the conformations of the CDR H2 loops in the two Mabs differ substantially (FIG. 2C). Upon aligning the variable domains of Mab 2B.1.3 onto those of R3Mab (FIG. 2B), the H3 loop also appears twisted by a few degrees, resulting in a distance of 2.6 Å between the Cα atoms of the H3 tip residue Y100b in both structures (FIG. 2C). Accordingly, the position of the FGFR2 D2 domain overall is shifted by ~3 Å from that of the FGFR3 D2 domain. Comparison of the interface between the variants and the FGFR antigens revealed that such reorganizations of the H2 and H3 CDR loops in Mab 2B.1.3 significantly improved packing against the FGFR2 surface. In the parental structure, the shape complementarity (sc) score between R3Mab and FGFR3-D2 is 0.731. If the D2 domain of FGFR2 is aligned onto and replaces FGFR3 D2, the sc between R3Mab and FGFR2 D2 drops to 0.685. This may explain the lack of R3Mab binding to FGFR2 (Table 6). However, in the new crystal structure, the sc score between 2B.1.3 and FGFR2-D2 dramatically increased to 0.768, which is consistent with the gain of high-affinity binding to FGFR2 through re-engineering of R3Mab.

Due to the remarkable similarity among FGFRs, 2B.1.3 cross-reacts with multiple homologs in the family. Although FGFR1 binding was not acquired along with FGFR2 binding, FGFR4 interaction was. Considering that FGFR4 inhibition carries an increased risk of toxicity (Pai, R., D. French, N. Ma, K. Hotzel, E. Plise, L. Salphati, K. D. Setchell, J. Ware, V. Lauriault, L. Schutt, D. Hartley and D. Dambach (2012). "Antibody-mediated inhibition of fibroblast growth factor 19 results in increased bile acids synthesis and ileal malabsorption of bile acids in cynomolgus monkeys." *Toxicol Sci* 126(2): 446-456), a second round of re-engineering was undertaken to eliminate FGFR4 binding.

Example 3. Further Re-Engineering of the FGFR3 Antibody was Performed to Remove FGFR4 Binding To generate a Mab 2B.1.3 derivative that binds FGFR2 and FGFR3 but not FGFR4, it antigen residues were identified that likely interacted with the antibody but differ between the various FGFRs (Table 9), assuming that Mab 2B.1.3 recognizes all FGFRs in an analogous mode to its interaction with FGFR2. Three phage display libraries were constructed based on the 2B.1.3 template, with random mutagenesis at selected positions on the contacted CDRs H1, H3 and L2 (Table 10). During engineering, we tried to focus on binding to FGFR2 instead of maintaining both FGFR2 and FGFR3, as we did in the previous engineering. Therefore, selection was undertaken with immobilized FGFR2-IIIb alone during panning. To counter-select FGFR4 binders, phage particles were incubated with excessive amount of soluble FGFR4-Fc proteins. The concentrations of FGFR4-Fc were increased up to 0.46 µM for successive rounds of selection (see Methods). Individual clones from round 4 (n=96) were assayed by ELISA with FGFR2-IIIb and FGFR4, and ranked by the ratio of FGFR2 to FGFR4 binding-ELISA values. Six clones with the highest FGFR2/FGFR4 binding ratios were sequenced, expressed as IgG and characterized for binding to FGFR2-IIIb and FGFR4 (Table 11). Characterized clones from the H3/L2 libraries 2B.1.3.2, 2B.1.3.4 and 2B.1.3.6 contained mutations only in CDR H3, not CDR L2, whereas characterized clones from the H1/H3 library 2B.1.3.8, 2B.1.3.10 and 2B.1.3.12 contained mutations in both CDR H1 and H3. Although the 4 residues in H3 from L100a to D100d were fully randomized, Y100b remained unchanged, suggesting that the interaction of Y100b with FGFR2 is crucial for binding. In addition, L100a was conservatively mutated to Thr or Ile, and V100c mostly to Asp. The H1/H3 mutants containing an additional H1 mutation of T28P displayed slightly higher affinities for FGFR2. These antibodies bind FGFR2 with $K_D$ values of 1.4 to 6.6 nM, but showed minimal binding to FGFR4 when using concentrations as high as 1 µM for measurements, except that clone 2B.1.3.8 still retained detectable yet weak affinity for FGFR4 (Table 11). Residues that are the same as those in R3Mab are underlined and those residues that differ from those in R3Mab are in bold (Table 11). The convergence in both sequences and affinities of the 2B.1.3 variants indicated that the last rounds of phage selection had reached the limit of enrichment for binders with desired functions, i.e., diminished FGFR4 binding and retention of tight FGFR2 binding.

TABLE 9

Residue variations between FGFR2 and FGFR4 at the positions that make potential contacts to 2B.1.3.

| Residues | 155 | 158 | 162 | 169 | 205 | 214 |
| --- | --- | --- | --- | --- | --- | --- |
| FGFR2 | N | K | R | A | K | I |
| FGFR3 | R | R | K | A | K | V |

TABLE 9-continued

Residue variations between FGFR2 and FGFR4 at the positions that make potential contacts to 2B.1.3.

| Residues | 155 | 158 | 162 | 169 | 205 | 214 |
| --- | --- | --- | --- | --- | --- | --- |
| FGFR4 | H | R | K | G | R | V |
| CDR | H3 | H3 | H3 | H1 | L2 | L2 |
| Contacts* | Y100b | Y100b | L100a | T32 | Y49, F53 | F53 |

*Cut-off distance for contacts is 4.5 Å.

TABLE 10

Library design for removing FGFR4 binding specificity from the engineered antibody 2B.1.3

CDR H1

| Residue | 28 | 29 | 30 | 31 | 32 |
| --- | --- | --- | --- | --- | --- |
| Codons (SEQ ID NO: 303) | ACC | TTC | ACT | AGT | ACT |
| Amino acid (SEQ ID NO: 284) | T | F | T | S | T |
| Lib. H1 + H3 | NNK | | | | NNK |
| Lib. H1 + L2 | NNK | | | | NNK |
| Lib. H3 + L2 | | | | | |

CDR H2

| Residue | 100a | 100b | 100c | 100d |
| --- | --- | --- | --- | --- |
| Codons (SEQ ID NO: 304) | CTG | TAC | GTG | GAC |
| Amino acid (SEQ ID NO: 288) | L | Y | V | D |
| Lib. H1 + H3 | NNK | NNK | NNK | NNK |
| Lib. H1 + L2 | | | | |
| Lib. H3 + L2 | NNK | NNK | NNK | NNK |

CDR H1

| Residue | 49 | 50 | 51 | 52 | 53 | 54 | 55 | 56 |
| --- | --- | --- | --- | --- | --- | --- | --- | --- |
| Codons (SEQ ID NO: 305) | TAC | TCG | GCA | TCC | TTC | CTC | TAC | TCT |
| Amino acid (SEQ ID NO: 306) | Y | S | A | S | F | L | Y | S |
| Lib. H1 + H3 | | | | | | | | |
| Lib. H1 + L2 | NNK | | | | NNK | NNK | | NNK |
| Lib. H3 + L2 | NNK | | | | NNK | NNK | | NNK |

N = G, A, T or C;
K = G or T

TABLE 11

2B.1.3 variants with minimal FGFR4 binding and maintained FGFR2 binding

| Clone | CDR H1 | SEQ ID NO: | CDR H3 | SEQ ID NO: | FGFR2-IIIb $K_D$ (nM) | FGFR4 $K_D$ (nM) |
| --- | --- | --- | --- | --- | --- | --- |
| 2B.1.3 | TFTST | 284 | LYVD | 288 | 2.6 | 32 |
| 2B.1.3.2 | TFTST | 284 | TYDN | 289 | 6.6 | >1,000 |
| 2B.1.3.4 | TFTST | 284 | IYGG | 290 | 5.8 | >1,000 |

TABLE 11-continued 2B.1.3 variants with minimal FGFR4 binding
and maintained FGFR2 binding

| Clone | CDR H1 | SEQ ID NO: | CDR H3 | SEQ ID NO: | FGFR2-IIIb $K_D$ (nM) | FGFR4 $K_D$ (nM) |
|---|---|---|---|---|---|---|
| 2B.1.3.6 | TFTST | 284 | TYDE | 291 | 5.9 | >1,000 |
| 2B.1.3.8 | PFTSL | 285 | IYEK | 295 | 1.4 | ~300 |
| 2B.1.3.10 | PFTSQ | 286 | TYDK | 293 | 2.9 | >1,000 |
| 2B.1.3.12 | PFTST | 287 | TYDM | 294 | 3.0 | >1,000 |

Considering that greater differential in binding to FGFR2 and FGFR4 as well as fewer mutations are preferable, Mab 2B.1.3.10 and 2B.1.3.12 were selected for further characterization. Both antibodies showed no binding to FGFR1 and retained strong binding to FGFR3 with affinities slightly weaker than 2B.1.3 (Table 6). Therefore, after the second-step engineering, the 2B.1.3 derivatives Mab 2B.1.3.10 and 2B.1.3.12 cross-react with FGFR2 and FGFR3, but do not recognize FGFR4.

We next checked the abilities of the R3Mab variants to block FGF ligand binding to the specific FGFRs. R3Mab blocks FGF ligand binding to both the FGFR3-IIIb and -IIIc isoforms. Owing to their different specificities for different FGFRs, the blocking spectrum of each of the new antibodies varied (FIG. 3). All the engineered antibodies showed blocking activities for both FGFR2 and FGFR3, while R3Mab did not inhibit FGF7 binding to FGFR2-IIIb or FGF1 binding to FGFR2-IIIc. Whereas 2B.1.3 strongly inhibited FGF19 binding to FGFR4, 2B.1.3.10 and 2B.1.3.12 did not block the latter interaction, due to substantially diminished FGFR4 affinity.

Figure 4A:
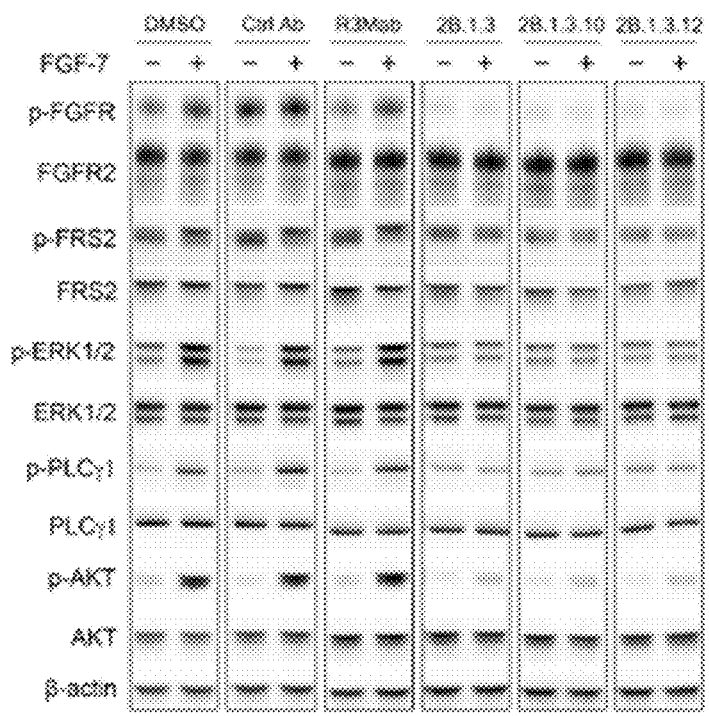
FIGS. 4A-4C show that the 2B.1 variants inhibit FGFR2 signaling in vitro and suppress in vivo xenograft growth.

Example 4. Re-Engineered Mab Variants Inhibit FGFR2- or FGFR3-Dependent Tumor-Cell Growth The newly engineered variants 2B.1.3.10 and 2B.1.3.12 display dual specificity for FGFR2 and FGFR3. To investigate their biological activities, we examined their effects on receptor-dependent signaling and proliferation in different types of tumor cells. First the new variants were assessed for inhibition of growth of FGFR2-overexpressing tumor cells in vitro. Both the SNU-16 gastric carcinoma and MFM-223x2.2 triple-negative breast carcinoma cell lines have amplification of FGFR2, evident by increased FGFR2 gene-copy numbers and protein over-expression (Kunii, K., L. Davis, J. Gorenstein, H. Hatch, M. Yashiro, A. Di Bacco, C. Elbi and B. Lutterbach (2008). "FGFR2-amplified gastric cancer cell lines require FGFR2 and Erbb3 signaling for growth and survival." Cancer research 68(7): 2340-2348.). In SNU-16 cells, 2B.1.3.10 and 2B.1.3.12 substantially suppressed FGF7-induced FGFR2 phosphorylation. In addition, the two 2B.1.3 variants markedly reduced phosphorylation of the downstream signaling molecules FRS2α, MAPK, PLCγ1 and AKT (FIG. 4A). Similarly, both variants diminished phosphorylation of FGFR2, FRS2α, MAPK and Her3 in FGF7-treated MFM-223x2.2 cells (FIG. 8).

Figure 4B:
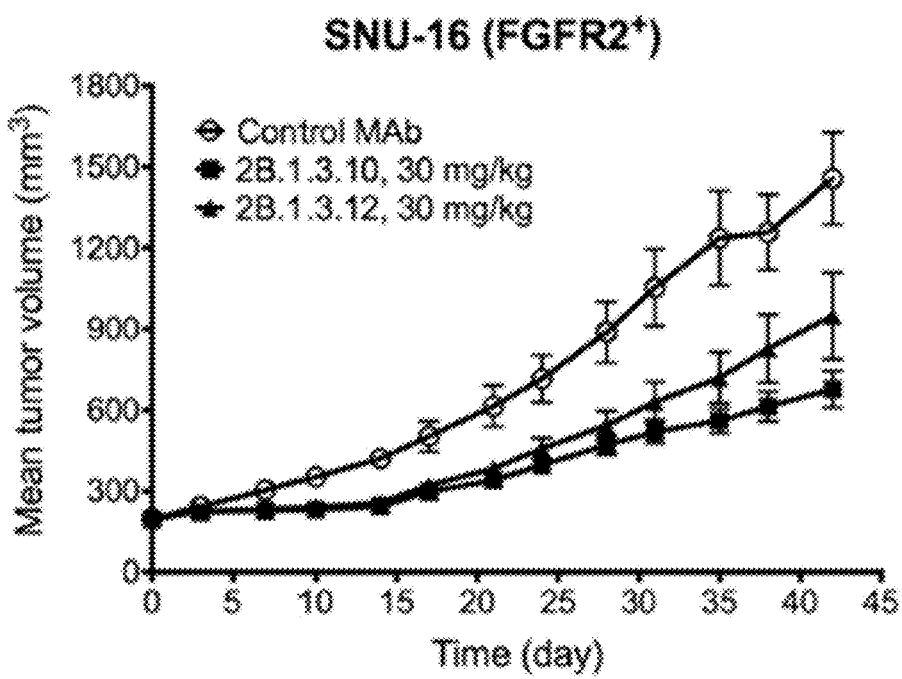
Figure 4C:
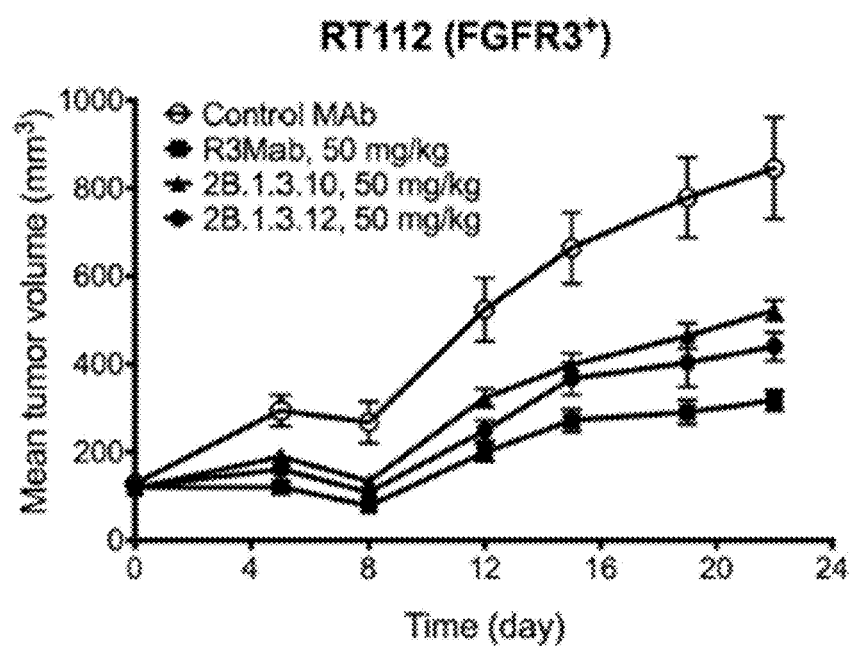

Next, the ability of the dual-specific Mab 2B.1.3.10 and 2B.1.3.12 to inhibit in vivo FGFR2-dependent or FGFR3-dependent growth of tumor xenografts was investigated. For FGFR2-specific treatment, mice injected with the human gastric cancer cells SNU-16 were dosed with non-specific IgG control antibody and the dual-specific Mabs, 2B.1.3.10 and 2B.1.3.12. Compared with the control antibody, the dual-specific antibodies displayed about 67% and 57% of tumor growth inhibition (FIG. 4B). In another experiment, 2B.1.3.10 and 2B.1.3.12 also retarded the growth of MFM-223x2.2 tumor xenografts in mice (FIG. 8). Therefore, these two engineered antibodies showed potency in inhibiting FGFR2-dependent tumor growth. Since they retain the parental specificity for FGFR3 after engineering, inhibition of FGFR3-dependent tumor growth was investigated. As anticipated, both Mab 2B.1.3.10 and 2B.1.3.12 suppressed the growth of RT 112 tumor xenografts (FIG. 4C). Collectively, the engineered antibodies can serve as dual agents to effectively inhibit both FGFR2- and FGFR3-dependent cancer cell growth. However, the potencies of the engineered variants in the RT112 model were reduced compared to the parental R3Mab, possibly due to modified pharmacokinetics.

Figure 8A:
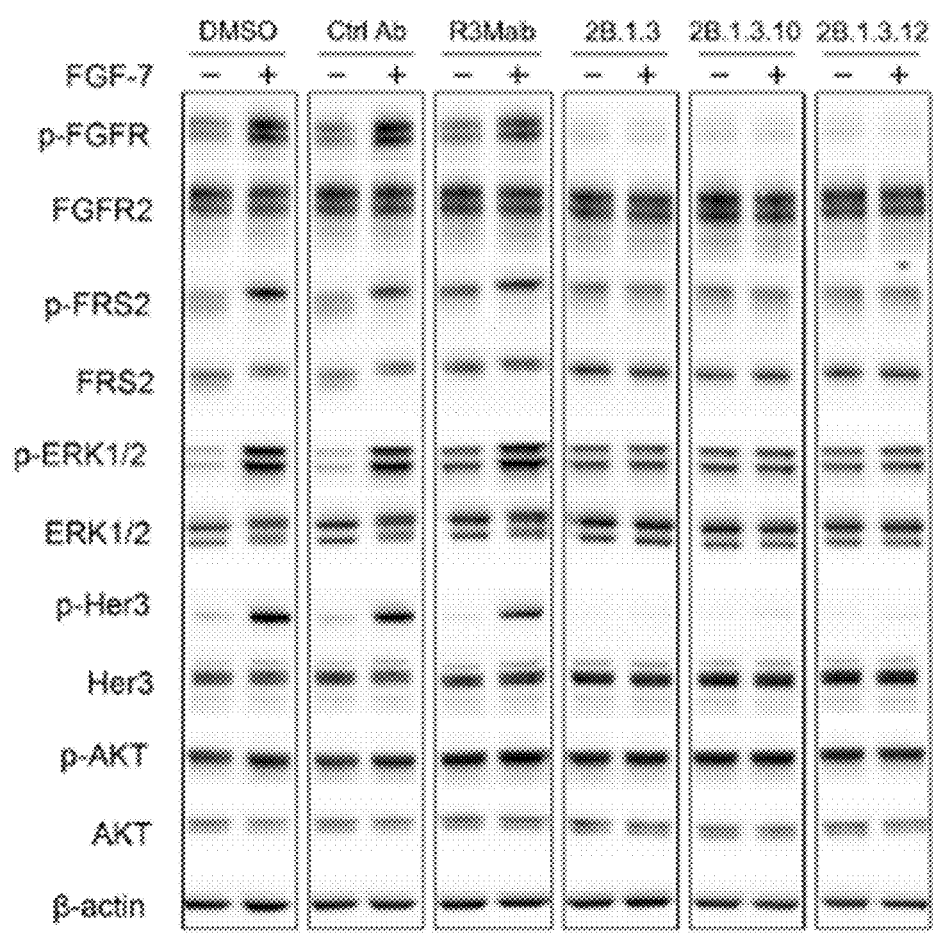
FIG. 8A show blocking of FGF7-stimulated FGFR2 signaling by 2B.1 variants in breast cancer cell line MFM-223x2.2.
Figure 8B:
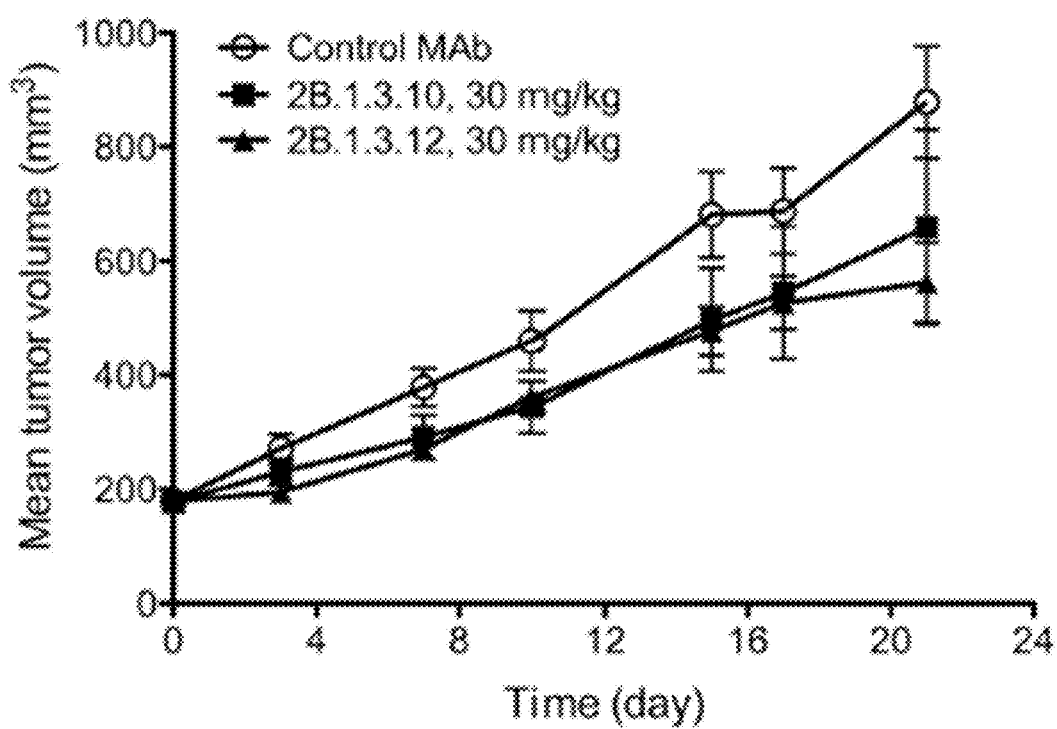
FIG. 8B shows the effects of 2B.1.3.10 and 2B.1.3.12 on the growth of FGFR2-dependent MFM-223x2.2 breast cancer xenografts. Mice under experiment showed estrogen toxicity. n=10 per group; error bars represent SEM.
Figure 12:
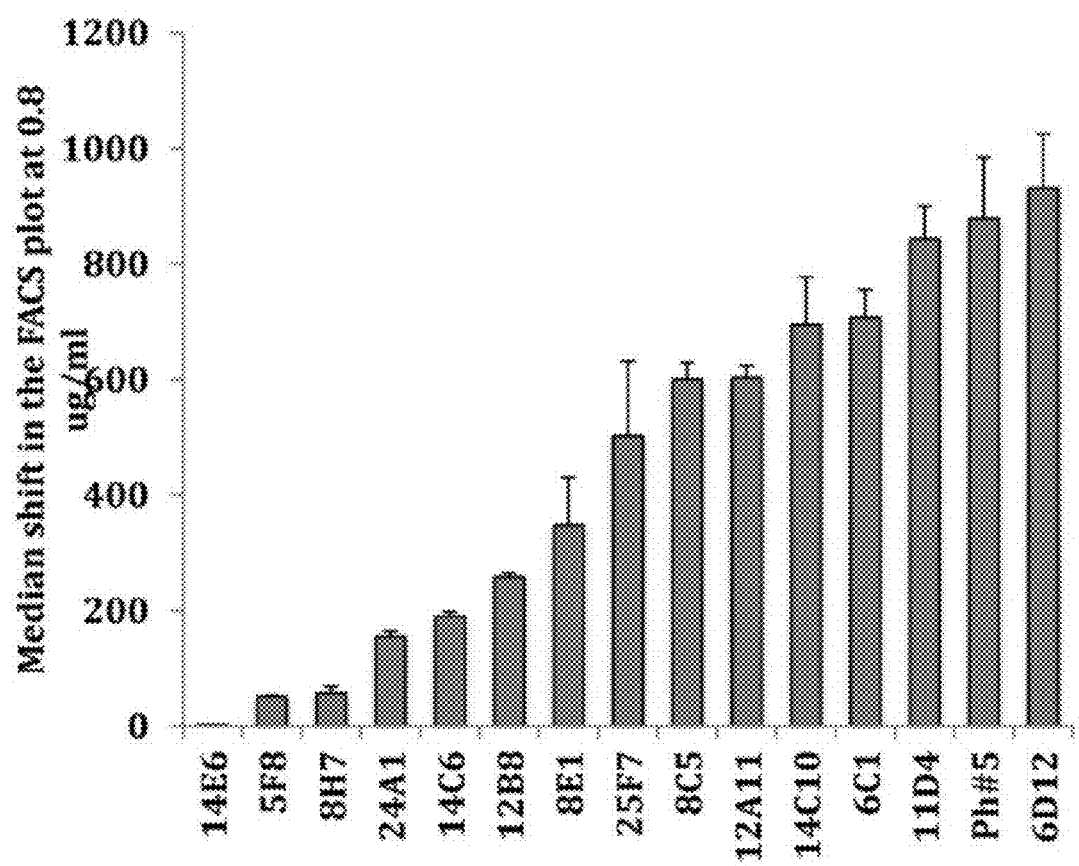
FIG. 12 depicts the median shift observed in the FACS plot at 0.8 µg/ml measuring binding of various anti-KLB antibodies to 293 cells expressing hKLB.
Figure 13:
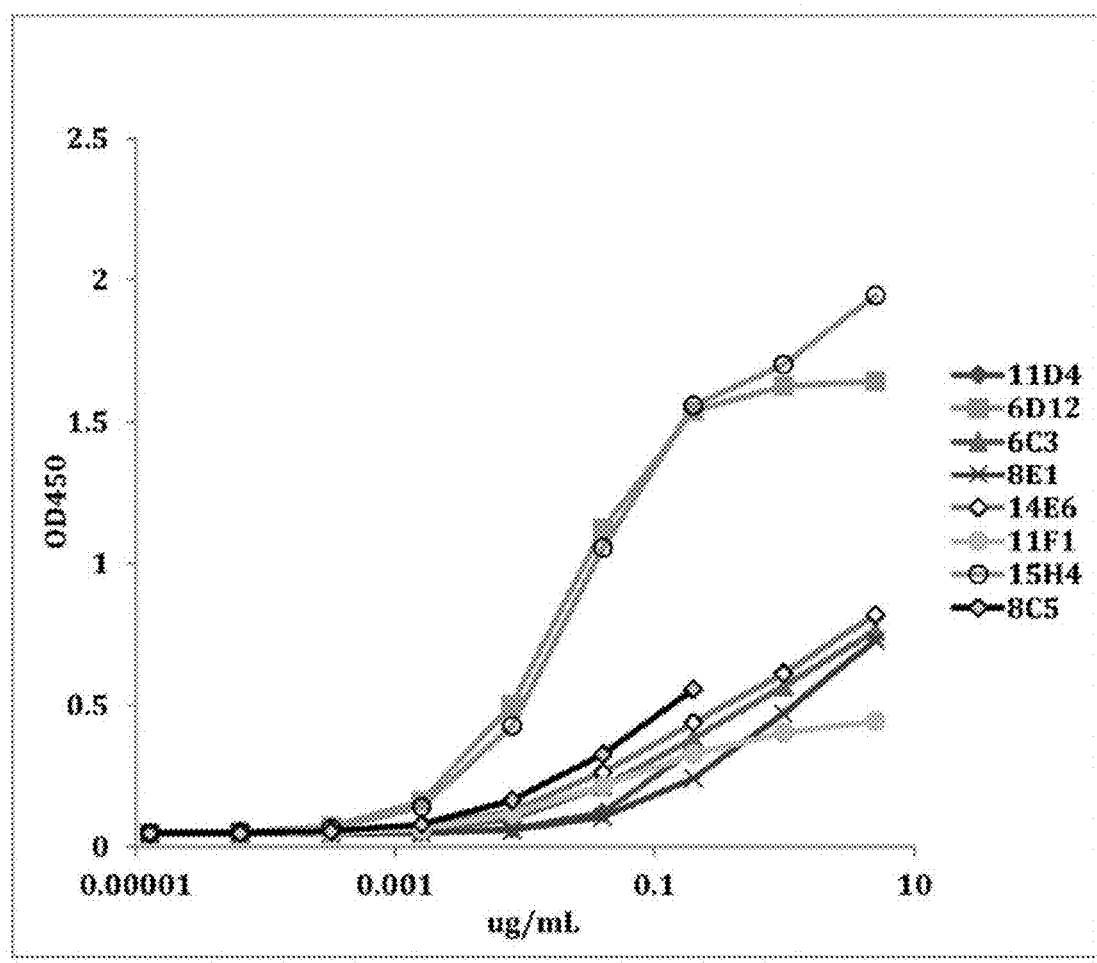
FIG. 13 depicts the relative binding of various anti-KLB antibodies to hKLB-ECD-HIS protein.
Figure 14D:
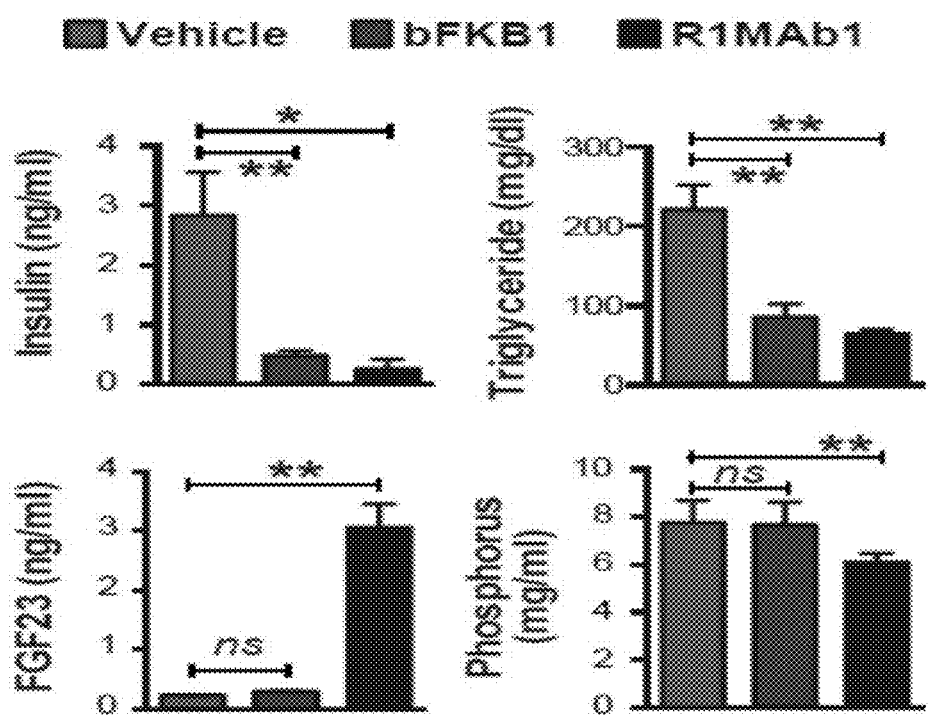
FIG. 14D shows insulin, triglyceride, FGF23 and phosphorous levels following administration of bFKB1 or R1MAB1 as compared to the control.
Figure 15A:
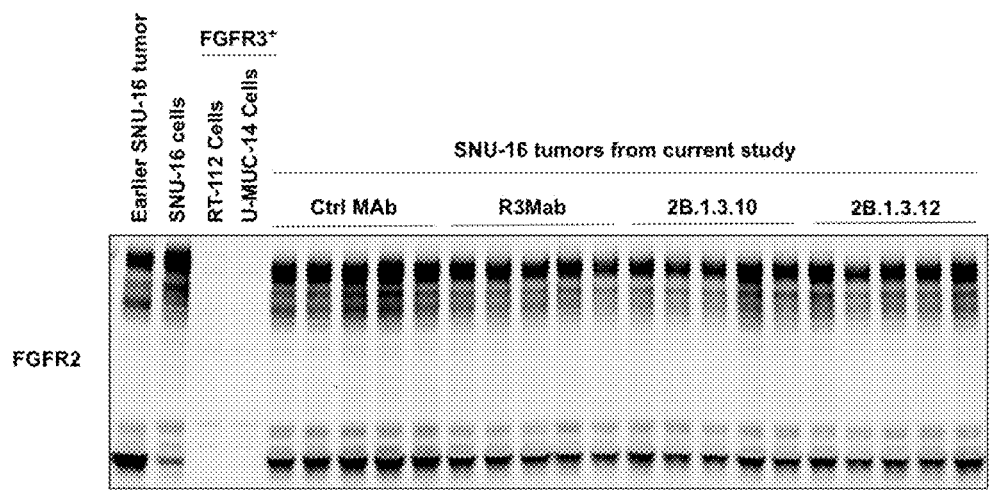
FIGS. 15A and 15B show detection of human FGFR2 (FIG. 15A) and FGFR3 (FIG. 15B) in SNU-16 xenograft tumors. Tumor samples were lysed and subjected to Western blot analysis for human FGFR2 and FGFR3 proteins. Tumors collected from the current study showed signal for FGFR3 (FIG. 15B, Lane 5-24). In addition, tumors collected from a previous SNU-16 study (FIG. 15B, Lane 3) and the in vitro-cultured SNU-16 cells (FIG. 15B, Lane 4) also showed detectable but weaker FGFR3 expression.
Figure 15B:
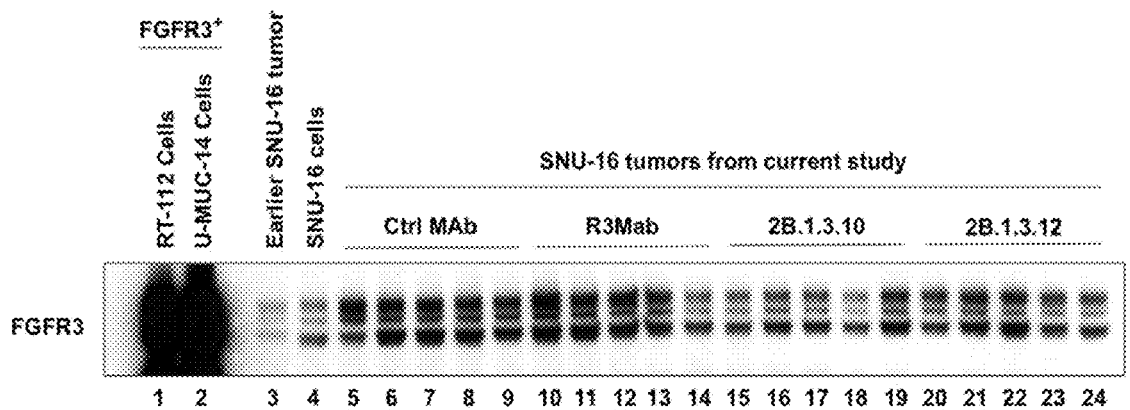

The RT112 cell line expresses FGFR3 but not FGFR2. As anticipated, both Mab 2B.1.3.10 and 2B.1.3.12, which retained the parental specificity for FGFR3 after engineering, as well as the parental antibody R3Mab, suppressed the growth of FGFR3-overexpressing RT112 tumor xenografts (FIG. 4B). The engineered variants 2B.1.3.10 and 2B.1.3.12 in the study, with tumor growth inhibition (TGI) values of 48% and 64%, displayed weaker potency than the parental R3Mab (TGI 82%), which could be possibly due to modified pharmacokinetics. For FGFR2-based efficacy, we turned to the SNU-16 cell line, which expresses readily detectable FGFR2 along with very low FGFR3 levels. Mice bearing SNU-16 xenografts were dosed with non-specific IgG control antibody, the parental R3Mab, or the engineered variants 2B.1.3.10 or 2B.1.3.12. The engineered variants displayed similar TGI values of 63% and 61%, respectively (FIG. 4C). Surprisingly, R3Mab, although not binding to FGFR2, also showed a measurable TGI of 44%. The tumor samples were then collected and analyzed for FGFR2 and FGFR3 expression (FIG. 15). FGFR3 was upregulated in the SNU-16 tumor xenografts in vivo, which may explain the observed inhibitory effect of R3Mab in this model. Regardless, the engineered variants showed significantly stronger activity as compared to R3Mab (p<0.001, day 31). In another experiment, 2B.1.3.10 and 2B.1.3.12 also retarded the growth of MFM-223x2.2 tumor xenografts in mice (FIG. 8A and FIG. 8B). Collectively, the engineered antibodies can serve as dual agents to effectively inhibit both FGFR2- and FGFR3-dependent cancer cell growth.

Example 5. FGFR2-Binding R3Mab Variants were Generated by Phage Library Selection Phagemid displaying R3Mab Fab fragment have been previously described (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4; 14)-positive multiple myeloma in mice." The Journal of clinical investigation 119(5): 1216-1229.). Three consecutive stop codons were introduced to replace 3 residues in each of the H1, H2, H3 or L2 CDR loops of R3Mab, which served as the template for constructing phage display library. Random mutations were then incorporated into each of the above CDR loops (Table 3) using the method of Kunkel et al. (Kunkel T A, Bebenek K, & McClary J (1991) Efficient site-directed mutagenesis using uracil-containing DNA. Methods Enzymol 204:125-139.). Purified library DNA was then transformed into SS320 competent cells by electroporation (BTX ECM 630) (Clackson T & Lowman H B (2004) Phage display: A practical approach (Oxford University Press). The transformed library cells were grown overnight in 2YT medium at 37° C. to allow the propagation of phage particles (Clackson T & Lowman H B (2004) *Phage display: A practical approach* (Oxford University Press). To sort for FGFR2 binders, 2 μg/mL of His-tagged FGFR2-IIIb, was coated on the 96-well MaxiSorp plates. 1 OD of purified phage suspensions from each library was incubated separately with the immobilized antigen for the first round of panning. After brief washing with phosphate buffer saline plus 0.05% Tween 20 (PBST), bound phage particles were eluted with low pH. Collected phage from individual libraries were pooled together and propagated in XL1-Blue cells for subsequent rounds of panning. For the fourth round of panning, the washing step was extended to three 15-time washings with intervals of 30-min PBST incubations so as to enrich the tight binders. XL1-Blue cells were infected with the recovered phage particles from round 4 and plated on 2YT agar. 96 randomly picked colonies were cultured individually for phage production. The supernatants were assayed to verify FGFR2-IIIb binding by phage ELISA. Meanwhile, phagemid DNA was extracted from each clone and sequenced.

Example 6. A Library was Construction and FGFR2 Binders that Did not Bind FGFR4 were Selected The phage display libraries were constructed based on the phagemid displaying the Fab fragment of antibody 2B.1.3. Stop templates for Kunkel mutagenesis included 3 stop codons in either the CDR H1 or H3 loops or both. Selected positions in CDR H1, H3 or L2 loops were subject to random mutagenesis (Table 10). Library preparation procedures were the same as described above. For selection of clones that have reduced FGFR4 binding while retaining FGFR2 specificity, in the first round, 1.5 OD of phage library was mixed with 0.5 nM FGFR4-Fc proteins. The mixture was incubated overnight at 4° C. in a MaxiSorp plate that was pre-coated with 2 μg/mL FGFR2-IIIb. Bound phage particles were washed briefly, eluted and propagated for the next round of selection. In the second round, 1.5 OD of phage preparations were mixed with 10 nM FGFR4-Fc and incubated at 4° C. overnight. For the third and fourth rounds, 0.5 OD of phage preparations were mixed with 460 nM FGFR4-Fc proteins, and shaken at room temperature (RT) for 20 min before being incubated with coated FGFR2-IIIb. After being incubated with FGFR2-IIIb for 30 min at RT, the MaxiSorp plates were washed 3 times with 10-min intervals of PB ST incubations. Eluted phage particles were used to infect XL1-Blue cells and plated on 2YT agar. Randomly picked clones were cultured for phage ELISA assays and DNA sequencing as described above.

Example 7. Phage ELISA Binding Assays were Performed

A 384-well MaxiSorp plate was coated overnight at 4° C. with 30 μL 1 μg/mL E25 (control antibody), FGFR2-IIIb-His, FGFR2-IIIc-His or FGFR4-His in each quadrant. After blocking with 2% BSA in PBS for 1 h at RT, 30 μL of 10-fold diluted phage supernatant was added into quadrant. The plate was shaken at RT for 2 h. To detect the bound phage particles, HRP-conjugated anti-M13 monoclonal antibody (GE Healthcare) was 1:3000 diluted and incubated in the plate for 15 min. TMB peroxidase substrate was added into each well to allow color development. The reaction was stopped by the addition of 100 μL 1M phosphoric acid before the plate was read at the absorbance of 450 nM.

Example 8. Surface Plasmon Resonance (SPR) Assays were Performed

The binding affinities of R3Mab variants for FGFR antigens were determined using a Biacore T100 (GE Healthcare). A saturated amount of anti-human Fc monoclonal antibody was immobilized onto a CM5 biosensor chip by following the product instructions. About 500 resonance units of R3Mab-derived antibody molecules were captured in each flow cell. FGFR antigens of various concentrations were injected at a flow rate 30 μL/min. After each binding cycle, flow cells were regenerated using 3M $MgCl_2$. Kinetic analyses were performed using the T100 evaluation software to obtain the kinetic and affinity constants.

Example 9. Protein Expression, Purification and Structure Determination

The human FGFR2-IIIb ECD (residue 140-369) was amplified by PCR and subcloned into pET-21b(+) vector (Novagen). The protein was expressed as inclusion bodies in *E. coli* BL21(DE3)pLysS cells. The inclusion bodies were washed with 20 mM Tris pH7.5, 5% Glycerol, 1 mM EDTA and 2% Triton X-100, before being dissolved in 6 M Guanidine-HCl, 20 mM Tris pH8, 10 mM TCEP. For in vitro folding, inclusion body was rapidly diluted to 50 mg/L into the refolding buffer containing 100 mM Tris pH 8.0, 0.4 M L-arginine HCl, 2 mM EDTA, 3.7 mM cystamine and 6.6 mM cysteamine. After 72 h at 4° C., the folding mixture was concentrated and passed through a 5 mL Heparin HP column (GE Healthcare). The sample was further purified with a MonoS column and a Superdex 200 column. The 2B.1.3 Fab was expressed and purified as described (Qing, J., X. Du, Y. Chen, P. Chan, H. Li, P. Wu, S. Marsters, S. Stawicki, J. Tien, K. Totpal, S. Ross, S. Stinson, D. Dornan, D. French, Q. R. Wang, J. P. Stephan, Y. Wu, C. Wiesmann and A. Ashkenazi (2009). "Antibody-based targeting of FGFR3 in bladder carcinoma and t(4; 14)-positive multiple myeloma in mice." The Journal of clinical investigation 119(5): 1216-1229). The FGFR2 and Fab proteins were separately dialyzed against 10 mM Tris pH 7.0, 5 mM NaCl before being mixed together at a molar ratio of 1:1. The protein mixture was diluted to 2 mg/mL for crystallization. Crystals were grown at 20% (w/v) PEG3350, 0.1 M sodium citrate pH 5.5, 0.2 M ammonium sulfate using vapor diffusion method. As the crystals were sensitive to cryoprotection solutions and cracked once being transferred out of the mother liquor, a diffractable crystal was eventually harvested from a tray that were left untouched for four months with the concentration of PEG3350 high enough to serve cryoprotection. Thus the crystals were directly taken out of the drop and flash frozen in liquid nitrogen. Diffraction data was collected with a beam wavelength of 1 Å at the Advanced Light Source of the Lawrence Berkeley National Laboratory. Data processing was carried out using HKL2000 and Scalepack (Otwinowski Z & Minor W (1997) Processing of X-ray diffraction data collected in oscillation mode. Methods in enzymology 276: 307-326.). The structure was solved with molecular replacement using the program Phaser in the CCP4 suite (McCoy A J, et al. (2007) Phaser crystallographic software. J Appl Crystallogr 40(Pt 4):658-674. Winn M D, et al. (2011) Overview of the CCP4 suite and current developments. Acta Crystallogr D Biol Crystallogr 67(Pt 4):235-242). The search models for Fab and FGFR2-D2 were PDB 3GRW and 3CU1, respectively. Two complexes were found in an asymmetric unit cell. Rigid body and simulated annealing refinements were conducted using Phenix (Adams P D, et al. (2010) PHENIX: a comprehensive Python-based system for macromolecular structure solution. *Acta Crystallogr D Biol Crystallogr* 66(Pt 2):213-221). Manual model building was performed with the program Coot (Emsley P, Lohkamp B, Scott W G, & Cowtan K (2010) Features and development of Coot. *Acta Crystallogr D Biol Crystallogr* 66(Pt 4):486-501). Subsequent refinements of positional and atomic displacement parameters were carried out using Phenix. Water molecules were added with a distance cutoff of 3.4 Å. The final model was validated by the program MolProbity (Chen V B, et al. (2010) MolProbity: all-atom structure validation for macromolecular crystallography. Acta Crystallogr D Biol Crystallogr 66(Pt 1): 12-21). Ramachandran outliers were not detected.

Example 10. FGF Ligand-Blocking ELISA

A 96-well MaxiSorp plate was coated overnight at 4° C. with 1.5 µg/mL anti-human Fc antibody (Jackson ImmunoResearch Lab). After blocking with 2% BSA in PBS for 1 h at RT, 0.25 µg/mL FGFR-Fc fusion proteins were incubated at RT for 2 h. The plate was washed 5 times before being added with the antibody and FGF ligand mixtures, which was prepared as 49 µL 100 ng/mL FGF ligand, 1 µL 25 mg/mL Heparin (Sigma-Aldrich) and 50 µL antibody dilutions. After shaking at RT for 2 h, the plate was washed 5 times. Bound ligand was detected by subsequent incubations at RT with 0.5 µg/mL biotinylated anti-FGF antibodies (R&D Biosystems) for 0.5 h, 1:2,500-diluted Streptavidin-HRP (Invitrogen) for 0.5 h and the TMB substrate until enough color development.

Example 11. Cell Lines

SNU16 and MFM-223x2.2 cell lines were obtained from an internal cell bank. The cell line RT112 was obtained from ATCC. The cells were cultured in RPMI medium supplemented with 10% FBS. All cell lines are tested for mycoplasma, cross contamination and genetically fingerprinted when new stocks are generated to ensure quality and confirm ancestry. *Cell line fingerprinting: SNP fingerprinting*. SNP genotypes are performed each time new stocks are expanded for cryopreservation. Cell line identity is verified by high-throughput SNP genotyping using Fluidigm multiplexed assays. SNPs were selected based on minor allele frequency and presence on commercial genotyping platforms. SNP profiles are compared to SNP calls from available internal and external data (when available) to determine or confirm ancestry. In cases where data is unavailable or cell line ancestry is questionable, DNA or cell lines are re-purchased to perform profiling to confirm cell line ancestry. SNPs. rs11746396, rs16928965, rs2172614, rs10050093, rs10828176, rs16888998, rs16999576, rs1912640, rs2355988, rs3125842, rs10018359, rs10410468, rs10834627, rs11083145, rs11100847, rs11638893, rs12537, rs1956898, rs2069492, rs10740186, rs12486048, rs13032222, rs1635191, rs17174920, rs2590442, rs2714679, rs2928432, rs2999156, rs10461909, rs11180435, rs1784232, rs3783412, rs10885378, rs1726254, rs2391691, rs3739422, rs10108245, rs1425916, rs1325922, rs1709795, rs1934395, rs2280916, rs2563263, rs10755578, rs1529192, rs2927899, rs2848745, rs10977980. Short Tandem Repeat (STR) Profiling. STR profiles are determined for each line using the Promega PowerPlex 16 System. This is performed once and compared to external STR profiles of cell lines (when available) to determine cell line ancestry. Loci analyzed. Detection of sixteen loci (15 STR loci and Amelogenin for gender identification), including D3S1358, TH01, D21S11, D18S51, Penta E, D5S818, D13S317, D7S820, D16S539, CSF1PO, Penta D, AMEL, vWA, D8S1179 and TPOX.

Example 12. Immunoblotting

Cells were seeded on tissue culture plates for 24 hours, pre-treated with 10 µg/ml FGFR blocking or control anti-gD antibody, then stimulated with 25 ng/ml FGF-7 (R&D Systems) in the presence of 20 µg/ml heparin (Sigma) for 15 minutes. Cells were placed on ice and protein immediately harvested with IP lysis buffer (Thermo Scientific). Protein lysates were passed through a syringe, cleared by centrifugation, then quantified using BCA protein assay (Thermo Scientific). Protein was separated on 4-12% Bis-Tris gels (Life Technologies), transferred to nitrocellulose membranes, blocked with 5% BSA or milk in TBST for 30 minutes, then blotted with primary antibody overnight at 4 C. Antibodies used: phospho-FGFR (Y653/654), phospho-FRS2 (Y196), phospho-ERK1/2 (T202/Y204), ERK1/2, phospho-AKT (S473), AKT, phospho-HER3 (Y1289), HER3, phospho-PLCgammal (Y783), PLCgammal (Cell Signaling); FGFR2, FRS2 (Santa Cruz Biotechnology); beta-actin (Sigma). Membranes were washed and incubated with appropriate HRP conjugated secondary antibodies for 1 hour, then washed and detected with SuperSignal West Femto Chemiluminescent Substrate (Thermo Scientific). Luminescence signal was acquired with FluorChem Q (Alpha Innotech).

Example 13. Xenograft Experiments

All procedures were approved by and conformed to the guidelines and principles set by the Institutional Animal Care and Use Committee of Genentech and were carried out in an Association for the Assessment and Accreditation of Laboratory Animal Care (AAALAC)-accredited facility. 0.36 mg estrogen pellets were implanted subcutaneously (s.c.) 1 day prior to cell inoculation. 10 million MFM-223 x2.2 breast cancer cells suspended in HBSS with matrigel were inoculated in the mammary fat pad #4 of 6-8-week-old female NCR nude mice (Taconicm). SNU-16 tumor fragments of about 15-30 $mm^3$ were implanted s.c. into right flanks of 6-8-week-old female Balb/c nude mice (Shanghai Laboratory Animal). 7 million RT-112 bladder carcinoma cells suspended in HBSS with matrigel were inoculated s.c. in the 6-8-week-old female C.B-17 SCID mice (Charles River Lab). When the mean tumor volume reached 100-200 $mm^3$ (day 0), mice were randomized into groups of 6 (SNU-16, RT 112) or 7 (MFM-223 x2.2) and were treated starting on day 1 with twice weekly intraperitoneal (i.p.) injections of 2B1.3.10 or 2B1.3.12 (10, 30 or 50 mg/kg). Control groups were treated with a control human IgG1 antibody diluted in PBS (30 mg/kg). Tumor volumes were measured in two dimensions (length and width) using Ultra Cal IV calipers (Model 54 10 111, Fred V. Fowler Company). The tumor volume was calculated using the following formula: Tumor volume $(mm^3)$=(length×$width^2$)×0.5. Animal body weights were measured using an Adventurer Pro AV812 scale (Ohaus). Percent body weight change was calculated using the following formula: Body weight change (%)=[(WeightDay new−WeightDay 0)/WeightDay 0]×100%. Percent body weight was tracked for each animal during the study and percent body weight change for each group was calculated and plotted.

Example 14. Identification FGFR2/3+KLB Bispecific Antibodies

Along with the anti-tumor activity of the anti-FGFR2/3 antibodies described here, bispecific antibodies directed to FGFR2/3 and KLB ("FGFR2/3+KLB bispecific antibodies") can be made for use in treating proliferative disorders and diseases associated with FGFR2 and/or FGFR3 expression and more specifically for metabolic diseases. Metabolic diseases that may be treated by FGFR2/3+KLB bispecific antibodies include but are not limited to: polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), maturity onset diabetes of the young (MODY), type 2 diabetes, obesity, Bardet-Biedl syndrome, Prader-Willi syndrome, Alstrom syndrome, Cohen syndrome, Albright's hereditary osteodystrophy (pseudohypoparathyroidism), Carpenter syndrome, MOMO syndrome, Rubinstein-Taybi syndrome, fragile X syndrome and Borjeson-Forssman-Lehman syndrome. More specifically, the FGFR2/3+KLB bispecific antibodies may be used for the treatment of NASH.

Figure 17A:
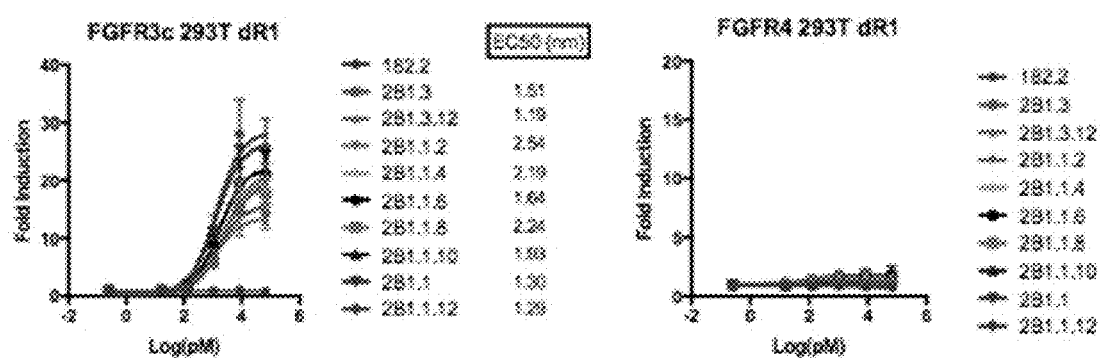
FIGS. 17A and 17B show a comparison of anti-FGFR2/3 antibody variant activity against the FGFRs using a luciferase assay.
Figure 17B:
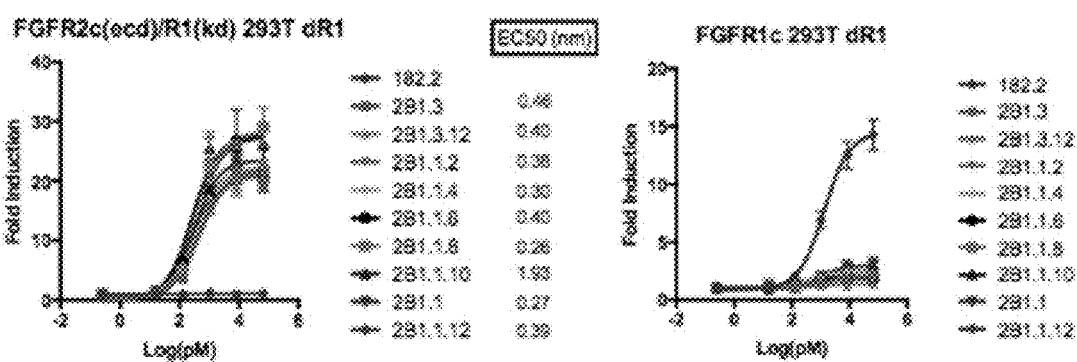

Initially, experiments were performed to compare the activity of the anti-FGFR2/3 antibody variants (FIGS. 17A and 17B). Specifically, 239T FGFR1 deletion cells were seeded at a density of $0.9 \times 10^6$ in 96 well plates on Day 1. On Day 2, the cells were transfected with constructs including FGFR, FF Luciferase, Renilla Luciferase (transfection efficiency control), and Elk1. On Day 3, the cells were stimulated in serum-free media with anti-FGFR2/3 antibody variants 2B1.3, 2B1.3.12, 2B1.1.2, 2B1.1.4, 2B1.1.6, 2B1.1.8, 2B1.1.10, 2B1.1, and 2B1.1.12. Initial concentrations were 10 µg/mL and a series of dilutions were performed ⅕. Reactions were carried out for 7.5 hrs and were stopped by removing media from the plates and addint 1× Passive Lysis buffer. The plates were then analyzed using a Wallace Envision plate reader after adding Luciferase substrate and normalized to Renilla expression.

Based in part on the Luciferase assay in addition to other assays performed but not described herein, an anti-FGFR2/3 antibody variant decision matrix was assembled (FIG. 18). 2B1.3 was shown to block growth in MCF-7/FGF7 assay and showed FGF19 blocking. 2B1.3.12 blocked tumor progression.

Figure 19A:
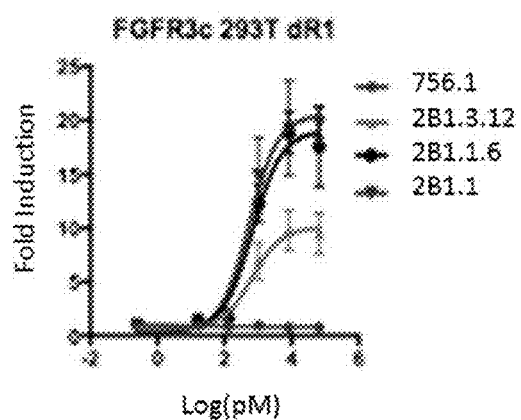
FIGS. 19A-19C show FGFR activity of selected anti-FGFR2/3 antibody variants.
Figure 19B:
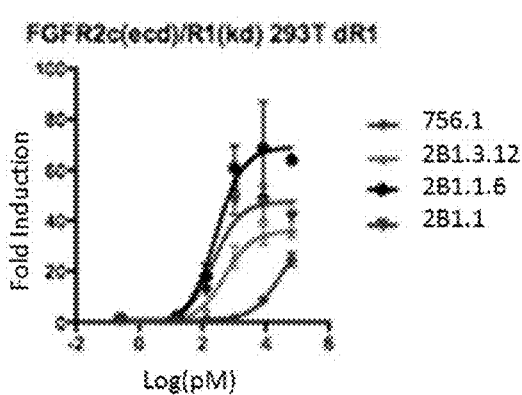
Figure 19C:
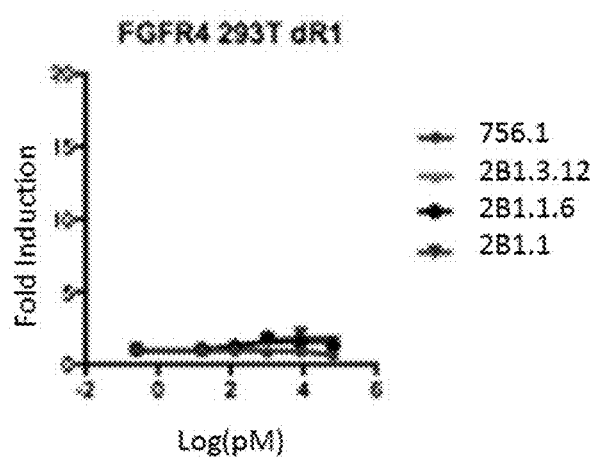

Based on the decision matrix, variants 2B1.3.12, 2B1.1.6, and 2B1.1 were further examined (FIGS. 19A-19C) and the activity of each was tested. Furthermore, FGFR binding was examined for 2B1.1, 2B1.3, and 2B1.3.12 (Table 12). In Table 12, NB refers to no binding and ND refers to not determined. 2B.1.1 for FGFR4 was measured by capturing IgG and flowing the FGFR4-6×His ("6×His" disclosed as SEQ ID NO: 307) (experiment identified with a * in Table 12). Later, the KD for the 2B.1.3 variants were determined by capturing FGFR4-Fc and flowing the antibody Fab fragments (Table 12).

TABLE 12

Binding affinities of R3Mab variants for human FGFR.

| Clone | FGFR1-IIIb, IIIc | FGFR2-IIIb | FGFR2-IIIc | FGFR3-IIIb | FGFR3-IIIc | FGFR4 |
|---|---|---|---|---|---|---|
| R3Mab | NB | NB | NB | 0.24 | 0.61 | NB |
| 2B.1.1 | NB | 0.29 | 2.8 | ND | ND | 2.8* |
| 2B.1.3 | NB | 2.6 | 2.0 | 0.09 | 0.07 | 32 |
| 2B.1.3.12 | NB | 3.0 | 6.1 | 0.50 | 0.72 | >1,000 |

Thereafter, seven 2B1.1 variants were expressed and agonist activity for FGFR2, FGFR3, and FGFR4 binding was tested (FIGS. 16A-16C). All 2B1.1 variants showed sub-nM to low-pM affinity ranges to FGFR3 using the Biacore assay. Due to FGFR4 protein stickiness, the binding affinity is best determined by Biacore with Fabs as the analyte. Most of the variants showed weak binding to FGFR4 by ELISA except for 2B1.1 and 2B1.1.4.

Based on the experiments described in this Example 14, variants 2B1.3.12 and 2B1.1.6 were selected for bispecific assembly with an anti-KLB antibody.

Example 14. Generation of FGFR2/3+KLB Bispecific Antibodies

FGFR2/3+KLB bispecific antibodies can be made using any bispecific antibody production method. In specific examples, FGFR2/3+KLB bispecific antibodies of this invention can be made using the the knob and hole technique.

HEK293 cells can be co-transfected with a mixture of four expression vectors encoding the heavy and light chains of anti-FGFR2/3 antibody variant 2B1.3.12 or 2B1.1.6 and the heavy and light chains of one of the anti-KLB antibodies described herein (see e.g., Tables 13 and 14).

TABLE 13

CDR H sequences for murine anti-KLB monoclonal antibodies.

| Antibody | CDR H1 | CDR H2 | CDR H3 |
|---|---|---|---|
| 11F1 | SYGIS (SEQ ID NO: 108) | TVSSGGRYTYYPDSVKG (SEQ ID NO: 138) | GGDGYALDY (SEQ ID NO: 154) |
| 6D12 | DYYMN (SEQ ID NO: 109) | WIDPENDDTIYDPKFQG (SEQ ID NO: 139) | FTTVFAY (SEQ ID NO: 155) |
| 11D4 | NYGVS (SEQ ID NO: 110) | VIWGDGSINYHSALIS (SEQ ID NO: 140) | THDWFDY (SEQ ID NO: 156) |
| 8E1 | DTYMN (SEQ ID NO: 111) | RIDPSNGNAKYDPKFQG (SEQ ID NO: 141) | RALGNGYALGY (SEQ ID NO: 157) |
| 46C3 | DTYIH (SEQ ID NO: 112) | RIDPANGNTKYDPKFQD (SEQ ID NO: 142) | GTSYSWFAY (SEQ ID NO: 158) |

TABLE 13-continued

CDR H sequences for murine anti-KLB monoclonal antibodies.

| Antibody | CDR H1 | CDR H2 | CDR H3 |
|---|---|---|---|
| 8H7 | SYWIH (SEQ ID NO: 113) | EIDPSVSNSNYNQKFKG (SEQ ID NO: 143) | LGVMVYGSSPFWFAY (SEQ ID NO: 159) |
| 21H3 | SYWIH (SEQ ID NO: 113) | EIDPSVSNSNYNQKFKG (SEQ ID NO: 143) | LGVMVYGSSPFWFAY (SEQ ID NO: 159) |
| 25F7 | DTFTH (SEQ ID NO: 114) | RIDPSNGNTKYDPKFQG (SEQ ID NO: 144) | RALGNGYAMDY (SEQ ID NO: 160) |
| 14E6 | EYTMN (SEQ ID NO: 115) | GINPNNGETSYNQKFKG (SEQ ID NO: 145) | KTTNY (SEQ ID NO: 161) |
| 14C6 | SYWIE (SEQ ID NO: 116) | EIFPGGGSTIYNENFRD (SEQ ID NO: 146) | RGYYDAAWFDY (SEQ ID NO: 162) |
| 24A1 | DYEMH (SEQ ID NO: 117) | AIWPENADSVYNQKFKG (SEQ ID NO: 147) | EGGNY (SEQ ID NO: 163) |
| 5F8 | DTYIH (SEQ ID NO: 118) | RIDPANGNTKYDPKFQG (SEQ ID NO: 148) | SGNYGAMDY (SEQ ID NO: 164) |
| 6C1 | SYWIE (SEQ ID NO: 116) | EILPGSDSTKYVEKFKV (SEQ ID NO: 149) | GGYHYPGWLVY (SEQ ID NO: 165) |
| 12A11 | RYWMS (SEQ ID NO: 119) | EISPDSSTINYTPSLKD (SEQ ID NO: 150) | PSPALDY (SEQ ID NO: 166) |
| 12B8 | NYGMN (SEQ ID NO: 120) | WIDTDTGEATYTDDFKG (SEQ ID NO: 151) | EEYGLFGFPY (SEQ ID NO: 167) |
| 14C10 | TSAMGIG (SEQ ID NO: 121) | HIWWDDDKRYNPALKS (SEQ ID NO: 152) | IDGIYDGSFYAMDY (SEQ ID NO: 168) |
| 8C5 | TYGVH (SEQ ID NO: 122) | VIWSGGSTDYNAAFIS (SEQ ID NO: 153) | DYGSTYVDAIDY (SEQ ID NO: 169) |

TABLE 14

CDR L sequences for murine anti-KLB monoclonal antibodies.

| Antibody | CDR L1 | CDR L2 | CDR L3 |
|---|---|---|---|
| 11F1 | SASQVISNYLN (SEQ ID NO: 170) | FTSSLRS (SEQ ID NO: 185) | QQYSKLPWT (SEQ ID NO: 201) |
| 6D12 | SASSSGRYTF (SEQ ID NO: 171) | DTSKLAS (SEQ ID NO: 186) | FQGTGYPLT (SEQ ID NO: 202) |
| 11D4 | RASQDISNYFN (SEQ ID NO: 172) | YTSRLQS (SEQ ID NO: 187) | HQVRTLPWT (SEQ ID NO: 203) |
| 8E1 | KASDHINNWLA (SEQ ID NO: 173) | GTTNLET (SEQ ID NO: 188) | QQYWNTPFT (SEQ ID NO: 204) |
| 46C3 | RSSQNIVHSDGNTYLE (SEQ ID NO: 174) | KVSNRFS (SEQ ID NO: 189) | FQGSHVLT (SEQ ID NO: 205) |
| 8H7 | KASQFVSDAVA (SEQ ID NO: 175) | SASYRYT (SEQ ID NO: 190) | QQHYIVPYT (SEQ ID NO: 206) |
| 21H3 | KASQFVSDAVA (SEQ ID NO: 175) | SASYRYT (SEQ ID NO: 190) | QQHYIVPYT (SEQ ID NO: 206) |
| 25F7 | KASDHINNWLA (SEQ ID NO: 173) | GASNLET (SEQ ID NO: 191) | QQYWNTPFT (SEQ ID NO: 204) |
| 14E6 | RASQEISGYLS (SEQ ID NO: 176) | AASTLDS (SEQ ID NO: 192) | LQYGSYPWT (SEQ ID NO: 207) |
| 14C6 | SASSSLSSSYLY (SEQ ID NO: 177) | GASNLAS (SEQ ID NO: 193) | HQWSSYPLT (SEQ ID NO: 208) |

TABLE 14-continued

CDR L sequences for murine anti-KLB monoclonal antibodies.

| Antibody | CDR L1 | CDR L2 | CDR L3 |
|---|---|---|---|
| 24A1 | KSSQSLLNSGNQKNSLA (SEQ ID NO: 178) | LASTRES (SEQ ID NO: 194) | QQHHSTPYT (SEQ ID NO: 209) |
| 5F8 | RASSSVNHMY (SEQ ID NO: 179) | YTSTLAP (SEQ ID NO: 195) | QQFTISPSMYT (SEQ ID NO: 210) |
| 6C1 | KASQNVDSYVA (SEQ ID NO: 180) | SASYRFS (SEQ ID NO: 196) | QQYNISPYT (SEQ ID NO: 211) |
| 12A11 | RASQSISDYVY (SEQ ID NO: 181) | YASQSIS (SEQ ID NO: 197) | QNGHNFPYT (SEQ ID NO: 212) |
| 12B8 | KASEDIYNRLA (SEQ ID NO: 182) | AATSLET (SEQ ID NO: 198) | QQYWSNPLT (SEQ ID NO: 213) |
| 14C10 | RASESVDSYGNSFMH (SEQ ID NO: 183) | RASNLES (SEQ ID NO: 199) | QQSNEDYT (SEQ ID NO: 214) |
| 8C5 | RASESVESYGNRYMT (SEQ ID NO: 184) | RAANLQS (SEQ ID NO: 200) | QQSNEDPWT (SEQ ID NO: 215) |

The heavy chain of anti-FFR2/3 and anti-KLB can be respectively tagged with the Flag peptide and Oct-Histidine (SEQ ID NO: 292) so that heterodimeric IgG can be purified by sequential affinity purification from conditioned medium. Partially purified heterodimeric IgG can then be analyzed in a GAL-ELK1 based luciferase assay to identify KLB-dependent agonists. To minimize mispairing of heavy and light chains, anti-FGFR2/3 can be expressed with human Fab constant region, and anti-KLB can be expressed with mouse Fab constant region. The tagged-bispecific IgGs can then be initially tested in a crude form using combinations of one arm from either FGFR2/3 antibody variant 2B1.3.12 or 2B1.1.6 and one arm from any of the KLB antibodies described herein. Specifically, the the anti-KLB antibody from which the KLB arm originates may comprise:

8C5.K4.M4L.H3.KNV Heavy Chain Variable Region
(SEQ ID NO: 104)
EVQLVESGGGLVQPGGSLRLSCAASDFSLTTYGVHWVRQAPGKGLEWLGV

IWSGGSTDYNAAFISRLTISKDNSKNTVYLQMNSLRAEDTAVYYCARDYG

STYVDAIDYWGQGTLVTVSS

8C5.K4.M4L.H3.KNV Full Heavy Chain
(SEQ ID NO: 106)
EVQLVESGGGLVQPGGSLRLSCAASDFSLTTYGVHWVRQAPGKGLEWLGV

IWSGGSTDYNAAFISRLTISKDNSKNTVYLQMNSLRAEDTAVYYCARDYG

STYVDAIDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLEPPKP

KDTLMISRTPEVTCVVVDVSHEDPEVKFNWYVDGVEVHNAKTKPREEQYG

STYRVVSVLTVLHQDWLNGKEYKCKVSNKALPAPIEKTISKAKGQPREPQ

VYTLPPSREEMTKNQVSLSCAVKGFYPSDIAVEWESNGQPENNYKTTPPV

LDSDGSFFLVSKLTVDKSRWQQGNVFSCSVMHEALHNHYTQKSLSLSPGK

8C5.K4.M4L.H3.KNV Light Chain Variable Region
(SEQ ID NO: 105)
DIVLTQSPDSLAVSLGERATINCRASESVESYGNRYMTWYQQKPGQPPKL -continued
LIYRAANLQSGVPDRFSGSGSGTDFTLTISSLQAEDVAVYYCQQSNEDPW

TFGQGTKVEIK

8C5.K4.M4L.H3.KNV Full Light Chain
(SEQ ID NO: 107)
DIVLTQSPDSLAVSLGERATINCRASESVESYGNRYMTWYQQKPGQPPKL

LIYRAANLQSGVPDRFSGSGSGTDFTLTISSLQAEDVAVYYCQQSNEDPW

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSENRGEC

Furthermore, bispecific antibodies can be produced with human IgG1 constant region (wild-type, with effector function) and with human IgG1 constant region with N297G mutation to eliminate the effector function, or mouse constant region with dual [D265G/N297G] mutations (DANG) to eliminate effector function.

Example 15: Testing of Bispecific Antibodies

Various bispecific antibody combinations of 8C5.K4H3.M4L.KNV (see Example 14 above) and different anti-FGFR2/3 arms can be made and tested in the GAL-ELK1-based luciferase assay in HEK293 cells with or without KLB. Each bispecific antibody combination can induced luciferase activity in a dose-dependent manner in cells expressing recombinant FGFR2 or 3 and KLB, but not in cells without KLB expression. This data can confirm that the FGFR2/3+KLB bispecifics retain the advantages of the parent antibodies, e.g., 2B1.3.12 or 2B1.1.6. Furthermore, the binding affinity of an FGFR2/3+KLB bispecific antibody that has a humanized 8C5 arm (8C5.K4.M4L.H3.KNV) and an arm of either the 2B1.3.12 or 2B1.1.6 variant can be determined for KLB binding, FGFR2 binding, and FGFR3 binding.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

Various publications, patents and patent applications are cited herein, the contents of which are hereby incorporated by reference in their entireties.

| SEQUENCES |
|---|

```
SEQ ID NO: 1
2B.1.3.10 HVR-L1
RASQDVDTSLA

SEQ ID NO: 2
2B.1.3.10 HVR-L2
SASFLYS

SEQ ID NO: 3
2B.1.3.10 HVR-L3
QQSTGHPQT

SEQ ID NO: 4
2B.1.3.10 HVR-H1
GFPFTSQGIS

SEQ ID NO: 5
2B.1.3.10 HVR-H2
RTHLGDGSTNYADSVKG

SEQ ID NO: 6
2B.1.3.10 HVR-H3
ARTYGIYDTYDKYTEYVMDY

SEQ ID NO: 7
2B.1.3.12 HVR-L1
RASQDVDTSLA

SEQ ID NO: 8
2B.1.3.12 HVR-L2
SASFLYS

SEQ ID NO: 9
2B.1.3.12 HVR-L3
QQSTGHPQT

SEQ ID NO: 10
2B.1.3.12 HVR-H1
GFPFTSTGIS

SEQ ID NO: 11
2B.1.3.12 HVR-H2
RTHLGDGSTNYADSVKG

SEQ ID NO: 12
2B.1.3.12 HVR-H3
ARTYGIYDTYDMYTEYVMDY

SEQ ID NO: 13
2B.1.1 HVR-H2
YWAWD

SEQ ID NO: 14
2B.1.88 HVR-H2
IWMFT

SEQ ID NO: 15
2B.1.38 HVR-H2
FWAYD

SEQ ID NO: 16
2B.1.20 HVR-H2
LDVFW

SEQ ID NO: 17
2B.1.32 HVR-H2
WVGFT
```

| SEQUENCES |
| --- |
| SEQ ID NO: 18<br>2B.1.49 HVR-H2<br>LSFFS |
| SEQ ID NO: 19<br>2B.1.86 HVR-H2<br>LSFWT |
| SEQ ID NO: 20<br>2B.1.9 HVR-H2<br>YHPYL |
| SEQ ID NO: 21<br>2B.1.73 HVR-H2<br>MIFYN |
| SEQ ID NO: 22<br>2B.1.74 HVR-H2<br>YHPFR |
| SEQ ID NO: 23<br>2B.1.14 HVR-H2<br>LWYFD |
| SEQ ID NO: 24<br>2B.1.71 HVR-H2<br>VWMFD |
| SEQ ID NO: 25<br>2B.1.28 HVR-H2<br>FWAWS |
| SEQ ID NO: 26<br>2B.1.95 HVR-H2<br>LIFFT |
| SEQ ID NO: 27<br>2B.1.50 HVR-H2<br>LNFYS |
| SEQ ID NO: 28<br>2B.1.81 HVR-H2<br>VNNFY |
| SEQ ID NO: 29<br>2B.1.25 HVR-H2<br>WHPWM |
| SEQ ID NO: 30<br>2B.1.3 HVR-H2<br>THLGD |
| SEQ ID NO: 31<br>2B.1.65 HVR-H2<br>YNAYT |
| SEQ ID NO: 32<br>2B.1.94 HVR-H2<br>LVFFS |
| SEQ ID NO: 33<br>2B.1.78 HVR-H2<br>LSFYS |
| SEQ ID NO: 34<br>2B.1.72 HVR-H2<br>VHPFE |
| SEQ ID NO: 35<br>2B.1.44 HVR-H2<br>WWSWG |
| SEQ ID NO: 36<br>2B.1.52 HVR-H2<br>FSLGD |

| SEQUENCES |
|---|
| SEQ ID NO: 37<br>2B.1.30 HVR-H2<br>VSFFS<br><br>SEQ ID NO: 38<br>2B.1.82 HVR-H2<br>INFFS<br><br>SEQ ID NO: 39<br>2B.1.93 HVR-H2<br>IDNYW<br><br>SEQ ID NO: 40<br>2B.1.55 HVR-H2<br>VDVFW<br><br>SEQ ID NO: 41<br>2B.1.35 HVR-H2<br>WHPFR<br><br>SEQ ID NO: 42<br>2B.1.33 HVR-H2<br>YHPFH<br><br>SEQ ID NO: 43<br>2B.1.80 HVR-H2<br>YWAFS<br><br>SEQ ID NO: 44<br>2B.1.92 HVR-H2<br>WVAFS<br><br>SEQ ID NO: 45<br>2B.1.3 HVR-H2<br>THLGD<br><br>SEQ ID NO: 46<br>2B.1.95 HVR-H2<br>LIFFT<br><br>SEQ ID NO: 47<br>2B.1.73 HVR-H2<br>MIFYN<br><br>SEQ ID NO: 48<br>2B.1.32 HVR-H2<br>WVGFT<br><br>SEQ ID NO: 49<br>2B.1.88 HVR-H2<br>IWMFT<br><br>SEQ ID NO: 50<br>2B.1.1 HVR-H2<br>YWAWD<br><br>SEQ ID NO: 51<br>FGFR2-IIIb nucleic acid sequence<br>ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCCGACGGGCTGCCCTACC<br>TCAAGGTTCTCAAGCACTCGGGGATAAATAGTTCCAATGCAGAAGTGCTGGCTCT<br>GTTCAATGTGACCGAGGCGGATGCTGGGGAATATATATGTAAGGTCTCCAATTAT |

| SEQUENCES |
|---|
| ATAGGGCAGGCCAACCAGTCTGCCTGGCTCACTGTCCTGCCAAAACAGCAAGCG<br>CCTGGAAGAGAAAAGGAGATTACAGCTTCCCCAGACTACCTGGAGATAGCCATT<br>TACTGCATAGGGGTCTTCTTAATCGCCTGTATGGTGGTAACAGTCATCCTGTGCC<br>GAATGAAGAACACGACCAAGAAGCCAGACTTCAGCAGCCAGCCGGCTGTGCACA<br>AGCTGACCAAACGTATCCCCCTGCGGAGACAGGTAACAGTTTCGGCTGAGTCCA<br>GCTCCTCCATGAACTCCAACACCCCGCTGGTGAGGATAACAACACGCCTCTCTTC<br>AACGGCAGACACCCCCATGCTGGCAGGGGTCTCCGAGTATGAACTTCCAGAGGA<br>CCCAAAATGGGAGTTTCCAAGAGATAAGCTGACACTGGGCAAGCCCCTGGGAGA<br>AGGTTGCTTTGGGCAAGTGGTCATGGCGGAAGCAGTGGGAATTGACAAAGACAA<br>GCCCAAGGAGGCGGTCACCGTGGCCGTGAAGATGTTGAAAGATGATGCCACAGA<br>GAAAGACCTTTCTGATCTGGTGTCAGAGATGGAGATGATGAAGATGATTGGGAA<br>ACACAAGAATATCATAAATCTTCTTGGAGCCTGCACACAGGATGGGCCTCTCTAT<br>GTCATAGTTGAGTATGCCTCTAAAGGCAACCTCCGAGAATACCTCCGAGCCCGGA<br>GGCCACCCGGGATGGAGTACTCCTATGACATTAACCGTGTTCCTGAGGAGCAGAT<br>GACCTTCAAGGACTTGGTGTCATGCACCTACCAGCTGGCCAGAGGCATGGAGTA<br>CTTGGCTTCCCAAAAATGTATTCATCGAGATTTAGCAGCCAGAAATGTTTTGGTA<br>ACAGAAAACAATGTGATGAAAATAGCAGACTTTGGACTCGCCAGAGATATCAAC<br>AATATAGACTATTACAAAAGACCACCAATGGGCGGCTTCCAGTCAAGTGGATG<br>GCTCCAGAAGCCCTGTTTGATAGAGTATACACTCATCAGAGTGATGTCTGGTCCT<br>TCGGGGTGTTAATGTGGGAGATCTTCACTTTAGGGGGCTTCGGCCCTACCCAGGGAT<br>TCCCGTGGAGGAACTTTTTAAGCTGCTGAAGGAAGGACACAGAATGGATAAGCC<br>AGCCAACTGCACCAACGAACTGTACATGATGATGAGGGACTGTTGGCATGCAGT<br>GCCCTCCCAGAGACCAACGTTCAAGCAGTTGGTAGAAGCTTGGATCGAATTCTC<br>ACTCTCACAACCAATGAGGAATACTTGGACCTCAGCCAACCTCTCGAACAGTATT<br>CACCTAGTTACCCTGACACAAGAAGTTCTTGTTCTTCAGGAGATGATTCTGTTTTT<br>TCTCCAGACCCCATGCCTTACGAACCATGCCTTCCTCAGTATCCACACATAAACG<br>GCAGTGTTAAAACATGA<br><br>SEQ ID NO: 52<br>FGFR2-IIIb amino acid sequence<br>MVSWGRFICLVVVTMATLSLARPSFSLVEDTTLEPEEPPTKYQISQPEVYVAAPGESL<br>EVRCLLKDAAVISWTKDGVHLGPNNRTVLIGEYLQIKGATPRDSGLYACTASRTVDS<br>ETWYFMVNVTDAISSGDDEDDTDGAEDFVSENSNNKRAPYWTNTEKMEKRLHAVP<br>AANTVKFRCPAGGNPMPTMRWLKNGKEFKQEHRIGGYKVRNQHWSLIMESVVPSD<br>KGNYTCVVENEYGSINHTYHLDVVERSPHRPILQAGLPANASTVVGGDVEFVCKVY<br>SDAQPHIQWIKHVEKNGSKYGPDGLPYLKVLKHSGINSSNAEVLALFNVTEADAGEY<br>ICKVSNYIGQANQSAWLTVLPKQQAPGREKEITASPDYLEIAIYCIGVFLIACMVVTVI<br>LCRMKNTTKKPDFSSQPAVHKLTKRIPLRRQVTVSAESSSSMNSNTPLVRITTRLSST<br>ADTPMLAGVSEYELPEDPKWEFPRDKLTLGKPLGEGCFGQVVMAEAVGIDKDKPKE<br>AVTVAVKMLKDDATEKDLSDLVSEMEMMKMIGKHKNIINLLGACTQDGPLYVIVE<br>YASKGNLREYLRARRPPGMEYSYDINRVPEEQMTFKDLVSCTYQLARGMEYLASQK<br>CIHRDLAARNVLVTENNVMKIADFGLARDINNIDYYKKTTNGRLPVKWMAPEALFD<br>RVYTHQSDVWSFGVLMWEIFTLGGSPYPGIPVEELFKLLKEGHRMDKPANCTNELY<br>MMMRDCWHAVPSQRPTFKQLVEDLDRILTLTTNEEYLDLSQPLEQYSPSYPDTRSSC<br>SSGDDSVFSPDPMPYEPCLPQYPHINGSVKT<br><br>SEQ ID NO: 53<br>FGFR2-IIIc nucleic acid sequence<br>ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCCGACGGGCTGCCCTACC<br>TCAAGGTTCTCAAGGCCGCCGGTGTTAACACCACGGACAAAGAGATTGAGGTTC<br>TCTATATTCGGAATGTAACTTTTGAGGACGCTGGGGAATATACGTGCTTGGCGGG<br>TAATTCTATTGGGATATCCTTTCACTCTGCATGGTTGACAGTTCTGCCAGCGCCTG<br>GAAGAGAAAGGAGATTACAGCTTCCCCAGACTACCTGGAGATAGCCATTTACT<br>GCATAGGGGTCTTCTTAATCGCCTGTATGGTGGTAACAGTCATCCTGTGCCGAAT<br>GAAGAACACGACCAAGAAGCCAGACTTCAGCAGCCAGCCGGCTGTGCACAAGCT<br>GACCAAACGTATCCCCCTGCGGAGACAGGTAACAGTTTCGGCTGAGTCCAGCTC<br>CTCCATGAACTCCAACACCCCGCTGGTGAGGATAACAACACGCCTCTCTTCAACG<br>GCAGACACCCCCATGCTGGCAGGGGTCTCCGAGTATGAACTTCCAGAGGACCCA<br>AAATGGGAGTTTCCAAGAGATAAGCTGACACTGGGCAAGCCCCTGGGAGAAGGT<br>TGCTTTGGGCAAGTGGTCATGGCGGAAGCAGTGGGAATTGACAAAGACAAGCCC<br>AAGGAGGCGGTCACCGTGGCCGTGAAGATGTTGAAAGATGATGCCACAGAGAAA |

| SEQUENCES |
| --- |
| GACCTTTCTGATCTGGTGTCAGAGATGGAGATGATGAAGATGATTGGGAAACAC
AAGAATATCATAAATCTTCTTGGAGCCTGCACACAGGATGGGCCTCTCTATGTCA
TAGTTGAGTATGCCTCTAAAGGCAACCTCCGAGAATACCTCCGAGCCCGGAGGC
CACCCGGGATGGAGTACTCCTATGACATTAACCGTGTTCCTGAGGAGCAGATGAC
CTTCAAGGACTTGGTGTCATGCACCTACCAGCTGGCCAGAGGCATGGAGTACTTG
GCTTCCCAAAAATGTATTCATCGAGATTTAGCAGCCAGAAATGTTTTGGTAACAG
AAAACAATGTGATGAAAATAGCAGACTTTGGACTCGCCAGAGATATCAACAATA
TAGACTATTACAAAAAGACCACCAATGGGCGGCTTCCAGTCAAGTGGATGGCTC
CAGAAGCCCTGTTTGATAGAGTATACACTCATCAGAGTGATGTCTGGTCCTTCGG
GGTGTTAATGTGGGAGATCTTCACTTTAGGGGCTCGCCCTACCCAGGGATTCCC
GTGGAGGAACTTTTTAAGCTGCTGAAGGAAGGACACAGAATGGATAAGCCAGCC
AACTGCACCAACGAACTGTACATGATGATGAGGGACTGTTGGCATGCAGTGCCC
TCCCAGAGACCAACGTTCAAGCAGTTGGTAGAAGACTTGGATCGAATTCTCACTC
TCACAACCAATGAGGAATACTTGGACCTCAGCCAACCTCTCGAACAGTATTCACC
TAGTTACCCTGACACAAGAAGTTCTTGTTCTTCAGGAGATGATTCTGTTTTTTCTC
CAGACCCCATGCCTTACGAACCATGCCTTCCTCAGTATCCACACATAAACGGCAG
TGTTAAAACATGA

SEQ ID NO: 54
FGFR2-IIIc amino acid sequence
MVSWGRFICLVVVTMATLSLARPSFSLVEDTTLEPEEPPTKYQISQPEVYVAAPGESL
EVRCLLKDAAVISWTKDGVHLGPNNRTVLIGEYLQIKGATPRDSGLYACTASRTVDS
ETWYFMVNVTDAISSGDDEDDTDGAEDFVSENSNNKRAPYWTNTEKMEKRLHAVP
AANTVKFRCPAGGNPMPTMRWLKNGKEFKQEHRIGGYKVRNQHWSLIMESVVPSD
KGNYTCVVENEYGSINHTYHLDVVERSPHRPILQAGLPANASTVVGGDVEFVCKVY
SDAQPHIQWIKHVEKNGSKYGPDGLPYLKVLKAAGVNTTDKEIEVLYIRNVTFEDAG
EYTCLAGNSIGISFHSAWLTVLPAPGREKEITASPDYLEIAIYCIGVFLIACMVVTVILC
RMKNTTKKPDFSSQPAVHKLTKRIPLRRQVTVSAESSSSMNSNTPLVRITTRLSSTAD
TPMLAGVSEYELPEDPKWEFPRDKLTLGKPLGEGCFGQVVMAEAVGIDKDKPKEAV
TVAVKMLKDDATEKDLSDLVSEMEMMKMIGKHKNIINLLGACTQDGPLYVIVEYAS
KGNLREYLRARRPPGMEYSYDINRVPEEQMTFKDLVSCTYQLARGMEYLASQKCIH
RDLAARNVLVTENNVMKIADFGLARDINNIDYYKKTTNGRLPVKWMAPEALFDRV
YTHQSDVWSFGVLMWEIFTLGGSPYPGIPVEELFKLLKEGHRMDKPANCTNELYMM
MRDCWHAVPSQRPTFKQLVEDLDRILTLTTNEEYLDLSQPLEQYSPSYPDTRSSCSSG
DDSVFSPDPMPYEPCLPQYPHINGSVKT SEQ ID NO: 55
FGFR3-IIIb nucleic acid sequence
ATGGGCGCCCCTGCCTGCGCCCTCGCGCTCTGCGTGGCCGTGGCCATCGTGGCCG
GCGCCTCCTCGGAGTCCTTGGGGACGGAGCAGCGCGTCGTGGGGCGAGCGGCAG
AAGTCCCGGGCCCAGAGCCCGGCCAGCAGGAGCAGTTGGTCTTCGGCAGCGGG
ATGCTGTGGAGCTGAGCTGTCCCCCGCCCGGGGGTGGTCCCATGGGGCCCACTGT
CTGGGTCAAGGATGGCACAGGGCTGGTGCCCTCGGAGCGTGTCCTGGTGGGGCC
CCAGCGGCTGCAGGTGCTGAATGCCTCCCACGAGGACTCCGGGGCCTACAGCTG
CCGGCAGCGGCTCACGCAGCGCGTACTGTGCCACTTCAGTGTGCGGGTGACAGA
CGCTCCATCCTCGGGAGATGACGAAGACGGGGAGGACGAGGCTGAGGACACAG
GTGTGGACACAGGGGCCCCTTACTGGACACGGCCCGAGCGGATGGACAAGAAGC
TGCTGGCCGTGCCGGCCGCCAACACCGTCCGCTTCCGCTGCCCAGCCGCTGGCAA
CCCCACTCCCTCCATCTCCTGGCTGAAGAACGGCAGGGAGTTCCGCGGCGAGCA
CCGCATTGGAGGCATCAAGCTGCGGCATCAGCAGTGGAGCCTGGTCATGGAAAG
CGTGGTGCCCTCGGACCGCGGCAACTACACCTGCGTCGTGGAGAACAAGTTTGG
CAGCATCCGGCAGACGTACACGCTGGACGTGCTGGAGCGCTCCCCGCACCGGCC
CATCCTGCAGGCGGGGCTGCCGGCCAACCAGACGGCGGTGCTGGGCAGCGACGT
GGAGTTCCACTGCAAGGTGTACAGTGACGCACAGCCCCACATCCAGTGGCTCAA
GCACGTGGAGGTGAATGGCAGCAAGGTGGGCCCGGACGGCACACCCTACGTTAC
CGTGCTCAAGTCCTGGATCAGTGAGAGTGTGGAGGCCGACGTGCGCCTCCGCCTG
GCCAATGTGTCGGAGCGGGACGGGGGCGAGTACCTCTGTCGAGCCACCAATTTC
ATAGGCGTGGCCGAGAAGGCCTTTTGGCTGAGCGTTCACGGGCCCCGAGCAGCC
GAGGAGGAGCTGGTGGAGGCTGACGAGGCGGGCAGTGTGTATGCAGGCATCCTC
AGCTACGGGGTGGGCTTCTTCCTGTTCATCCTGGTGGTGGCGGCTGTGACGCTCT
GCCGCCTGCGCAGCCCCCCCAAGAAAGGCCTGGGCTCCCCCACCGTGCACAAGA
TCTCCCGCTTCCCGCTCAAGCGACAGGTGTCCCTGGAGTCCAACGCGTCCATGAG
CTCCAACACACCACTGGTGCGCATCGCAAGGCTGTCCTCAGGGGAGGGCCCCAC
GCTGGCCAATGTCTCCGAGCTCGAGCTGCCTGCCGACCCCAAATGGGAGCTGTCT
CGGGCCCGGCTGACCCTGGGCAAGCCCCTTGGGGAGGGCTGCTTCGGCCAGGTG
GTCATGGCGGAGGCCATCGGCATTGACAAGGACCGGGCCGCCAAGCCTGTCACC
GTAGCCGTGAAGATGCTGAAAGACGATGCCACTGACAAGGACCTGTCGGACCTG
GTGTCTGAGATGGAGATGATGAAGATGATCGGGAAACACAAAAACATCATCAAC
CTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGAC
TACTCCTTCGACACCTGCAAGCCGCCCGAGGAGCAGCTCACCTTCAAGGACCTGG
TGTCCTGTGCCTACCAGGTGGCCCGGGGCATGGAGTACTTGGCCTCCCAGAAGTG
CATCCACAGGGACCTGGCTGCCCGCAATGTGCTGGTGACCGAGGACAACGTGAT
GAAGATCGCAGACTTCGGGCTGGCCCGGGACGTGCACAACCTCGACTACTACAA
GAAGACAACCAACGGCCGGCTGCCCGTGAAGTGGATGGCGCCTGAGGCCTTGTT
TGACCGAGTCTACACTCACCAGAGTGACGTCTGGTCCTTTGGGGTCCTGCTCTGG
GAGATCTTCACGCTGGGGGGCTCCCCGTACCCCGGCATCCCTGTGGAGGAGCTCT |

| SEQUENCES |
|---|
| TCAAGCTGCTGAAGGAGGGCCACCGCATGGACAAGCCCGCCAACTGCACACACG
ACCTGTACATGATCATGCGGGAGTGCTGGCATGCCGCGCCCTCCCAGAGGCCCA
CCTTCAAGCAGCTGGTGGAGGACCTGGACCGTGTCCTTACCGTGACGTCCACCGA
CGAGTACCTGGACCTGTCGGCGCCTTTCGAGCAGTACTCCCCGGGTGGCCAGGAC
ACCCCCAGCTCCAGCTCCTCAGGGGACGACTCCGTGTTTGCCCACGACCTGCTGC
CCCCGGCCCCACCCAGCAGTGGGGGCTCGCGGACGTGA

SEQ ID NO: 56
FGFR3-IIIb amino acid sequence
MGAPACALALCVAVAIVAGASSESLGTEQRVVGRAAEVPGPEPGQQEQLVFGSGDA
VELSCPPPGGGPMGPTVWVKDGTGLVPSERVLVGPQRLQVLNASHEDSGAYSCRQR
LTQRVLCHFSVRVTDAPSSGDDEDGEDEAEDTGVDTGAPYWTRPERMDKKLLAVP
AANTVRFRCPAAGNPTPSISWLKNGREFRGEHRIGGIKLRHQQWSLVMESVVPSDRG
NYTCVVENKFGSIRQTYTLDVLERSPHRPILQAGLPANQTAVLGSDVEFHCKVYSDA
QPHIQWLKHVEVNGSKVGPDGTPYVTVLKSWISESVEADVRLRLANVSERDGGEYL
CRATNFIGVAEKAFWLSVHGPRAAEEELVEADEAGSVYAGILSYGVGFFLFILVVAA
VTLCRLRSPPKKGLGSPTVHKISRFPLKRQVSLESNASMSSNTPLVRIARLSSGEGPTL
ANVSELELPADPKWELSRARLTLGKPLGEGCFGQVVMAEAIGIDKDRAAKPVTVAV
KMLKDDATDKDLSDLVSEMEMMKMIGKHKNIINLLGACTQGGPLYVLVEYAAKGN
LREFLRARRPPGLDYSFDTCKPPEEQLTFKDLVSCAYQVARGMEYLASQKCIHRDLA
ARNVLVTEDNVMKIADFGLARDVHNLDYYKKTTNGRLPVKWMAPEALFDRVYTH
QSDVWSFGVLLWEIFTLGGSPYPGIPVEELFKLLKEGHRMDKPANCTHDLYMIMREC
WHAAPSQRPTFKQLVEDLDRVLTVTSTDEYLDLSAPFEQYSPGGQDTPSSSSSGDDS
VFAHDLLPPAPPSSGGSRT SEQ ID NO: 57
FGFR3-IIIc nucleic acid sequence
ATGGGCGCCCCTGCCTGCGCCCTCGCGCTCTGCGTGGCCGTGGCCATCGTGGCCG
GCGCCTCCTCGGAGTCCTTGGGGACGGAGCAGCGCGTCGTGGGGCGAGCGGCAG
AAGTCCCGGGCCCAGAGCCCGGCCAGCAGGAGCAGTTGGTCTTCGGCAGCGGGG
ATGCTGTGGAGCTGAGCTGTCCCCGCCCGGGGGTGGTCCCATGGGGCCCACTGT
CTGGGTCAAGGATGGCACAGGGCTGGTGCCCTCGGAGCGTGTCCTGGTGGGGCC
CCAGCGGCTGCAGGTGCTGAATGCCTCCCACGAGGACTCCGGGGCCTACAGCTG
CCGGCAGCGGCTCACGCAGCGCGTACTGTGCCACTTCAGTGTGCGGGTGACAGA
CGCTCCATCCTCGGGAGATGACGAAGACGGGGAGGACGAGGCTGAGGACACAG
GTGTGGACACAGGGGCCCCTTACTGGACACGCCCGAGCGGATGGACAAGAAGC
TGCTGGCCGTGCCGGCCGCCAACACCGTCCGCTTCCGCTGCCCAGCCGCTGGCAA
CCCCACTCCCTCCATCTCCTGGCTGAAGAACGGCAGGGAGTTCCGCGGCGAGCA
CCGCATTGGAGGCATCAAGCTGCGGCATCAGCAGTGGAGCCTGGTCATGGAAAG
CGTGGTGCCCTCGGACCGCGGCAACTACACCTGCGTCGTGGAGAACAAGTTTGG
CAGCATCCGGCAGACGTACACGCTGGACGTGCTGGAGCGCTCCCCGCACCGGCC
CATCCTGCAGGCGGGGCTGCCGGCCAACCAGACGGCGGTGCTGGGCAGCGACGT
GGAGTTCCACTGCAAGGTGTACAGTGACGCACAGCCCCACATCCAGTGGCTCAA
GCACGTGGAGGTGAATGGCAGCAAGGTGGGCCCGGACGGCACACCCTACGTTAC
CGTGCTCAAGACGGCGGGCGCTAACACCACCGACAAGGAGCTAGAGGTTCTCTC
CTTGCACAACGTCACCTTTGAGGACGCCGGGGAGTACACCTGCCTGGCGGGCAA
TTCTATTGGGTTTTCTCATCACTCTGCGTGGCTGGTGGTGCTGCCAGCCGAGGAG
GAGCTGGTGGAGGCTGACGAGGCGGGCAGTGTGTATGCAGGCATCCTCAGCTAC
GGGGTGGGCTTCTTCCTGTTCATCCTGGTGGTGGCGGCTGTGACGCTCTGCCGCC
TGCGCAGCCCCCCCAAGAAAGGCCTGGGCTCCCCCACCGTGCACAAGATCTCCC
GCTTCCCGCTCAAGCGACAGGTGTCCCTGGAGTCCAACGCGTCCATGAGCTCCAA
CACACCACTGGTGCGCATCGCAAGGCTGTCCTCAGGGGAGGGCCCCACGCTGGC
CAATGTCTCCGAGCTCGAGCTGCCTGCCGACCCCAAATGGGAGCTGTCTCGGGCC
CGGCTGACCCTGGGCAAGCCCCTTGGGGAGGGCTGCTTCGGCCAGGTGGTCATG
GCGGAGGCCATCGGCATTGACAAGGACCGGGCCGCCAAGCCTGTCACCGTAGCC
GTGAAGATGCTGAAAGACGATGCCACTGACAAGGACCTGTCGGACCTGGTGTCT
GAGATGGAGATGATGAAGATGATCGGGAAACACAAAAACATCATCAACCTGCTG
GGCGCCTGCACGCAGGGCGGGCCCCTGTACGTGCTGGTGGAGTACGCGGCCAAG
GGTAACCTGCGGGAGTTTCTGCGGGCGCGGCGCCCCGGGCTGGACTACTCCT
TCGACACCTGCAAGCCGCCCGAGGAGCAGCTCACCTTCAAGGACCTGGTGTCCT
GTGCCTACCAGGTGGCCCGGGGCATGGAGTACTTGGCCTCCCAGAAGTGCATCC
ACAGGGACCTGGCTGCCCGCAATGTGCTGGTGACCGAGGACAACGTGATGAAGA
TCGCAGACTTCGGGCTGGCCCGGGACGTGCACAACCTCGACTACTACAAGAAGA
CAACCAACGGCCGGCTGCCCGTGAAGTGGATGGCGCCTGAGGCCTTGTTTGACC
GAGTCTACACTCACCAGAGTGACGTCTGGTCCTTTGGGGTCCTGCTCTGGGAGAT
CTTCACGCTGGGGGCTCCCCGTACCCCGGCATCCCTGTGGAGGAGCTCTTCAAG
CTGCTGAAGGAGGGCCACCGCATGGACAAGCCCGCCAACTGCACACACGACCTG
TACATGATCATGCGGGAGTGCTGGCATGCCGCGCCCTCCCAGAGGCCCACCTTCA
AGCAGCTGGTGGAGGACCTGGACCGTGTCCTTACCGTGACGTCCACCGACGAGT
ACCTGGACCTGTCGGCGCCTTTCGAGCAGTACTCCCCGGGTGGCCAGGACACCCC
CAGCTCCAGCTCCTCAGGGGACGACTCCGTGTTTGCCCACGACCTGCTGCCCCCG
GCCCCACCCAGCAGTGGGGGCTCGCGGACGTGA SEQ ID NO: 58
FGFR3-IIIc amino acid sequence
MGAPACALALCVAVAIVAGASSESLGTEQRVVGRAAEVPGPEPGQQEQLVFGSGDA
VELSCPPPGGGPMGPTVWVKDGTGLVPSERVLVGPQRLQVLNASHEDSGAYSCRQR |

| SEQUENCES |
| --- |
| LTQRVLCHFSVRVTDAPSSGDDEDGEDEAEDTGVDTGAPYWTRPERMDKKLLAVP
AANTVRFRCPAAGNPTPSISWLKNGREFRGEHRIGGIKLRHQQWSLVMESVVPSDRG
NYTCVVENKFGSIRQTYTLDVLERSPHRPILQAGLPANQTAVLGSDVEFHCKVYSDA
QPHIQWLKHVEVNGSKVGPDGTPYVTVLKTAGANTTDKELEVLSLHNVTFEDAGEY
TCLAGNSIGFSHHSAWLVVLPAEEELVEADEAGSVYAGILSYGVGFFLFILVVAAVTL
CRLRSPPKKGLGSPTVHKISRFPLKRQVSLESNASMSSNTPLVRIARLSSGEGPTLANV
SELELPADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKGNLRE
FLRARRPPGLDYSFDTCKPPEEQLTFKDLVSCAYQVARGMEYLASQKCIHRDLAARN
VLVTEDNVMKIADFGLARDVHNLDYYKKTTNGRLPVKWMAPEALFDRVYTHQSD
VWSFGVLLWEIFTLGGSPYPGIPVEELFKLLKEGHRMDKPANCTHDLYMIMRECWH
AAPSQRPTFKQLVEDLDRVLTVTSTDEYLDLSAPFEQYSPGGQDTPSSSSSGDDSVFA
HDLLPPAPPSSGGSRT

SEQ ID NO: 59
2B.1.3 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 60
2B.1.95 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 61
2B.1.73 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 62
2B.1.32 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 63
2B.1.88 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 64
2B.1.1 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGECC SEQ ID NO: 65
2B.1.3.10 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 66
2B.1.3.12 light chain, amino acid
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 67
2B.1.3 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC |

| SEQUENCES |
|---|
| GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT

SEQ ID NO: 68
2B.1.95 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT SEQ ID NO: 69
2B.1.73 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT SEQ ID NO: 70
2B.1.32 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT SEQ ID NO: 71
2B.1.88 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT SEQ ID NO: 72
2B.1.1 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA |

| SEQUENCES |
|---|

CTGCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT

SEQ ID NO: 73
2B.1.3.10 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT SEQ ID NO: 74
2B.1.3.12 light chain, nucleic acid
GATATCCAGATGACCCAGTCCCCGAGCTCCCTGTCCGCCTCTGTGGGCGATAGGG
TCACCATCACCTGCCGTGCCAGTCAGGATGTTGATACTTCTCTGGCCTGGTATAA
ACAGAAACCAGGAAAAGCTCCGAAGCTTCTGATTTACTCGGCATCCTTCCTCTAC
TCTGGAGTCCCTTCTCGCTTCTCTGGTAGCGGTTCCGGGACGGATTTCACTCTGAC
CATCAGCAGTCTGCAGCCGGAAGACTTCGCAACTTATTACTGTCAGCAATCTACC
GGTCATCCTCAGACGTTCGGACAGGGTACCAAGGTGGAGATCAAACGAACTGTG
GCTGCACCATCTGTCTTCATCTTCCCGCCATCTGATGAGCAGTTGAAATCTGGAA
CTGCTTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCT
GAGCTCGCCCGTCACAAAGAGCTTCAACAGGGGAGAGTGT SEQ ID NO: 75
2B.1.3 heavy chain, amino acid
EVQLVESGGGLVQPGGSLRLSCAASGFTFTSTGISWVRQAPGKGLEWVGRTHLGDG
STNYADSVKGRFTISADTSKNTAYLQMNSLRAEDTAVYYCARTYGIYDLYVDYTEY
VMDYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSL
SLSPGK SEQ ID NO: 76
2B.1.95 heavy chain, amino acid
EVQLVESGGGLVQPGGSLRLSCAASGFTFTSTGISWVRQAPGKGLEWVGRLIFFTGS
TNYADSVKGRFTISADTSKNTAYLQMNSLRAEDTAVYYCARTYGIYDLYVDYTEYV
MDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSL
SPGK SEQ ID NO: 77
2B.1.73 heavy chain, amino acid
EVQLVESGGGLVQPGGSLRLSCAASGFTFTSTGISWVRQAPGKGLEWVGRMIFYNGS
TNYADSVKGRFTISADTSKNTAYLQMNSLRAEDTAVYYCARTYGIYDLYVDYTEYV
MDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSL
SPGK SEQ ID NO: 78
2B.1.32 heavy chain, amino acid
EVQLVESGGGLVQPGGSLRLSCAASGFTFTSTGISWVRQAPGKGLEWVGRWVGFTG
STNYADSVKGRFTISADTSKNTAYLQMNSLRAEDTAVYYCARTYGIYDLYVDYTEY
VMDYWGQGTLVTVSSASTKGPSVFPLAPSSKSTSGGTAALGCLVKDYFPEPVTVSW

| SEQUENCES |
| --- |
| NSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKSL<br>SLSPGK<br><br>SEQ ID NO: 79<br>2B.1.88 heavy chain, amino acid<br>EVQLVESGGGLVQPGGSLRLSCAASGFTFTSTGISWVRQAPGKGLEWVGRIWMFTG<br>STNYADSVKGRFTISADTSKNTAYLQMNSLRAEDTAVYYCARTYGIYDLYVDYTEY<br>VMDYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKSL<br>SLSPGK<br><br>SEQ ID NO: 80<br>2B.1.1 heavy chain, amino acid<br>EVQLVESGGGLVQPGGSLRLSCAASGFTFTSTGISWVRQAPGKGLEWVGRYWAWD<br>GSTNYADSVKGRFTISADTSKNTAYLQMNSLRAEDTAVYYCARTYGIYDLYVDYTE<br>YVMDYWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHNHYTQKS<br>LSLSPGK<br><br>SEQ ID NO: 81<br>2B.1.3.10 heavy chain, amino acid<br>EVQLVESGGGLVQPGGSLRLSCAASGFPFTSQGISWVRQAPGKGLEWVGRTHLGDG<br>STNYADSVKGRFTISADTSKNTAYLQMNSLRAEDTAVYYCARTYGIYDTYDKYTEY<br>VMDYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKSL<br>SLSPGK<br><br>SEQ ID NO: 82<br>2B.1.3.12 heavy chain, amino acid<br>EVQLVESGGGLVQPGGSLRLSCAASGFPFTSTGISWVRQAPGKGLEWVGRTHLGDG<br>STNYADSVKGRFTISADTSKNTAYLQMNSLRAEDTAVYYCARTYGIYDTYDMYTEY<br>VMDYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKSL<br>SLSPGK<br><br>SEQ ID NO: 83<br>2B.1.3 heavy chain, nucleic acid<br>GAGGTTCAGCTGGTGGAGTCTGGCGGTGGCCTGGTGCAGCCAGGGGGCTCACTC<br>CGTTTGTCCTGTGCAGCTTCTGGCTTCACCTTCACTAGTACTGGGATTAGCTGGGT<br>GCGTCAGGCCCCGGGTAAGGGCCTGGAATGGGTTGGTAGGACGCATTTGGGTGA<br>TGGTTCTACTAACTATGCCGATAGCGTCAAGGGCCGTTTCACTATAAGCGCAGAC<br>ACATCCAAAAACACAGCCTACCTACAAATGAACAGCTTAAGAGCTGAGGACACT<br>GCCGTCTATTATTGTGCTCGTACCTACGGCATCTACGACCTGTACGTGGACTACA<br>CGGAGTACGTTATGGACTACTGGGGTCAAGGAACCCTGGTCACCGTCTCCTCGGC<br>CTCCACCAAGGGCCCATCGGTCTTCCCCCTGGCACCCTCCTCCAAGAGCACCTCT<br>GGGGGCACAGCGGCCCTGGGCTGCCTGGTCAAGGACTACTTCCCCGAACCGGTG<br>ACGGTGTCGTGGAACTCAGGCGCCCTGACCAGCGGCGTGCACACCTTCCCGGCT<br>GTCCTACAGTCCTCAGGACTCTACTCCCTCAGCAGCGTGGTGACTGTGCCCTCTA<br>GCAGCTTGGGCACCCAGACCTACATCTGCAACGTGAATCACAAGCCCAGCAACA<br>CCAAGGTGGACAAGAAAGTTGAGCCCAAATCTTGTGACAAAACTCACACATGCC<br>CACCGTGCCCAGCACCTGAACTCCTGGGGGGACCGTCAGTCTTCCTCTTCCCCCC<br>AAAACCCAAGGACACCCTCATGATCTCCCGGACCCCTGAGGTCACATGCGTGGT<br>GGTGGACGTGAGCCACGAAGACCCTGAGGTCAAGTTCAACTGGTACGTGGACGG<br>CGTGGAGGTGCATAATGCCAAGACAAAGCCGCGGGAGGAGCAGTACAACAGCA<br>CGTACCGGGTGGTCAGCGTCCTCACCGTCCTGCACCAGGACTGGCTGAATGGCA<br>AGGAGTACAAGTGCAAGGTCTCCAACAAAGCCCTCCCAGCCCCCATCGAGAAAA<br>CCATCTCCAAAGCCAAAGGGCAGCCCCGAGAACCACAGGTGTACACCCTGCCCC |

| SEQUENCES |
| --- |
| CATCCCGGGAAGAGATGACCAAGAACCAGGTCAGCCTGACCTGCCTGGTCAAAG
GCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTG
TCTCCGGGTAAA

SEQ ID NO: 84
2B.1.95 heavy chain, nucleic acid
GAGGTTCAGCTGGTGGAGTCTGGCGGTGGCCTGGTGCAGCCAGGGGGCTCACTC
CGTTTGTCCTGTGCAGCTTCTGGCTTCACCTTCACTAGTACTGGGATTAGCTGGGT
GCGTCAGGCCCCGGGTAAGGGCCTGGAATGGGTTGGTAGGTTAATTTTTTTTACA
GGTTCTACTAACTATGCCGATAGCGTCAAGGGCCGTTTCACTATAAGCGCAGACA
CATCCAAAAACACAGCCTACCTACAAATGAACAGCTTAAGAGCTGAGGACACTG
CCGTCTATTATTGTGCTCGTACCTACGGCATCTACGACCTGTACGTGGACTACAC
GGAGTACGTTATGGACTACTGGGTCAAGGAACCCTGGTCACCGTCTCCTCGGCCT
CCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTC
CTACAGTCCTCAGGACTCTACTCCCTCAGCAGCGTGGTGACTGTGCCCTCTAGCA
GCTTGGGCACCCAGACCTACATCTGCAACGTGAATCACAAGCCCAGCAACACCA
AGGTGGACAAGAAAGTTGAGCCCAAATCTTGTGACAAAACTCACACATGCCCAC
CGTGCCCAGCACCTGAACTCCTGGGGGACCGTCAGTCTTCCTCTTCCCCCCAAA
ACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTG
GAGGTGCATAATGCCAAGACAAAGCCGCGGGAGGAGCAGTACAACAGCACGTA
CCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCCCATC
CCGGGAAGAGATGACCAAGAACCAGGTCAGCCTGACCTGCCTGGTCAAAGGCTT
CTATCCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTACAGC
AAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTC
CGGGTAAA SEQ ID NO: 85
2B.1.73 heavy chain, nucleic acid
GAGGTTCAGCTGGTGGAGTCTGGCGGTGGCCTGGTGCAGCCAGGGGGCTCACTC
CGTTTGTCCTGTGCAGCTTCTGGCTTCACCTTCACTAGTACTGGGATTAGCTGGGT
GCGTCAGGCCCCGGGTAAGGGCCTGGAATGGGTTGGTAGGATGATTTTTTATAAT
GGTTCTACTAACTATGCCGATAGCGTCAAGGGCCGTTTCACTATAAGCGCAGACA
CATCCAAAAACACAGCCTACCTACAAATGAACAGCTTAAGAGCTGAGGACACTG
CCGTCTATTATTGTGCTCGTACCTACGGCATCTACGACCTGTACGTGGACTACAC
GGAGTACGTTATGGACTACTGGGGTCAAGGAACCCTGGTCACCGTCTCCTCGGCC
TCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCGGCTGT
CCTACAGTCCTCAGGACTCTACTCCCTCAGCAGCGTGGTGACTGTGCCCTCTAGC
AGCTTGGGCACCCAGACCTACATCTGCAACGTGAATCACAAGCCCAGCAACACC
AAGGTGGACAAGAAAGTTGAGCCCAAATCTTGTGACAAAACTCACACATGCCCA
CCGTGCCCAGCACCTGAACTCCTGGGGGACCGTCAGTCTTCCTCTTCCCCCCAA
AACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGT
ACCGGGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCCCCAT
CCCGGGAAGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCT
CCGGGTAAA SEQ ID NO: 86
2B.1.32 heavy chain, nucleic acid
GAGGTTCAGCTGGTGGAGTCTGGCGGTGGCCTGGTGCAGCCAGGGGGCTCACTC
CGTTTGTCCTGTGCAGCTTCTGGCTTCACCTTCACTAGTACTGGGATTAGCTGGGT
GCGTCAGGCCCCGGGTAAGGGCCTGGAATGGGTTGGTAGGTGGGTCGGATTTAC
AGGTTCTACTAACTATGCCGATAGCGTCAAGGGCCGTTTCACTATAAGCGCAGAC
ACATCCAAAAACACAGCCTACCTACAAATGAACAGCTTAAGAGCTGAGGACACT
GCCGTCTATTATTGTGCTCGTACCTACGGCATCTACGACCTGTACGTGGACTACA
CGGAGTACGTTATGGACTACTGGGGTCAAGGAACCCTGGTCACCGTCTCCTCGGC
CTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCT |

| SEQUENCES |
|---|
| GTCCTACAGTCCTCAGGACTCTACTCCCTCAGCAGCGTGGTGACTGTGCCCTCTA
GCAGCTTGGGCACCCAGACCTACATCTGCAACGTGAATCACAAGCCCAGCAACA
CCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCA
CGTACCGGGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCC
CATCCCGGGAAGAGATGACCAAGAACCAGGTCAGCCTGACCTGCCTGGTCAAAG
GCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTG
TCTCCGGGTAAA |

SEQ ID NO: 87
2B.1.88 heavy chain, nucleic acid
GAGGTTCAGCTGGTGGAGTCTGGCGGTGGCCTGGTGCAGCCAGGGGGCTCACTC
CGTTTGTCCTGTGCAGCTTCTGGCTTCACCTTCACTAGTACTGGGATTAGCTGGGT
GCGTCAGGCCCCGGGTAAGGGCCTGGAATGGGTTGGTAGGATTTGGATGTTTAC
AGGTTCTACTAACTATGCCGATAGCGTCAAGGGCCGTTTCACTATAAGCGCAGAC
ACATCCAAAAACACAGCCTACCTACAAATGAACAGCTTAAGAGCTGAGGACACT
GCCGTCTATTATTGTGCTCGTACCTACGGCATCTACGACCTGTACGTGGACTACA
CGGAGTACGTTATGGACTACTGGGGTCAAGGAACCCTGGTCACCGTCTCCTCGGC
CTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACTGTGCCCTCTA
GCAGCTTGGGCACCCAGACCTACATCTGCAACGTGAATCACAAGCCCAGCAACA
CCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCA
CGTACCGGGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCC
CATCCCGGGAAGAGATGACCAAGAACCAGGTCAGCCTGACCTGCCTGGTCAAAG
GCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTG
TCTCCGGGTAAA SEQ ID NO: 88
2B.1.1 heavy chain, nucleic acid
GAGGTTCAGCTGGTGGAGTCTGGCGGTGGCCTGGTGCAGCCAGGGGGCTCACTC
CGTTTGTCCTGTGCAGCTTCTGGCTTCCCGTTCACTAGTCAGGGGATTAGCTGGGT
GCGTCAGGCCCCGGGTAAGGGCCTGGAATGGGTTGGTAGGACGCATTTGGGTGA
TGGTTCTACTAACTATGCCGATAGCGTCAAGGGCCGTTTCACTATAAGCGCAGAC
ACATCCAAAAACACAGCCTACCTACAAATGAACAGCTTAAGAGCTGAGGACACT
GCCGTCTATTATTGTGCTCGTACCTACGGCATCTACGACACGTATGATAAGTACA
CGGAGTACGTTATGGACTACTGGGGTCAAGGAACCCTGGTCACCGTCTCCTCGGC
CTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACTGTGCCCTCTA
GCAGCTTGGGCACCCAGACCTACATCTGCAACGTGAATCACAAGCCCAGCAACA
CCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCA
CGTACCGGGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCC
CATCCCGGGAAGAGATGACCAAGAACCAGGTCAGCCTGACCTGCCTGGTCAAAG
GCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTG
TCTCCGGGTAAA -continued

SEQUENCES

SEQ ID NO: 89
2B.1.3.10 heavy chain, nucleic acid
GAGGTTCAGCTGGTGGAGTCTGGCGGTGGCCTGGTGCAGCCAGGGGCTCACTC
CGTTTGTCCTGTGCAGCTTCTGGCTTCCCGTTCACTAGTCAGGGGATTAGCTGGGT
GCGTCAGGCCCCGGGTAAGGGCCTGGAATGGGTTGGTAGGACGCATTTGGGTGA
TGGTTCTACTAACTATGCCGATAGCGTCAAGGGCCGTTTCACTATAAGCGCAGAC
ACATCCAAAAACACAGCCTACCTACAAATGAACAGCTTAAGAGCTGAGGACACT
GCCGTCTATTATTGTGCTCGTACCTACGGCATCTACGACACGTATGATAAGTACA
CGGAGTACGTTATGGACTACTGGGGTCAAGGAACCCTGGTCACCGTCTCCTCGGC
CTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACTGTGCCCTCTA
GCAGCTTGGGCACCCAGACCTACATCTGCAACGTGAATCACAAGCCCAGCAACA
CCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCA
CGTACCGGGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCC
CATCCCGGGAAGAGATGACCAAGAACCAGGTCAGCCTGACCTGCCTGGTCAAAG
GCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTG
TCTCCGGGTAAA SEQ ID NO: 90
2B.1.3.12 heavy chain, nucleic acid
GAGGTTCAGCTGGTGGAGTCTGGCGGTGGCCTGGTGCAGCCAGGGGCTCACTC
CGTTTGTCCTGTGCAGCTTCTGGCTTCCCGTTCACTAGTACGGGGATTAGCTGGGT
GCGTCAGGCCCCGGGTAAGGGCCTGGAATGGGTTGGTAGGACGCATTTGGGTGA
TGGTTCTACTAACTATGCCGATAGCGTCAAGGGCCGTTTCACTATAAGCGCAGAC
ACATCCAAAAACACAGCCTACCTACAAATGAACAGCTTAAGAGCTGAGGACACT
GCCGTCTATTATTGTGCTCGTACCTACGGCATCTACGACACGTATGATATGTACA
CGGAGTACGTTATGGACTACTGGGGTCAAGGAACCCTGGTCACCGTCTCCTCGGC
CTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACTGTGCCCTCTA
GCAGCTTGGGCACCCAGACCTACATCTGCAACGTGAATCACAAGCCCAGCAACA
CCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCA
CGTACCGGGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCC
CATCCCGGGAAGAGATGACCAAGAACCAGGTCAGCCTGACCTGCCTGGTCAAAG
GCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTG
TCTCCGGGTAAA SEQ ID NO: 91
2B.1.3.10 FGFR2-IIIb and FGFR2-IIIc epitope 1
TNTEKMEKRLHAVPAANTVKFRCPA SEQ ID NO: 92
2B.1.3.10 FGFR2-IIIb and FGFR2-IIIc epitope 2
YKVRNQHWSLIMES SEQ ID NO: 93
2B.1.3.10 FGFR3-IIIb and FGFR3-IIIc epitope 1
TRPERMDKKLLAVPAANTVRFRCPA SEQ ID NO: 94
2B.1.3.10 FGFR3-IIIb and FGFR3-IIIc epitope 2
IKLRHQQWSLVMES

| SEQUENCES |
|---|

SEQ ID NO: 95
VH subgroup III consensus framework
EVQLVESGGGLVQPGGSLRLSCAAS

SEQ ID NO: 96
VH subgroup III consensus framework
WVRQAPGKGLEWV

SEQ ID NO: 97
VH subgroup III consensus framework
RFTISRDNSKNTLYLQMNSLRAEDTAVYYC SEQ ID NO: 98
VH subgroup III consensus framework
WGQGTLVTVSS SEQ ID NO: 99
VL subgroup I consensus framework
DIQMTQSPSSLSASVGDRVTITC SEQ ID NO: 100
VL subgroup I consensus framework
WYQQKPGKAPKLLIY SEQ ID NO: 101
VL subgroup I consensus framework
GVPSRFSGSGSGTDFTLTISSLQPEDFATYYC SEQ ID NO: 102
VL subgroup I consensus framework
FGQGTKVEIK SEQ ID NO: 103
Ser Ser Pro Thr Arg Leu Ala Val Ile Pro Trp Gly Val Arg Lys Leu Leu Arg Trp Val Arg Arg
Asn Tyr Gly Asp Met Asp Ile Tyr Ile Thr Ala Ser SEQ ID NO: 104
Glu Val Gln Leu Val Glu Ser Gly Gly Gly Leu Val Gln Pro Gly Gly Ser Leu Arg Leu Ser
Cys Ala Ala Ser Asp Phe Ser Leu Thr Thr Tyr Gly Val His Trp Val Arg Gln Ala Pro Gly Lys
Gly Leu Glu Trp Leu Gly Val Ile Trp Ser Gly Gly Ser Thr Asp Tyr Asn Ala Ala Phe Ile Ser
Arg Leu Thr Ile Ser Lys Asp Asn Ser Lys Asn Thr Val Tyr Leu Gln Met Asn Ser Leu Arg
Ala Glu Asp Thr Ala Val Tyr Tyr Cys Ala Arg Asp Tyr Gly Ser Thr Tyr Val Asp Ala Ile Asp
Tyr Trp Gly Gln Gly Thr Leu Val Thr Val Ser Ser SEQ ID NO: 105
Asp Ile Val Leu Thr Gln Ser Pro Asp Ser Leu Ala Val Ser Leu Gly Glu Arg Ala Thr Ile Asn
Cys Arg Ala Ser Glu Ser Val Glu Ser Tyr Gly Asn Arg Tyr Met Thr Trp Tyr Gln Gln Lys
Pro Gly Gln Pro Pro Lys Leu Leu Ile Tyr Arg Ala Ala Asn Leu Gln Ser Gly Val Pro Asp Arg
Phe Ser Gly Ser Gly Ser Gly Thr Asp Phe Thr Leu Thr Ile Ser Ser Leu Gln Ala Glu Asp Val
Ala Val Tyr Tyr Cys Gln Gln Ser Asn Glu Asp Pro Trp Thr Phe Gly Gln Gly Thr Lys Val
Glu Ile Lys SEQ ID NO: 106
Glu Val Gln Leu Val Glu Ser Gly Gly Gly Leu Val Gln Pro Gly Gly Ser Leu Arg Leu Ser
Cys Ala Ala Ser Asp Phe Ser Leu Thr Thr Tyr Gly Val His Trp Val Arg Gln Ala Pro Gly Lys
Gly Leu Glu Trp Leu Gly Val Ile Trp Ser Gly Gly Ser Thr Asp Tyr Asn Ala Ala Phe Ile Ser
Arg Leu Thr Ile Ser Lys Asp Asn Ser Lys Asn Thr Val Tyr Leu Gln Met Asn Ser Leu Arg
Ala Glu Asp Thr Ala Val Tyr Tyr Cys Ala Arg Asp Tyr Gly Ser Thr Tyr Val Asp Ala Ile Asp
Tyr Trp Gly Gln Gly Thr Leu Val Thr Val Ser Ser Ala Ser Thr Lys Gly Pro Ser Val Phe Pro
Leu Ala Pro Ser Ser Lys Ser Thr Ser Gly Gly Thr Ala Ala Leu Gly Cys Leu Val Lys Asp Tyr
Phe Pro Glu Pro Val Thr Val Ser Trp Asn Ser Gly Ala Leu Thr Ser Gly Val His Thr Phe Pro
Ala Val Leu Gln Ser Ser Gly Leu Tyr Ser Leu Ser Ser Val Val Thr Val Pro Ser Ser Ser Leu
Gly Thr Gln Thr Tyr Ile Cys Asn Val Asn His Lys Pro Ser Asn Thr Lys Val Asp Lys Lys Val
Glu Pro Lys Ser Cys Asp Lys Thr His Thr Cys Pro Pro Cys Pro Ala Pro Glu Leu Leu Gly
Gly Pro Ser Val Phe Leu Phe Pro Pro Lys Pro Lys Asp Thr Leu Met Ile Ser Arg Thr Pro Glu
Val Thr Cys Val Val Val Asp Val Ser His Glu Asp Pro Glu Val Lys Phe Asn Trp Tyr Val
Asp Gly Val Glu Val His Asn Ala Lys Thr Lys Pro Arg Glu Glu Gln Tyr Gly Ser Thr Tyr
Arg Val Val Ser Val Leu Thr Val Leu His Gln Asp Trp Leu Asn Gly Lys Glu Tyr Lys Cys
Lys Val Ser Asn Lys Ala Leu Pro Ala Pro Ile Glu Lys Thr Ile Ser Lys Ala Lys Gly Gln Pro
Arg Glu Pro Gln Val Tyr Thr Leu Pro Pro Ser Arg Glu Glu Met Thr Lys Asn Gln Val Ser
Leu Ser Cys Ala Val Lys Gly Phe Tyr Pro Ser Asp Ile Ala Val Glu Trp Glu Ser Asn Gly Gln
Pro Glu Asn Asn Tyr Lys Thr Thr Pro Pro Val Leu Asp Ser Asp Gly Ser Phe Phe Leu Val
Ser Lys Leu Thr Val Asp Lys Ser Arg Trp Gln Gln Gly Asn Val Phe Ser Cys Ser Val Met
His Glu Ala Leu His Asn His Tyr Thr Gln Lys Ser Leu Ser Leu Ser Pro Gly Lys

SEQUENCES

SEQ ID NO: 107
Asp Ile Val Leu Thr Gln Ser Pro Asp Ser Leu Ala Val Ser Leu Gly Glu Arg Ala Thr Ile Asn
Cys Arg Ala Ser Glu Ser Val Glu Ser Tyr Gly Asn Arg Tyr Met Thr Trp Tyr Gln Gln Lys
Pro Gly Gln Pro Pro Lys Leu Leu Ile Tyr Arg Ala Ala Asn Leu Gln Ser Gly Val Pro Asp Arg
Phe Ser Gly Ser Gly Ser Gly Thr Asp Phe Thr Leu Thr Ile Ser Ser Leu Gln Ala Glu Asp Val
Ala Val Tyr Tyr Cys Gln Gln Ser Asn Glu Asp Pro Trp Thr Phe Gly Gln Gly Thr Lys Val
Glu Ile Lys Arg Thr Val Ala Ala Pro Ser Val Phe Ile Phe Pro Pro Ser Asp Glu Gln Leu Lys
Ser Gly Thr Ala Ser Val Val Cys Leu Leu Asn Asn Phe Tyr Pro Arg Glu Ala Lys Val Gln
Trp Lys Val Asp Asn Ala Leu Gln Ser Gly Asn Ser Gln Glu Ser Val Thr Glu Gln Asp Ser
Lys Asp Ser Thr Tyr Ser Leu Ser Ser Thr Leu Thr Leu Ser Lys Ala Asp Tyr Glu Lys His Lys
Val Tyr Ala Cys Glu Val Thr His Gln Gly Leu Ser Ser Pro Val Thr Lys Ser Phe Asn Arg Gly
Glu Cys

SEQ ID NO: 108
Ser Tyr Gly Ile Ser

SEQ ID NO: 109
Asp Tyr Tyr Met Asn

SEQ ID NO: 110
Asn Tyr Gly Val Ser

SEQ ID NO: 111
Asp Thr Tyr Met Asn

SEQ ID NO: 112
Asp Thr Tyr Ile His

SEQ ID NO: 113
Ser Tyr Trp Ile His

SEQ ID NO: 114
Asp Thr Phe Thr His

SEQ ID NO: 115
Glu Tyr Thr Met Asn

SEQ ID NO: 116
Ser Tyr Trp Ile Glu

SEQ ID NO: 117
Asp Tyr Glu Met His

SEQ ID NO: 118
Asp Thr Tyr Ile His

SEQ ID NO: 119
Arg Tyr Trp Met Ser

SEQ ID NO: 120
Asn Tyr Gly Met Asn

SEQ ID NO: 121
Thr Ser Ala Met Gly Ile Gly

SEQ ID NO: 122
Thr Tyr Gly Val His

SEQ ID NO: 123
Gln Gln Tyr Ser Lys Leu Pro Trp Thr

SEQ ID NO: 124
Phe Gln Gly Thr Gly Tyr Pro Leu Thr

SEQ ID NO: 125
His Gln Val Arg Thr Leu Pro Trp Thr

SEQ ID NO: 126
Gln Gln Tyr Trp Asn Thr Pro Phe Thr

SEQ ID NO: 127
Phe Gln Gly Ser His Val Leu Thr

SEQ ID NO: 128
Gln Gln His Tyr Ile Val Pro Tyr Thr

|  SEQUENCES |
| --- |

SEQ ID NO: 129
Leu Gln Tyr Gly Ser Tyr Pro Trp Thr

SEQ ID NO: 130
His Gln Trp Ser Ser Tyr Pro Leu Thr

SEQ ID NO: 131
Gln Gln His His Ser Thr Pro Tyr Thr

SEQ ID NO: 132
Gln Gln Phe Thr Ile Ser Pro Ser Met Tyr Thr

SEQ ID NO: 133
Gln Gln Tyr Asn Ile Ser Pro Tyr Thr

SEQ ID NO: 134
Gln Asn Gly His Asn Phe Pro Tyr Thr

SEQ ID NO: 135
Gln Gln Tyr Trp Ser Asn Pro Leu Thr

SEQ ID NO: 136
Gln Gln Ser Asn Glu Asp Tyr Thr

SEQ ID NO: 137
Gln Gln Ser Asn Glu Asp Pro Trp Thr

SEQ ID NO: 138
Thr Val Ser Ser Gly Gly Arg Tyr Thr Tyr Tyr Pro Asp Ser Val Lys Gly

SEQ ID NO: 139
Trp Ile Asp Pro Glu Asn Asp Asp Thr Ile Tyr Asp Pro Lys Phe Gln Gly

SEQ ID NO: 140
Val Ile Trp Gly Asp Gly Ser Ile Asn Tyr His Ser Ala Leu Ile Ser

SEQ ID NO: 141
Arg Ile Asp Pro Ser Asn Gly Asn Ala Lys Tyr Asp Pro Lys Phe Gln Gly

SEQ ID NO: 142
Arg Ile Asp Pro Ala Asn Gly Asn Thr Lys Tyr Asp Pro Lys Phe Gln Asp

SEQ ID NO: 143
Glu Ile Asp Pro Ser Val Ser Asn Ser Asn Tyr Asn Gln Lys Phe Lys Gly

SEQ ID NO: 144
Arg Ile Asp Pro Ser Asn Gly Asn Thr Lys Tyr Asp Pro Lys Phe Gln Gly

SEQ ID NO: 145
Gly Ile Asn Pro Asn Asn Gly Glu Thr Ser Tyr Asn Gln Lys Phe Lys Gly

SEQ ID NO: 146
Glu Ile Phe Pro Gly Gly Gly Ser Thr Ile Tyr Asn Glu Asn Phe Arg Asp

SEQ ID NO: 147
Ala Ile Trp Pro Glu Asn Ala Asp Ser Val Tyr Asn Gln Lys Phe Lys Gly

SEQ ID NO: 148
Arg Ile Asp Pro Ala Asn Gly Asn Thr Lys Tyr Asp Pro Lys Phe Gln Gly

SEQ ID NO: 149
Glu Ile Leu Pro Gly Ser Asp Ser Thr Lys Tyr Val Glu Lys Phe Lys Val

SEQ ID NO: 150
Glu Ile Ser Pro Asp Ser Ser Thr Ile Asn Tyr Thr Pro Ser Leu Lys Asp

SEQ ID NO: 151
Trp Ile Asp Thr Asp Thr Gly Glu Ala Thr Tyr Thr Asp Asp Phe Lys Gly

SEQ ID NO: 152
SEQ ID NO: 152
His Ile Trp Trp Asp Asp Asp Lys Arg Tyr Asn Pro Ala Leu Lys Ser

SEQ ID NO: 153
Val Ile Trp Ser Gly Gly Ser Thr Asp Tyr Asn Ala Ala Phe Ile Ser

| SEQUENCES |
|---|

SEQ ID NO: 154
Gly Gly Asp Gly Tyr Ala Leu Asp Tyr

SEQ ID NO: 155
Phe Thr Thr Val Phe Ala Tyr

SEQ ID NO: 156
Thr His Asp Trp Phe Asp Tyr

SEQ ID NO: 157
Arg Ala Leu Gly Asn Gly Tyr Ala Leu Gly Tyr

SEQ ID NO: 158
Gly Thr Ser Tyr Ser Trp Phe Ala Tyr

SEQ ID NO: 159
Leu Gly Val Met Val Tyr Gly Ser Ser Pro Phe Trp Phe Ala Tyr

SEQ ID NO: 160
Arg Ala Leu Gly Asn Gly Tyr Ala Met Asp Tyr

SEQ ID NO: 161
Lys Thr Thr Asn Tyr

SEQ ID NO: 162
Arg Gly Tyr Tyr Asp Ala Ala Trp Phe Asp Tyr

SEQ ID NO: 163
Glu Gly Gly Asn Tyr

SEQ ID NO: 164
Ser Gly Asn Tyr Gly Ala Met Asp Tyr

SEQ ID NO: 165
Gly Gly Tyr His Tyr Pro Gly Trp Leu Val Tyr

SEQ ID NO: 166
Pro Ser Pro Ala Leu Asp Tyr

SEQ ID NO: 167
Glu Glu Tyr Gly Leu Phe Gly Phe Pro Tyr

SEQ ID NO: 168
Ile Asp Gly Ile Tyr Asp Gly Ser Phe Tyr Ala Met Asp Tyr

SEQ ID NO: 169
Asp Tyr Gly Ser Thr Tyr Val Asp Ala Ile Asp Tyr

SEQ ID NO: 170
Ser Ala Ser Gln Val Ile Ser Asn Tyr Leu Asn

SEQ ID NO: 171
Ser Ala Ser Ser Ser Gly Arg Tyr Thr Phe

SEQ ID NO: 172
Arg Ala Ser Gln Asp Ile Ser Asn Tyr Phe Asn

SEQ ID NO: 173
Lys Ala Ser Asp His Ile Asn Asn Trp Leu Ala

SEQ ID NO: 174
Arg Ser Ser Gln Asn Ile Val His Ser Asp Gly Asn Thr Tyr Leu Glu

SEQ ID NO: 175
Lys Ala Ser Gln Phe Val Ser Asp Ala Val Ala

SEQ ID NO: 176
Arg Ala Ser Gln Glu Ile Ser Gly Tyr Leu Ser

SEQ ID NO: 177
Ser Ala Ser Ser Ser Leu Ser Ser Ser Tyr Leu Tyr

SEQ ID NO: 178
Lys Ser Ser Gln Ser Leu Leu Asn Ser Gly Asn Gln Lys Asn Ser Leu Ala

SEQ ID NO: 179
Arg Ala Ser Ser Ser Val Asn His Met Tyr

SEQ ID NO: 180
Lys Ala Ser Gln Asn Val Asp Ser Tyr Val Ala

SEQ ID NO: 181
Arg Ala Ser Gln Ser Ile Ser Asp Tyr Val Tyr

SEQ ID NO: 182
Lys Ala Ser Glu Asp Ile Tyr Asn Arg Leu Ala

SEQ ID NO: 183
Arg Ala Ser Glu Ser Val Asp Ser Tyr Gly Asn Ser Phe Met His

SEQ ID NO: 184
Arg Ala Ser Glu Ser Val Glu Ser Tyr Gly Asn Arg Tyr Met Thr

SEQ ID NO: 185
Phe Thr Ser Ser Leu Arg Ser

SEQ ID NO: 186
Asp Thr Ser Lys Leu Ala Ser

SEQ ID NO: 187
Tyr Thr Ser Arg Leu Gln Ser

SEQ ID NO: 188
Gly Thr Thr Asn Leu Glu Thr

SEQ ID NO: 189
Lys Val Ser Asn Arg Phe Ser

SEQ ID NO: 190
Ser Ala Ser Tyr Arg Tyr Thr

SEQ ID NO: 191
Gly Ala Ser Asn Leu Glu Thr

SEQ ID NO: 192
Ala Ala Ser Thr Leu Asp Ser

SEQ ID NO: 193
Gly Ala Ser Asn Leu Ala Ser

SEQ ID NO: 194
Leu Ala Ser Thr Arg Glu Ser

SEQ ID NO: 195
Tyr Thr Ser Thr Leu Ala Pro

SEQ ID NO: 196
Ser Ala Ser Tyr Arg Phe Ser

SEQ ID NO: 197
Tyr Ala Ser Gln Ser Ile Ser

SEQ ID NO: 198
Ala Ala Thr Ser Leu Glu Thr

SEQ ID NO: 199
Arg Ala Ser Asn Leu Glu Ser

SEQ ID NO: 200
Arg Ala Ala Asn Leu Gln Ser

SEQ ID NO: 201
Gln Gln Tyr Ser Lys Leu Pro Trp Thr

SEQ ID NO: 202
Phe Gln Gly Thr Gly Tyr Pro Leu Thr

SEQ ID NO: 203
His Gln Val Arg Thr Leu Pro Trp Thr

SEQ ID NO: 204
Gln Gln Tyr Trp Asn Thr Pro Phe Thr

SEQ ID NO: 205
Phe Gln Gly Ser His Val Leu Thr

SEQ ID NO: 206
Gln Gln His Tyr Ile Val Pro Tyr Thr

SEQ ID NO: 207
Leu Gln Tyr Gly Ser Tyr Pro Trp Thr

SEQ ID NO: 208
His Gln Trp Ser Ser Tyr Pro Leu Thr

SEQ ID NO: 209
Gln Gln His His Ser Thr Pro Tyr Thr

SEQ ID NO: 210
Gln Gln Phe Thr Ile Ser Pro Ser Met Tyr Thr

SEQ ID NO: 211
Gln Gln Tyr Asn Ile Ser Pro Tyr Thr

SEQ ID NO: 212
Gln Asn Gly His Asn Phe Pro Tyr Thr

SEQ ID NO: 213
Gln Gln Tyr Trp Ser Asn Pro Leu Thr

SEQ ID NO: 214
Gln Gln Ser Asn Glu Asp Tyr Thr

SEQ ID NO: 215
Gln Gln Ser Asn Glu Asp Pro Trp Thr

SEQ ID NO: 216
Glu Val Gln Leu Val Glu Ser Gly Gly Gly Leu Val Lys Pro Gly Gly Ser Leu Lys Leu Ser
Cys Ala Pro Ser Gly Phe Thr Phe Ser Ser Tyr Gly Ile Ser Trp Val Arg Gln Thr Pro Glu Lys
Arg Leu Glu Trp Val Ala Thr Val Ser Ser Gly Gly Arg Tyr Thr Tyr Tyr Pro Asp Ser Val Lys
Gly Arg Phe Thr Ile Ser Arg Asp Asn Ala Glu Asn Thr Leu Tyr Leu Gln Met Ser Ser Leu
Arg Ser Glu Asp Thr Ala Met Tyr Tyr Cys Thr Arg Gly Gly Asp Gly Tyr Ala Leu Asp Tyr
Trp Gly Gln Gly Thr Ser Val Thr Val Ser Ser

SEQ ID NO: 217
Glu Val Gln Leu Gln Gln Ser Gly Ala Glu Leu Val Arg Pro Gly Ala Leu Val Asn Leu Ser
Cys Lys Ala Ser Gly Phe Asn Ile Lys Asp Tyr Tyr Met Asn Trp Val Lys Gln Arg Pro Glu
Gln Gly Leu Glu Trp Thr Gly Trp Ile Asp Pro Glu Asn Asp Asp Thr Ile Tyr Asp Pro Lys Phe
Gln Gly Lys Ala Thr Ile Thr Ala Asp Thr Ser Ser Asn Thr Val Tyr Leu Gln Leu Thr Ser Leu
Thr Ser Glu Asp Thr Ala Val Tyr Tyr Cys Ala Ala Phe Thr Thr Val Phe Ala Tyr Trp Gly His
Gln Thr Met Val Thr Val Ser Ala

SEQ ID NO: 218
Gln Val Gln Val Lys Glu Ser Gly Pro Gly Leu Val Ala Pro Ser Gln Ser Leu Ser Ile Thr Cys
Thr Val Ser Gly Phe Ser Leu Thr Asn Tyr Gly Val Ser Trp Ile Arg Gln Pro Pro Gly Lys Gly
Leu Glu Trp Leu Gly Val Ile Trp Gly Asp Gly Ser Ile Glu Asn Tyr His Ser Ala Leu Ile Ser Arg
Leu Thr Ile Thr Lys Asp Asn Ser Lys Ser Gln Val Phe Leu Lys Leu Asn Ser Leu Glu Ala
Asp Asp Thr AlaThr Tyr Tyr Cys Ala Lys Thr His Asp Trp Phe Asp Tyr Trp Gly Gln Gly
Thr Leu Val Thr Val Ser Ala

SEQ ID NO: 219
Glu Val Gln Leu Gln Gln Ser Gly Ala Glu Leu Val Lys Pro Gly Ala Ser Val Lys Leu Ser Cys
Thr Ala Ala Asp Phe Asn Ile Lys Asp Thr Tyr Met His Trp Val Lys Gln Arg Pro Glu Gln
Gly Leu Glu Trp Ile Gly Arg Ile Asp Pro Ser Asn Gly Asn Ala Lys Tyr Asp Pro Lys Phe Gln
Gly Lys Ala Ser Ile Thr Ala Asp Ser Ser Ser Asn Thr Ala Tyr Leu His Leu Ser Ser Leu Thr
Ser Glu Asp Thr Ala Val Tyr Tyr CysAla Ser Arg Ala Leu Gly Asn Gly Tyr Ala Leu Gly Tyr
Trp Gly Gln Gly Thr Ser Val Thr Val Ser Ser

SEQ ID NO: 220
Glu Val Gln Leu Gln Gln Ser Gly Ala Glu Leu Val Lys Pro Gly Ala Ser Val Lys Leu Ser Cys
Thr Ala Ser Asp Phe Asn Ile Ile Asp Thr Tyr Ile His Trp Val Lys Gln Arg Pro Glu Gln Gly
Leu Glu Trp Ile Gly Arg Ile Asp Pro Ala Asn Gly Asn Thr Lys Tyr Asp Pro Lys Phe Gln Asp
Lys Ala Ala Leu Thr Ser Asp Thr Asp Ser Asn Thr Ala Tyr Leu Leu Phe Asn Ser Leu Thr
Ser Glu Asp Thr Ala Val Tyr Tyr Cys Ala Arg Gly Thr Ser Tyr Ser Trp Phe Ala Tyr Trp Gly
Gln Gly Thr Leu Val Ser Val Ser Ala

| SEQUENCES |
|---|
| SEQ ID NO: 221<br>Gln Val Gln Leu Gln Gln Pro Gly Ala Glu Ile Val Lys Pro Gly Ala Ser Val Arg Leu Ser Cys<br>Lys Ala Ser Gly Tyr Ser Phe Thr Ser Tyr Trp Ile His Trp Val Lys Gln Arg Pro Gly Gln Gly<br>Leu Glu Trp Ile Gly Glu Ile Asp Pro Ser Val Ser Asn Ser Asn Tyr Asn Gln Lys Phe Lys Gly<br>Lys Ala Thr Leu Thr Ala Asp Lys Ser Ser Thr Ala Tyr Met Gln Leu Ser Gly Leu Thr Ser<br>Glu Asp Ser Ala Val Tyr Phe Cys Val Arg Leu Gly Val Met Val Tyr Gly Ser Ser Pro Phe Trp<br>Phe Ala Tyr Trp Gly Gln Gly Thr Leu Val Thr Val Ser Ala |
| SEQ ID NO: 222<br>Gln Val Gln Leu Gln Gln Pro Gly Ala Glu Ile Val Lys Pro Gly Ala Ser Val Arg Leu Ser Cys<br>Lys Ala Ser Gly Tyr Ser Phe Thr Ser Tyr Trp Ile His Trp Val Lys Gln Arg Pro Gly Gln Gly<br>Leu Glu Trp Ile Gly Glu Ile Asp Pro Ser Val Ser Asn Ser Asn Tyr Asn Gln Lys Phe Lys Gly<br>Lys Ala Thr Leu Thr Ala Asp Lys Ser Ser Thr Ala Tyr Met Gln Leu Ser Gly Leu Thr Ser<br>Glu Asp Ser Ala Val Tyr Phe CysVal Arg Leu Gly Val Met Val Tyr Gly Ser Ser Pro Phe Trp<br>Phe Ala Tyr Trp Gly Gln Gly Thr Leu Val Thr Val Ser Ala |
| SEQ ID NO: 223<br>Glu Val Gln Leu Gln Gln Ser Gly Ala Glu Leu Leu Lys Pro Gly Ala Ser Val Arg Leu Ser<br>Cys Thr Ala Ser Gly Phe Asn Ile Gln Asp Thr Phe Thr His Trp Val Arg Gln Arg Pro Glu Gln<br>Gly Leu Glu Trp Ile Gly Arg Ile Asp Pro Ser Asn Gly Asn Thr Lys Tyr Asp Pro Lys Phe Gln<br>Gly Lys Ala Lys Ile Leu Ala Asp Thr Ser Ser Asn Thr Ala Tyr Leu Gln Leu Ile Gly Leu Thr<br>Ser Glu Asp Thr Ala Val Tyr Tyr Cys Ala Ser Arg Ala Leu Gly Asn Gly Tyr Ala Met Asp<br>Tyr Trp Gly Gln Gly Thr Ser Val Thr Val Ser Ser |
| SEQ ID NO: 224<br>Glu Val Pro Leu Gln Gln Ser Gly Pro Glu Leu Val Lys Pro Gly Ala Thr Val Lys Ile Ser Cys<br>Lys Pro Ser Gly Asp Thr Phe Thr Glu Tyr Thr Met Asn Trp Val Arg Gln Ser His Gly Lys Ser<br>Leu Glu Trp Ile Gly Gly Ile Asn Pro Asn Asn Gly Glu Thr Ser Tyr Asn Gln Lys Phe Lys Gly<br>Lys Ala Thr Leu Thr Val Asp Lys Ser Ser Ser Thr Ala Phe Met Asp Leu Arg Ile Leu Thr Ser<br>Glu Asp Ser Ala Val Tyr Phe Cys Ala Arg Lys Thr Thr Asn Tyr Trp Gly Gln Gly Thr Thr<br>Leu Ile Val Ser Ser |
| SEQ ID NO: 225<br>Gln Ile Gln Leu Gln Gln Ser Gly Ala Glu Leu Met Lys Pro Gly Ala Ser Val Arg Met Ser Cys<br>Lys Ala Ser Gly Tyr Thr Phe Ser Ser Tyr Trp Ile Glu Trp Val Lys Gln Arg Ser Gly His Gly<br>Leu Glu Trp Ile Gly Glu Ile Phe Pro Gly Gly Gly Ser Thr Ile Tyr Asn Glu Asn Phe Arg Asp<br>Lys Ala Thr Phe Thr Ala Asp Thr Ser Ser Asn Thr Ala Tyr Met Gln Leu Ser Ser Leu Thr Ser<br>Glu Asp Ser Ala Val Tyr Phe Cys Ala Arg Arg Gly Tyr Tyr Asp Ala Ala Trp Phe Asp Tyr<br>Trp Gly Gln Gly Thr Leu Val Thr Val Ser Ala |
| SEQ ID NO: 226<br>Gln Val Gln Leu Lys Gln Ser Gly Ala Glu Leu Val Arg Pro Gly Thr Ser Val Thr Leu Ser Cys<br>Lys Ala Ser Gly Tyr Thr Phe Thr Asp Tyr Glu Met His Trp Met Lys Gln Thr Pro Val Tyr<br>Gly Leu Glu Trp Ile Gly Ala Ile Trp Pro Glu Asn Ala Asp Ser Val Tyr Asn Gln Lys Phe Lys<br>Gly Lys Val Thr Leu Thr Ala Asp Lys Ser Ser Ser Thr Ala Tyr Met Asp Leu Arg Ser Leu<br>Thr Ser Glu Asp Ser Ala Val Tyr Tyr Cys Thr Arg Glu Gly Gly Asn Tyr Trp Gly Gln Gly<br>Thr Thr Leu Thr Val Ser Ser |
| SEQ ID NO: 227<br>Glu Val Gln Leu Gln Gln Ser Gly Thr Glu Leu Val Arg Pro Gly Ala Ser Val Lys Leu Ser<br>Cys Thr Ser Ser Asp Phe Asn Ile Lys Asp Thr Tyr Ile His Trp Val Lys Gln Arg Pro Glu Gln<br>Gly Leu Asp Trp Leu Gly Arg Ile Asp Pro Ala Asn Gly Asn Thr Lys Tyr Asp Pro Lys Phe<br>Gln Gly Lys Ala Ala Met Thr Ser Asp Thr Ser Ser Asn Thr Ala Tyr Leu Arg Leu Ser Ser Leu<br>Thr Ser Glu Asp Thr Ala Val Tyr Tyr Cys Ala Ser Ser Gly Asn Tyr Gly Ala Met Asp Tyr<br>Trp Gly Gln Gly Thr Ser Val Thr Val Ser Ser |
| SEQ ID NO: 228<br>Gln Val Gln Leu Gln Gln Ser Gly Asp Glu Leu Met Lys Pro Gly Ala Ser Val Lys Ile Ser Cys<br>Lys Val Thr Gly Asn Thr Phe Ser Ser Tyr Trp Ile Glu Trp Val Lys Gln Arg Pro Gly His Gly<br>Leu Glu Trp Ile Gly Glu Ile Leu Pro Gly Ser Asp Ser Thr Lys Tyr Val Glu Lys Phe Lys Val<br>Lys Ala Thr Phe Thr Ala Asp Thr Ser Ser Asn Thr Ala Tyr Met Gln Leu Ser Ser Leu Thr Ser<br>Glu Asp Ser Ala Val Tyr Tyr CysAla Arg Gly Gly Tyr His Tyr Pro Gly Trp Leu Val Tyr Trp<br>Gly Gln Gly Thr Leu Val Thr Val Ser Ala |
| SEQ ID NO: 229<br>Glu Val Lys Phe Leu Glu Ser Gly Gly Gly Leu Val Gln Pro Gly Gly Ser Leu Arg Leu Ser<br>Cys Ala Val Ser Gly Ile Asp Phe Ser Arg Tyr Trp Met Ser Trp Val Arg Gln Ala Pro Gly Lys<br>Gly Leu Glu Trp Ile Gly Glu Ile Ser Pro Asp Ser Ser Thr Ile Asn Tyr Thr Pro Ser Leu Lys<br>Asp Lys Phe Val Ile Ser Arg Asp Asn Ala Lys Asn Thr Leu Tyr Leu Gln Met Ser Lys Val<br>Arg Ser Ala Asp Thr Ala Leu Tyr Tyr Cys Ala Arg Pro Ser Pro Ala Leu Asp Tyr Trp Gly<br>Gln Gly Thr Leu Val Thr Val Ser Ala |
| SEQ ID NO: 230<br>Gln Ile Gln Leu Val Gln Ser Gly Pro Glu Leu Lys Lys Pro Gly Glu Thr Ala Lys Ile Ser Cys<br>Lys Ala Ser Gly Tyr Ala Phe Ser Asn Tyr Gly Met Asn Trp Val Lys Gln Ala Pro Gly Lys<br>Asp Leu Lys Trp Met Gly Trp Ile Asp Thr Asp Thr Gly Glu Ala Thr Tyr Thr Asp Asp Phe<br>Lys Gly Arg Phe Val Phe Ser Leu Glu Thr Ser Ala Ser Thr Ala Tyr Leu Gln Ile Asn Asn Leu |

-continued

SEQUENCES

Lys Asn Glu Asp Met Ala Thr Tyr Phe Cys Ala Arg Glu Glu Tyr Gly Leu Phe Gly Phe Pro
Tyr Trp Gly His Gly Thr Leu Val Thr Val Ser Ala

SEQ ID NO: 231
Gln Val Thr Leu Lys Glu Ser Gly Pro Gly Ile Leu Gln Pro Ser Gln Thr Leu Ser Leu Thr Cys
Ser Phe Ser Gly Phe Ser Leu Ser Thr Ser Ala Met Gly Ile Gly Trp Ile Arg Gln Pro Ser Gly
Lys Gly Leu Glu Trp Leu Ala His Ile Trp Trp Asp Asp Lys Arg Tyr Asn Pro Ala Leu
Lys Ser Arg Leu Thr Ile Ser Lys Asp Thr Ser Arg Asn Gln Val Phe Leu Lys Ile Ala Ser Val
Asp Thr Ala Asp Thr Ala Thr Tyr Phe Cys Ala Arg Ile Asp Gly Ile Tyr Asp Gly Ser Phe Tyr
Ala Met Asp Tyr Trp Gly Gln Gly Thr Ser Val Thr Val Ser Ser

SEQ ID NO: 232
Gln Val Gln Leu Lys Gln Ser Gly Pro Gly Leu Val Gln Pro Ser Gln Ser Leu Ser Val Ala Cys
Thr Val Ser Asp Phe Ser Leu Thr Thr Tyr Gly Val His Trp Val Arg Gln Ser Pro Gly Lys Gly
Leu Glu Trp Leu Gly Val Ile Trp Ser Gly Gly Ser Thr Asp Tyr Asn Ala Ala Phe Ile Ser Arg
Leu Thr Ile Ser Lys Asp Asn Ser Lys Ser Gln Val Phe Phe Lys Met Asn Ser Leu Gln Thr Thr
Asp Thr Ala Ile Tyr Tyr Cys Ala Arg Asp Tyr Gly Ser Thr Tyr Val Asp Ala Ile Asp Tyr Trp
Gly Gln Gly Thr Ser Val Thr Val Ser Ser

SEQ ID NO: 233
Phe Ser Gly Asp Gly Arg Ala Ile Trp Ser Lys Asn Pro Asn Phe Thr Pro Val Asn Glu Ser Gln
Leu Phe Leu Tyr Asp Thr Phe Pro Lys Asn Phe Phe Trp Gly Ile Gly Thr Gly Ala Leu Gln
Val Glu Gly Ser Trp Lys Lys Asp Gly Lys Gly Pro Ser Ile Trp Asp His Phe Ile His Thr His
Leu Lys Asn Val Ser Ser Thr Asn Gly Ser Ser Ser Tyr Ile Phe Leu Glu Lys Asp Leu Ser
Ala Leu Asp Phe Ile Gly Val Ser Phe Tyr Gln Phe Ser Ile Ser Trp Pro Arg Leu Phe Pro Asp
Gly Ile Val Thr Val Ala Asn Ala Lys Gly Leu Gln Tyr Tyr Ser Thr Leu Leu Asp Ala Leu Val
Leu Arg Asn Ile Glu Pro Ile Val Thr Leu Tyr His Trp Asp Leu Pro Leu Ala Leu Gln Glu Lys
Tyr Gly Gly Trp Lys Asn Asp Thr Ile Ile Asp Phe Asn Asp Tyr Ala Thr Tyr Cys Phe Gln
Met Phe Gly Asp Arg Val Lys Tyr Trp Ile Thr Ile His Asn Pro Tyr Leu Val Ala Trp His Gly
Tyr Gly Thr Gly Met His Ala Pro Gly Glu Lys Gly Asn Leu Ala Ala Val Tyr Thr Val Gly
His Asn Leu Ile Lys Ala His Ser Lys Val Trp His Asn Tyr Asn Thr His Phe Arg Pro His Gln
Lys Gly Trp Leu Ser Ile Leu Thr Leu Gly Ser His Trp Ile Glu Pro Asn Arg Ser Glu Asn Thr Met
Asp Ile Phe Lys Cys Gln Gln Ser Met Val Ser Val Leu Gly Trp Phe Ala Asn Pro Ile His Gly
Asp Gly Asp Tyr Pro Glu Gly Met Arg Lys Lys Leu Phe Ser Val Leu Pro Ile Phe Ser Glu Ala
Glu Lys His Glu Met Arg Gly Thr Ala Asp Phe Phe Ala Phe Ser Phe Gly Pro Asn Asn Phe
Lys Pro Leu Asn Thr Met Ala Lys Met Gly Gln Asn Val Ser Leu Asn Leu Arg Glu Ala Leu
Asn Trp Ile Lys Leu Glu Tyr Asn Asn Pro Arg Ile Leu Ile Ala Glu Asn Gly Trp Phe Thr Asp
Ser Arg Val Lys Thr Glu Asp Thr Thr Ala Ile Tyr Met Met Lys Asn Phe Leu Ser Gln Val
Leu Gln Ala Ile Arg Leu Asp Glu Ile Arg Val Phe Gly Tyr Thr Ala Trp Ser Leu Leu Asp Gly
Phe Glu Trp Gln Asp Ala Tyr Thr Ile Arg Arg Gly Leu Phe Tyr Val Asp Phe Asn Ser Lys
Gln Lys Glu Arg Lys Pro Lys Ser Ser Ala His Tyr Tyr Lys Gln Ile Ile Arg Glu Asn Gly Phe
Ser Leu Lys Glu Ser Thr Pro Asp Val Gln Gly Gln Phe Pro Cys Asp Phe Ser Trp Gly Val Thr
Glu Ser Val Leu Lys Pro Glu Ser Val Ala Ser Ser Pro Gln Phe Ser Asp Pro His Leu Tyr Val
Trp Asn Ala Thr Gly Asn Arg Leu Leu His Arg Val Glu Gly Val Arg Leu Lys Thr Arg Pro
Ala Gln Cys Thr Asp Phe Val Asn Ile Lys Lys Gln Leu Glu Met Leu Ala Arg Met Lys Val
Thr His Tyr Arg Phe Ala Leu Asp Trp Ala Ser Val Leu Pro Thr Gly Asn Leu Ser Ala Val
Asn Arg Gln Ala Leu Arg Tyr Tyr Arg Cys Val Val Ser Glu Gly Leu Lys Leu Gly Ile Ser
Ala Met Val Thr Leu Tyr Tyr Pro Thr His Ala His Leu Gly Leu Pro Glu Pro Leu Leu His Ala
Asp Gly Trp Leu Asn Pro Ser Thr Ala Glu Ala Phe Gln Ala Tyr Ala Gly Leu Cys Phe Gln
Glu Leu Gly Asp Leu Val Lys Leu Trp Ile Thr Ile Asn Glu Pro Asn Arg Leu Ser Asp Ile Tyr
Asn Arg Ser Gly Asn Asp Thr Tyr Gly Ala Ala His Asn Leu Leu Val Ala His Ala Leu Ala
Trp Arg Leu Tyr Asp Arg Gln Phe Arg Pro Ser Gln Arg Gly Ala Val Ser Leu Ser Leu His
Ala Asp Trp Ala Glu Pro Ala Asn Pro Tyr Ala Asp Ser His Trp Arg Ala Ala Ala Glu Arg Phe
Leu Gln Phe Glu Ile Ala Trp Phe Ala Glu Pro Leu Phe Lys Thr Gly Asp Tyr Pro Ala Ala Met
Arg Glu Tyr Ile Ala Ser Lys His Arg Arg Gly Leu Ser Ser Ser Ala Leu Pro Arg Leu Thr Glu
Ala Glu Arg Arg Leu Leu Lys Gly Thr Val Asp Phe Cys Ala Leu Asn His Phe Thr Thr Arg
Phe Val Met His Gly Gln Leu Ala Gly Ser Arg Tyr Asp Ser Asp Arg Asp Ile Gln Phe Leu
Gln Asp Ile Thr Arg Leu Ser Ser Pro Thr Arg Leu Ala Val Ile Pro Trp Gly Val Arg Lys Leu
Leu Arg Trp Val Arg Arg Asn Tyr Gly Asp Met Asp Ile Tyr Ile Thr Ala Ser Gly Ile Asp Asp
Gln Ala Leu Glu Asp Asp Arg Leu Arg Lys Tyr Tyr Leu Gly Lys Tyr Leu Gln Glu Val Leu
Lys Ala Tyr Leu Ile Asp Lys Val Arg Ile Lys Gly Tyr Tyr Ala Phe Lys Leu Ala Glu Glu Lys
Ser Lys Pro Arg Phe Gly Phe Phe Thr Ser Asp Phe Lys Ala Lys Ser Ser Ile Gln Phe Tyr Asn
Lys Val Ile Ser Ser Arg Gly Phe Pro Phe Glu Asn Ser Ser Ser Arg Cys Ser Gln Thr Gln Glu
Asn Thr Glu Cys Thr Val Cys Leu Phe Leu Val Gln Lys Lys Pro Leu Ile Phe Leu Gly Cys
Cys Phe Phe Ser Thr Leu Val Leu Leu Leu Ser Ile Ala Ile Phe Gln Arg Gln Lys Arg Arg Lys
Phe Trp Lys Ala Lys Asn Leu Gln His Ile Pro Leu Lys Lys Gly Lys Arg Val Val Ser

SEQ ID NO: 234
Met Lys Pro Gly Cys Ala Ala Gly Ser Pro Gly Asn Glu Trp Ile Phe Phe Ser Thr Asp Glu Ile
Thr Thr Arg Tyr Arg Asn Thr Met Ser Asn Gly Gly Leu Gln Arg Ser Val Ile Leu Ser Ala
Leu Ile Leu Leu Arg Ala Val Thr Gly

SEQ ID NO: 235
Phe Pro Cys Asp Phe Ser Trp Gly Val Thr Glu Ser Val Leu Lys Pro Glu Ser Val Ala Ser Ser
Pro Gln Phe Ser Asp Pro His Leu Tyr Val Trp Asn Ala Thr Gly Asn Arg Leu Leu His Arg
Val Glu Gly Val Arg Leu Lys Thr Arg Pro Ala Gln Cys Thr Asp Phe Val Asn Ile Lys Lys
Gln Leu Glu Met Leu Ala Arg Met Lys Val Thr His Tyr Arg Phe Ala Leu Asp Trp Ala Ser

SEQUENCES

Val Leu Pro Thr Gly Asn Leu Ser Ala Val Asn Arg Gln Ala Leu Arg Tyr Tyr Arg Cys Val
Val Ser Glu Gly Leu Lys Leu Gly Ile Ser Ala Met Val Thr Leu Tyr Tyr Pro Thr His Ala His
Leu Gly Leu Pro Gly Pro Leu Leu His Ala Asp Gly Trp Leu Asn Pro Ser Thr Ala Glu Ala
Phe Gln Ala Tyr Ala Gly Leu Cys Phe Gln Glu Leu Gly Asp Leu Val Lys Leu Trp Ile Thr Ile
Asn Glu Pro Asn Arg Leu Ser Asp Ile Tyr Asn Arg Ser Gly Asn Asp Thr Tyr Gly Ala Ala
His Asn Leu Leu Val Ala His Ala Leu Ala Trp Arg Leu Tyr Asp Arg Gln Phe Arg Pro Ser
Gln Arg Gly Ala Val Ser Leu Ser Leu His Ala His Asp Pro Ala Asn Pro Tyr Ala
Asp Ser His Trp Arg Ala Ala Glu Arg Phe Leu Gln Phe Glu Ile Ala Trp Phe Ala Glu Pro Leu
Phe Lys Thr Gly Asp Tyr Pro Ala Ala Met Arg Glu Tyr Ile Ala Ser Lys His Arg Arg Gly Leu
Ser Ser Ser Ala Leu Pro Arg Leu Thr Glu Ala Glu Arg Arg Leu Leu Lys Gly Thr Val Asp
Phe Cys Ala Leu Asn His Phe Thr Thr Arg Phe Val Met His Glu Gln Leu Ala Gly Ser Arg
Tyr Asp Ser Asp Arg Asp Ile Gln Phe Leu Gln Asp Ile Thr Arg Leu Ser Ser Pro Thr Arg Leu
Ala Val Ile Pro Trp Gly Val Arg Lys Leu Leu Arg Trp Val Arg Arg Asn Tyr Gly Asp Met
Asp Ile Tyr Ile Thr Ala Ser Gly Ile Asp Asp Gln Ala Leu Glu Asp Asp Arg Leu Arg Lys Tyr
Tyr Leu Gly Lys Tyr Leu Gln Glu Val Leu Lys Ala Tyr Leu Ile Asp Lys Val Arg Ile Lys Gly
Tyr Tyr Ala Phe Lys Leu Ala Glu Glu Lys Ser Lys Pro Arg Phe Gly Phe Thr Ser Asp
Phe Lys Ala Lys Ser Ser Ile Gln Phe Tyr Asn Lys Val Ile Ser Ser Arg Gly Phe Pro Phe Glu
Asn Ser Ser Ser Arg

SEQ ID NO: 236
Asp Ile Gln Met Thr Gln Thr Thr Ser Ser Leu Ser Ala Ser Leu Gly Asp Arg Val Thr Ile Ile
Cys Ser Ala Ser Gln Val Ile Ser Asn Tyr Leu Asn Trp Tyr Gln Gln Lys Pro Asp Gly Thr Val
Lys Leu Leu Ile Tyr Phe Thr Ser Ser Leu Arg Ser Gly Val Pro Ser Arg Phe Ser Gly Ser Gly
Ser Gly Thr Asp Tyr Ser Leu Thr Ile Ser Asn Leu Glu Pro Glu Asp Val Ala Thr Tyr Phe Cys
Gln Gln Tyr Ser Lys Leu Pro Trp Thr Phe Gly Gly Gly Thr Lys Leu Glu Leu Lys

SEQ ID NO: 237
Glu Asn Val Leu Thr Gln Ser Pro Ala Ile Met Ser Ala Ser Pro GlyGlu Lys Val Thr Met Thr
Cys Ser Ala Ser Ser Ser Gly Arg Tyr Thr Phe Trp Tyr Gln Gln Lys Ser Asn Thr Ala Pro Lys
Leu Trp Ile Tyr Asp Thr Ser Lys Leu Ala Ser Gly Val Pro Gly Arg Phe Ser Gly Ser Gly Ser
Gly Asn Ser Tyr Ser Leu Thr Ile Ser Ser Met Glu Ala Glu Asp Val Ala Thr Tyr Tyr Cys Phe
Gln Gly Thr Gly Tyr Pro Leu Thr Phe Gly Ala Gly Thr Lys Leu Glu Leu Lys

SEQ ID NO: 238
Asp Ile Gln Met Thr Gln Thr Pro Ser Ser Leu Ser Ala Ser Leu Gly Asp Arg Val Thr Ile Asn
Cys Arg Ala Ser Gln Asp Ile Ser Asn Tyr Phe Asn Trp Tyr Gln Gln Lys Pro Asn Gly Thr Ile
Lys Leu Leu Ile Tyr Tyr Thr Ser Arg Leu Gln Ser Gly Val Pro Ser Arg Phe Ser Gly Ser Gly
Ser Gly Thr Asp Tyr Ser Leu Thr Ile Ser Asn Leu Glu Gln Glu Asp Lys Ala Thr Tyr Phe Cys
His Gln Val Arg Thr Leu Pro Trp Thr Phe Gly Gly Gly Thr Lys Leu Glu Ile Lys

SEQ ID NO: 239
Asp Ile Gln Met Thr Gln Ser Ser Ser Tyr Leu Ser Val Ser Leu Gly Gly Ser Val Thr Ile Thr
Cys Lys Ala Ser Asp His Ile Asn Asn Trp Leu Ala Trp Tyr Gln Gln Lys Pro Gly Asn Ala Pro
Arg Leu Leu Ile Tyr Gly Thr Thr Asn Leu Glu Thr Gly Val Pro Ser Arg Phe Ser Gly Ser Gly
Ser Gly Arg Asp Tyr Ile Leu Ser Ile Thr Ser Leu Gln Ser Glu Asp Val Ala Ser Tyr Tyr Cys
Gln Gln Tyr Trp Asn Thr Pro Phe Thr Phe Gly Ser Gly Thr Lys Leu Glu Ile Lys

SEQ ID NO: 240
Ala Val Leu Met Thr Gln Thr Pro Leu Ser Leu Pro Val Ser Leu Gly Asp Gln Ala Ser Ile Ser
Cys Arg Ser Ser Gln Asn Ile Val His Ser Asp Gly Asn Thr Tyr Leu Glu Trp Tyr Leu Gln Lys
Pro Gly Gln Ser Pro Lys Leu Leu Ile Tyr Lys Val Ser Asn Arg Phe Ser Gly Val Pro Asp Arg
Phe Ser Gly Ser Gly Ser Gly Arg Asp Phe Thr Leu Lys Ile Ser Arg Val Glu Ala Gly Asp Leu
Gly Val Tyr Tyr Cys Phe Gln GlySer His Val Leu Thr Phe Gly Ala Gly Thr Arg Leu Glu Leu
Lys

SEQ ID NO: 241
Asp Ile Val Met Thr Gln Ser Gln Lys Phe Met Ser Thr Ser Val Gly Asp Arg Val Ser Ile Thr
Cys Lys Ala Ser Gln Phe Val Ser Asp Ala Val Ala Trp Tyr Gln Gln Lys Pro Gly Gln Ser Pro
Lys Leu Leu Ile Cys Ser Ala Ser Tyr Arg Tyr Thr Gly Val Pro Asp Arg Phe Thr Gly Ser Gly
Ser Gly Thr Asp Phe Thr Phe Thr Ile Ser Ser Val Arg Thr Glu Asp Leu Ala Val Tyr Tyr Cys
Gln Gln His Tyr Ile Val Pro Tyr Thr Phe Gly Gly Gly Thr Thr Leu Glu Ile Glu

SEQ ID NO: 242
Asp Ile Val Met Thr Gln Ser Gln Lys Phe Met Ser Thr Ser Val Gly Asp Arg Val Ser Ile Thr
Cys Lys Ala Ser Gln Phe Val Ser Asp Ala Val Ala Trp Tyr Gln Gln Lys Pro Gly Gln Ser Pro
Lys Leu Leu Ile Cys Ser Ala Ser Tyr Arg Tyr Thr Gly Val Pro Asp Arg Phe Thr Gly Ser Gly
Ser Gly Thr Asp Phe Thr Phe Thr Ile Ser Ser Val Arg Thr Glu Asp Leu Ala Val Tyr Tyr Cys
Gln Gln His Tyr Ile Val Pro Tyr Thr Phe Gly Gly Gly Thr Thr Leu Glu Ile Glu

SEQ ID NO: 243
Asp Ile Gln Met Thr Gln Ser Ser Ser Tyr Leu Ser Val Ser Leu Gly Gly Arg Val Thr Ile Thr
Cys Lys Ala Ser Asp His Ile Asn Asn Trp Leu Ala Trp Tyr Gln Gln Lys Pro Gly Asn Ala Pro
Arg Leu Leu Ile Ser Gly Ala Ser Asn Leu Glu Thr Gly Ile Pro Ser Arg Phe Ser Gly Ser Gly
Ser Gly Lys Asp Tyr Thr Leu Thr Ile Thr Ser Leu Gln Thr Glu Asp Val Ala Thr Tyr Tyr Cys
Gln Gln Tyr Trp Asn Thr Pro Phe Thr Phe Gly Ser Gly Thr Lys Leu Glu Ile Lys

SEQUENCES

SEQ ID NO: 244
Asp Ile Gln Met Thr Gln Ser Pro Ser Ser Leu Ser Ala Ser Leu Gly Glu Arg Val Ser Leu Thr
Cys Arg Ala Ser Gln Glu Ile Ser Gly Tyr Leu Ser Trp Leu Gln Gln Lys Pro Asp Gly Thr Ile
Lys Arg Leu Ile Tyr Ala Ala Ser Thr Leu Asp Ser Gly Val Pro Arg Arg Phe Ser Gly Ser Arg
Ser Gly Ser Asp Tyr Ser Leu Thr Ile Ser Ser Leu Glu Ser Glu Asp Phe Ala Asp Tyr Tyr Cys
Leu Gln Tyr Gly Ser Tyr Pro Trp Thr Phe Gly Gly Gly Thr Lys Leu Glu Leu Lys

SEQ ID NO: 245
Gln Ile Val Leu Thr Gln Ser Pro Ala Ile Met Ser Ala Ser Pro Gly Glu Arg Val Thr Leu Thr
Cys Ser Ala Ser Ser Ser Ser Leu Ser Tyr Leu Tyr Trp Tyr Gln Gln Lys Pro Gly Ser Ser
Pro Lys Leu Trp Ile Tyr Gly Ala Ser Asn Leu Ala Ser Gly Val Pro Gly Arg Phe Ser Gly Ser
Gly Ser Gly Thr Ser Tyr Ser Leu Thr Ile Ser Ser Met Glu Ala Glu Asp Ala Ala Ser Tyr Phe
Cys His Gln Trp Ser Ser Tyr Pro Leu Thr Phe Gly Ser Gly Thr Lys Leu Glu Leu Lys

SEQ ID NO: 246
Asp Ile Val Met Thr Gln Ser Pro Ser Ser Leu Pro Met Ser Val Gly Gln Lys Val Thr Met Ser
Cys Lys Ser Ser Gln Ser Leu Leu Asn Ser Gly Asn Gln Lys Asn Ser Leu Ala Trp Tyr Gln
Gln Lys Pro Gly Gln Ser Pro Lys Leu Leu Val Tyr Leu Ala Ser Thr Arg Glu Ser Gly Val Pro
Asp Arg Phe Ile Gly Ser Gly Ser Gly Thr Asp Phe Thr Leu Thr Ile Ser Ser Val Gln Ala Glu
Asp Leu Ala Asp Tyr Phe Cys Gln Gln His His Ser Thr Pro Tyr Thr Phe Gly Gly Gly Thr
Lys Leu Glu Leu Lys

SEQ ID NO: 247
Glu Ser Val Leu Thr Gln Ser Pro Ala Leu Met Ser Ala Ser Leu Gly Glu Lys Val Thr Met Thr
Cys Arg Ala Ser Ser Ser Val Asn His Met Tyr Trp Tyr Gln Gln Lys Ser Asp Ala Ser Pro Lys
Leu Trp Ile Tyr Tyr Thr Ser Thr Leu Ala Pro Gly Val Pro Ala Arg Phe Ser Gly Ser Gly Ser
Gly Asn Ser Tyr Ser Leu Thr Ile Ser Ser Met Glu Gly Glu Asp Ala Ala Thr Tyr Tyr Cys Gln
Gln Phe Thr Ile Ser Pro Ser Met Tyr Thr Phe Gly Gly Gly Thr Lys Leu Glu Ile Lys

SEQ ID NO: 248
Gly Thr Asp Val Met Asp Tyr

SEQ ID NO: 249
Arg Ala Ser Gln Asp Val Ser Thr Ala Val Ala

SEQ ID NO: 250
Ser Ala Ser Phe Leu Tyr Ser

SEQ ID NO: 251
Gln Gln Ser Tyr Thr Thr Pro Pro Thr

SEQ ID NO: 252
Lys Leu His Ala Val Pro Ala Ala Lys Thr Val Lys Phe Lys Cys Pro

SEQ ID NO: 253
Phe Lys Pro Asp His Arg Ile Gly Gly Tyr Lys Val Arg Tyr

SEQ ID NO: 254
Phe Ser Gly Asp Gly Arg Ala Ile Trp Ser Lys Asn Pro Asn Phe Thr Pro Val Asn Glu Ser Gln
Leu Phe Leu Tyr Asp Thr Phe Pro Lys Asn Phe Phe Trp Gly Ile Gly Thr Gly Ala Leu Gln
Val Glu Gly Ser Trp Lys Lys Asp Gly Lys Gly Pro Ser Ile Trp Asp His Phe Ile His Thr His
Leu Lys Asn Val Ser Ser Thr Asn Gly Ser Ser Asp Ser Tyr Ile Phe Leu Glu Lys Asp Leu Ser
Ala Leu Asp Phe Ile Gly Val Ser Phe Tyr Gln Phe Ser Ile Ser Trp Pro Arg Leu Phe Pro Asp
Gly Ile Val Thr Val Ala Asn Ala Lys Gly Leu Gln Tyr Tyr Ser Thr Leu Leu Asp Ala Leu Val
Leu Arg Asn Ile Glu Pro Ile Val Thr Leu Tyr His Trp Asp Leu Pro Leu Ala Leu Gln Glu Lys
Tyr Gly Gly Trp Lys Asn Asp Thr Ile Ile Asp Ile Phe Asn Asp Tyr Ala Thr Tyr Cys Phe Gln
Met Phe Gly Asp Arg Val Lys Tyr Trp Ile Thr Ile His Asn Pro Tyr Leu Val Ala Trp His Gly
Tyr Gly Thr Gly Met His Ala Pro Gly Glu Lys Gly Asn Leu Ala Ala Val Tyr Thr Val Gly
His Asn Leu Ile Lys Ala His Ser Lys Val Trp His Asn Tyr Asn Thr His Phe Arg Pro His Gln
Lys Gly Trp Leu Ser Ile Thr Leu Gly Ser His Trp Ile Glu Pro Asn Arg Ser Glu Asn Thr Met
Asp Ile Phe Lys Cys Gln Gln Ser Met Val Ser Val Leu Gly Trp Phe Ala Asn Pro Ile His Gly
Asp Gly Asp Tyr Pro Glu Gly Met Arg Lys Lys Leu Phe Ser Val Leu Pro Ile Phe Ser Glu Ala
Glu Lys His Glu Met Arg Gly Thr Ala Asp Phe Phe Ala Phe Ser Phe Gly Pro Asn Asn Phe
Lys Pro Leu Asn Thr Met Ala Lys Met Gly Gln Asn Val Ser Leu Asn Leu Arg Glu Ala Leu
Asn Trp Ile Lys Leu Glu Tyr Asn Asn Pro Arg Ile Leu Ile Ala Glu Asn Gly Trp Phe Thr Asp
Ser Arg Val Lys Thr Glu Asp Thr Thr Ala Ile Tyr Met Met Lys Asn Phe Leu Ser Gln Val
Leu Gln Ala Ile Arg Leu Asp Glu Ile Arg Val Phe Gly Tyr Thr Ala Trp Ser Leu Leu Asp Gly
Phe Glu Trp Gln Asp Ala Tyr Thr Ile Arg Arg Gly Leu Phe Tyr Val Asp Phe Asn Ser Lys
Gln Lys Glu Arg Lys Pro Lys Ser Ser Ala His Tyr Tyr Lys Gln Ile Ile Arg Glu Asn Gly Phe
Ser Leu Lys Glu Ser Thr Pro Asp Val Gln Gly Gln Phe Pro Cys Asp Phe Ser Trp Gly Val Thr
Glu Ser Val Leu Lys Pro Glu Ser Val Ala Ser Ser Pro Gln Phe Ser Asp Pro His Leu Tyr Val
Trp Asn Ala Thr Gly Asn Arg Leu Leu His Arg Val Glu Gly Val Arg Leu Lys Thr Arg Pro
Ala Gln Cys Thr Asp Phe Val Asn Ile Lys Lys Gln Leu Glu Met Leu Ala Arg Met Lys Val
Thr His Tyr Arg Phe Ala Leu Asp Trp Ala Ser Val Leu Pro Thr Gly Asn Leu Ser Ala Val
Asn Arg Gln Ala Leu Arg Tyr Tyr Arg Cys Val Val Ser Glu Gly Leu Lys Leu Gly Ile Ser
Ala Met Val Thr Leu Tyr Tyr Pro Thr His Ala His Leu Gly Leu Pro Glu Pro Leu Leu His Ala

```
                                SEQUENCES
Asp Gly Trp Leu Asn Pro Ser Thr Ala Glu Ala Phe Gln Ala Tyr Ala Gly Leu Cys Phe Gln
Glu Leu Gly Asp Leu Val Lys Leu Trp Ile Thr Ile Asn Glu Pro Asn Arg Leu Ser Asp Ile Tyr
Asn Arg Ser Gly Asn Asp Thr Tyr Gly Ala Ala His Asn Leu Leu Val Ala His Ala Leu Ala
Trp Arg Leu Tyr Asp Arg Gln Phe Arg Pro Ser Gln Arg Gly Ala Val Ser Leu Ser Leu His
Ala Asp Trp Ala Glu Pro Ala Asn Pro Tyr Ala Asp Ser His Trp Arg Ala Ala Glu Arg Phe
Leu Gln Phe Glu Ile Ala Trp Phe Ala Glu Pro Leu Phe Lys Thr Gly Asp Tyr Pro Ala Ala Met
Arg Glu Tyr Ile Ala Ser Lys His Arg Arg Gly Leu Ser Ser Ala Leu Pro Arg Leu Thr Glu
Ala Glu Arg Arg Leu Leu Lys Gly Thr Val Asp Phe Cys Ala Leu Asn His Phe Thr Thr Arg
Phe Val Met His Glu Gln Leu Ala Gly Ser Arg Tyr Asp Ser Asp Arg Asp Ile Gln Phe Leu
Gln Asp Ile Thr Arg Leu Ser Ser Pro Thr Arg Leu Ala Val Ile Pro Trp Gly Val Arg Lys Leu
Leu Arg Trp Val Arg Arg Asn Tyr Gly Asp Met Asp Ile Tyr Ile Thr Ala Ser Gly Ile Asp Asp
Gln Ala Leu Glu Asp Asp Arg Leu Ala Lys Tyr Tyr Leu Gly Lys Tyr Leu Gln Glu Val Leu
Lys Ala Tyr Leu Ile Asp Lys Val Arg Ile Lys Gly Tyr Tyr Ala Phe Lys Leu Ala Glu Glu Lys
Ser Lys Pro Arg Phe Gly Phe Phe Thr Ser Asp Phe Lys Ala Lys Ser Ser Ile Gln Phe Tyr Asn
Lys Val Ile Ser Ser Arg Gly Phe Pro Phe Glu Asn Ser Ser Ser Arg Cys Ser Gln Thr Gln Glu
Asn Thr Glu Cys Thr Val Cys Leu Phe Leu Val Gln Lys Lys Pro Leu Ile Phe Leu Gly Cys
Cys Phe Phe Ser Thr Leu Val Leu Leu Leu Ser Ile Ala Ile Phe Gln Arg Gln Lys Arg Arg Lys
Phe Trp Lys Ala Lys Asn Leu Gln His Ile Pro Leu Lys Lys Gly Lys Arg Val Val Ser

SEQ ID NO: 255
Met Trp Ser Trp Lys Cys Leu Leu Phe Trp Ala Val Leu Val Thr Ala Thr Leu Cys Thr Ala
Arg Pro Ser Pro Thr Leu Pro Glu Gln Ala Gln Pro Trp Gly Ala Pro Val Glu Val Glu Ser Phe
Leu Val His Pro Gly Asp Leu Leu Gln Leu Arg Cys Arg Leu Arg Asp Asp Val Gln Ser Ile
Asn Trp Leu Arg Asp Gly Val Gln Leu Ala Glu Ser Asn Arg Thr Arg Ile Thr Gly Glu Glu
Val Glu Val Gln Asp Ser Val Pro Ala Asp Ser Gly Leu Tyr Ala Cys Val Thr Ser Ser Pro Ser
Gly Ser Asp Thr Thr Tyr Phe Ser Val Asn Val Ser Asp Ala Leu Pro Ser Ser Glu Asp Asp
Asp Asp Asp Asp Asp Ser Ser Ser Glu Glu Lys Glu Thr Asp Asn Thr Lys Pro Asn Pro Val
Ala Pro Tyr Trp Thr Ser Pro Glu Lys Met Glu Lys Lys Leu His Ala Val Pro Ala Ala Lys Thr
Val Lys Phe Lys Cys Pro Ser Ser Gly Thr Pro Asn Pro Thr Leu Arg Trp Leu Lys Asn Gly
Lys Glu Phe Lys Pro Asp His Arg Ile Gly Gly Tyr Lys Val Arg Tyr Ala Thr Trp Ser Ile Ile
Met Asp Ser Val Val Pro Ser Asp Lys Gly Asn Tyr Thr Cys Ile Val Glu Asn Glu Tyr Gly Ser
Ile Asn His Thr Tyr Gln Leu Asp Val Val Glu Arg Ser Pro His Arg Pro Ile Leu Gln Ala Gly
Leu Pro Ala Asn Lys Thr Val Ala Leu Gly Ser Asn Val Glu Phe Met Cys Lys Val Tyr Ser
Asp Pro Gln Pro His Ile Gln Trp Leu Lys His Ile Glu Val Asn Gly Ser Lys Ile Gly Pro Asp
Asn Leu Pro Tyr Val Gln Ile Leu Lys Thr Ala Gly Val Asn Thr Thr Asp Lys Glu Met Glu
Val Leu His Leu Arg Asn Val Ser Phe Glu Asp Ala Gly Glu Tyr Thr Cys Leu Ala Gly Asn
Ser Ile Gly Leu Ser His His Ser Ala Trp Leu Thr Val Leu Glu Ala Leu Glu Glu Arg Pro Ala
Val Met Thr Ser Pro Leu Tyr Leu Glu Ile Ile Ile Tyr Cys Thr Gly Ala Phe Leu Ile Ser Cys
Met Val Gly Ser Val Ile Val Tyr Lys Met Lys Ser Gly Thr Lys Lys Ser Asp Phe His Ser Gln
Met Ala Val His Lys Leu Ala Lys Ser Ile Pro Leu Arg Arg Gln Val Thr Val Ser Ala Asp Ser
Ser Ala Ser Met Asn Ser Gly Val Leu Leu Val Arg Pro Ser Arg Leu Ser Ser Ser Gly Thr Pro
Met Leu Ala Gly Val Ser Glu Tyr Glu Leu Pro Glu Asp Pro Arg Trp Glu Leu Pro Arg Asp
Arg Leu Val Leu Gly Lys Pro Leu Gly Glu Gly Cys Phe Gly Gln Val Val Leu Ala Glu Ala
Ile Gly Leu Asp Lys Asp Lys Pro Asn Arg Val Thr Lys Val Ala Val Lys Met Leu Lys Ser
Asp Ala Thr Glu Lys Asp Leu Ser Asp Leu Ile Ser Glu Met Glu Met Met Lys Met Ile Gly
Lys His Lys Asn Ile Ile Asn Leu Leu Gly Ala Cys Thr Gln Asp Gly Pro Leu Tyr Val Ile Val
Glu Tyr Ala Ser Lys Gly Asn Leu Arg Glu Tyr Leu Gln Ala Arg Arg Pro Pro Gly Leu Glu
Tyr Cys Tyr Asn Pro Ser His Asn Pro Glu Glu Gln Leu Ser Ser Lys Asp Leu Val Ser Cys Ala
Tyr Gln Val Ala Arg Gly Met Glu Tyr Leu Ala Ser Lys Lys Cys Ile His Arg Asp Leu Ala
Ala Arg Asn Val Leu Val Thr Glu Asp Asn Val Met Lys Ile Ala Asp Phe Gly Leu Ala Arg
Asp Ile His His Ile Asp Tyr Tyr Lys Lys Thr Thr Asn Gly Arg Leu Pro Val Lys Trp Met Ala
Pro Glu Ala Leu Phe Asp Arg Ile Tyr Thr His Gln Ser Asp Val Trp Ser Phe Gly Val Leu Leu
Trp Glu Ile Phe Thr Leu Gly Gly Ser Pro Tyr Pro Gly Val Pro Val Glu Glu Leu Phe Lys Leu
Leu Lys Glu Gly His Arg Met Asp Lys Pro Ser Asn Cys Thr Asn Glu Leu Tyr Met Met Met
Arg Asp Cys Trp His Ala Val Pro Ser Gln Arg Pro Thr Phe Lys Gln Leu Val Glu Asp Leu
Asp Arg Ile Val Ala Leu Thr Ser Asn Gln Glu Tyr Leu Asp Leu Ser Met Pro Leu Asp Gln
Tyr Ser Pro Ser Phe Pro Asp Thr Arg Ser Ser Thr Cys Ser Ser Gly Glu Asp Ser Val Phe Ser
His Glu Pro Leu Pro Glu Glu Pro Cys Leu Pro Arg His Pro Ala Gln Leu Ala Asn Gly Gly
Leu Lys Arg Arg

SEQ ID NO: 256
Asp Tyr Lys Asp Asp Asp Asp Lys Leu Glu Phe Ser Gly Asp Gly Lys Ala Ile Trp Asp Lys
Lys Gln Tyr Val Ser Pro Val Asn Pro Gly Gln Leu Phe Leu Tyr Asp Thr Phe Pro Lys Asn
Phe Ser Trp Gly Val Gly Thr Gly Ala Phe Gln Val Glu Gly Ser Trp Lys Ala Asp Gly Arg
Gly Pro Ser Ile Trp Asp Arg Tyr Val Asp Ser His Leu Arg Gly Val Asn Ser Thr Asp Arg Ser
Thr Asp Ser Tyr Val Phe Leu Glu Lys Asp Leu Leu Ala Leu Asp Phe Leu Gly Val Ser Phe
Tyr Gln Phe Ser Ile Ser Trp Pro Arg Leu Phe Pro Asn Gly Thr Val Ala Ala Val Asn Ala Lys
Gly Leu Gln Tyr Tyr Arg Ala Leu Leu Asp Ser Leu Val Leu Arg Asn Ile Glu Pro Ile Val Thr
Leu Tyr His Trp Asp Leu Pro Leu Thr Leu Gln Glu Glu Tyr Gly Gly Trp Lys Asn Ala Thr
Met Ile Asp Leu Phe Asn Asp Tyr Ala Thr Tyr Cys Phe Gln Thr Phe Gly Asp Arg Val Lys
Tyr Trp Ile Thr Ile His Asn Pro Tyr Leu Val Ala Trp His Gly Phe Gly Thr Gly Met His Ala
Pro Gly Gln Lys Gly Asn Leu Thr Ala Val Tyr Thr Val Gly His Asn Leu Ile Lys Ala His Ser
Lys Val Trp His Asn Tyr Asp Lys Asn Phe Arg Pro His Gln Lys Gly Trp Leu Ser Ile Thr Leu
Gly Ser His Trp Ile Glu Pro Asn Arg Thr Glu Asn Met Glu Asp Val Ile Asn Cys Gln His Ser
Met Ser Ser Val Leu Gly Trp Phe Ala Asn Pro Ile His Gly Asp Gly Asp Tyr Pro Glu Phe Met
Lys Thr Ser Ser Val Ile Pro Glu Phe Ser Glu Ala Glu Lys Glu Glu Val Arg Gly Thr Ala Asp
Phe Phe Ala Phe Ser Phe Gly Pro Asn Asn Phe Arg Pro Ser Asn Thr Val Val Lys Met Gly
```

| SEQUENCES |
|---|
| Gln Asn Val Ser Leu Asn Leu Arg Gln Val Leu Asn Trp Ile Lys Leu Glu Tyr Asp Asn Pro
Arg Ile Leu Ile Ser Glu Asn Gly Trp Phe Thr Asp Ser Tyr Ile Lys Thr Glu Asp Thr Thr Ala
Ile Tyr Met Met Lys Asn Phe Leu Asn Gln Val Leu Gln Ala Ile Lys Phe Asp Glu Ile Gln Val
Phe Gly Tyr Thr Ala Trp Thr Leu Leu Asp Gly Phe Glu Trp Gln Asp Ala Tyr Thr Thr Arg
Arg Gly Leu Phe Tyr Val Asp Phe Asn Ser Glu Gln Lys Glu Arg Lys Pro Lys Ser Ser Ala
His Tyr Tyr Lys Gln Ile Ile Gln Asp Asn Gly Phe Pro Leu Gln Glu Ser Thr Pro Asp Met Lys
Gly Gln Phe Pro Cys Asp Phe Ser Trp Gly Val Thr Glu Ser Val Leu Lys Pro Glu Phe Thr Val
Ser Ser Pro Gln Phe Thr Asp Pro His Leu Tyr Val Trp Asn Val Thr Gly Asn Arg Leu Leu
Tyr Arg Val Glu Gly Val Arg Leu Lys Thr Arg Pro Ser Gln Cys Thr Asp Tyr Val Ser Ile Lys
Lys Arg Val Glu Met Leu Ala Lys Met Lys Val Thr His Tyr Gln Phe Ala Leu Asp Trp Thr
Ser Ile Leu Pro Thr Gly Asn Leu Ser Lys Ile Asn Arg Gln Val Leu Arg Tyr Tyr Arg Cys Val
Val Ser Glu Gly Leu Lys Leu Gly Ile Ser Pro Met Val Thr Leu Tyr His Pro Thr His Ser His
Leu Gly Leu Pro Met Pro Leu Leu Ser Ser Gly Gly Trp Leu Asn Thr Asn Thr Ala Lys Ala
Phe Gln Asp Tyr Ala Gly Leu Cys Phe Lys Glu Leu Gly Asp Leu Val Lys Leu Trp Ile Thr Ile
Asn Glu Pro Asn Arg Leu Ser Asp Met Tyr Asn Arg Thr Ser Asn Asp Thr Tyr Arg Ala Ala
His Asn Leu Met Ile Ala His Ala Gln Val Trp His Leu Tyr Asp Arg Gln Tyr Arg Pro Val Gln
His Gly Ala Val Ser Leu Ser Leu His Ser Asp Trp Ala Glu Pro Ala Asn Pro Tyr Val Glu Ser
His Trp Lys Ala Ala Glu Arg Phe Leu Gln Phe Glu Ile Ala Trp Phe Ala Asp Pro Leu Phe Lys
Thr Gly Asp Tyr Pro Leu Ala Met Lys Glu Tyr Ile Ala Ser Lys Lys Gln Arg Gly Leu Ser Ser
Ser Val Leu Pro Arg Phe Thr Leu Lys Glu Ser Ala Arg Leu Val Lys Gly Thr Tyr Ile Asp Phe Tyr Ala
Leu Asn His Phe Thr Thr Arg Phe Val Ile His Lys Gln Leu Asn Thr Asn Cys Ser Val Ala
Asp Arg Asp Val Gln Phe Leu Gln Asp Ile Thr Arg Leu Ser Ser Pro Ser Arg Leu Ala Val
Thr Pro Trp Gly Met Arg Lys Leu Leu Gly Trp Ile Arg Arg Asn Tyr Arg Asp Met Asp Ile
Tyr Val Thr Ala Asn Gly Ile Asp Asp Leu Ala Leu Glu Asp Asp Gln Ile Leu Arg Lys Tyr Tyr
Leu Glu Lys Tyr Val Gln Glu Ala Leu Lys Ala Tyr Leu Ile Asp Lys Val Lys Ile Lys Gly
Tyr Tyr Ala Phe Lys Leu Thr Glu Glu Lys Ser Lys Pro Arg Phe Gly Phe Phe Thr Ser Asp
Phe Lys Ala Lys Ser Ser Val Gln Phe Tyr Ser Lys Leu Ile Ser Ser Ser Gly Phe Ser Ser Glu
Asn Arg Ser Pro Ala Cys Gly Gln Pro Pro Glu Asp Thr Glu Cys Ala Ile Cys Ser Phe Leu
Thr |

SEQ ID NO: 257
Asp Tyr Lys Asp Asp Asp Asp Lys Leu Asp Phe Pro Gly Asp Gly Arg Ala Val Trp Ser Gln
Asn Pro Asn Leu Ser Pro Val Asn Glu Ser Gln Leu Phe Leu Tyr Asp Thr Phe Pro Lys Asn
Phe Phe Trp Gly Val Gly Thr Gly Ala Phe Gln Val Glu Gly Ser Trp Lys Lys Asp Gly Lys
Gly Leu Ser Val Trp Asp His Phe Ile Ala Thr His Leu Asn Val Ser Ser Arg Asp Gly Ser Ser
Asp Ser Tyr Ile Phe Leu Glu Lys Asp Leu Ser Ala Leu Asp Phe Leu Gly Val Ser Phe Tyr
Gln Phe Ser Ile Ser Trp Pro Arg Leu Phe Pro Asp Gly Thr Val Ala Val Ala Asn Ala Lys Gly
Leu Gln Tyr Tyr Asn Arg Leu Leu Asp Ser Leu Leu Leu Arg Asn Ile Glu Pro Val Val Thr
Leu Tyr His Trp Asp Leu Pro Trp Ala Leu Gln Glu Lys Tyr Gly Gly Trp Lys Asn Glu Thr
Leu Ile Asp Leu Phe Asn Asp Tyr Ala Thr Tyr Cys Phe Gln Thr Phe Gly Asp Arg Val Lys
Tyr Trp Ile Thr Ile His Asn Pro Tyr Leu Val Ala Trp His Gly Tyr Gly Thr Gly Leu His Ala
Pro Gly Glu Lys Gly Asn Val Ala Ala Val Tyr Thr Val Gly His Asn Leu Leu Lys Ala His
Ser Lys Val Trp His Asn Tyr Asn Arg Asn Phe Arg Pro His Gln Lys Gly Trp Leu Ser Ile Thr
Leu Gly Ser His Trp Ile Glu Pro Asn Arg Ala Glu Ser Ile Val Asp Ile Leu Lys Cys Gln Gln
Ser Met Val Ser Arg Leu Gly Trp Phe Ala Asn Pro Ile His Gly Asp Gly Asp Tyr Pro Glu Val
Met Thr Lys Lys Leu Leu Ser Val Leu Pro Ala Phe Ser Glu Ala Glu Lys Asn Glu Val Arg
Gly Thr Ala Asp Phe Phe Ala Phe Ser Phe Gly Pro Asn Asn Phe Lys Pro Leu Asn Thr Met
Ala Lys Met Gly Gln Asn Val Ser Leu Asn Leu Arg Gln Val Leu Asn Trp Ile Lys Leu Glu
Tyr Gly Asn Pro Arg Ile Leu Ile Ala Glu Asn Gly Trp Phe Thr Asp Ser Tyr Val Gln Thr Glu
Asp Thr Thr Ala Ile Tyr Met Met Lys Asn Phe Leu Asn Gln Val Leu Gln Ala Ile Arg Leu
Asp Gly Val Arg Val Phe Gly Tyr Thr Ala Trp Ser Leu Leu Asp Gly Phe Glu Trp Gln Asp
Ala Tyr Asn Thr Arg Arg Gly Leu Phe Tyr Val Asp Phe Asn Ser Glu Gln Arg Glu Arg Arg
Pro Lys Ser Ser Ala His Tyr Tyr Lys Gln Ile Ile Gly Val Asn Gly Phe Pro Thr Leu Arg Glu Ala
Thr Pro Asp Leu Gln Gly Gln Phe Pro Cys Asp Phe Ser Trp Gly Val Thr Glu Ser Val Leu
Lys Pro Glu Ser Val Ala Ser Ser Pro Gln Phe Ser Asp Pro His Leu Tyr Val Trp Asn Ala Thr
Gly Asn Arg Met Leu His Arg Val Glu Gly Val Arg Leu Lys Thr Arg Pro Ala Gln Cys Thr
Asp Phe Ile Thr Ile Lys Lys Gln Leu Glu Met Leu Ala Arg Met Lys Val Thr His Tyr Arg Phe
Ala Leu Asp Trp Ala Ser Val Leu Pro Thr Gly Asn Leu Ser Glu Val Asn Arg Gln Ala Leu
Arg Tyr Tyr Arg Cys Val Val Thr Glu Gly Leu Lys Leu Asn Ile Ser Pro Met Val Thr Leu
Tyr Tyr Pro Thr His Ala His Leu Gly Leu Pro Ala Pro Leu Leu His Ser Gly Gly Trp Leu Asp
Pro Ser Thr Ala Lys Ala Phe Ala Arg Asp Tyr Ala Gly Leu Cys Phe Arg Gln Leu Gly Asp Leu
Val Lys Leu Trp Ile Thr Ile Asn Glu Pro Asn Arg Leu Ser Asp Val Tyr Asn Arg Thr Ser Asn
Asp Thr Tyr Gln Ala Ala His Asn Leu Leu Ile Ala His Ala Ile Val Trp His Leu Tyr Asp Arg
Gln Tyr Arg Pro Ser Gln Arg Gly Ala Leu Ser Leu Ser Leu His Ser Asp Trp Ala Glu Pro Ala
Asn Pro Tyr Val Ala Ser His Trp Gln Ala Ala Glu Arg Phe Leu Gln Phe Glu Ile Ala Trp Phe
Ala Glu Pro Leu Phe Lys Thr Gly Asp Tyr Pro Ala Ala Met Arg Glu Tyr Ile Ala Ser Lys Thr
Arg Arg Gly Leu Ser Ser Ser Val Leu Pro Arg Phe Ser Asp Ala Glu Arg Arg Leu Val Lys
Gly Ala Ala Asp Phe Tyr Ala Leu Asn His Phe Thr Thr Arg Phe Val Met His Glu Gln Gln
Asn Gly Ser Arg Tyr Asp Ser Asp Arg Asp Val Gln Phe Leu Gln Asp Ile Thr Arg Leu Ala
Ser Pro Ser Arg Leu Ala Val Met Pro Trp Gly Glu Gly Lys Leu Leu Arg Trp Met Arg Asn
Asn Tyr Gly Asp Leu Asp Val Tyr Ile Thr Ala Asn Gly Ile Asp Asp Ala Leu Asn Asp
Asp Gln Leu Arg Gln Tyr Tyr Leu Glu Lys Tyr Val Gln Glu Ala Leu Lys Ala Tyr Leu Ile
Asp Lys Ile Lys Ile Lys Gly Tyr Tyr Ala Phe Lys Leu Thr Glu Glu Lys Ser Lys Pro Arg Phe
Gly Phe Phe Thr Ser Asp Phe Lys Ala Lys Ser Ser Ile Gln Phe Tyr Asn Lys Leu Ile Thr Ser
Asn Gly Phe Pro Ser Glu Asn Gly Gly Pro Arg Cys Asn Gln Thr Gln Gly Asn Pro Glu Cys
Thr Val Cys Leu Leu Leu Leu

-continued

SEQUENCES

SEQ ID NO: 258
Asp Tyr Lys Asp Asp Asp Asp Lys Leu Glu Phe Ser Gly Asp Gly Arg Ala Val Trp Ser Lys
Asn Pro Asn Phe Thr Pro Val Asn Glu Ser Gln Leu Phe Leu Tyr Asp Thr Phe Pro Lys Asn
Phe Phe Trp Gly Val Gly Thr Gly Ala Leu Gln Val Glu Gly Ser Trp Lys Lys Asp Gly Lys
Gly Pro Ser Ile Trp Asp His Phe Val His Thr His Leu Lys Asn Val Ser Ser Thr Asn Gly Ser
Ser Asp Ser Tyr Ile Phe Leu Glu Lys Asp Leu Ser Ala Leu Asp Phe Ile Gly Val Ser Phe Tyr
Gln Phe Ser Ile Ser Trp Pro Arg Leu Phe Pro Asp Gly Ile Val Thr Val Ala Asn Ala Lys Gly
Leu Gln Tyr Tyr Asn Thr Leu Leu Asp Ser Leu Val Leu Arg Asn
Ile Glu Pro Ile Val Thr Leu Tyr His Trp Asp Leu Pro Leu Ala Leu Gln Glu Lys Tyr Gly Gly
Trp Lys Asn Asp Thr Ile Ile Asp Ile Phe Asn Asp Tyr Ala Thr Tyr Cys Phe Gln Thr Phe Gly
Asp Arg Val Lys Tyr Trp Ile Thr Ile His Asn Pro Tyr Leu Val Ala Trp His Gly Tyr Gly Thr
Gly Met His Ala Pro Gly Glu Lys Gly Asn Leu Ala Ala Val Tyr Thr Val Gly His Asn Leu Ile
Lys Ala His Ser Lys Val Trp His Asn Tyr Asn Thr His Phe Arg Pro His Gln Lys Gly Trp Leu
Ser Ile Thr Leu Gly Ser His Trp Ile Glu Pro Asn Arg Ser Glu Asn Thr Met Asp Ile Leu Lys
Cys Gln Gln Ser Met Val Ser Val Leu Gly Trp Phe Ala Ser Pro Ile His Gly Asp Gly Asp Tyr
Pro Glu Gly Met Lys Lys Leu Leu Ser Ile Leu Leu Pro Leu Phe Ser Glu Ala Glu Lys Asn
Glu Val Arg Gly Thr Ala Asp Phe Phe Ala Phe Ser Phe Gly Pro Asn Asn Phe Lys Pro Leu
Asn Thr Met Ala Lys Met Gly Gln Asn Val Ser Leu Asn Leu Arg Glu Ala Leu Asn Trp Ile
Lys Leu Glu Tyr Asn Asn Pro Arg Ile Leu Ile Ala Glu Asn Gly Trp Phe Thr Asp Ser His Val
Lys Thr Glu Asp Thr Ala Ile Tyr Met Met Lys Asn Phe Leu Ser Gln Val Leu Gln Ala Ile
Arg Leu Asp Glu Ile Arg Val Phe Gly Tyr Thr Ala Trp Ser Leu Leu Asp Gly Phe Glu Trp
Gln Asp Ala Tyr Thr Ile Arg Arg Gly Leu Phe Tyr Val Asp Phe Asn Ser Lys Gln Lys Glu
Arg Lys Pro Lys Ser Ser Ala His Tyr Tyr Lys Gln Ile Ile Arg Glu Asn Gly Phe Ser Leu Lys
Glu Ala Thr Pro Asp Pro Val Gly Gln Phe Pro Cys Asp Phe Ser Trp Gly Val Thr Glu Ser Val
Leu Lys Pro Glu Ser Val Ala Ser Ser Pro Gln Phe Ser Asp Pro Tyr Leu Tyr Val Trp Asn Ala
Thr Gly Asn Arg Leu Leu His Arg Val Glu Gly Val Arg Leu Lys Thr Arg Pro Ala Gln Cys
Thr Asp Phe Val Asn Ile Lys Lys Gln Leu Glu Met Leu Ala Arg Met Lys Val Thr His Tyr
Arg Phe Ala Leu Asp Trp Ala Ser Val Leu Pro Thr Gly Asn Leu Ser Ala Val Asn Arg Gln
Ala Leu Arg Tyr Tyr Arg Cys Val Val Ser Glu Gly Leu Lys Leu Gly Ile Ser Ala Met Val Thr
Leu Tyr Tyr Pro Thr His Ala His Leu Gly Leu Pro Glu Pro Leu Leu His Ala Gly Gly Trp Leu
Asn Pro Ser Thr Val Glu Ala Phe Gln Ala Tyr Ala Gly Leu Cys Phe Gln Glu Leu Gly Asp
Leu Val Lys Leu Trp Ile Thr Ile Asn Glu Pro Asn Arg Leu Ser Asp Ile Tyr Asn Arg Ser Gly
Asn Asp Thr Tyr Gly Ala Ala His Asn Leu Leu Val Ala His Ala Leu Ala Trp Arg Leu Tyr
Asp Arg Gln Phe Arg Pro Ser Gln Arg Gly Ala Val Ser Leu Ser Leu His Ala Asp Trp Ala
Glu Pro Ala Asn Pro Tyr Ala Asp Ser His Trp Arg Ala Ala Glu Arg Phe Leu Gln Phe Glu Ile
Ala Trp Phe Ala Glu Pro Leu Phe Lys Thr Gly Asp Tyr Pro Ala Ala Met Arg Glu Tyr Ile Ala
Ser Lys His Arg Arg Gly Leu Ser Ser Ser Ala Leu Pro Arg Leu Thr Glu Ala Glu Arg Arg
Leu Leu Lys Gly Thr Val Asp Phe Cys Ala Leu Asn His Phe Thr Thr Arg Phe Val Met His
Glu Gln Leu Ala Gly Ser Arg Tyr Asp Ser Asp Arg Asp Ile Gln Phe Leu Gln Asp Ile Thr Arg
Leu Ser Ser Pro Thr Arg Leu Ala Val Ile Pro Trp Gly Val Arg Lys Leu Leu Arg Trp Val Arg
Arg Asn Tyr Gly Asp Met Asp Ile Tyr Ile Thr Ala Ser Gly Ile Asp Asp Gln Ala Leu Glu Asp
Asp Arg Leu Arg Lys Tyr Tyr Leu Glu Lys Tyr Leu Gln Glu Val Leu Lys Ala Tyr Leu Ile
Asp Lys Val Arg Ile Lys Gly Tyr Tyr Ala Phe Lys Leu Ala Glu Glu Lys Ser Lys Pro Arg Phe
Gly Phe Phe Thr Ser Asp Phe Lys Ala Lys Ser Ser Ile Gln Phe Tyr Asn Lys Met Ile Ser Ser
Ser Gly Phe Pro Ser Glu Asn Ser Ser Ser Arg Cys Ser Gln Thr Gln Lys Asn Thr Glu Cys Thr
Val Cys Leu Phe Leu Ala

SEQ ID NO: 259
Asp Tyr Lys Asp Asp Asp Asp Lys Leu Glu Phe Ser Gly Asp Gly Arg Ala Val Trp Ser Lys
Asn Pro Asn Phe Thr Pro Val Asn Glu Ser Gln Leu Phe Leu Tyr Asp Thr Phe Pro Lys Asn
Phe Phe Trp Gly Val Gly Thr Gly Ala Leu Gln Val Glu Gly Ser Trp Lys Lys Asp Gly Lys
Gly Pro Ser Ile Trp Asp His Phe Val His Thr His Leu Lys Asn Val Ser Ser Thr Asn Gly Ser
Ser Asp Ser Tyr Ile Phe Leu Glu Lys Asp Leu Ser Ala Leu Asp Phe Ile Gly Val Ser Phe Tyr
Gln Phe Ser Ile Ser Trp Pro Arg Leu Phe Pro Asp Gly Ile Val Thr Val Ala Asn Ala Lys Gly
Leu Gln Tyr Tyr Asn Ala Leu Leu Asp Ser Leu Val Leu Arg Asn Ile Glu Pro Ile Val Thr Leu
Tyr His Trp Asp Leu Pro Leu Ala Leu Gln Glu Lys Tyr Gly Gly Trp Lys Asn Asp Thr Ile Ile
Asp Ile Phe Asn Asp Tyr Ala Thr Tyr Cys Phe Gln Thr Phe Gly Asp Arg Val Lys Tyr Trp Ile
Thr Ile His Asn Pro Tyr Leu Val Ala Trp His Gly Tyr Gly Thr Gly Met His Ala Pro Gly Glu
Lys Gly Asn Leu Ala Ala Val Tyr Thr Val Gly His Asn Leu Ile Lys Ala His Ser Lys Val Trp
His Asn Tyr Asn Thr His Phe Arg Pro His Gln Lys Gly Trp Leu Ser Ile Thr Leu Gly Ser His
Trp Ile Glu Pro Asn Arg Ser Glu Asn Thr Met Asp Ile Leu Lys Cys Gln Gln Ser Met Val Ser
Val Leu Gly Trp Phe Ala Asn Pro Ile His Gly Asp Gly Asp Tyr Pro Gln Gly Met Lys Lys
Leu Leu Ser Ile Leu Pro Leu Phe Ser Glu Ala Glu Lys Asn Glu Val Arg Gly Thr Ala
Asp Phe Phe Ala Phe Ser Phe Gly Pro Asn Asn Phe Lys Pro Leu Asn Thr Met Ala Lys Met
Gly Gln Asn Val Ser Leu Asn Leu Arg Glu Ala Leu Asn Trp Ile Lys Leu Glu Tyr Asn Asn
Pro Gln Ile Leu Ile Ala Glu Asn Gly Trp Phe Thr Asp Ser His Val Lys Thr Glu Asp Thr Thr
Ala Ile Tyr Met Met Lys Asn Phe Leu Ser Gln Val Leu Gln Ala Ile Arg Leu Asp Glu Ile Arg
Val Phe Gly Tyr Thr Ala Trp Ser Leu Leu Asp Gly Phe Glu Trp Gln Asp Ala Tyr Thr Ile Arg
Arg Gly Leu Phe Tyr Val Asp Phe Asn Ser Lys Gln Lys Glu Arg Lys Pro Lys Ser Ser Ala
His Tyr Tyr Lys Gln Ile Ile Arg Glu Asn Gly Phe Ser Leu Lys Glu Ala Thr Pro Asp Val Gln
Gly Gln Phe Pro Cys Asp Phe Ser Trp Gly Val Thr Glu Ser Val Leu Lys Pro Glu Ser Val Ala
Ser Ser Pro Gln Phe Ser Asp Pro Tyr Leu Tyr Val Trp Asn Ala Thr Gly Asn Arg Leu Leu
His Arg Val Glu Gly Val Arg Leu Lys Thr Arg Pro Ala Gln Cys Thr Asp Phe Val Asn Ile
Lys Lys Gln Leu Glu Met Leu Ala Arg Met Lys Val Thr His Tyr Arg Phe Ala Leu Asp Trp
Ala Ser Val Leu Pro Thr Gly Asn Leu Ser Ala Val Asn Arg Gln Ala Leu Arg Tyr Tyr Arg
Cys Val Val Ser Glu Gly Leu Lys Leu Gly Ile Ser Ala Met Val Thr Leu Tyr Tyr Pro Thr His
Ala His Leu Gly Leu Pro Glu Pro Leu Leu His Ala Gly Gly Trp Leu Asn Pro Ser Thr Val

| SEQUENCES |
|---|
| Glu Ala Phe Gln Ala Tyr Ala Gly Leu Cys Phe Gln Glu Leu Gly Asp Leu Val Lys Leu Trp
Ile Thr Ile Asn Glu Pro Asn Arg Leu Ser Asp Ile Tyr Asn Arg Ser Gly Asn Asp Thr Tyr Gly
Ala Ala His Asn Leu Leu Val Ala His Ala Leu Ala Trp Arg Leu Tyr Arg Asp Arg Leu Arg
Pro Ser Gln Arg Gly Ala Val Ser Leu Ser Leu His Ala Asp Trp Ala Glu Pro Ala Asn Pro Tyr
Ala Asp Ser His Trp Arg Ala Ala Glu Arg Phe Leu Gln Phe Glu Ile Ala Trp Phe Ala Glu Pro
Leu Phe Lys Thr Gly Asp Tyr Pro Ala Ala Met Arg Glu Tyr Ile Ala Ser Lys His Arg Arg Gly
Leu Ser Ser Ser Ala Leu Pro Arg Leu Thr Glu Ala Glu Arg Arg Leu Leu Lys Gly Thr Val
Asp Phe Cys Ala Leu Asn His Phe Thr Thr Arg Phe Val Met His Glu Gln Leu Ala Gly Ser
Arg Tyr Asp Ser Asp Arg Asp Ile Gln Phe Leu Gln Asp Ile Thr Arg Leu Ser Ser Pro Thr Arg
Leu Ala Val Ile Pro Trp Gly Val Arg Lys Leu Leu Arg Trp Val Arg Arg Asn Tyr Gly Asp
Met Asp Ile Tyr Ile Thr Ala Ser Gly Ile Asp Gln Ala Leu Glu Asp Ala Asp Arg Leu Arg Lys
Tyr Tyr Leu Glu Lys Tyr Leu Gln Glu Val Leu Lys Ala Tyr Leu Ile Asp Lys Val Arg Ile Lys
Gly Tyr Tyr Ala Phe Lys Leu Ala Glu Glu Lys Ser Lys Pro Arg Phe Gly Phe Phe Thr Ser
Asp Phe Lys Ala Lys Ser Ser Ile Gln Phe Tyr Asn Lys Met Ile Ser Ser Ser Gly Phe Pro Ser
Glu Asn Ser Ser Ser Arg Cys Ser Gln Thr Gln Lys Asn Thr Glu Cys Thr Val Cys Leu Phe
Leu Val

SEQ ID NO: 260
Glu Pro Gly Asp Gly Ala Gln Thr Trp Ala Arg Phe Ser Arg Pro Pro Ala Pro Glu Ala Ala Gly
Leu Phe Gln Gly Thr Phe Pro Asp Gly Phe Leu Trp Ala Val Gly Ser Ala Ala Tyr Gln Thr
Glu Gly Gly Trp Gln Gln His Gly Lys Gly Ala Ser Ile Trp Asp Thr Phe Thr His His Pro Leu
Ala Pro Pro Gly Asp Ser Arg Asn Ala Ser Leu Pro Leu Gly Ala Pro Ser Pro Leu Gln Pro Ala
Thr Gly Asp Val Ala Ser Asp Ser Tyr Asn Asn Val Phe Arg Asp Thr Glu Ala Leu Arg Glu
Leu Gly Val Thr His Tyr Arg Phe Ser Ile Ser Trp Pro Arg Ala Val Leu Pro Asn Gly Ser Ala Gly
Val Pro Asn Arg Glu Gly Leu Arg Tyr Tyr Arg Arg Leu Leu Glu Arg Leu Arg Glu Leu Gly
Val Gln Pro Val Val Thr Leu Tyr His Trp Asp Leu Pro Gln Arg Leu Gln Asp Ala Tyr Gly
Gly Trp Ala Asn Arg Ala Leu Ala Asp His Phe Arg Asp Tyr Ala Glu Leu Cys Phe Arg His
Phe Gly Gly Gln Val Lys Tyr Trp Ile Thr Ile Asp Glu Pro Asn Pro Tyr Val Val Ala Trp His Gly Tyr
Ala Thr Gly Arg Leu Ala Pro Gly Ile Arg Gly Ser Pro Arg Leu Gly Tyr Leu Val Ala His Asn
Leu Leu Leu Ala His Ala Lys Val Trp His Leu Tyr Asn Thr Ser Phe Arg Pro Thr Gln Gly
Gly Gln Val Ser Ile Ala Leu Ser Ser His Trp Ile Asn Pro Arg Arg Met Thr Asp His Ser Ile
Lys Glu Cys Gln Lys Ser Leu Asp Phe Val Leu Gly Trp Phe Ala Lys Pro Val Phe Ile Asp
Gly Asp Tyr Pro Glu Ser Met Lys Asn Asn Leu Ser Ser Ile Leu Pro Asp Phe Thr Glu Ser Glu
Lys Lys Phe Ile Lys Gly Thr Ala Asp Phe Phe Ala Leu Cys Phe Gly Pro Thr Leu Ser Phe Gln
Leu Leu Asp Pro His Met Lys Phe Arg Gln Leu Glu Ser Pro Asn Leu Arg Gln Leu Leu Ser
Trp Ile Asp Leu Glu Phe Asn His Pro Gln Ile Phe Ile Val Glu Asn Gly Trp Phe Val Ser Gly
Thr Thr Lys Arg Asp Asp Ala Lys Tyr Met Tyr Tyr Leu Lys Lys Phe Ile Met Glu Thr Leu
Lys Ala Ile Lys Leu Asp Gly Val Asp Val Ile Gly Tyr Thr Ala Trp Ser Leu Met Asp Gly Phe
Glu Trp His Arg Gly Tyr Ser Ile Arg Arg Gly Leu Phe Tyr Val Asp Phe Leu Ser Gln Asp
Lys Met Leu Leu Pro Lys Ser Ser Ala Leu Phe Tyr Gln Lys Leu Ile Glu Lys Asn Gly Phe Pro
Pro Leu Pro Glu Asn Gln Pro Leu Glu Gly Thr Phe Pro Cys Asp Phe Ala Trp Gly Val Val Asp
Asp Asn Tyr Ile Gln Val Asp Thr Thr Leu Ser Gln Phe Thr Asp Leu Asn Val Tyr Leu Trp
Asp Val His His Ser Lys Arg Leu Ile Lys Val Asp Gly Val Val Thr Lys Arg Lys Ser Tyr
Cys Val Asp Phe Ala Ala Ile Gln Pro Gln Ile Ala Leu Leu Gln Glu Met His Val Thr His Phe
Arg Phe Ser Leu Asp Trp Ala Leu Ile Leu Pro Leu Gly Asn Gln Ser Gln Val Asn His Thr Ile
Leu Gln Tyr Tyr Arg Cys Met Ala Ser Glu Leu Val Arg Val Asn Ile Thr Pro Val Val Ala Leu
Trp Gln Pro Met Ala Pro Asn Gln Gly Leu Pro Arg Leu Leu Ala Arg Gln Gly Ala Trp Glu
Asn Pro Tyr Thr Ala Leu Ala Phe Ala Glu Tyr Ala Arg Leu Cys Phe Gln Glu Leu Gly His
His Val Lys Leu Trp Ile Thr Met Asn Glu Pro Tyr Thr Arg Asn Met Thr Tyr Ser Ala Gly His
Asn Leu Leu Lys Ala His Ala Leu Ala Trp His Val Tyr Asn Glu Lys Phe Arg His Ala Gln
Asn Gly Lys Ile Ser Ile Ala Leu Gln Ala Asp Trp Ile Glu Pro Ala Cys Pro Phe Ser Gln Lys
Asp Lys Glu Val Ala Glu Arg Val Leu Glu Phe Asp Ile Gly Trp Leu Ala Glu Pro Ile Phe Gly
Ser Gly Asp Tyr Pro Trp Val Met Arg Asp Trp Leu Asn Gln Arg Asn Asn Phe Leu Leu Pro
Tyr Phe Thr Glu Asp Glu Lys Lys Leu Ile Gln Gly Thr Phe Asp Phe Leu Ala Leu Ser His
Tyr Thr Thr Ile Leu Val Asp Ser Glu Lys Glu Asp Pro Ile Lys Tyr Asn Asp Tyr Leu Glu Val
Gln Glu Met Thr Asp Ile Thr Trp Leu Asn Ser Pro Ser Gln Val Ala Val Val Pro Trp Gly Leu
Arg Lys Val Leu Asn Trp Leu Lys Phe Lys Tyr Gly Asp Leu Pro Met Tyr Ile Ile Ser Asn Gly
Ile Asp Asp Gly Leu His Ala Glu Asp Asp Gln Leu Arg Val Tyr Tyr Met Gln Asn Tyr Ile
Asn Glu Ala Leu Lys Ala His Ile Leu Asp Gly Ile Asn Leu Cys Gly Tyr Phe Ala Tyr Ser Phe
Asn Asp Arg Thr Ala Pro Arg Phe Gly Leu Tyr Arg Tyr Ala Ala Asp Gln Phe Glu Pro Lys
Ala Ser Met Lys His Tyr Arg Lys Ile Ile Asp Ser Asn Gly Phe Pro Gly Pro Glu Thr Leu Glu
Arg Phe Cys Pro Glu Glu Phe Thr Val Cys Thr Glu Cys Ser Phe Phe His Thr Arg Lys Ser
Leu Leu Ala Phe Ile Ala Phe Leu Phe Phe Ala Ser Ile Ile Ser Leu Ser Leu Ile Phe Tyr Tyr Ser
Lys Lys Gly Arg Arg Ser Tyr Lys Leu Glu Asp Tyr Lys Asp Asp Asp Asp Lys

SEQ ID NO: 261
Ser Thr Tyr Ile Ser

SEQ ID NO: 262
Glu Ile Asp Pro Tyr Asp Gly Ala Thr Asp Tyr Ala Asp Ser Val Lys Gly

SEQ ID NO: 263
Glu His Phe Asp Ala Trp Val His Tyr Tyr Val Met Asp Tyr

SEQ ID NO: 264
Phe Pro Cys Asp Phe Ser Trp Gly Val Thr Glu Ser Val Leu Lys Pro Glu Ser Val Ala Ser Ser
Pro Gln Phe Ser Asp Pro His Leu Tyr Val Trp Asn Ala Thr Gly Asn Arg Leu Leu His Arg |

SEQUENCES

Val Glu Gly Val Arg Leu Lys Thr Arg Pro Ala Gln Cys Thr Asp Phe Val Asn Ile Lys Lys
Gln Leu Glu Met Leu Ala Arg Met Lys Val Thr His Tyr Arg Phe Ala Leu Asp Trp Ala Ser
Val Leu Pro Thr Gly Asn Leu Ser Ala Val Asn Arg Gln Ala Leu Arg Tyr Tyr Arg Cys Val
Val Ser Glu Gly Leu Lys Leu Gly Ile Ser Ala Met Val Thr Leu Tyr Tyr Pro Thr His Ala His
Leu Gly Leu Pro Glu Pro Leu Leu His Ala Asp Gly Trp Leu Asn Pro Ser Thr Ala Glu Ala
Phe Gln Ala Tyr Ala Gly Leu Cys Phe Gln Glu Leu Gly Asp Leu Val Lys Leu Trp Ile Thr Ile
Asn Glu Pro Asn Arg Leu Ser Asp Ile Tyr Asn Asn Ser Gly Asn Asp Thr Tyr Gly Ala Ala
His Asn Leu Leu Val Ala His Ala Leu Ala Trp Arg Leu Tyr Asp Arg Gln Phe Arg Pro Ser
Gln Arg Gly Ala Val Ser Leu Ser Leu His Ala Asp Trp Ala Glu Pro Ala Asn Pro Tyr Ala
Asp Ser His Trp Arg Ala Ala Glu Arg Phe Leu Gln Phe Glu Ile Ala Trp Phe Ala Glu Pro Leu
Phe Lys Thr Gly Asp Tyr Pro Ala Ala Met Arg Gly Tyr Ile Ala Ser Lys His Arg Arg Gly Leu
Ser Ser Ser Ala Leu Pro Arg Leu Thr Glu Ala Glu Arg Leu Leu Lys Gly Thr Val Asp
Phe Cys Ala Leu Asn His Phe Thr Thr Arg Phe Val Met His Glu Gln Leu Ala Gly Ser Arg
Tyr Asp Ser Asp Arg Asp Ile Gln Phe Leu Gln Asp Ile Thr Arg Leu Ser Ser Pro Thr Arg Leu
Ala Val Ile Pro Trp Gly Val Arg Lys Leu Leu Arg Trp Val Arg Arg Asn Tyr Gly Asp Met
Asp Ile Tyr Ile Thr Ala Ser Gly Ile Asp Asp Gln Ala Leu Glu Asp Asp Arg Leu Arg Lys Tyr
Tyr Leu Gly Lys Tyr Leu Gln Glu Val Leu Lys Ala Tyr Leu Ile Asp Lys Val Lys Arg Ile Lys Lys Gly
Tyr Tyr Ala Phe Lys Leu Ala Glu Glu Lys Ser Lys Pro Arg Phe Gly Phe Phe Thr Ser Asp
Phe Lys Ala Lys Ser Ser Ile Gln Phe Tyr Asn Lys Val Ile Ser Ser Arg Gly Phe Pro Phe Glu
Asn Ser Ser Ser Arg

SEQ ID NO: 265
gttaccggct tctccggaga cgggaaagca atatgg

SEQ ID NO: 266
Met Lys Pro Gly Cys Ala Ala Gly Ser Pro Gly Asn Glu Trp Ile Phe Phe Ser Thr Asp Glu Ile
Thr Thr Arg Tyr Arg Asn Thr Met Ser Asn Gly Gly Leu Gln Arg Ser Val Ile Leu Ser Ala
Leu Ile Leu Leu Arg Ala Val Thr Gly

SEQ ID NO: 267
Phe Ser Gly Asp Gly Lys Ala Ile Trp Asp Lys Lys Gln Tyr Val Ser Pro Val Asn Pro Ser Gln
Leu Phe Leu Tyr Asp Thr Phe Pro Lys Asn Phe Ser Trp Gly Val Gly Thr Gly Ala Phe Gln
Val Glu Gly Ser Trp Lys Thr Asp Gly Arg Gly Pro Ser Ile Trp Asp Arg Tyr Val Tyr Ser His
Leu Arg Gly Val Asn Gly Thr Asp Arg Ser Thr Asp Ser Tyr Ile Phe Leu Glu Lys Asp Leu
Leu Ala Leu Asp Phe Leu Gly Val Ser Phe Tyr Gln Phe Ser Ile Ser Trp Pro Arg Leu Phe Pro
Asn Gly Thr Val Ala Ala Val Asn Ala Gln Gly Leu Arg Tyr Tyr Arg Ala Leu Leu Asp Ser
Leu Val Leu Arg Asn Ile Glu Pro Ile Val Thr Leu Tyr His Trp Asp Leu Pro Leu Thr Leu Gln
Glu Glu Tyr Gly Gly Trp Lys Asn Ala Thr Met Ile Asp Leu Phe Asn Asp Tyr Ala Thr Tyr
Cys Phe Gln Thr Phe Gly Asp Arg Val Lys Tyr Trp Ile Thr Ile His Asn Pro Tyr Leu Val Ala
Trp His Gly Phe Gly Thr Gly Met His Ala Pro Gly Glu Lys Gly Asn Leu Thr Ala Val Tyr
Thr Val Gly His Asn Leu Ile Lys Ala His Ser Lys Val Trp His Asn Tyr Asp Lys Asn Phe Arg
Pro His Gln Lys Gly Trp Leu Ser Ile Thr Leu Gly Ser His Trp Ile Glu Leu Pro Asn Arg Thr Asp
Asn Met Glu Asp Val Ile Asn Cys Gln His Ser Met Ser Ser Val Leu Gly Trp Phe Ala Asn
Pro Ile His Gly Asp Gly Asp Tyr Pro Glu Phe Met Lys Thr Gly Ala Met Ile Pro Glu Phe Ser
Glu Ala Glu Lys Glu Glu Val Arg Gly Thr Ala Asp Phe Phe Ala Phe Ser Phe Gly Pro Asn
Asn Phe Arg Pro Ser Asn Thr Val Val Lys Met Gly Gln Asn Val Ser Leu Asn Leu Arg Gln
Val Leu Asn Trp Ile Lys Leu Glu Tyr Asp Asp Pro Gln Ile Leu Ile Ser Glu Asn Gly Trp Phe
Thr Asp Ser Tyr Ile Lys Thr Glu Asp Thr Thr Ala Ile Tyr Met Met Lys Asn Phe Leu Asn Gln
Val Leu Gln Ala Ile Lys Phe Asp Glu Ile Arg Val Phe Gly Tyr Thr Ala Trp Thr Leu Leu Asp
Gly Phe Glu Trp Gln Asp Ala Tyr Thr Thr Arg Arg Gly Leu Phe Tyr Val Asp Phe Asn Ser
Glu Gln Lys Glu Arg Lys Pro Lys Ser Ser Ala His Tyr Tyr Lys Gln Ile Ile Gln Asp Asn Gly
Phe Pro Leu Lys Glu Ser Thr Pro Asp Met Lys Gly Arg Phe Pro Cys Asp Phe Ser Trp Gly
Val Thr Glu Ser Val Leu Lys Pro Glu Phe Thr Val Ser Ser Pro Gln Phe Thr Asp Pro His Leu
Tyr Val Trp Asn Val Thr Gly Asn Arg Leu Leu Tyr Arg Val Glu Gly Val Arg Leu Lys Thr
Arg Pro Ser Gln Cys Thr Asp Tyr Val Ser Ile Lys Lys Arg Val Glu Met Leu Ala Lys Met
Lys Val Thr His Tyr Gln Phe Ala Leu Asp Trp Thr Ser Ile Leu Pro Thr Gly Asn Leu Ser Lys
Val Asn Arg Gln Val Leu Arg Tyr Tyr Arg Cys Val Val Ser Glu Gly Leu Lys Leu Gly Val
Phe Pro Met Val Thr Leu Tyr His Pro Thr His Leu Pro Leu Pro Leu Pro Leu Ser
Ser Gly Gly Trp Leu Asn Met Asn Thr Ala Lys Ala Phe Gln Asp Tyr Ala Glu Leu Cys Phe
Arg Glu Leu Gly Asp Leu Val Lys Leu Trp Ile Thr Ile Asn Glu Pro Asn Arg Leu Ser Asp
Met Tyr Asn Arg Thr Ser Asn Asp Thr Tyr Arg Ala Ala His Asn Leu Met Ile Ala His Ala
Gln Val Trp His Leu Tyr Asp Arg Gln Tyr Arg Pro Val Gln His Gly Ala Val Ser Leu Ser Leu
His Cys Asp Trp Ala Glu Pro Ala Asn Pro Phe Val Asp Ser His Trp Lys Ala Ala Glu Arg Arg
Phe Leu Gln Phe Glu Ile Ala Trp Phe Ala Asp Pro Leu Phe Lys Thr Gly Asp Tyr Pro Ser Val
Met Lys Glu Tyr Ile Ala Ser Lys Asn Gln Arg Gly Leu Ser Ser Ser Val Leu Pro Arg Phe Thr
Ala Lys Glu Ser Arg Leu Val Lys Gly Thr Val Asp Phe Tyr Ala Leu Asn His Phe Thr Thr
Arg Phe Val Ile His Lys Gln Leu Asn Thr Asn Arg Ser Val Ala Asp Arg Asp Val Gln Phe
Leu Gln Asp Ile Thr Arg Leu Ser Ser Pro Ser Arg Leu Ala Val Thr Pro Trp Gly Val Arg Lys
Leu Leu Ala Trp Ile Arg Arg Asn Tyr Arg Asp Arg Asp Ile Tyr Ile Thr Ala Asn Gly Ile Asp
Asp Leu Ala Leu Glu Asp Asp Gln Ile Arg Lys Tyr Tyr Leu Glu Lys Tyr Val Gln Glu Ala
Leu Lys Ala Tyr Leu Ile Asp Lys Val Lys Ile Lys Gly Tyr Tyr Ala Phe Lys Leu Thr Glu Glu
Lys Ser Lys Pro Arg Phe Gly Phe Phe Thr Ser Asp Phe Arg Ala Lys Ser Ser Val Gln Phe Tyr
Ser Lys Leu Ile Ser Ser Ser Gly Leu Pro Ala Glu Asn Arg Ser Pro Ala Cys Gly Gln Pro Ala
Glu Asp Thr Asp Cys Thr Ile Cys Ser Phe Leu Val

SEQUENCES

SEQ ID NO: 268
Met Glu Lys Lys Leu His Ala Val Pro Ala Ala Lys Thr Val Lys Phe Lys Cys Pro Ser Ser Gly
Thr Pro Asn Pro Thr Leu Arg Trp Leu Lys Asn Gly Lys Glu Phe Lys Pro Asp His Arg Ile
Gly Gly Tyr Lys Val Arg Tyr Ala Thr Trp

SEQ ID NO: 269
Ser Ser Pro Thr Arg Leu Ala Val Ile Pro Trp Gly Val Arg Lys Leu Leu Arg Trp Val Arg Arg
Asn Tyr Gly Asp Met Asp Ile Tyr Ile Thr Ala Ser

SEQ ID NO: 270
Ser Ser Pro Thr Arg Leu Ala Val Ile Pro Trp Gly Val Arg Lys Leu Leu Arg Trp Val Arg Arg
Asn Tyr Gly Asp Met Asp Ile Tyr Ile Thr Ala Ser

SEQ ID NO: 271
Ser Ser Pro Ser Arg Leu Ala Val Thr Pro Trp Gly Met Arg Lys Leu Leu Gly Trp Ile Arg Arg
Asn Tyr Arg Asp Met Asp Ile Tyr Val Thr Ala Asn

SEQ ID NO: 272
Ser Ser Pro Ser Arg Leu Ala Val Thr Pro Trp Gly Val Arg Lys Leu Leu Ala Trp Ile Arg Arg
Asn Tyr Arg Asp Arg Asp Ile Tyr Ile Thr Ala Asn

SEQ ID NO: 273
Ala Ser Pro Ser Arg Leu Ala Val Met Pro Trp Gly Glu Gly Lys Leu Leu Arg Trp Met Arg
Asn Asn Tyr Gly Asp Leu Asp Val Tyr Ile Thr Ala Asn

SEQ ID NO: 274
Phe Ser Gly Asp Gly Lys Ala Ile Trp Asp Lys Lys Gln Tyr Val Ser Pro

SEQ ID NO: 275
Phe Ser Glu Thr Gly Lys Gln Tyr Gly Ile Lys Asn Ser Thr

SEQ ID NO: 276
2B.1.1.6 HVR-L1
RASQDVDTSLA

SEQ ID NO: 277
2B.1.1.6 HVR-L2
SASFLYS

SEQ ID NO: 278
2B.1.1.6 HVR-L3
QQSTGHPQT

SEQ ID NO: 279
2B.1.1.6 HVR-H1
GFTFTSTGIS

SEQ ID NO: 280
2B.1.1.6 HVR-H2
RYWAWDGSTNYADSVKG

SEQ ID NO: 281
2B.1.1.6 HVR-H3
ARTYGIYDTYDEYTEYVMDY

SEQ ID NO: 282
2B.1.1.6 HC
EVQLVESGGGLVQPGGSLRLSCAASGFTFTSTGISWVRQAPGKGLEWVGRYWAWD
GSTNYADSVKGRFTISADTSKNTAYLQMNSLRAEDTAVYYCARTYGIYDTYDEYTE
YVMDYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKS
LSLSPGK

SEQ ID NO: 283
2B.1.1.6 LC
DIQMTQSPSSLSASVGDRVTITCRASQDVDTSLAWYKQKPGKAPKLLIYSASFLYSG
VPSRFSGSGSGTDFTLTISSLQPEDFATYYCQQSTGHPQTFGQGTKVEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC

What is claimed is:

1. An isolated antibody, or antigen-binding portion thereof, that binds to FGFR2 and FGFR3, wherein binding of the antibody, or antigen-binding portion thereof, to FGFR1 or FGFR4 is not detectable by surface plasmon resonance, and wherein the antibody, or antigen-binding portion thereof, comprises:
   a. a heavy chain variable region CDR1 domain comprising an amino acid sequence selected from the group consisting of SEQ ID NOs: 4 and 10;
   b. a heavy chain variable region CDR2 domain comprising the amino acid sequence of SEQ ID NO: 5;
   c. a heavy chain variable region CDR3 domain comprising an amino acid sequence selected from the group consisting of SEQ ID NOs: 6 and 12;
   d. a light chain variable region CDR1 domain comprising the amino acid sequence of SEQ ID NO: 1;
   e. a light chain variable region CDR2 domain comprising the amino acid sequence of SEQ ID NO: 2; and
   f. a light chain variable region CDR3 domain comprising the amino acid sequence of SEQ ID NO: 3.

2. The isolated antibody, or antigen-binding portion thereof, of claim 1, wherein the antibody, or antigen-binding portion thereof, is selected from the group consisting of a chimeric antibody, a humanized antibody, an affinity matured antibody, a human antibody and a bispecific antibody.

3. The isolated antibody, or antigen-binding portion thereof, of claim 1, wherein the antibody, or antigen-binding portion thereof, is an antibody fragment.

4. A pharmaceutical composition comprising an antibody, or an antigen-binding portion thereof, that binds to FGFR2 and FGFR3, and a pharmaceutically acceptable carrier, wherein binding of the antibody, or antigen-binding portion thereof, to FGFR1 or FGFR4 is not detectable by surface plasmon resonance, and wherein the antibody, or antigen-binding portion thereof, comprises:
   a. a heavy chain variable region CDR1 domain comprising an amino acid sequence selected from the group consisting of SEQ ID NOs: 4 and 10;
   b. a heavy chain variable region CDR2 domain comprising the amino acid sequence of SEQ ID NO: 5;
   c. a heavy chain variable region CDR3 domain comprising an amino acid sequence selected from the group consisting of SEQ ID NOs: 6 and 12;
   d. a light chain variable region CDR1 domain comprising the amino acid sequence of SEQ ID NO: 1;
   e. a light chain variable region CDR2 domain comprising the amino acid sequence of SEQ ID NO: 2; and
   f. a light chain variable region CDR3 domain comprising the amino acid sequence of SEQ ID NO: 3.

5. The pharmaceutical composition of claim 4, wherein the antibody, or antigen-binding portion thereof, is selected from the group consisting of a chimeric antibody, a humanized antibody, an affinity matured antibody, a human antibody and a bispecific antibody.

6. The pharmaceutical composition of claim 4, wherein the antibody, or antigen-binding portion thereof, is an antibody fragment.

7. An isolated antibody, or an antigen-binding portion thereof, that binds to FGFR2 and FGFR3, wherein binding of the antibody, or antigen-binding portion thereof, to FGFR1 or FGFR4 is not detectable by surface plasmon resonance, and wherein the antibody, or antigen-binding portion thereof, comprises:
   a. a light chain variable region CDR1 domain comprising the amino acid sequence of SEQ ID NO: 1;
   b. a light chain variable region CDR2 domain comprising the amino acid sequence of SEQ ID NO: 2;
   c. a light chain variable region CDR3 domain comprising the amino acid sequence of SEQ ID NO: 3;
   d. a heavy chain variable region CDR1 domain comprising the amino acid sequence of SEQ ID NO: 4;
   e. a heavy chain variable region CDR2 domain comprising the amino acid sequence of SEQ ID NO: 5; and
   f. a heavy chain variable region CDR3 domain comprising the amino acid sequence of SEQ ID NO: 6.

8. An isolated antibody, or an antigen-binding portion thereof, that binds to FGFR2 and FGFR3, wherein binding of the antibody, or antigen-binding portion thereof, to FGFR1 or FGFR4 is not detectable by surface plasmon resonance, and wherein the antibody, or antigen-binding portion thereof, comprises:
   a. a light chain variable region CDR1 domain comprising the amino acid sequence of SEQ ID NO: 1;
   b. a light chain variable region CDR2 domain comprising the amino acid sequence of SEQ ID NO: 2;
   c. a light chain variable region CDR3 domain comprising the amino acid sequence of SEQ ID NO: 3;
   d. a heavy chain variable region CDR1 domain comprising the amino acid sequence of SEQ ID NO: 10;
   e. a heavy chain variable region CDR2 domain comprising the amino acid sequence of SEQ ID NO: 5; and
   f. a heavy chain variable region CDR3 domain comprising the amino acid sequence of SEQ ID NO: 12.

9. A pharmaceutical composition comprising an antibody, or an antigen-binding portion thereof, that binds to FGFR2 and FGFR3 and a pharmaceutically acceptable carrier, wherein binding of the antibody, or antigen-binding portion thereof, to FGFR1 or FGFR4 is not detectable by surface plasmon resonance, and wherein the antibody, or antigen-binding portion thereof, comprises:
   a. a light chain variable region CDR1 domain comprising the amino acid sequence of SEQ ID NO: 1;
   b. a light chain variable region CDR2 domain comprising the amino acid sequence of SEQ ID NO: 2;
   c. a light chain variable region CDR3 domain comprising the amino acid sequence of SEQ ID NO: 3;
   d. a heavy chain variable region CDR1 domain comprising the amino acid sequence of SEQ ID NO: 4;
   e. a heavy chain variable region CDR2 domain comprising the amino acid sequence of SEQ ID NO: 5; and
   f. a heavy chain variable region CDR3 domain comprising the amino acid sequence of SEQ ID NO: 6.

10. A pharmaceutical composition comprising an antibody, or an antigen-binding portion thereof, that binds to FGFR2 and FGFR3 and a pharmaceutically acceptable carrier, wherein binding of the antibody, or antigen-binding portion thereof, to FGFR1 or FGFR4 is not detectable by surface plasmon resonance, and wherein the antibody, or antigen-binding portion thereof, comprises:
   a. a light chain variable region CDR1 domain comprising the amino acid sequence of SEQ ID NO: 1;
   b. a light chain variable region CDR2 domain comprising the amino acid sequence of SEQ ID NO: 2;
   c. a light chain variable region CDR3 domain comprising the amino acid sequence of SEQ ID NO: 3;
   d. a heavy chain variable region CDR1 domain comprising the amino acid sequence of SEQ ID NO: 10;
   e. a heavy chain variable region CDR2 domain comprising the amino acid sequence of SEQ ID NO: 5; and
   f. a heavy chain variable region CDR3 domain comprising the amino acid sequence of SEQ ID NO: 12.

* * * * *